(12) United States Patent
Takahashi et al.

(10) Patent No.: US 11,135,234 B2
(45) Date of Patent: Oct. 5, 2021

(54) EFFECTIVE AMINOGLYCOSIDE ANTIBIOTIC FOR MULTIDRUG-RESISTANT BACTERIA

(71) Applicants: MICROBIAL CHEMISTRY RESEARCH FOUNDATION, Tokyo (JP); MEIJI SEIKA PHARMA CO., LTD., Tokyo (JP)

(72) Inventors: Yoshiaki Takahashi, Tokyo (JP); Eijiro Umemura, Kanagawa (JP); Takashi Ida, Kanagawa (JP); Masayuki Igarashi, Tokyo (JP)

(73) Assignees: MICROBIAL CHEMISTRY RESEARCH FOUNDATION, Tokyo (JP); MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 16/749,191

(22) Filed: Jan. 22, 2020

(65) Prior Publication Data
US 2020/0155582 A1 May 21, 2020

Related U.S. Application Data

(62) Division of application No. 15/747,581, filed as application No. PCT/JP2016/072400 on Jul. 29, 2016, now Pat. No. 10,617,704.

(30) Foreign Application Priority Data

Jul. 30, 2015 (JP) .................. 2015-151250

(51) Int. Cl.
  *A61K 31/7036* (2006.01)
  *C07H 15/224* (2006.01)
  *A61P 31/04* (2006.01)

(52) U.S. Cl.
  CPC .......... *A61K 31/7036* (2013.01); *A61P 31/04* (2018.01); *C07H 15/224* (2013.01); *Y02A 50/30* (2018.01)

(58) Field of Classification Search
  CPC .................. A61K 31/7036; C07H 15/224
  See application file for complete search history.

(56) References Cited

U.S. PATENT DOCUMENTS

| | | | |
|---|---|---|---|
| 4,358,585 A | 11/1982 | Igarashi et al. | |
| 4,360,665 A | 11/1982 | Kirst | |
| 4,370,475 A | 1/1983 | Igarashi et al. | |
| 4,379,917 A | 4/1983 | Kirst | |
| 4,424,344 A | 1/1984 | Kirst et al. | |
| 4,424,345 A | 1/1984 | Kirst et al. | |
| 4,458,065 A | 7/1984 | Kirst | |
| 4,468,513 A | 8/1984 | Kirst et al. | |
| 8,148,504 B2 | 4/2012 | Kobayashi | |
| 9,260,465 B2 | 2/2016 | Kobayashi | |
| 10,617,704 B2* | 4/2020 | Takahashi | C07H 15/224 |
| 2013/0165397 A1 | 6/2013 | Boettger et al. | |

FOREIGN PATENT DOCUMENTS

| | | |
|---|---|---|
| CN | 103228282 | 7/2013 |
| EP | 0 048 613 | 3/1982 |
| EP | 0 048 614 | 3/1982 |
| GB | 2 086 383 | 5/1982 |
| GB | 2 086 388 | 5/1982 |
| JP | 57-72998 | 5/1982 |
| JP | 57-72999 | 5/1982 |
| JP | 57-082398 | 5/1982 |
| JP | 57-082399 | 5/1982 |
| JP | 2013-537177 | 9/2013 |
| RU | 2 491 921 | 9/2013 |
| WO | 2007/117500 | 10/2007 |

(Continued)

OTHER PUBLICATIONS

International Search Report dated Sep. 6, 2016 in International Application No. PCT/JP2016/072400.
Dobutsuyo Iyaku Hyokasho Apramycin, Food Safety Commission, Jul. 2013, pp. 1 to 33.
Introduction to modern pharmaceutics, revised 3$^{rd}$ edition, Nankodo Co., Ltd., Apr. 10, 1987 (Apr. 10, 1987), pp. 273-274.
Modern pharmaceutics, revised 3$^{rd}$ edition, Nankodo Co., Ltd., Dec. 15, 2011 (Dec. 15, 2011), pp. 381-386.
RN: 1192350-04-01, Registry, STN [online], Nov. 13, 2009.
Kondo, S. et al., "Synthesis of 1-N-{(S)-4-Amino-2-Hydroxybutyryl}-Kanamycinb and -3', 4'-Dideoxykanamycin B Active Against Kanamycin-Resistant Bacteria", The Journal of Antibiotics, vol. 26, pp. 412-415, 1973.

(Continued)

*Primary Examiner* — Golam M Shameem
(74) *Attorney, Agent, or Firm* — Wenderoth, Lind & Ponack, L.L.P.

(57) ABSTRACT

A compound represented by the following general formula (I) or a pharmaceutically acceptable salt or solvate thereof, and a pharmaceutical composition thereof, and the use thereof to prevent or treat infectious diseases and a method to prevent or treat infectious diseases using those regimen are disclosed. The compound represented by formula (I) has an antibacterial activity against both gram-positive and gram-negative bacteria, and is useful in the prevention or treatment of infectious diseases caused by these bacteria.

(I)

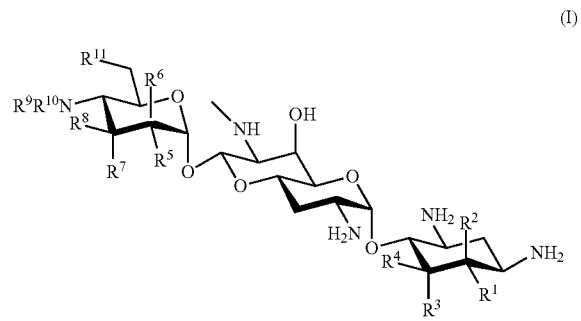

1 Claim, No Drawings

(56) References Cited

FOREIGN PATENT DOCUMENTS

| | | |
|---|---|---|
| WO | 2009/067692 | 5/2009 |
| WO | 2012/034955 | 3/2012 |
| WO | 2013/191550 | 12/2013 |

OTHER PUBLICATIONS

D.M. Livermore et al., "Activity of aminoglycosides, including ACHN-490, against carbapenem-resistant Enterobacteriaceae isolates", Journal of Antimicrobial Chemotherapy, vol. 66, pp. 48-53, 2011.
International Preliminary Report on Patentability dated Feb. 8, 2018 in International Application No. PCT/JP2016/072400.
English Abstract (p. 4) of Dobutsuyo Iyaku Hyokasho Apramycin, Food Safety Commisson, Jul. 2013, pp. 1 to 33, previously cited in the IDS filed on Jan. 25, 2018.
English translation of Introduction to modern pharmaceutics, revised $3^{rd}$ edition, Nankodo Co., Ltd., Apr. 10, 1987, pp. 273-274, previously cited in the IDS filed on Jan. 25, 2018.
English translation of Modern pharmaceutics, revised $3^{rd}$ edition, Nankodo Co., Ltd., Dec. 15, 2011, pp. 381-386, previously cited in the IDS filed on Jan. 25, 2018.
Extended European Search Report dated Aug. 1, 2018 in European Application No. 16830631.4.
Extended European Search Report dated Nov. 6, 2018 in European Patent Application No. 16830631.4.
Extended European Search Report dated Apr. 25, 2019 in European Patent Application No. 19154615.9.
Kirst et al. (1983), STN International (Columbus, Ohio) HCAPLUS database, Accession No. 1983: 107687.
Harvey et al. (2000), STN International (Columbus, Ohio), HCAPLUS database, Accession No. 2000: 31060.
Office Action dated Dec. 27, 2019 in Russian Patent Application No. 2018107150 with English-language translation.
Office Action dated Feb. 11, 2021 in corresponding Indonesian Application No. PID201801382, with English Translation, 6 pages.
Office Action dated Feb. 8, 2021 in corresponding Malaysian Application No. PI2018700342, 3 pages.
Office Action dated Jul. 15, 2020 in corresponding Chinese Patent Application No. 201680044421.1, with English translation.

\* cited by examiner

EFFECTIVE AMINOGLYCOSIDE ANTIBIOTIC FOR MULTIDRUG-RESISTANT BACTERIA

CROSS-REFERENCE TO RELATED APPLICATION

The present application claims priority to Japanese Patent Application No. 2015-151250 (filing date: Jul. 30, 2015) which is a prior application applied to Japan. The entire contents of the prior application are incorporated by reference herein.

BACKGROUND OF THE INVENTION

Field of the Invention

The present invention relates to a new aminoglycoside antibiotics and a pharmaceutical composition comprising thereof.

Background Art

Aminoglycoside antibiotics have, similar to beta-lactams and quinolones, antibacterial activities against both gram-positive and gram-negative bacteria. However, there is no currently available medicine including these antibacterial agents mentioned above having a broad-spectrum activity coping with antibiotic-resistant bacteria. As described below, the development of such medicine also faces difficulties.

Recently, there have been rapidly increasing cases of infectious diseases caused by methicillin-resistant *Staphylococcus aureus* (referred to as "MRSA" as follows) both in Japan and abroad. MRSA poses clinical problems as a causative bacterium to result in serious infectious diseases, and studies to exploit therapeutic agents for these infectious diseases have been made.

It has been reported that (S)-1-N-(4-amino-2-hydroxybutyryl) dibekacin (arbekacin), which is obtained by acylation of an amino group at 1-position of dibekacin (a type of aminoglycosides) with aminohydroxybutyric acid (HABA), is effective against methicillin-resistant *Staphylococcus aureus* (MRSA) (Non-patent Document 1). Actually, arbekacin has been used as a magic bullet for MRSA infection in Japan since the end of 1990.

However, arbekacin has been used as a therapeutic agent for treatment of MRSA for more than 20 years, and emerging arbekacin-resistant MRSA poses issues in clinical practices.

Also, recently, multidrug-resistant bacteria have increased including not only gram-positive bacteria, such as MRSA, but also gram-negative bacteria, such as *Escherichia coli, Klebsiella pneumoniae, Serratia, Acinetobacter, Pseudomonas aeruginosa*. Among these bacteria, many have resistance against conventional aminoglycoside antibiotics, beta-lactam antibiotics and new quinolone antibiotics and often cause intractable infectious diseases.

For the multidrug-resistant gram-negative bacteria such as multidrug-resistant *Escherichia coli* and multidrug-resistant *Acinetobacter*, it has been reported that (S)-1-N-(4-amino-2-hydroxybutyryl)-6'-N-hydroxyethylsisomicin (Plazomicin) is effective, which is produced from sisomicin (a type of aminoglycoside antibiotics) by acylation of the amino group at 1-position of sisomicin with amino hydroxybutyric acid (HABA) and alkylation of the amino group at 6'-position of sisomicin (Patent Document 1).

However, Plazomicin is ineffective against resistant methylase-producing gram-negative bacteria although it shows efficacy against some multidrug-resistant gram-negative bacteria. Also, the fundamental antimicrobial activity and safety thereof are not sufficient.

Furthermore, it is described that apramycin is moderately effective against carbapenem-resistant gram-negative bacteria for which most aminoglycoside antibiotics are found ineffective (Non-patent Document 2). A compound produced by chemical modification of the hydroxyl group at 5-, 6- or 6"-position of this apramycin is disclosed (Patent Documents 2, 3 and 4). A compound produced by chemical modification of the amino group at 1- or 4"-position of apramycin is also disclosed (Patent Documents 5 and 6). However, neither of the compounds has been clearly disclosed regarding their efficacies against resistant bacteria.

PRIOR ART DOCUMENT

Patent Document

Patent Document 1: WO 2009/067692

Patent Document 2: Japanese Unexamined Patent Application Publication No. 57-72998

Patent Document 3: Japanese Unexamined Patent Application Publication No. 57-72999

Patent Document 4: U.S. Pat. No. 4,379,917

Patent Document 5: U.S. Pat. No. 4,424,345

Patent Document 6: U.S. Pat. No. 4,360,665

Non Patent Document

Non Patent Document 1: Kondo, S. et al., The Journal of Antibiotics, Vol. 26, pp. 412-415, 1973

Non Patent Document 2: J Antimicrob Chemother, Vol. 66, pp. 48-53, 2011

SUMMARY OF THE INVENTION

The present invention is intended to provide a new aminoglycoside antibiotic, which is effective against both gram-positive and gram-negative bacteria, especially against multidrug-resistant gram-negative and gram-positive bacteria.

The inventors of the present invention found compounds having antibacterial activities against gram-positive and gram-negative bacteria as a result of their earnest investigation of derivatives of apramycin, a type of aminoglycoside antibiotics. These compounds proved to be also effective against resistant bacteria such as MRSA and multidrug-resistant gram-negative bacteria. The present invention is based on these findings.

Therefore, the present invention includes the following invention.

(1) A compound represented by a general formula (I) or a pharmaceutically acceptable salt or solvate thereof:

[Chem. 1]

(I)

Wherein,
$R^1$ is a hydrogen atom or a hydroxyl group,
$R^2$ is a hydrogen atom or an amino group,
$R^3$ is a hydrogen atom, a halogen atom, a hydroxyl group or an amino group,
$R^4$ is a hydrogen atom, a halogen atom, a hydroxyl group or an amino group,
wherein $R^1$ and $R^4$ may form a double bond together,
$R^5$ is a hydrogen atom, a hydroxyl group or an amino group,
$R^6$ is a hydrogen atom, a hydroxyl group or an amino group,
$R^7$ is a hydrogen atom, a hydroxyl group or an amino group,
$R^8$ is a hydrogen atom, a hydroxyl group or an amino group,
$R^9$ and $R^{10}$ are each independently a hydrogen atom, a $C_{1-6}$ alkyl group, an amino-$C_{1-6}$ alkyl group, a guanidino-$C_{1-6}$ alkyl group, an amino-$C_{3-7}$ cycloalkyl group, an amino-$C_{3-7}$ cycloalkyl-$C_{1-6}$ alkyl group, an amidino group, an azetidino group optionally substituted with a $C_{1-6}$ alkyl group, a glycyl group, a sarcosyl group, an L-alanyl group, a D-alanyl group, an L-seryl group, a D-seryl group, a β-alanyl group, an L-isoseryl group or a D-isoseryl group; and
$R^{11}$ is a hydrogen atom, a hydroxyl group or a fluorine atom, except when
(i) $R^1$, $R^4$, $R^5$, $R^8$, and $R^{11}$ are hydroxyl groups, $R^2$, $R^3$, $R^6$, $R^7$, $R^9$, and $R^{10}$ are hydrogen atoms (apramycin),
(ii) $R^5$, $R^8$, and $R^{1"}$ are hydroxyl groups, $R^1$, $R^2$, $R^3$, $R^4$, $R^6$, $R^7$, $R^9$, and $R^{10}$ are hydrogen atoms (5,6-dideoxyapramycin),
(iii) $R^1$, $R^5$, $R^8$, and $R^{11}$ are hydroxyl groups, $R^2$, $R^3$, $R^4$, $R^6$, $R^7$, $R^9$, and $R^{10}$ are hydrogen atoms (5-deoxyapramycin),
(iv) $R^1$, $R^4$, $R^5$, and $R^8$ are hydroxyl groups, $R^2$, $R^3$, $R^6$, $R^7$, $R^9$, $R^{10}$, and $R^{11}$ are hydrogen atoms (6"-deoxyapramycin),
(v) $R^1$, $R^4$, $R^5$, $R^8$, and $R^1$ are hydroxyl groups, $R^2$, $R^3$, $R^6$, and $R^7$ are hydrogen atoms, either one of $R^9$ or $R^{10}$ is a hydrogen atom, the other is an ethyl group or a 2-aminoethyl group.

(2) The compound according to (1) represented by a general formula (I-1) or a pharmaceutically acceptable salt or solvate thereof:

[Chem. 2]

(I-1)

wherein,
$R^1$ is a hydrogen atom or a hydroxyl group,
$R^2$ is a hydrogen atom or an amino group,
$R^3$ is a hydrogen atom, a halogen atom, a hydroxyl group or an amino group,
$R^4$ is a hydrogen atom, a halogen atom or an amino group,
wherein $R^1$ and $R^4$ may form a double bond together,
$R^5$ is a hydrogen atom, a hydroxyl group or an amino group,
$R^6$ is a hydrogen atom, a hydroxyl group or an amino group,
$R^7$ is a hydrogen atom, a hydroxyl group or an amino group,
$R^8$ is a hydrogen atom, a hydroxyl group or an amino group; and
$R^{11}$ is a hydrogen atom, a hydroxyl group or a fluorine atom, except when
(i) $R^5$, $R^8$, and $R^{11}$ are hydroxyl groups, $R^1$, $R^2$, $R^3$, $R^4$, $R^6$, and $R^7$ are hydrogen atoms (5,6-dideoxyapramycin),
(ii) $R^1$, $R^5$, $R^8$, and $R^{11}$ are hydroxyl groups, $R^2$, $R^3$, $R^4$, $R^6$, and $R^7$ are hydrogen atoms (5-deoxyapramycin),
(iii) $R^1$, $R^4$, $R^5$, and $R^8$ are hydroxyl groups, $R^2$, $R^3$, $R^6$, $R^7$, and $R^{11}$ are hydrogen atoms (6"-deoxyapramycin).

(3) The compound according to (1) represented by a general formula (I-2) or a pharmaceutically acceptable salt or solvate thereof:

[Chem. 3]

(I-2)

Wherein,
$R^1$ is a hydrogen atom or a hydroxyl group,
$R^2$ is a hydrogen atom or an amino group,
$R^3$ is a hydrogen atom, a halogen atom, a hydroxyl group or an amino group,
$R^4$ is a hydrogen atom, a halogen atom or an amino group,
wherein $R^1$ and $R^4$ may form a double bond together,
$R^7$ is a hydrogen atom, a hydroxyl group or an amino group,
$R^8$ is a hydrogen atom, a hydroxyl group or an amino group,
$R^9$ is a hydrogen atom, a $C_{1-6}$ alkyl group or an amino-$C_{1-6}$ alkyl group,
$R^{10}$ is a $C_{1-6}$ alkyl group, an amino-$C_{1-6}$ alkyl group, a guanidino-$C_{1-6}$ alkyl group, an amino-$C_{3-7}$ cycloalkyl group, an amino-$C_{3-7}$ cycloalkyl-$C_{1-6}$ alkyl group, an amidino group, an azetidino group optionally substituted with a $C_{1-6}$ alkyl group, a glycyl group, a sarcosyl group, an L-alanyl group, a D-alanyl group, an L-seryl group, a D-seryl group, a β-alanyl group, an L-isoseryl group or a D-isoseryl group; and
$R^{11}$ is a hydrogen atom or a hydroxyl group.

(4) The compound according to (1) represented by a general formula (I-3) or a pharmaceutically acceptable salt or solvate thereof:

[Chem. 4]

(I-3)

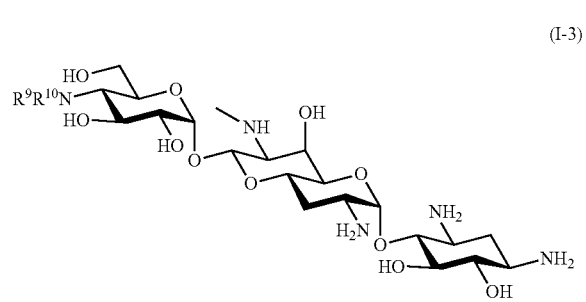

Wherein, $R^9$ is a hydrogen atom, a $C_{1-6}$ alkyl group or an amino-$C_{1-6}$ alkyl group, $R^{10}$ is a methyl group, a $C_{3-6}$ alkyl group, an amino-$C_{3-6}$ alkyl group, a guanidino-$C_{1-6}$ alkyl group, an amino-$C_{3-7}$ cycloalkyl group, an amino-$C_{3-7}$ cycloalkyl-$C_{1-6}$ alkyl group, an amidino group, an azetidino group optionally substituted with a $C_{1-6}$ alkyl group, a glycyl group, a sarcosyl group, an L-alanyl group, a D-alanyl group, an L-seryl group, a D-seryl group, a β-alanyl group, an L-isoseryl group or a D-isoseryl group. (5) The compound according to (1) represented by a general formula (I-4) or a pharmaceutically acceptable salt or solvate thereof:

[Chem. 5]

(I-4)

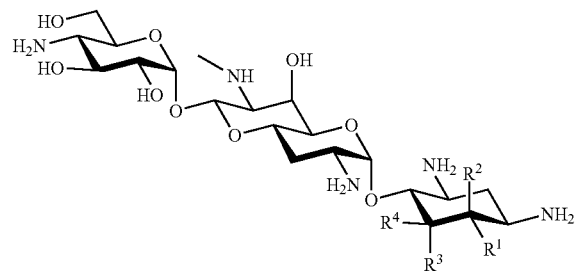

Wherein, $R^1$ is a hydrogen atom or a hydroxyl group, $R^2$ is a hydrogen atom or an amino group, $R^3$ is a hydrogen atom, a halogen atom, a hydroxyl group or an amino group, $R^4$ is a hydrogen atom, a halogen atom or an amino group; and wherein $R^1$ and $R^4$ may form a double bond together, except when (i) $R^1$, $R^2$, $R^3$, and $R^4$ are hydrogen atoms (5,6-dideoxyapramycin), (ii) $R^1$ is a hydroxyl group, and $R^2$, $R^3$, and $R^4$ are hydrogen atoms (5-deoxyapramycin).

(6) The compound according to (1) represented by a general formula (I-5) or a pharmaceutically acceptable salt or solvate thereof:

[Chem. 6]

(I-5)

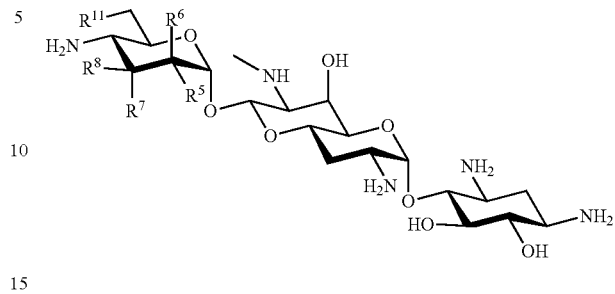

wherein, $R^5$ is a hydrogen atom, a hydroxyl group or an amino group,
$R^6$ is a hydrogen atom, a hydroxyl group or an amino group,
$R^7$ is a hydrogen atom, a hydroxyl group or an amino group,
$R^8$ is a hydrogen atom, a hydroxyl group or an amino group; and
$R^{11}$ is a hydrogen atom, a hydroxyl group or a fluorine atom,
except when
(i) $R^5$, $R^8$, and $R^{11}$ are hydroxyl groups, $R^6$, and $R^7$ are hydrogen atoms (apramycin),
(ii) $R^5$ and $R^8$ are hydroxyl groups, and $R^6$, $R^7$, and $R^{11}$ are hydrogen atoms (6"-deoxyapramycin).

(7) A compound according to (1) or a pharmaceutically acceptable salt or solvate thereof, wherein the compound is:

4"-N-methylapramycin,
4"-N-(3-aminopropyl)apramycin,
4"-N-((1-aminocyclopentyl)methyl)apramycin,
4"-N-(1,3-diaminopropan-2-yl)apramycin,
4"-N,N-bis(2-aminoethyl)apramycin,
4"-N-(cis-1,4-4-aminocyclohexyl)apramycin,
4"-N-(trans-1,4-4-aminocyclohexyl)apramycin,
4"-N-(azetidin-3-yl)apramycin,
4"-N-(1-methylazetidin-3-yl)apramycin,
4"-deamino-4"-guanidinoapramycin,
4"-N-guanidinoethylapramycin,
5-epiapramycin,
5-deoxy-5-epi-5-fluoroapramycin,
6-deoxy-5-epiapramycin,
5,6-dideoxy-5-fluoroapramycin,
5-amino-5-deoxy-5-epiapramycin,
5-amino-5-deoxyapramycin,
6-amino-5,6-dideoxy-5,6-diepi-5-fluoroapramycin,
5-amino-5,6-dideoxyapramycin,
2"-amino-2"-deoxy-2",3"-diepiapramycin,
3"-amino-3"-deoxyapramycin,
3"-epiapramycin,
2",3"-diepiapramycin,
6"-deoxy-6"-fluoroapramycin,
3",6"-dideoxyapramycin,
5,6"-dideoxyapramycin,
5,3"-dideoxyapramycin,
3"-deoxy-5-epiapramycin,
5,3"-dideoxy-5-epi-5-fluoroapramycin,
6,3"-dideoxy-5-epiapramycin,
5,6,3"-trideoxyapramycin,
5-amino-5,3"-dideoxy-5-epiapramycin,
5,2"-dideoxy-5,3"-diepi-5-fluoroapramycin,
5,3"-diepiapramycin,
6,6"-dideoxy-5-epiapramycin,
5-eno-5,6,6"-trideoxyapramycin,
5,6,6"-trideoxyapramycin,
5-deoxy-4"-N-methylapramycin,
4"-N-(2-aminoethyl)-5-deoxyapramycin, 4"-N-(3-aminopropyl)-5-deoxyapramycin,
5-deoxy-4"-N-(1,3-diaminopropan-2-yl)apramycin,
4"-deamino-5-deoxy-4"-guanidinoapramycin,
5-epi-4"-N-methylapramycin,
4"-N-(2-aminoethyl)-5-epiapramycin,
4"-N-(3-aminopropyl)-5-epiapramycin,
4"-N-(1,3-diaminopropan-2-yl)-5-epiapramycin,
4"-deamino-5-epi-4"-guanidinoapramycin,
4"-deamino-5-deoxy-5-epi-5-fluoro-4"-guanidinoapramycin,
5,6-dideoxy-4"-N-methylapramycin,
4"-N-(2-aminoethyl)-5,6-dideoxyapramycin,
4"-N-(3-aminopropyl)-5,6-dideoxyapramycin,
4"-N-(1,3-diaminopropan-2-yl)-5,6-dideoxyapramycin,
4"-deamino-5,6-dideoxy-4"-guanidinoapramycin,
6-deoxy-5-epi-4"-N-methylapramycin,
4"-N-(2-aminoethyl)-6-deoxy-5-epiapramycin,
4"-N-(3-aminopropyl)-6-deoxy-5-epiapramycin,
4"-deamino-6-deoxy-5-epi-4"-guanidinoapramycin,
4"-N-(1,3-diaminopropan-2-yl)-5,6"-dideoxyapramycin,
4"-deamino-5,6"-dideoxy-4"-guanidinoapramycin,
4"-deamino-5,3"-dideoxy-4"-guanidinoapramycin,
4"-N-glycylapramycin,
4"-N-sarcosylapramycin,
4"-N-(L-alanyl)apramycin,
4"-N-(D-alanyl)apramycin,
4"-N-(L-seryl)apramycin,
4"-N-(D-seryl)apramycin,
4"-N-(β-alanyl)apramycin,
4"-N-(L-isoseryl)apramycin,
5-epi-4"-N-glycylapramycin,
5-epi-4"-N-sarcosylapramycin,
4"-N-(L-alanyl)-5-epiapramycin,
5-epi-4"-N-(L-seryl)apramycin,
4"-N-(β-alanyl)-5-epiapramycin,
5-epi-4"-N-(L-isoseryl)apramycin,
5-epi-4"-N-(D-isoseryl)apramycin,
6-deoxy-5-epi-4"-N-glycylapramycin,
6-deoxy-5-epi-4"-N-sarcosylapramycin,
4"-N-(β-alanyl)-6-deoxy-5-epiapramycin,
6-deoxy-5-epi-4"-N-(L-isoseryl)apramycin,
5-amino-4"-deamino-5-deoxy-5-epi-4"-guanidinoapramycin,
5-amino-5-deoxy-5-epi-4"-N-glycylapramycin,
5-amino-5-deoxy-5-epi-4"-N-(L-isoseryl)apramycin,
4"-deamino-3"-deoxy-5-epi-4"-guanidinoapramycin,
4"-deamino-5,3"-dideoxy-5-epi-5-fluoro-4"-guanidinoapramycin
or
2"-deoxy-5,3"-diepiapramycin.

(8) A pharmaceutical composition comprising the compound according to any one of (1) to (7) or a pharmaceutically acceptable salt or solvate thereof.
(9) The pharmaceutical composition according to (8) for use in the prevention or treatment of infectious disease.
(10) The pharmaceutical composition according to (8) or (9), wherein the infectious disease is sepsis, infectious endocarditis, dermatological infections, surgical site infections, orthopedic surgical site infections, respiratory infections, urinary tract infections, enteral infections, peritonitis, meningitis, ophthalmological infections or otolaryngological infections.
(11) The pharmaceutical composition according to any one of (8) to (10), wherein the infectious disease is caused by methicillin-resistant *Staphylococcus aureus* (MRSA), *Staphylococcus aureus*, *Escherichia coli*, *Klebsiella pneumoniae* or *Pseudomonas aeruginosa*.
(12) The compound according to any one of (1) to (7) or a pharmaceutically acceptable salt or solvate thereof for use in therapy.
(13) The compound according to any one of (1) to (7) or a pharmaceutically acceptable salt or solvate thereof for use in the prevention or treatment of infectious disease.
(14) Use of the compound according to any one of (1) to (7) or a pharmaceutically acceptable salt or solvate thereof for the manufacture of a medicament for the prevention or treatment of infectious disease.
(15) Use of the compound according to any one of (1) to (7) or a pharmaceutically acceptable salt or solvate thereof for the prevention or treatment of infectious disease.
(16) The use according to (15), wherein other medicinal agents (e.g., antibiotics) are used in combination therewith.
(17) A method for the prevention or treatment of infectious disease, comprising administering a therapeutically effective dose of the compound according to any one of (1) to (7) or a pharmaceutically acceptable salt or solvate thereof to an animal including human.
(18) An antimicrobial agent comprising the compound of any one of (1) to (7) or a pharmaceutically acceptable salt or solvate thereof.

The compound of the present invention or a pharmaceutically acceptable salt or solvate thereof is advantageous in terms of a wide antibacterial spectrum against a variety of gram-positive bacteria and gram-negative bacteria. Also, it is advantageous from the viewpoint of an antibacterial activity against multidrug-resistant gram-positive and gram-negative bacteria, which are not treatable with currently available antibiotics. Particularly, it is advantageous to prevent or treat serious infectious diseases caused by MRSA or multidrug-resistant gram-negative bacteria.

DETAILED DESCRIPTION OF THE INVENTION

The present invention will be specifically explained as follows.

Definition

In a compound of the present invention, the halogen atom means a fluorine atom, a chlorine atom, a bromine atom or an iodine atom.

In a compound of the present invention, the $C_{1-6}$ alkyl group means a linear or branched-chain alkyl group having 1 to 6 carbon atoms. For example, the alkyl groups include methyl group, ethyl group, n-propyl group, isopropyl group, n-butyl group, isobutyl group, tert-butyl group, sec-butyl group, n-pentyl group, isopentyl group, 2-methylbutyl group, neopentyl group, 1-ethylpropyl group, n-hexyl group, 4-methylpentyl group, 3-methylpentyl group, 2-methylpentyl group, 1-methylpentyl group, 3,3-dimethylbutyl group, 2,2-dimethylbutyl group, 1,1-dimethylbutyl group, 1,2-dimethylbutyl group, 1,3-dimethylbutyl group, 2,3-dimethylbutyl group, 2-ethylbutyl group and the like.

In a compound of the present invention, the amino-$C_{1-6}$ alkyl group means the above-mentioned $C_{1-6}$ alkyl group of which 1 to 3 hydrogen atoms are substituted with (an) amino group(s), and the position of substitution is not particularly limited. For example, the amino-$C_{1-6}$ alkyl groups include aminomethyl group, aminoethyl group, aminopropyl group, aminobutyl group, aminopentyl group, aminohexyl group, 1,3-diaminopropanyl group and the like.

In a compound of the present invention, the guanidino-$C_{1-6}$ alkyl group means the above-mentioned $C_{1-6}$ alkyl group in which 1 to 2 hydrogen atoms are substituted with (a) guanidino group(s), and the position of substitution is not particularly limited. For example, the guanidino-$C_{1-6}$ alkyl groups include guanidinomethyl group, guanidinoethyl group, guanidinopropyl group, and the like.

In a compound of the present invention, the amino-$C_{3-7}$ cycloalkyl group means a cyclic alkyl group having 3 to 7 carbon atoms in which 1 to 2 hydrogen atoms are substituted with (an) amino group(s), and the position of substitution is not particularly limited. The amino-$C_{3-7}$ cycloalkyl groups include aminocyclopropyl group, aminocyclobutyl group, aminocyclopentyl group, aminocyclohexyl group, aminocycloheptyl group and the like.

In a compound of the present invention, the amino-$C_{3-7}$ cycloalkyl-$C_{1-6}$ alkyl group means the above-mentioned $C_{1-6}$ alkyl group substituted with the above-mentioned amino-$C_{3-7}$ cycloalkyl groups. The amino-$C_{3-7}$ cycloalkyl-$C_{1-6}$ alkyl groups include aminocyclopropylmethyl group, aminocyclobutylmethyl group, aminocyclopentylmethyl group, aminocyclohexylmethyl group, and the like.

In a compound of the present invention, the azetidino group optionally substituted with $C_{1-6}$ alkyl means an azetidino group unsubstituted or substituted with the $C_{1-6}$ alkyl group mentioned above. The azetidino groups substituted with $C_{1-6}$ alkyl include N-methylazetidino group, N-ethylazetidino group, N-propylazetidino group, N-isopropylazetidino group and the like.

In a compound of the present invention, "optionally substituted" means that it may be substituted with 1 or more substituents or may be unsubstituted.

Aminoglycoside Antibiotic

The compound of the present invention is a compound represented by above-mentioned general formula (I), (I-1), (I-2), (I-3), (I-4) or (I-5), or a pharmaceutically acceptable salt thereof or a solvate thereof.

In one embodiment, $R^9$ and $R^{10}$ in the above-mentioned general formula (I) each independently represent a hydrogen atom, a $C_{1-6}$ alkyl group, an amino-$C_{1-6}$ alkyl group, a guanidino-$C_{1-6}$ alkyl group, an amino-$C_{3-7}$ cycloalkyl group, an amino-$C_{3-7}$ cycloalkyl-$C_{1-6}$ alkyl group, an amidino group, an azetidino group optionally substituted with a $C_{1-6}$ alkyl group.

In one embodiment, $R^{10}$ in the above-mentioned general formula (I-2) represents an $C_{1-6}$ alkyl group, an amino-$C_{1-6}$ alkyl group, a guanidino-$C_{1-6}$ alkyl group, an amino-$C_{3-7}$ cycloalkyl group, an amino-$C_{3-7}$ cycloalkyl-$C_{1-6}$ alkyl group, an amidino group or an azetidino group optionally substituted with a $C_{1-6}$ alkyl group.

In one embodiment, $R^0$ in the above-mentioned general formula (I-3) represents a methyl group, a $C_{3-6}$ alkyl group, an amino-$C_{3-6}$ alkyl group, a guanidino-$C_{1-6}$ alkyl group, an amino-$C_{3-7}$ cycloalkyl group, an amino-$C_{3-7}$ cycloalkyl-$C_{1-6}$ alkyl group, an amidino group or an azetidino group optionally substituted with a $C_{1-6}$ alkyl group.

A compound of the present invention can be present as a salt. The salt includes, for example, a pharmaceutically acceptable nontoxic salt. Specific examples of the salt include hydrogen halide salt such as hydrogen fluoride salt, hydrogen chloride salt, hydrogen bromide salt and hydrogen iodide salt; inorganic acid salt such as sulfate, nitrate, phosphate, perchlorate and carbonate; carboxylates such as acetate, trichloroacetate, trifluoroacetate, hydroxyacetate, lactate, citrate, tartrate, oxalate, benzoate, mandelate, butyrate, maleate, propionate, formate and malate; amino acid salts such as argininate, aspartate and glutamate; sulfonates such as methanesulfonate, para-toluenesulfonate, and preferable examples include inorganic acid salts such as sulfate and the like.

A compound of the present invention can be present as a solvate. Preferable solvates includes hydrate and ethanol solvate.

A Method to Produce Aminoglycoside Antibiotic

Compounds of the present invention can be produced according to the following methods A to U, but the methods are not limited to these.

Method A

The method A is a way to produce a compound represented by a general formula (A4) comprising introducing a substituent at 4"-position of apramycin and subsequent deprotecting. The steps are shown as follows. In addition, the steps A1 to A3 were carried out according to a method described in US2013/0165395 A1.

[Chem. 7]

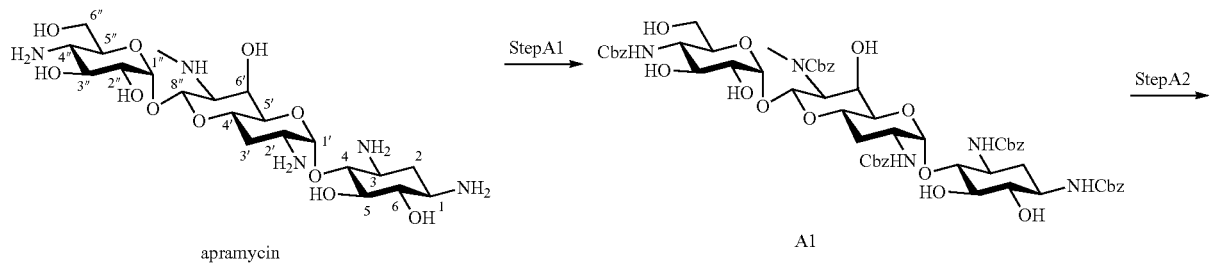

apramycin

A1

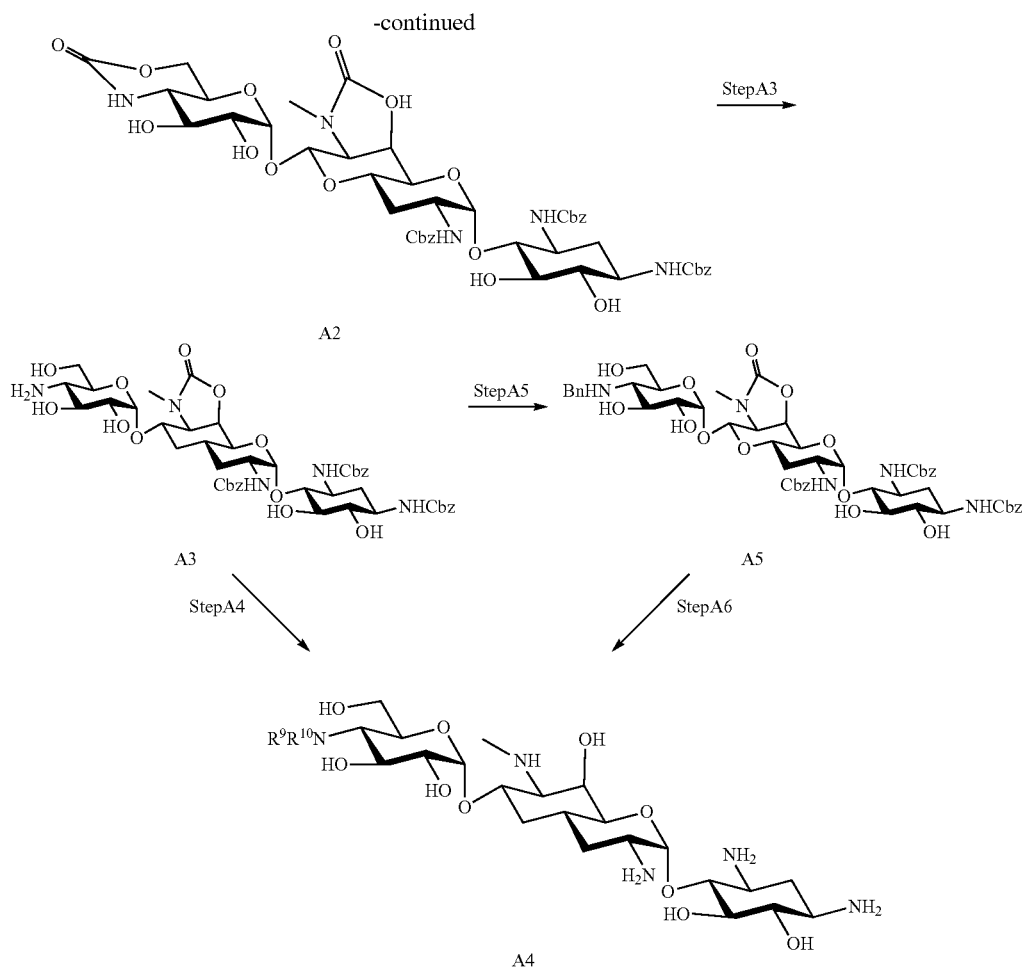

Step A4

The step A4 is a way to produce a compound represented by a general formula (A4) by alkylation or amidination of the amino group at 4″-position of a compound represented by formula (A3) followed by deprotection thereof. This step is achieved by the reaction of various ketones with a compound of formula (A3) and a reducing agent in the presence of an acid as for monoalkylation, by the reaction of various aldehydes with the compound of formula (A3) and a reducing agent in the presence of an acid as for dialkylation, and by the reaction with an amidino reacting reagent in the presence of a base as for amidination.

The reducing agents used in the present step include sodium borohydride, sodium cyanoborohydride and borane-2-methylpyridine complex, and preferably sodium cyanoborohydride. The solvents used include methanol, ethanol, isopropyl alcohol, dioxane, water or a mixed solvent thereof, and preferably a mixed solvent of methanol and dioxane. The reagents used in amidination include 1,3-bis (tert-butoxycarbonyl)-2-(trifluoromethanesulfonyl) guanidine (Goodman's reagent), N,N'-di-(t-butoxycarbonyl) thiourea, t-butyl-(Z)-(((t-butoxycarbonyl)imino)(1H-pyrazol-1-yl) methyl) carbamate and the like, and preferably Goodman's reagent, and the base is preferably triethylamine. All the reactions are conducted under the reaction temperature of 10° C. to 90° C. for the reaction time of 1 to 24 hours.

The benzyloxycarbonyl group can be eliminated by reacting with hydrogen and a catalytic reduction catalyst. The catalytic reduction catalysts used include palladium-carbon, palladium black, palladium hydroxide, platinum oxide and the like, and preferably palladium-carbon. The solvents used are not particularly limited if not involved in this reaction, and preferably methanol, ethanol, tetrahydrofuran, dioxane or a mixed solvent of these organic solvent and water. The reaction temperature is 10° C. to 30° C., and the reaction time is usually 1 to 24 hours. Cyclic carbamate can be eliminated by base hydrolysis. The bases include sodium hydroxide and potassium hydroxide. The reaction temperature is 20° C. to 110° C. and the reaction time is 0.5 to 48 hours.

Step A5

The step A5 is a way to produce a compound represented by formula (A5) by introducing a benzyl group for the monoalkylation of the amino group at 4″-position of a compound of formula (A3). This step is achieved by the reaction of the compound represented by formula (A3) with benzaldehyde and sodium borohydride in the presence of a base. The solvents used in the step A5 include methanol, tetrahydrofuran, dioxane and a mixed solvent thereof, and preferably methanol. The reaction temperature is 10° C. to 20° C. and the reaction time is 1 to 2 hours.

Step A6

The step A6 is a way to produce a compound represented by a general formula (A4) by alkylation of the benzylated amino group at 4″-position of a compound of formula (A5)

followed by deprotection thereof. This step is achieved by various kinds of aldehydes reacting with the compound of formula (A5) and a reducing agent in the presence of an acid.

The solvents used in the present step include tetrahydrofuran, dioxane, methanol and a mixed solvent thereof. The reducing agents include sodium cyanoborohydride and borane-2-methylpyridine complex. The deprotection of the benzyl group, benzyloxycarbonyl group and cyclic carbamate can be carried out under the conditions similar to those in the above-mentioned step A4.

Method B

The method B is a way to produce a compound represented by formulae (B5) and (B7) by chemically modifying the 5-position of a compound obtained by liberating a hydroxyl group only at 5-position of apramycin and subsequent deprotecting. The steps are shown as follows.

[Chem. 8]

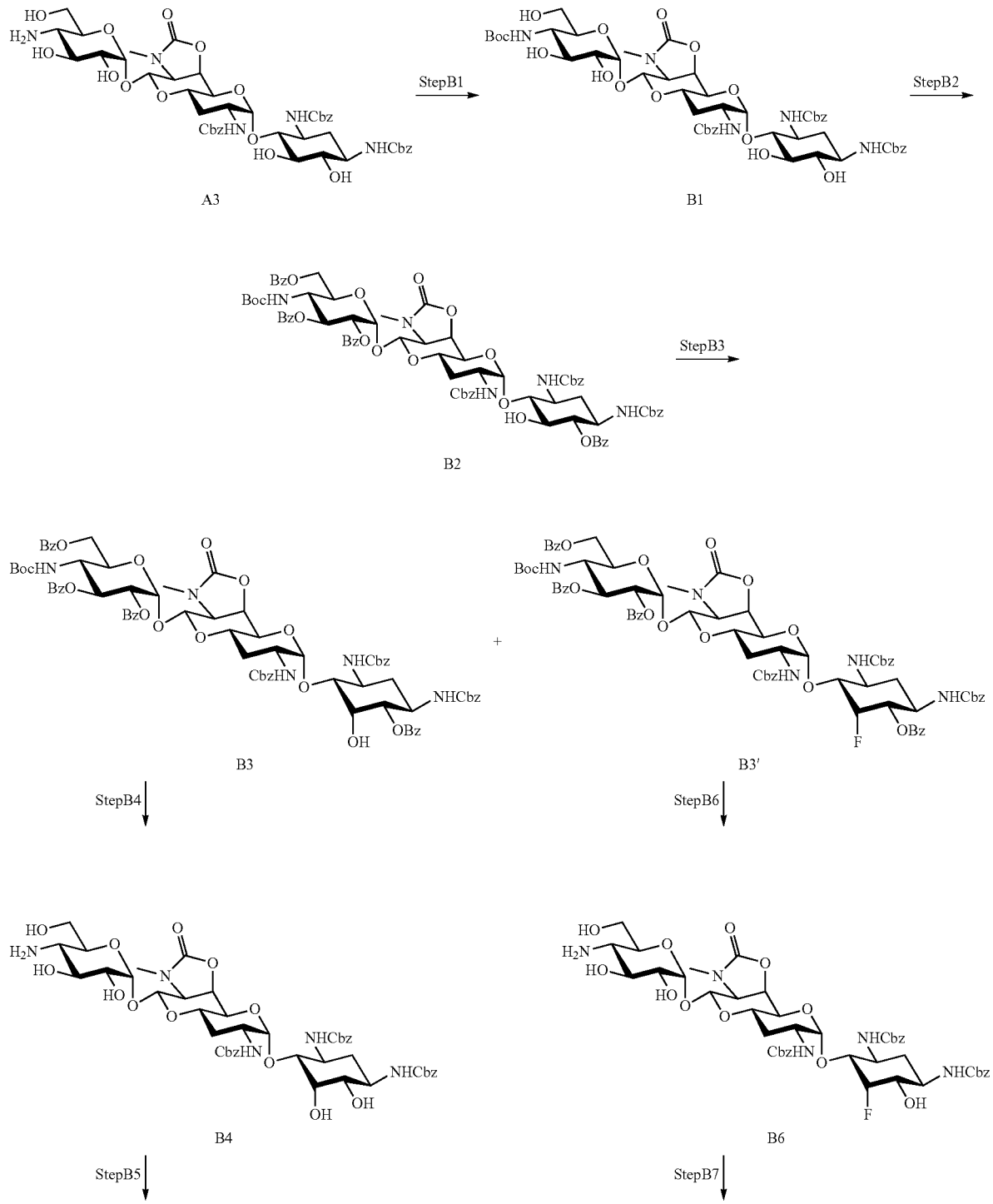

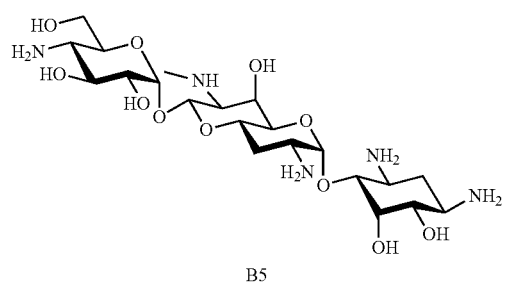

B5

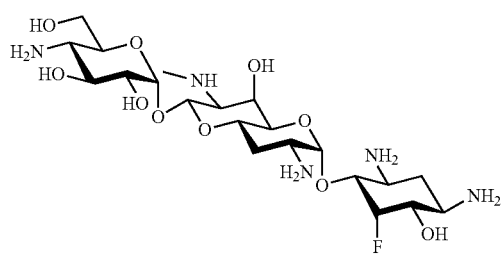

B7

Step B1

The step B1 is a way to produce a compound represented by formula (B1) by introducing a t-butoxycarbonyl group into the amino group at 4"-position of a compound represented by formula (A3). This step is achieved by reacting the compound of formula (A3) with di-t-butyl dicarbonate in the presence of a base.

The solvents used in the present step include water, N,N-dimethylformamide, tetrahydrofuran, dioxane and a mixed solvent thereof, and preferably a mixed solvent of water and N,N-dimethylformamide. The bases used can include sodium hydroxide, potassium carbonate, sodium carbonate, potassium bicarbonate, sodium bicarbonate, triethylamine and the like, and preferably triethylamine. The reaction temperature is 0° C. to 40° C. and the reaction time is 1 to 3 hours.

Step B2

The step B2 is a way to produce a compound represented by formula (B2) by selectively introducing a benzoyl protecting group into a hydroxyl group at 6-, 2"-, 3"-, and 6"-positions of a compound represented by formula (B1). This step is achieved by reacting the compound of formula (B1) with benzoyl chloride in the presence of a base.

The solvents used in the present step include pyridine, N,N-dimethylformamide, methylene chloride, chloroform, 1,2-dichloroethane and the like, and preferably pyridine. The bases used include triethylamine, pyridine, 4-dimethylaminopyridine and the like, and preferably pyridine. The reaction temperature is 0° C. to 30° C. and the reaction time is 1 to 5 hours.

Step B3

The step B3 is a way to produce compounds represented by formulae (B3) and (B3') by epimerizing or epi-fluorinating a hydroxyl group at 5-position of a compound represented by (B2). This step is achieved by reacting the compound represented by formula (B2) with diethylaminosulfur trifluoride (DAST).

The solvents used in the present step include toluene, methylene chloride, chloroform, 1,2-dichloroethane and the like, and preferably methylene chloride The reaction temperature is −5° C. to 5° C. and the reaction time is 1 to 5 hours.

Step B4

The step B4 is a way to produce a compound represented by formula (B4) by removing a benzoyl group and a t-butoxycarbonyl group of a compound represented by formula (B3). This step is achieved by reacting the compound of formula (B3) with a base to eliminate the protecting group of the hydroxyl group, and reacting the resultant compound with an acid to remove the protecting group of the amino group at 4"-position.

The solvents used in the step of removing the protecting group of the hydroxyl group include methanol, ethanol, isopropyl alcohol, tert-butyl alcohol, methylene chloride, chloroform and a mixed solvent thereof, and preferably a mixed solvent of methanol and chloroform. The bases used include potassium carbonate, sodium carbonate, potassium hydroxide, sodium hydroxide, sodium methoxide, sodium ethoxide, potassium tert-butoxide and the like, and preferably sodium methoxide. The reaction temperature is 0° C. to 30° C. and the reaction time is 1 to 5 hours.

The solvents used in the step of removing the protecting group of the amino group at 4"-position include ethyl acetate, methylene chloride, acetonitrile, acetone, methanol and like, and preferably methanol. The acids used include p-toluenesulfonic acid, methanesulfonic acid, acetic acid, trifluoroacetic acid and the like, and preferably trifluoroacetic acid. The reaction temperature is normally 0° C. to 50° C. and the reaction time is 1 to 5 hours.

Step B5

The step B5 is a way to produce a compound represented by formula (B5) by removing the benzyloxycarbonyl group and cyclic carbamate of the compound represented by formula (B4). The benzyloxycarbonyl group can be eliminated by reacting with hydrogen and a catalytic hydrogen reduction catalyst. The catalytic hydrogen reduction catalysts used include palladium-carbon, palladium black, palladium hydroxide, platinum oxide and the like, and preferably palladium-carbon. The solvents used are not particularly limited if not involved in this reaction, and preferably methanol, ethanol, tetrahydrofuran, dioxane or a mixed solvent of these organic solvents and water. The reaction temperature is 10° C. to 30° C., and the reaction time is usually 1 to 24 hours. Cyclic carbamate can be eliminated by hydrolysis with base. The bases include sodium hydroxide and potassium hydroxide. The reaction temperature is 90° C. to 110° C. and the reaction time is 0.5 to 1 hour.

Step B6

The step B6 is a way to produce a compound represented by formula (B6) by removing a benzoyl group and a t-butoxycarbonyl group of a compound represented by formula (B3'). The removal of the protecting group can be carried out under the conditions similar to those in the above-mentioned step B4.

Step B7

The step B7 is a way to produce a compound represented by formula (B7) by removing the benzyloxycarbonyl group and cyclic carbamate of the compound represented by formula (B6). The removal of the protecting group can be carried out under the conditions similar to those in the above-mentioned step B5.

Method C

The method C is a way to produce compounds represented by formulae (C6), (C8) and (C11) by first introducing a leaving group into the 5-position of apramycin and then obtaining 6-deoxy-5-epi, 6-deoxy-5-fluoro and 5-azido-6-deoxy derivatives, followed by deprotecting. The steps are shown as follows.

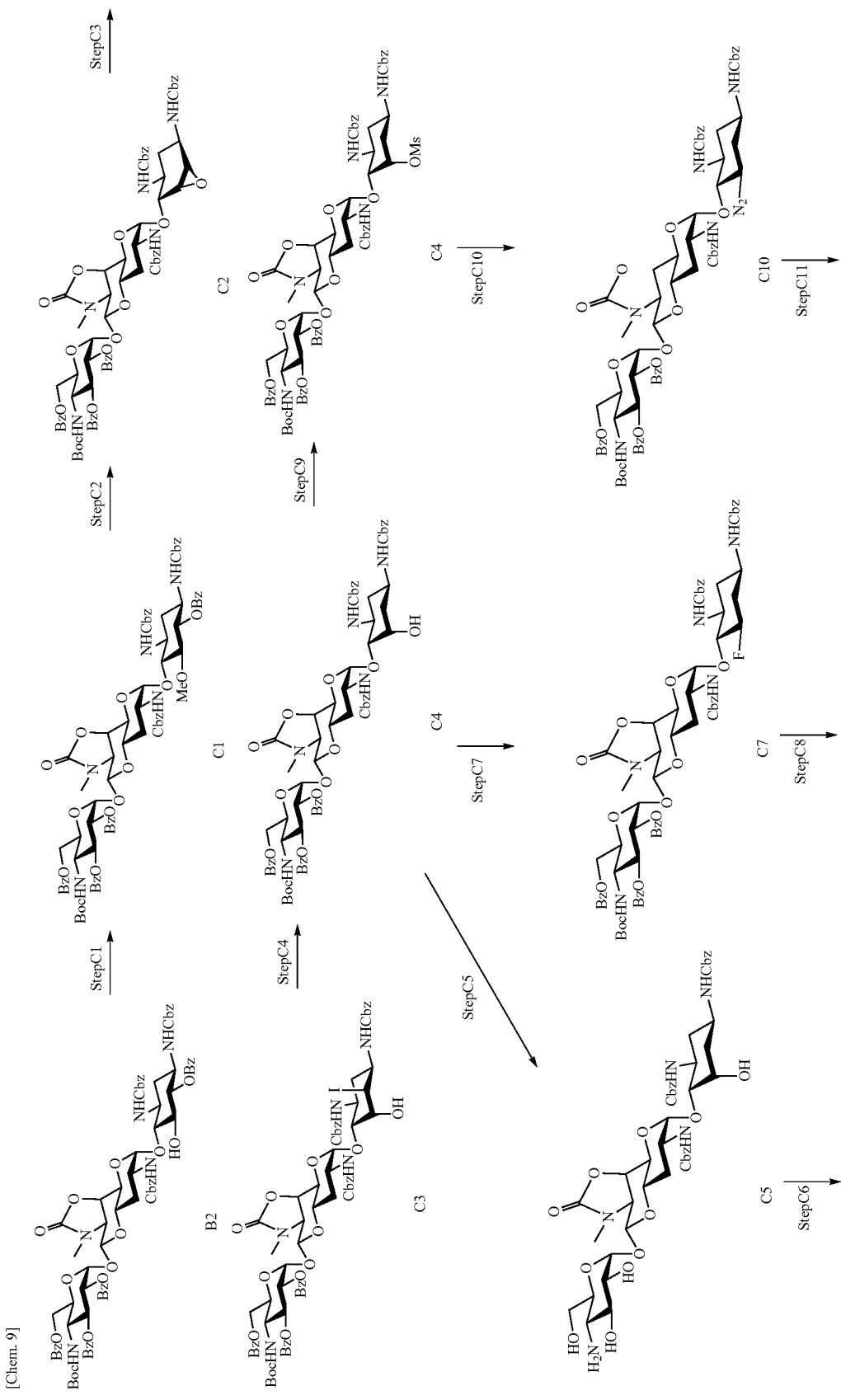

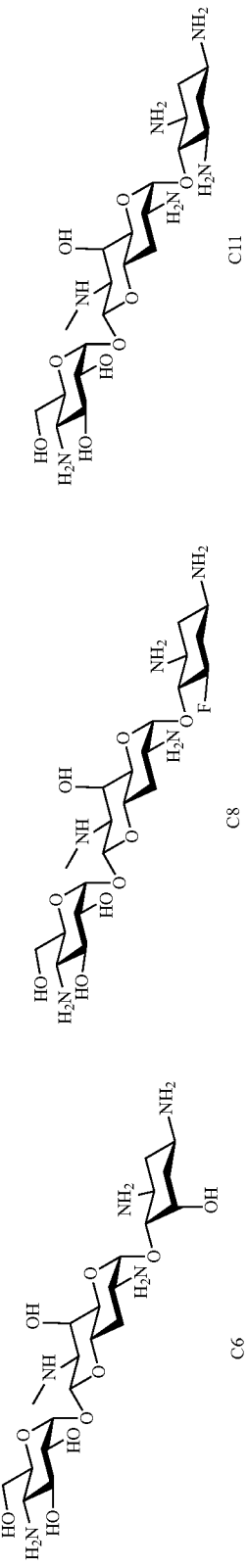

Step C1

The step C1 is a way to produce a compound represented by formula (C1) by introducing a methanesulphonyl group into a hydroxyl group at 5-position of a compound represented by formula (B2). This step is achieved by reacting the compound of formula (B2) with methanesulfonyl chloride in the presence of a base.

The solvents used in the present step include pyridine, methylene chloride, chloroform, 1,2-dichloroethane and the like, and preferably methylene chloride. The bases used include triethylamine, pyridine, 4-dimethylaminopyridine and the like, and preferably 4-dimethylaminopyridine. The reaction temperature is 0° C. to 30° C. and the reaction time is 1 to 2 hours.

Step C2

The step C2 is a way to produce a compound represented by formula (C2) by first removing the benzoyl group of the compound represented by formula (C1) and simultaneously performing anhydrization (epoxidation) of the 5- and 6-positions followed by introducing a benzoyl protecting group into the hydroxyl groups at 2"-, 3"- and 6"-positions. This step is achieved by reacting the compound represented by formula (C1) with a base and further reacting with benzoyl chloride in the presence of a base.

The solvents used in the step of debenzoylation and anhydrization include methanol, ethanol, methylene chloride, chloroform, 1,2-dichloroethane and the like, and preferably chloroform. The bases used include potassium carbonate, sodium carbonate, potassium hydroxide, sodium hydroxide, sodium methoxide, sodium ethoxide, potassium tert-butoxide and the like, and preferably sodium methoxide. The reaction temperature is 0° C. to 30° C. and the reaction time is 1 to 5 hours.

The benzoylation can be carried out under the conditions similar to those in the above-mentioned step B2.

Step C3

The step C3 is a way to produce a compound represented by formula (C3) by opening an epoxide of the compound represented by formula (C2). This step is achieved by reacting the compound represented by formula (C2) with sodium iodide in the presence of an acidic buffer solution. The solvents used in the present step include acetone, N,N-dimethylformamide, tetrahydrofuran, dioxane and the like, and preferably acetone. The acidic buffer solutions used include 5% sodium acetate-acetic acid solution and the like. The reaction temperature is 60° C. to 100° C. and the reaction time is 1 to 6 hours.

Step C4

The step C4 is a way to produce a compound represented by formula (C4) by reducing an iodine of the compound represented by formula (O3). This step is achieved by reacting a compound represented by formula (O3) with tributyltin hydride in the presence of 2,2'-azobis(isobutyronitrile).

The solvents used in the present step include toluene, tetrahydrofuran, dioxane and the like, and preferably dioxane. The reaction temperature is 60° C. to 100° C. and the reaction time is 3 to 8 hours.

Step C5

The step C5 is a way to produce a compound represented by formula (C5) by removing the benzoyl group and the t-butoxycarbonyl group of the compound represented by formula (C4). The removal of the protecting group can be carried out under the conditions similar to those in the above-mentioned step B4.

Step C6

The step C6 is a way to produce a compound represented by formula (C6) by removing the benzyloxycarbonyl group and cyclic carbamate of the compound represented by formula (C5). The removal of the protecting group can be carried out under the conditions similar to those in the above-mentioned step B5.

Step C7

The step C7 is a way to produce a compound represented by formula (C7) by epi-fluorinating the 5-position of the compound represented by formula (C4). The epi-fluorination can be carried out under the conditions similar to those in the above-mentioned step B3.

Step C8

The step C8 is a way to produce a compound represented by formula (C8) by removing the protecting group of the compound represented by formula (C7). The removal of protecting group can be carried out under the conditions similar to those in the above-mentioned steps B4 and B5.

Step C9

The step C9 is a way to produce a compound represented by formula (C9) by methanesulphonylating the hydroxyl group at 5-position of the compound represented by formula (C4). The methanesulphonylation can be carried out under the conditions similar to those in the above-mentioned step C1.

Step C10

The step C10 is a way to produce a compound represented by formula (C10) by azidating at 5-position of the compound represented by formula (C9). This step is achieved by reacting the compound represented by formula (C9) with sodium azide. The solvents used in the present step include acetone, N,N-dimethylformamide, tetrahydrofuran, dioxane and the like, and preferably N,N-dimethylformamide. The reaction temperature is 60° C. to 100° C. and the reaction time is 1 to 6 hours.

Step C11

The step C11 is a way to produce a compound represented by formula (C11) by removing the protecting group of the compound represented by formula (C10). The removal of protecting group can be carried out under the conditions similar to those in the above-mentioned steps B4 and B5.

Method D

The method D is a way to produce a compound represented by (D2) by azidation of the compound represented by formula (C1) at 5-position followed by reduction and deprotection. The steps are shown as follows.

[Chem. 10]

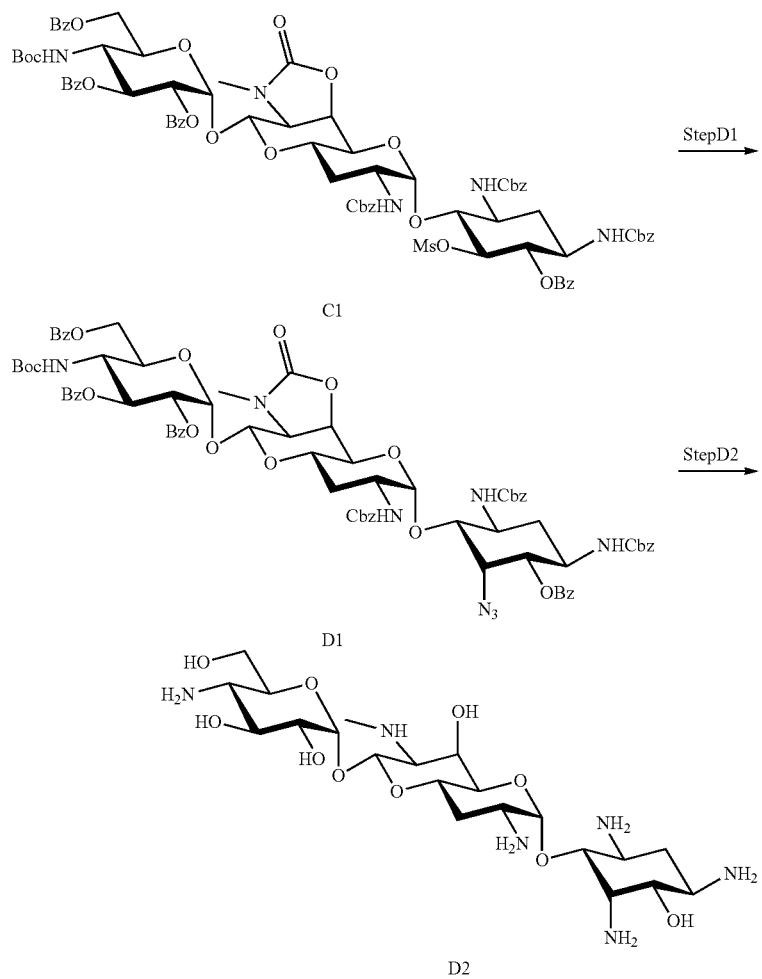

Step D1

The step D1 is a way to produce a compound represented by formula (D1) by azidating the 5-position of the compound represented by formula (C1). The azidation can be carried out under the conditions similar to those in the above-mentioned step C10.

Step D2

The step D2 is a way to produce a compound represented by formula (D2) by removing the protecting group of the compound represented by formula (D1). The removal of protecting group can be carried out under the conditions similar to those in the above-mentioned steps B4 and B5.

Method E

The method E is a way to produce a compound represented by formula (E3) by chlorinating of the 5-position of the compound represented by formula (B2) in the method B followed by azidation and deprotection. The steps are shown as follows.

[Chem. 11]

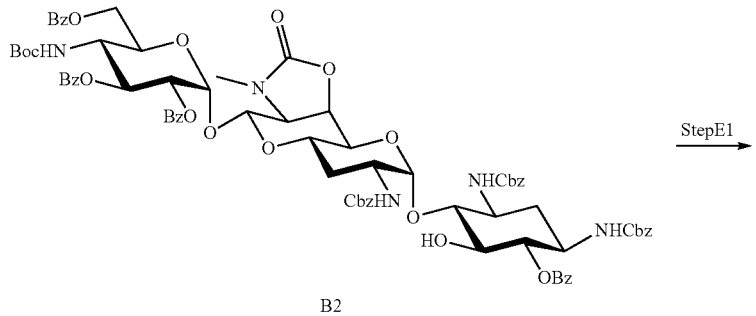

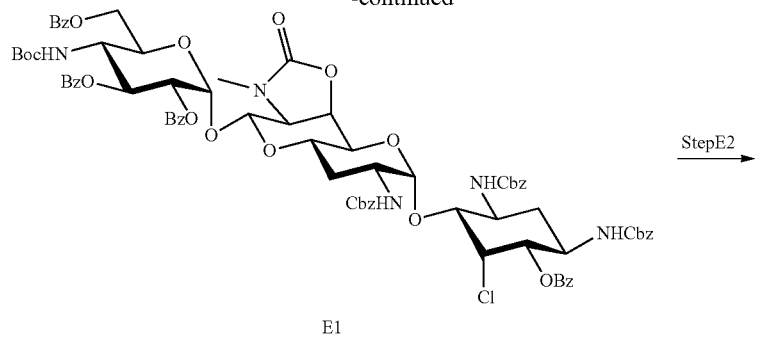

E1

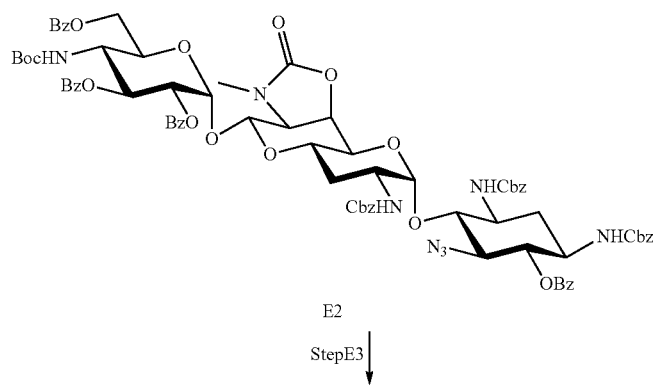

E2

StepE3

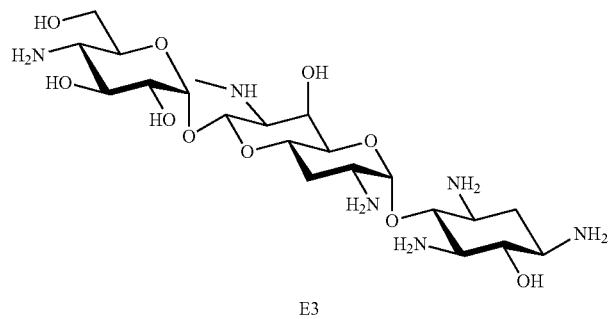

E3

Step E1

The step E1 is a way to produce a compound represented by formula (E1) by chlorinating the 5-position of the compound represented by formula (B2). This step is achieved by reacting the compound of formula (B2) with sulfuryl chloride in the presence of a base.

The solvents used in the present step include pyridine, methylene chloride, chloroform, 1,2-dichloroethane and the like, and preferably methylene chloride. The bases used include triethylamine, pyridine, 4-dimethylaminopyridine and the like, and preferably 4-dimethylaminopyridine. The reaction temperature is 0° C. to 30° C. and the reaction time is 1 to 2 hours.

Step E2

The step E2 is a way to produce a compound represented by formula (E2) by azidating the 5-position of the compound represented by formula (E1). The azidation can be carried out under the conditions similar to those in the above-mentioned step C10.

Step E3

The step E3 is a way to produce a compound represented by formula (E3) by removing the protecting group of the compound represented by formula (E2). The removal of protecting group can be carried out under the conditions similar to those in the above-mentioned step B4 and B5.

Method F

The method F is a way to produce a compound represented by (F3) by azidation at the 6-position of the compound represented by formula (C2), which is a common intermediate in the method C, followed by fluorination at the 5-position and deprotection. The steps are shown as follows.

[Chem. 12]

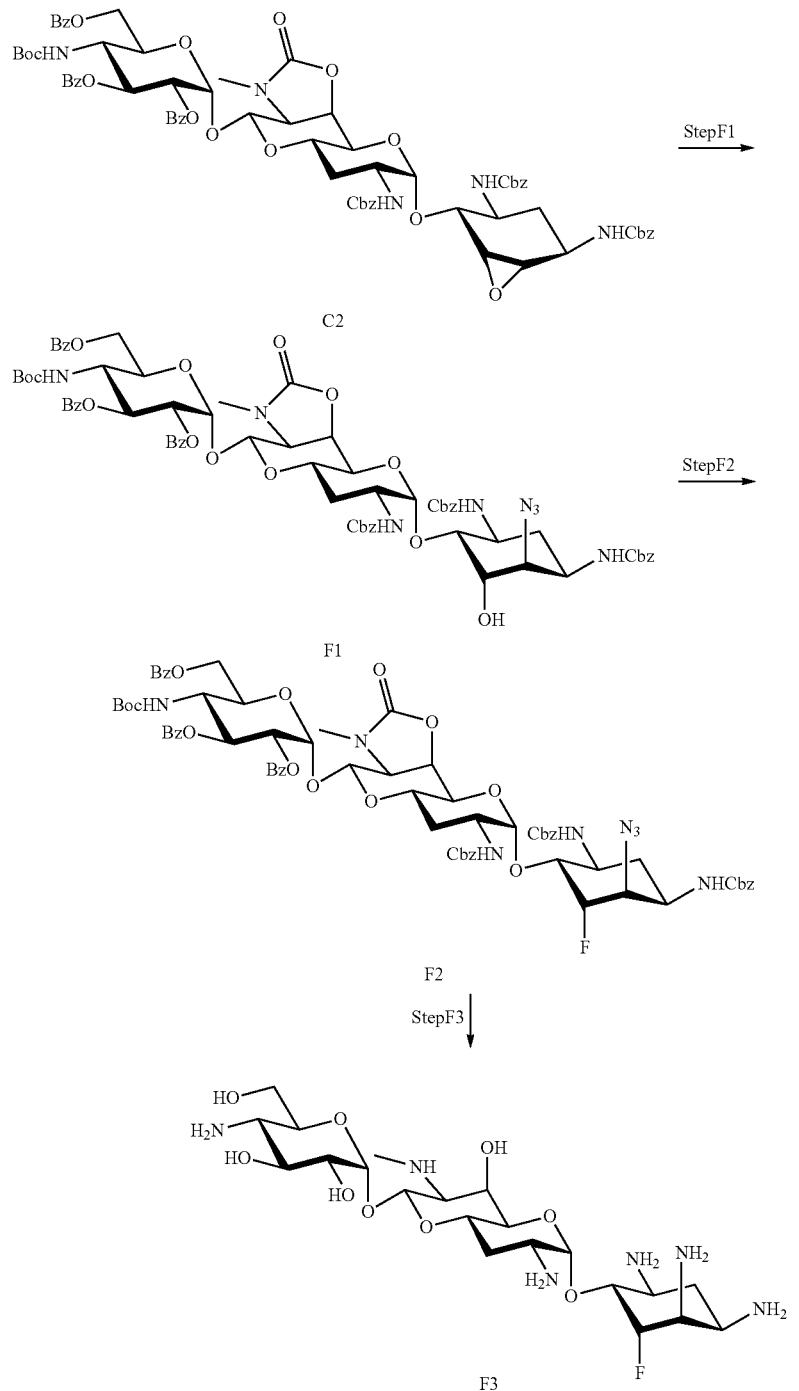

Step F1

The step F1 is a way to produce a compound represented by formula (F1) by opening the epoxide of the compound represented by formula (C2) to convert the epoxide into azide and a hydroxyl group. This step is achieved by reacting the compound represented by formula (C2) with sodium azide in the presence of ammonium chloride.

The solvents used in the present step include acetone, N,N-dimethylformamide, tetrahydrofuran, dioxane and the like, and preferably N,N-dimethylformamide. The reaction temperature is 60° C. to 100° C. and the reaction time is 1 to 6 hours.

Step F2

The step F2 is a way to produce a compound represented by formula (F2) by fluorinating the 5-position of the compound represented by formula (F1). The fluorination can be carried out under the conditions similar to those in the above-mentioned step B3.

Step F3

The step F3 is a way to produce a compound represented by formula (F3) by removing the protecting group of the compound represented by formula (F2). The removal of protecting group can be carried out under the conditions similar to those in the above-mentioned step B4 and B5.

Method G

The method G is a way to produce the compounds represented by formulae (G7) and (G8) by first introducing a leaving group into 3″-position of the compound represented by formula (G3) (in which only the hydroxyl group at 3″-position is present in a free state) obtained from apramycin in 4 steps, then by obtaining 3″-azide-3″-deoxy, and 2″-azide-2″, 3″-diepi-2″-deoxy derivatives, via 2″,3″-anhydro intermediate, followed by performing deprotection. The steps are shown as follows.

[Chem. 13]

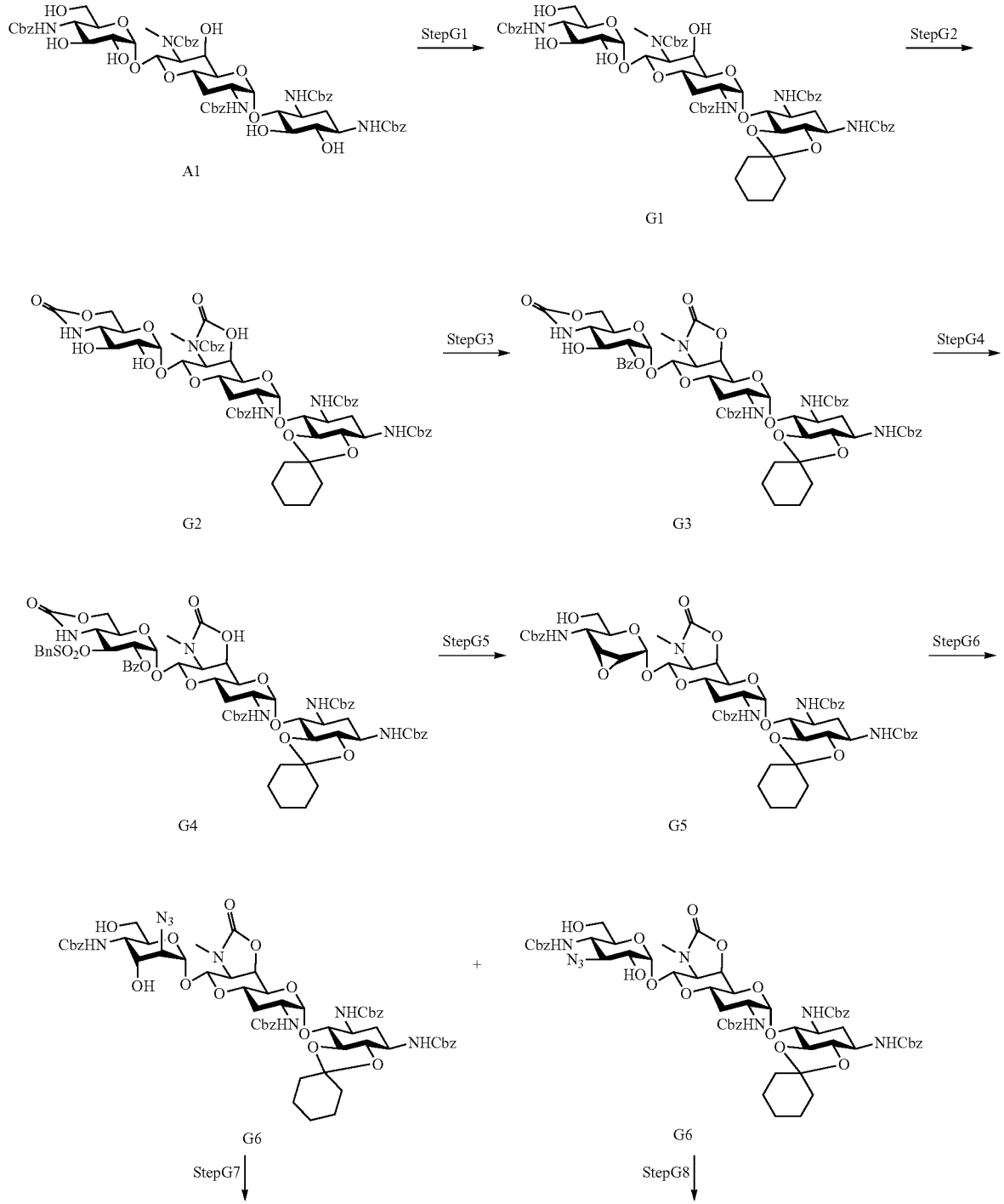

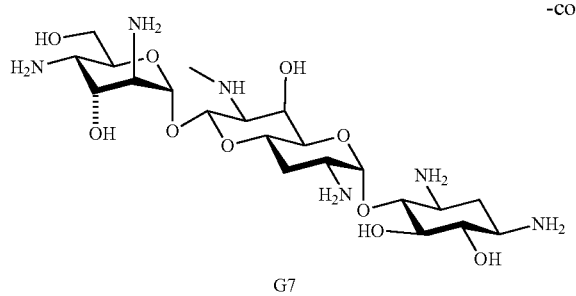

G7

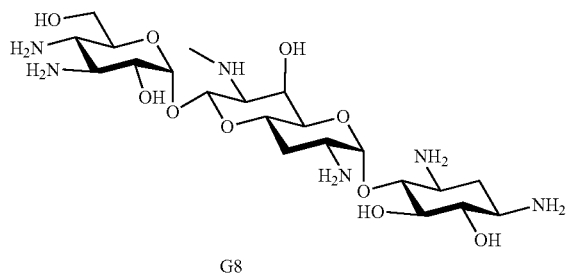

G8

Step G1

The step G1 is a way to produce a compound represented by formula (G1) by introducing protecting groups into hydroxyl groups at the 5- and 6-positions of the compound represented by formula (A1). This step is achieved by reacting the compound represented by formula (A1) with 1,1-dimethoxycyclohexane in the presence of an acid. The solvents used in the present step include N,N-dimethylformamide, methylene chloride, chloroform, 1,2-dichloroethane, ethyl acetate and the like, and preferably N,N-dimethylformamide. The acids used include p-toluenesulfonic acid, pyridinium p-toluenesulfonate, camphorsulfonic acid, hydrochloric acid and the like, and preferably p-toluenesulfonic acid. The reaction temperature is 20° C. to 60° C. and the reaction time is 1 to 8 hours.

Step G2

The step G2 is a way to produce a compound represented by formula (G2) by connecting the 6'- and 7'-positions, and 4"- and 6"-positions of the compound represented by formula (G1) into cyclic carbamates. The conversion into cyclic carbamate can be carried out under the conditions similar to those in the above-mentioned step A2.

Step G3

The step G3 is a way to produce a compound represented by formula (G3) by selectively introducing a benzoyl protecting group into the hydroxyl group at the 2"-position of the compound represented by formula (G2). The introduction of benzoyl protecting group can be carried out under the conditions similar to those in the above-mentioned step B2.

Step G4

The step G4 is a way to produce a compound represented by formula (G4) by introducing a benzylsulphonyl group into the hydroxyl group at the 3"-position of the compound represented by formula (G3). This step is achieved by reacting the compound of formula (G3) with benzylsulfonyl chloride in the presence of a base. The solvents used in the present step include pyridine, methylene chloride, chloroform, 1,2-dichloroethane and the like, and preferably pyridine. The bases used include triethylamine, pyridine, 4-dimethylaminopyridine and the like, and preferably pyridine. The reaction temperature is −20° C. to room temperature and the reaction time is 0.5 to 1 hour.

Step G5

The step G5 is a way to produce a compound represented by formula (G5) by removing the benzoyl group of the compound represented by formula (G4) and simultaneously performing anhydrization (epoxidation) at the 2"- and 3"-positions. This step is achieved by reacting the compound represented by formula (G4) with a base.

The solvents used in performing anhydrization include methanol, ethanol, methylene chloride, chloroform, 1,2-dichloroethane and the like, and preferably chloroform. The bases used include potassium carbonate, sodium carbonate, potassium hydroxide, sodium hydroxide, sodium methoxide, sodium ethoxide, potassium tert-butoxide and the like, and preferably sodium methoxide. The reaction temperature is 0° C. to 30° C. and the reaction time is 1 to 5 hours.

Step G6

The step G6 is a way to produce compounds represented by formulae (G6) and (G6') by opening the epoxide of the compound represented by formula (G5) to convert the epoxide into an azide and a hydroxyl group. The azidation can be carried out under the conditions similar to those in the above-mentioned step F1.

Step G7

The step G7 is a way to produce a compound represented by formula (G7) by removing the protecting group of the compound represented by formula (G6). This step is achieved by removing the protecting group of the hydroxyl group through acid hydrolysis of the compound represented by formula (G6), and next by removing the protecting group of the amino group through a catalytic reduction and alkaline hydrolysis of the compound obtained. The acids used in the acidic hydrolysis include 1 N hydrochloric acid, 1 N sulfuric acid, 80% aqueous acetic acid solution, 80% aqueous formic acid solution and the like, and preferably 80% aqueous acetic acid solution. The reaction temperature is 30° C. to 80° C. and the reaction time is 1 to 3 hours. The removal of protecting group of the amino group can be carried out under the conditions similar to those in the above-mentioned step B5.

Step G8

The step G8 is a way to produce a compound represented by formula (G8) by removing the protecting group of the compound represented by formula (G6'). The removal of protecting group can be carried out under the conditions similar to those in the above-mentioned step G7.

Method H

The method H is a way to produce the compound represented by formula (H3) by first introducing a leaving group into the 3"-position of the compound represented by formula (G3) (in which having only the hydroxyl group at the 3"-position is present in a free state) obtained from apramycin in 4 steps, then by inverting the hydroxyl group at the 3"-position, followed by performing deprotection. The steps are shown as follows.

[Chem. 14]
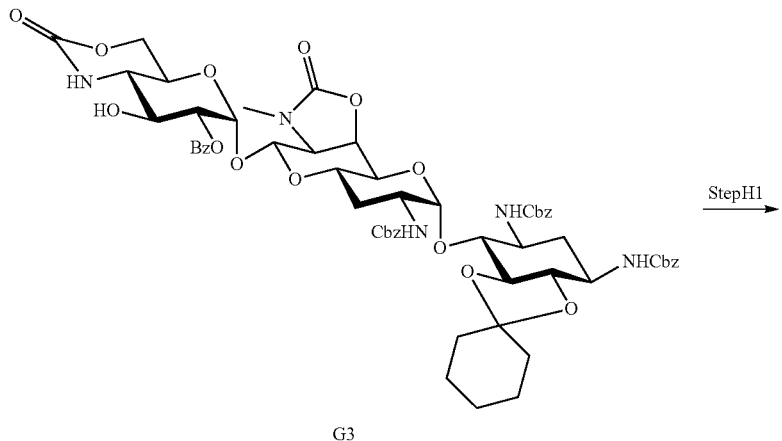
G3
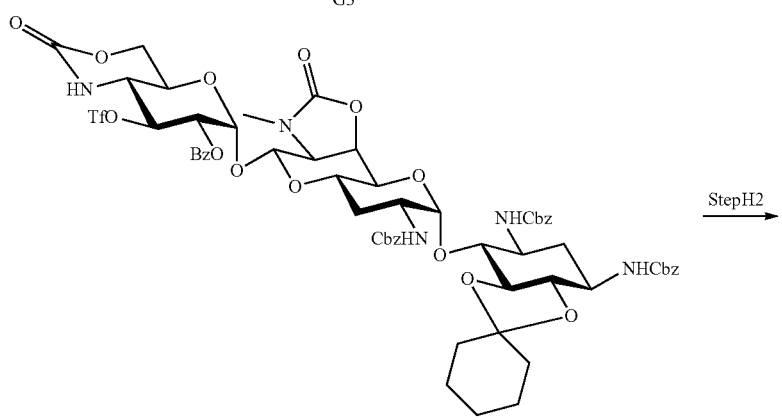
H1
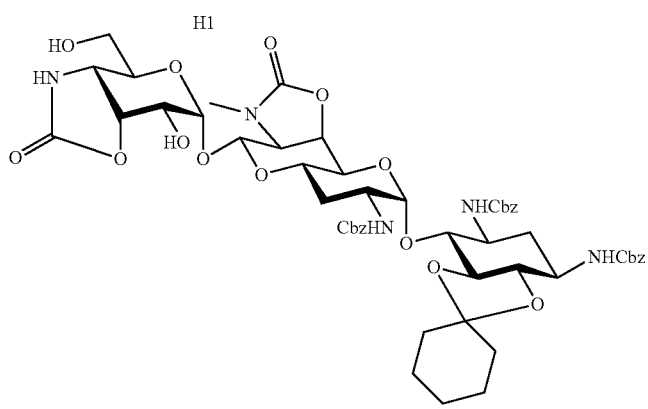
H2
StepH3 ↓
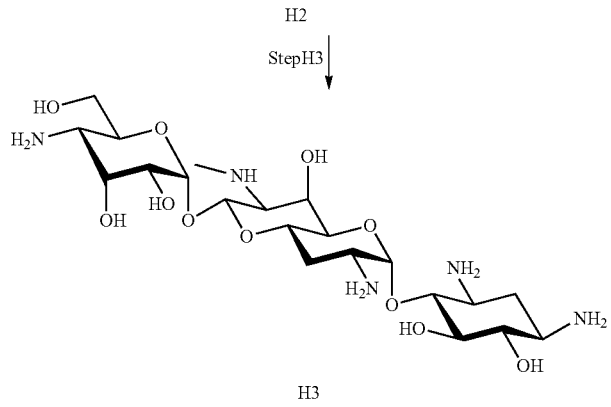
H3

Step H1

The step H1 is a way to produce a compound represented by formula (H1) by introducing a trifluoromethanesulfonyl group into the hydroxyl group at the 3"-position of the compound represented by formula (G3). This step is achieved by reacting the compound of formula (G3) with trifluoromethanesulfonic anhydride in the presence of a base.

The solvents used in the present step include pyridine, methylene chloride, chloroform, 1,2-dichloroethane and the like, and preferably methylene chloride. The bases used include triethylamine, pyridine, 4-dimethylaminopyridine and the like, and preferably pyridine. The reaction temperature is −10° C. to 5° C. and the reaction time is 0.5 to 1 hour.

Step H2

The step H2 is a way to produce a compound represented by formula (H2) by epimerizing the hydroxyl group at the 3"-position and by converting 4"-position together with 3"-position into cyclic carbamate in the compound represented by formula (H1). Epimerization in this step is achieved by reacting the compound represented by formula (H1) with cesium acetate followed by base treatment. The solvents used in the present step include dioxane, N,N-dimethylformamide, 1,2-dimethoxyethane and the like, and preferably N, N-dimethylformamide. The reaction temperature is 50° C. to 80° C. The reaction time is 1 to 3 hours.

The bases used for conversion to cyclic carbamate include potassium carbonate, sodium carbonate, potassium hydroxide, sodium hydroxide, sodium methoxide, sodium ethoxide, potassium tert-butoxide and the like, and preferably sodium methoxide. The reaction temperature is 0° C. to 30° C. and the reaction time is 1 to 3 hours.

Step H3

The step H3 is a way to produce a compound represented by formula (H3) by removing the protecting group of the compound represented by formula (H2). The removal of protecting group can be carried out under the conditions similar to those in the above-mentioned step G7.

Method I

The method I is a way to produce a compound represented by formula (I3) by diaxial cleavage of an epoxide of the compound represented by formula (G5) to obtain 2",3"-diepi derivative, and subsequent deprotection, wherein the compound (G5) is obtained from apramycin in 6 steps. The steps are shown as follows.

[Chem. 15]

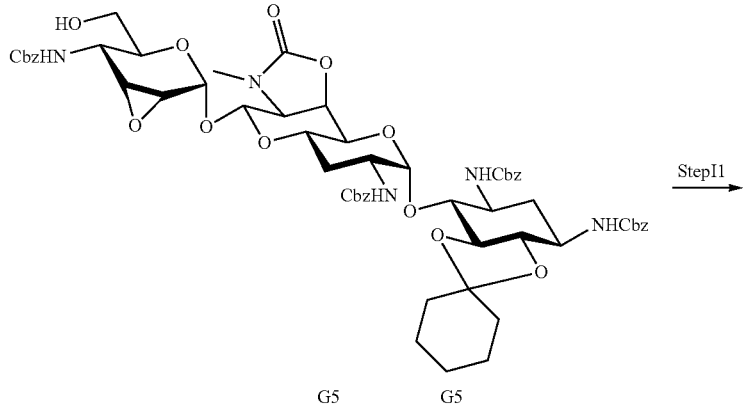

G5

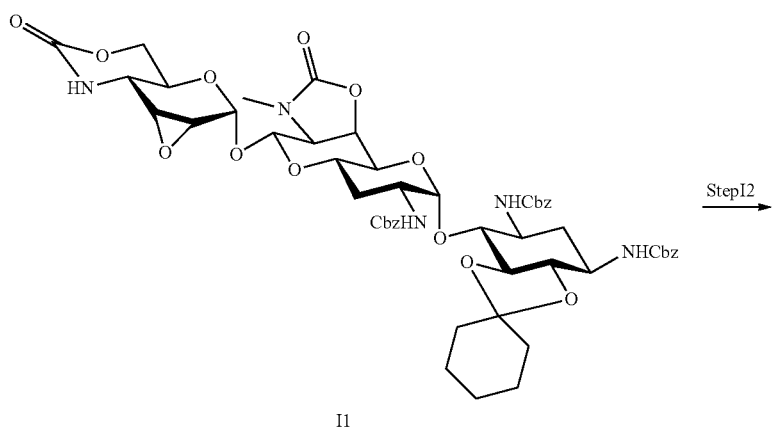

I1

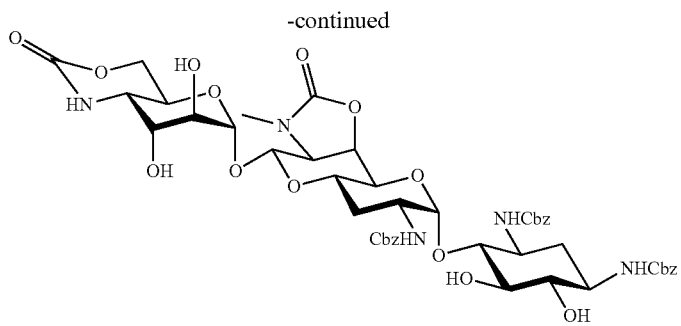

I2

Step I3 ↓

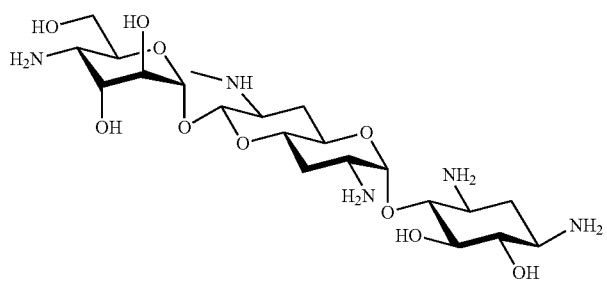

I3

Step I1

The step I1 is a way to produce a compound represented by formula (I1) by converting the 4"- and 6"-positions of the compound represented by formula (G5) into cyclic carbamate. The conversion into cyclic carbamate can be carried out under the conditions similar to those in the above-mentioned step A2.

Step I2

The step I2 is a way to produce a compound represented by formula (I2) by diepimerizing at the 2" and 3"-positions through acidic hydrolysis of the compound represented by formula (I1). The acids used for acidic hydrolysis include 1 N hydrochloric acid, 1 N sulfuric acid, 80% aqueous acetic acid solution, 80% aqueous formic acid solution and the like, and preferably 80% aqueous acetic acid solution. The reaction temperature is 30° C. to 80° C. and the reaction time is 1 to 3 hours.

Step I3

The step I3 is a way to produce a compound represented by formula (I3) by removing the benzyloxycarbonyl group and cyclic carbamate of the compound represented by formula (I2). The removal of protecting group can be carried out under the conditions similar to those in the above-mentioned step B5.

Method J

The method J is a way to produce a compound represented by formula (J4) by fluorinating the 6"-position of the compound represented by formula (A1) obtained from apramycin in 3 steps followed by deprotection. The steps are shown as follows.

[Chem. 16]

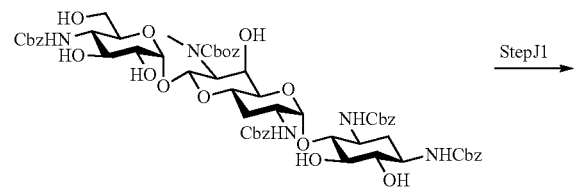

A1

StepJ1 →

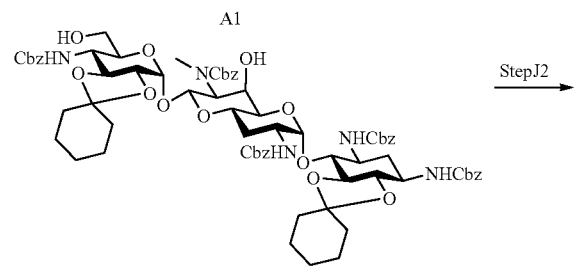

J1

StepJ2 →

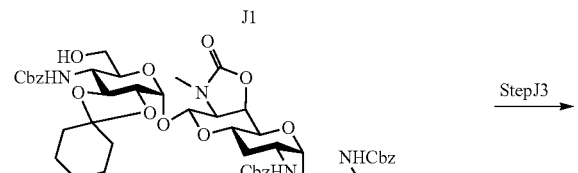

J2

StepJ3 →

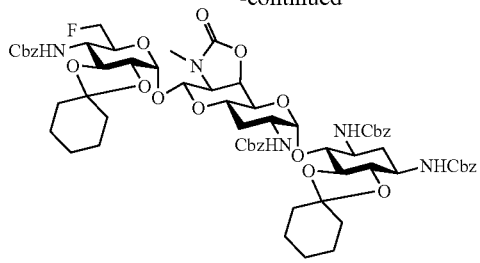

J3

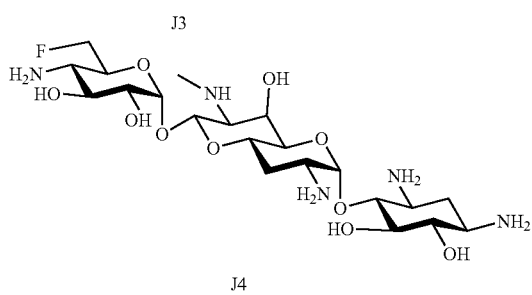

J4

Step J1

The step J1 is a way to produce a compound represented by formula (J1) by introducing protecting groups at hydroxyl groups at the 5-, 6-positions and, 2"-, 3"-positions of the compound represented by formula (A1). This step is achieved by reacting the compound represented by formula (A1) with 1,1-dimethoxycyclohexane in the presence of an acid.

The solvents used in the present step include N,N-dimethylformamide, methylene chloride, chloroform, 1,2-dichloroethane, ethyl acetate and the like, and preferably N,N-dimethylformamide. The acids used include p-toluenesulfonic acid, pyridinium p-toluenesulfonate, camphorsulfonic acid, hydrochloric acid and the like, and preferably p-toluenesulfonic acid. The reaction is performed at the temperature of 40° C. to 60° C., under the reduced pressure of 20 to 40 Torr, and the reaction time is 1 to 8 hours.

Step J2

The step J2 is a way to produce a compound represented by formula (J2) by converting the 6'- and 7'-positions of the compound represented by formula (J1) into a cyclic carbamate. The conversion into cyclic carbamate can be carried out under the conditions similar to those in the above-mentioned step A2.

Step J3

The step J3 is a way to produce a compound represented by formula (J3) by fluorinating the 6"-position of the compound represented by formula (J2). The fluorination can be carried out under the conditions similar to those in the above-mentioned step B3.

Step J4

The step J4 is a way to produce a compound represented by formula (J4) by removing the protecting group of the compound represented by formula (J3). The removal of protecting group can be carried out under the conditions similar to those in the above-mentioned step G7.

Method K

The method K is a way to produce a compound represented by formula (K4) by introducing a benzylsulfonyl group into a hydroxyl group at the 6"-position and by iodinating the 3"- and 6"-positions of the compound represented by formula (G5) obtained from apramycin in 6 steps, followed by reduction and deprotection. The steps are shown as follows.

[Chem. 17]

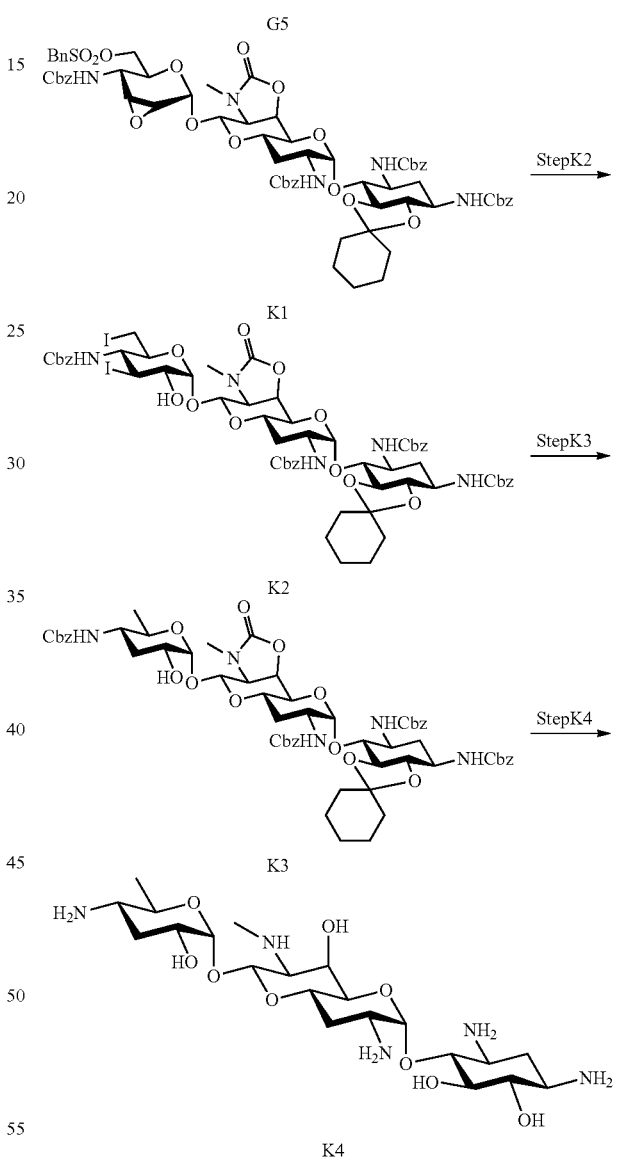

Step K1

The step K1 is a way to produce a compound represented by formula (K1) by introducing a benzylsulphonyl group into hydroxyl group at the 6"-position of the compound represented by formula (G5). The introduction of benzoylsulfonyl group can be carried out under the conditions similar to those in the above-mentioned step G4.

Step K2

The step K2 is a way to produce a compound represented by formula (K2) by opening the epoxide of the compound represented by formula (K1) to convert the epoxide to an iodide and a hydroxyl group and further converting the benzylsulfonyloxy group at the 6"-position into iodide. The iodination can be carried out under the conditions similar to those in the above-mentioned step C3.

Step K3

The step K3 is a way to produce a compound represented by formula (K3) by reducing the iodides of the compound represented by formula (K2). The reduction can be carried out under the conditions similar to those in the above-mentioned step C4.

Step K4

The step K4 is a way to produce a compound represented by formula (K4) by removing the protecting group of the compound represented by formula (K3). The removal of protecting group can be carried out under the conditions similar to those in the above-mentioned step G7.

Method L

The method L is a way to produce a compound represented by formula (L5) by selectively substituting the hydroxyl group at the 6-position with a chlorine of the compound represented by formula (E1) obtained from apramycin in 6 steps, followed by subsequent deprotection after reduction. The steps are shown as follows.

[Chem. 18]

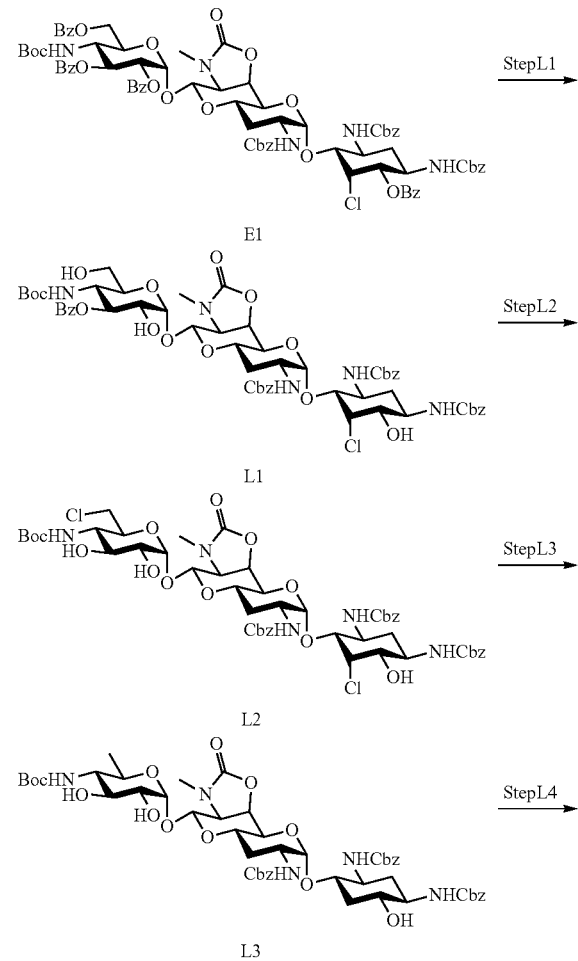

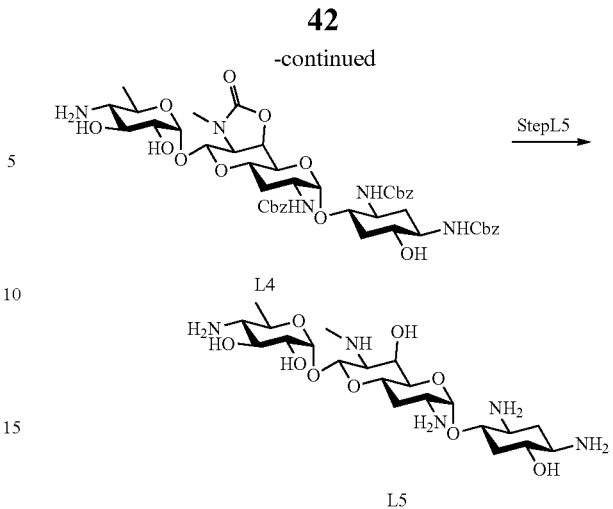

Step L1

The step L1 is a way to produce a compound represented by formula (L-1) by removing the benzoyl group of the compound represented by formula (E1). The removal of the benzoyl group can be carried out under the conditions similar to those in the above-mentioned step G5.

Step L2

The step L2 is a way to produce a compound represented by formula (L2) by selectively substituting the hydroxy group at the 6"-position with a chlorine of the compound represented by formula (L1). This step is achieved by the reaction of the compound represented by formula (L1) with triphenylphosphine and carbon tetrachloride. The solvents used in the present step include dioxane, N,N-dimethylformamide, pyridine, tetrahydrofuran and the like, and preferably N,N-dimethylformamide. The reaction temperature is 40° C. to 90° C. and the reaction time is 1 to 6 hours.

Step L3

The step L3 is a way to produce a compound represented by formula (L3) by reducing the chloro group at the 5- and 6"-positions of the compound represented by formula (L2). The reduction can be carried out under the conditions similar to those in the above-mentioned step C4.

Step L4

The step L4 is a way to produce a compound represented by formula (L4) by removing the t-butoxycarbonyl group at the 4"-position of the compound represented by formula (L3). The solvents used in the present step include ethyl acetate, methylene chloride, acetonitrile, acetone, methanol and the like, and preferably methanol. The acids used include p-toluenesulfonic acid, methanesulfonic acid, acetic acid, trifluoroacetic acid and the like, and preferably trifluoroacetic acid. The reaction temperature is 0° C. to 50° C. and the reaction time is 1 to 2 hours.

Step L5

The step L5 is a way to produce a compound represented by formula (L5) by removing the protecting group of the compound represented by formula (L4). The removal of protecting group can be carried out under the conditions similar to those in the above-mentioned step G7.

Method M

The method M is a way to produce compounds represented by formulae (M7), (M9) and (M10) by first obtaining a 3"-deoxy derivative via the compound represented by formula (G5) which is obtained in 6 steps from apramycin and converting it into a 5-OH derivative, and then by converting the 5-OH derivative into a 5-deoxy, a 5-epi and a 5-epifluorite derivatives, followed by performing deprotection. The steps are shown as follows.

[Chem. 19]
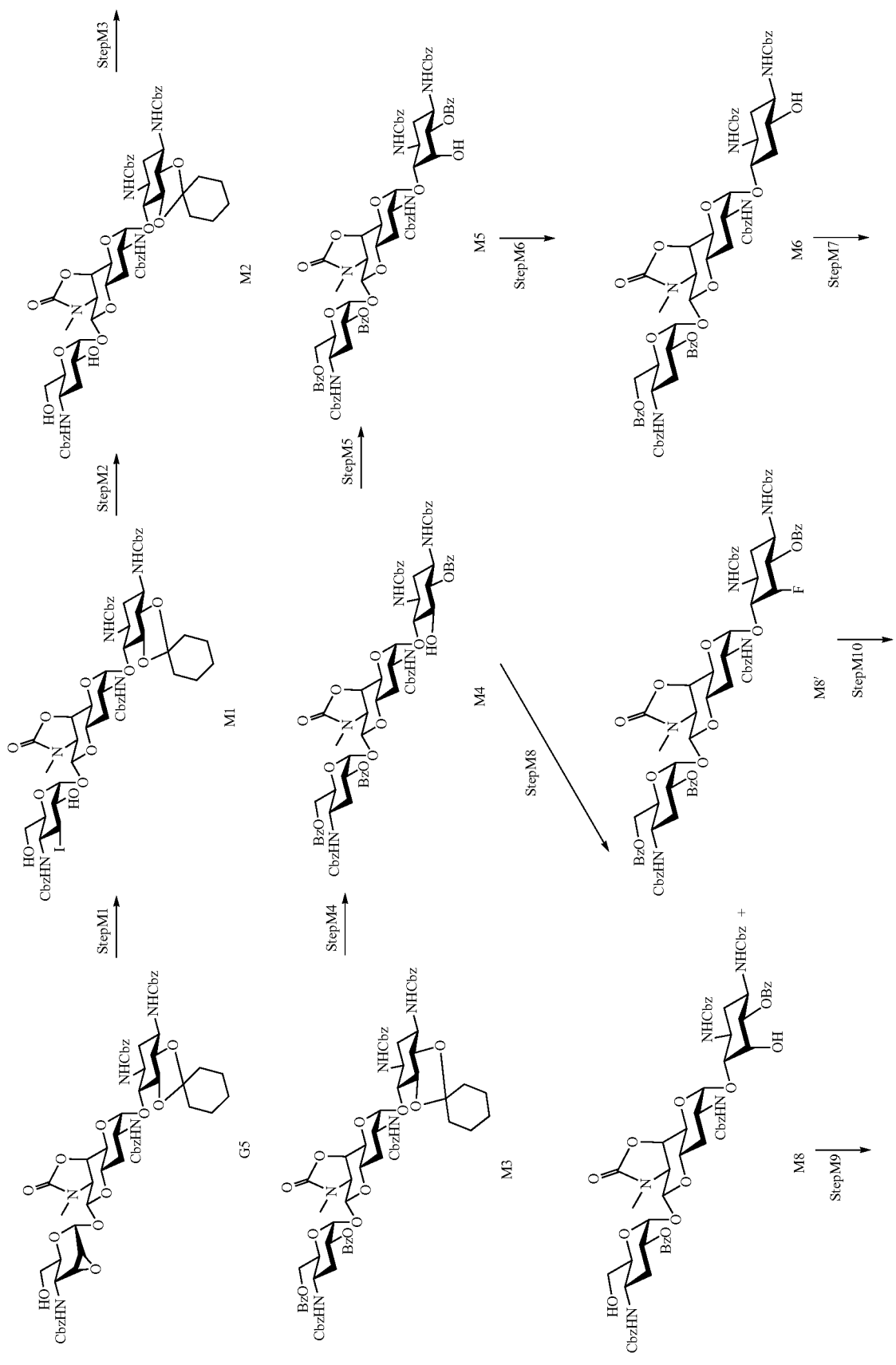

-continued
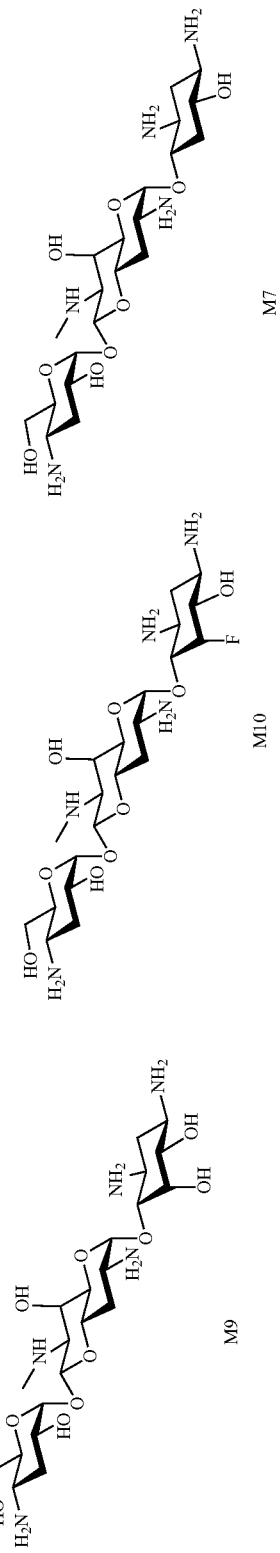
M7
M10
M9

Step M1

The step M1 is a way to produce a compound represented by formula (M1) by opening an epoxide of a compound represented by formula (G5) and converting it into an iodide and a hydroxyl group. The iodination can be carried out under the conditions similar to those in the above-mentioned step C3.

Step M2

The step M2 is a way to produce a compound represented by formula (M2) by reducing iodine of the compound represented by formula (M1). The reduction can be carried out under the conditions similar to those in the above-mentioned step C4.

Step M3

The step M3 is a way to produce a compound represented by formula (M3) by benzoylating the hydroxy groups at the 2"- and 6"-positions of the compound represented by formula (M2). The benzoylation can be carried out under the conditions similar to those in the above-mentioned step B2.

Step M4

The step M4 is a way to produce a compound represented by formula (M4) by selectively performing benzoylation at the 6-position of the compound represented by formula (M3) after removing cyclohexylidene group at the 5-, 6-position. The acids used for removal of cyclohexylidene group include 1 N hydrochloric acid, 1 N sulfuric acid, 80% aqueous acetic acid solution, 80% aqueous formic acid solution and the like, and preferably 80% aqueous acetic acid solution. The reaction temperature is 30° C. to 80° C. and the reaction time is 1 to 3 hours. The benzoylation can be carried out under the conditions similar to those in the above-mentioned step B2.

Step M5

The step M5 is a way to produce a compound represented by formula (M5) by chlorinating the 5-position of a compound represented by formula (M4). The chlorination can be carried out under the conditions similar to those in the above-mentioned step E1.

Step M6

The step M6 is a way to produce a compound represented by formula (M6) by reducing the chloro group at the 5-position of the compound represented by formula (M5). The reduction can be carried out under the conditions similar to those in the above-mentioned step C4.

Step M7

The step M7 is a way to produce a compound represented by formula (M7) by removing the protecting group of the compound represented by formula (M6). This step is achieved by removing the protecting group of the hydroxyl group of the compound represented by formula (M6) through a base treatment followed by removing the protecting group of the amino group through catalytic reduction and alkaline hydrolysis of the compound obtained. The removal of the protecting group of the hydroxyl group can be conducted under the conditions similar to those in the above-mentioned step B4, and the removal of the protecting group of the amino group can be conducted under the conditions similar to those in the step B5.

Step M8

The step M8 is a way to produce compounds represented by formulae (M8) and (M8') by epimerizing or epi-fluorinating the hydroxyl group at the 5-position of the compound represented by formula (M4). This step can be carried out under the conditions similar to those in the above-mentioned step B3.

Step M9

The step M9 is a way to produce a compound represented by formula (M9) by removing the protecting group of the compound represented by formula (M8). The removal of protecting group can be carried out under the conditions similar to those in the above-mentioned step M7.

Step M10

The step M10 is a way to produce a compound represented by formula (M10) by removing the protecting group of the compound represented by formula (M8'). The removal of protecting group can be carried out under the conditions similar to those in the above-mentioned step M7.

Method N

The method N is a way to produce compounds represented by formulae (N5), (N7) and (N9) by deriving a 5-epi-6-deoxy, a 5,6-dideoxy and a 5-epiamino derivatives from the compound represented by formula (M4) which is obtained from apramycin in 10 steps, followed by performing deprotection. The steps are shown as follows.

[Chem. 20]
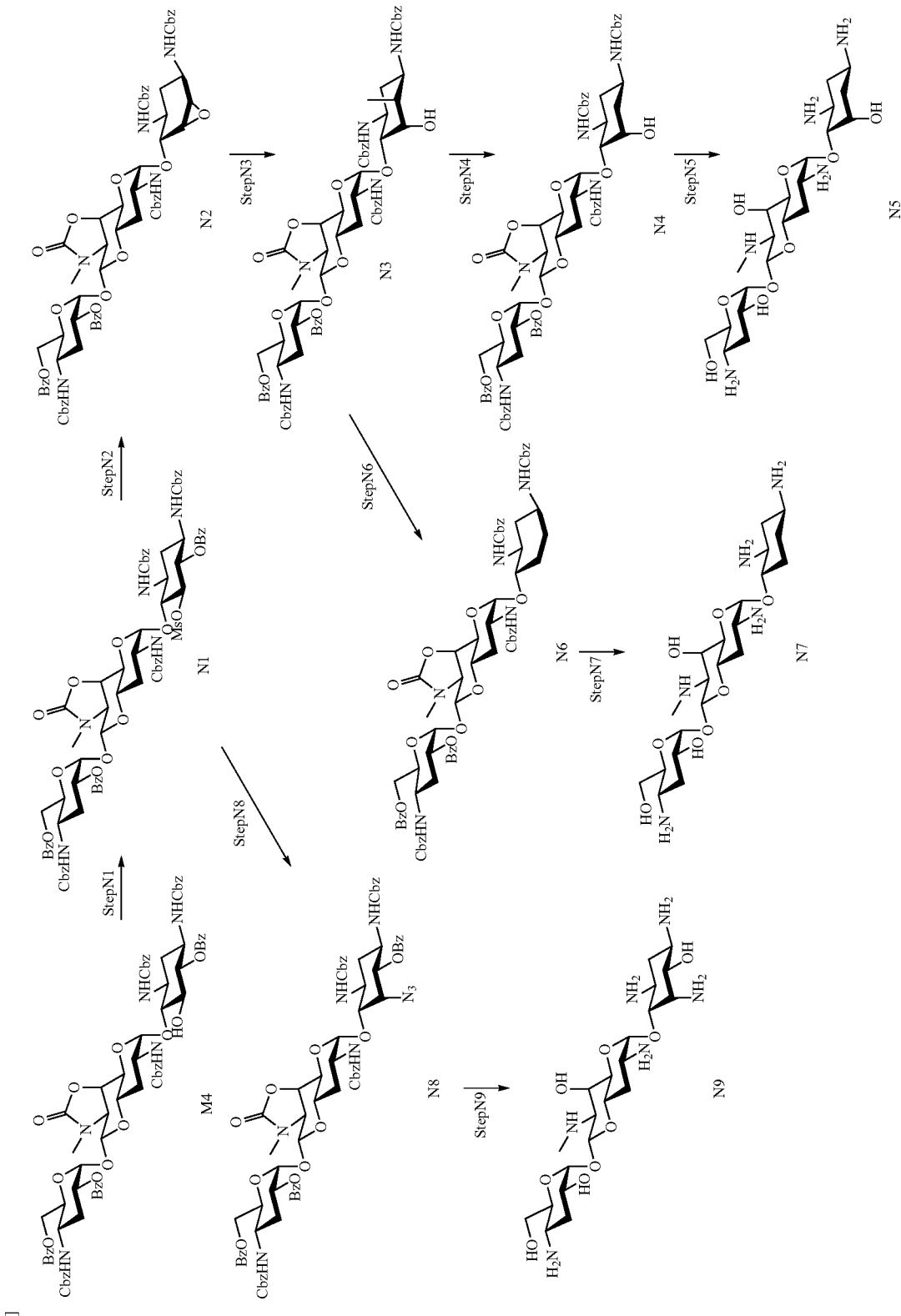

Step N1

The step N1 is a way to produce a compound represented by formula (N1) by introducing a methanesulphonyl group at the hydroxyl group at the 5-position of the compound represented by formula (M4). The introduction of the methanesulphonyl group can be carried out under the conditions similar to those in the above-mentioned step C1.

Step N2

The step N2 is a way to produce a compound represented by formula (N2) by first removing the benzoyl group of the compound represented by formula (N1) and simultaneously performing anhydrization (epoxidation) at the 5- and 6-positions, and then introducing a benzoyl protecting group into the hydroxyl group at the 2" and 6"-positions. The epoxidation and benzoylation can be carried out under the conditions similar to those in the above-mentioned step C2.

Step N3

The step N3 is a way to produce a compound represented by formula (N3) by opening the epoxide of the compound represented by formula (N2) to convert the epoxide into an iodide and a hydroxyl group. This step can be carried out under the conditions similar to those in the above-mentioned step C3.

Step N4

The step N4 is a way to produce a compound represented by formula (N4) by reducing the iodide at the 6-position of the compound represented by formula (N3). The reduction can be carried out under the conditions similar to those in the above-mentioned step C4.

Step N5

The step N5 is a way to produce a compound represented by formula (N5) by removing the protecting group of the compound represented by formula (N4). The removal of protecting group can be carried out under the conditions similar to those in the above-mentioned step M7.

Step N6

The step N6 is a way to produce a compound represented by formula (N6) by introducing a benzylsulfonyl group into the hydroxyl group at the 5-position of the compound represented by formula (N3), and then adding water, followed by an elimination reaction. The introduction of the benzylsulfonyl group can be carried out under the conditions similar to those in the above-mentioned step G4. The reaction temperature after adding water is 40° C. to 90° C. and the reaction time is 1 to 5 hours.

Step N7

The step N7 is a way to produce a compound represented by formula (N7) by removing the protecting group of the compound represented by formula (N6) and reducing a double bond. This step can be carried out under the conditions similar to those in the above-mentioned step M7.

Step N8

The step N8 is a way to produce a compound represented by formula (N8) by azidating the 5-position of the compound represented by formula (N1). The azidation can be carried out under the conditions similar to those in the above-mentioned step C10.

Step N9

The step N9 is a way to produce a compound represented by formula (N9) by removing the protecting group of the compound represented by formula (N8). The removal of protecting group and conversion of azide group to amino group can be carried out under the conditions similar to those in the above-mentioned step M7.

Method O

The method O is a way to produce a compound represented by (O5) from the compound represented by formula (I1). The steps are shown as follows.

[Chem. 21]

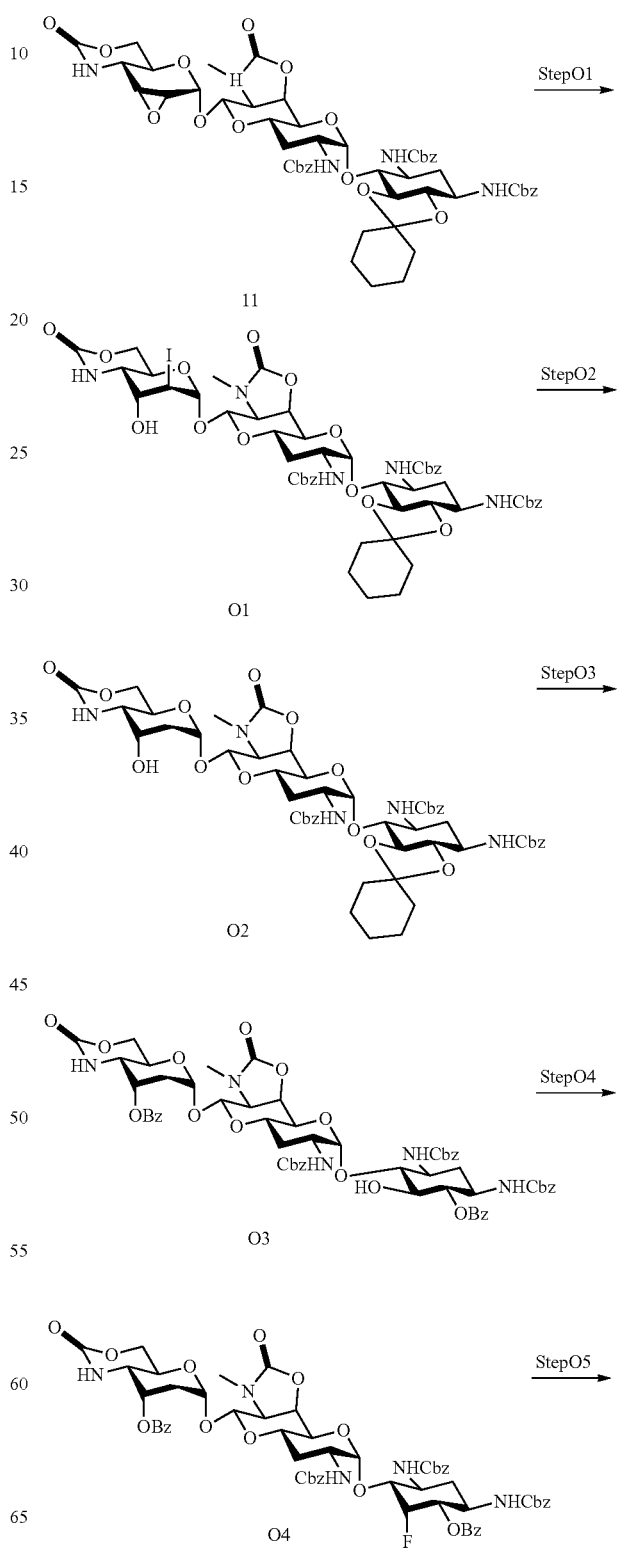

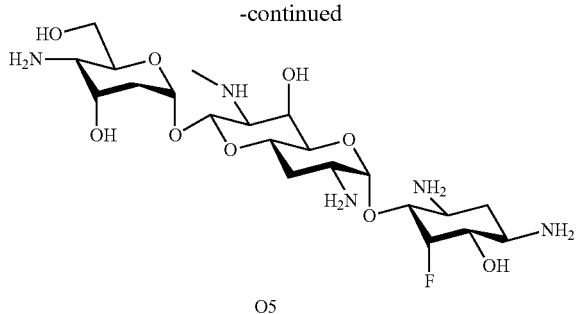

O5

Step O1
The step O1 is a way to produce a compound represented by formula (O1) by opening an epoxide of the compound represented by formula (I1) to convert the epoxide into an iodide and a hydroxyl group. This step can be carried out under the conditions similar to those in the above-mentioned step C3.

Step O2
The step O2 is a way to produce a compound represented by formula (O2) by reducing the iodine at the 2"-position of the compound represented by formula (O1). The reduction can be carried out under the conditions similar to those in the above-mentioned step C4.

Step O3
The step O3 is a way to produce a compound represented by formula (O3) by selectively performing 0-benzoylation at the 6- and 3"-positions of the compound represented by formula (O2) after removing of cyclohexylidene group at the 5- and 6-positions. The removal of cyclohexylidene group and benzoylation can be carried out under the conditions similar to those in the above-mentioned step M4.

Step O4
The step O4 is a way to produce a compound represented by formula (O4) by epi-fluorinating the hydroxyl group at the 5-position of the compound represented by (O3). This step can be carried out under the conditions similar to those in the above-mentioned step B3.

Step O5
The step O5 is a way to produce a compound represented by formula (O5) by removing the protecting group of the compound represented by formula (O4). The removal of protecting group can be carried out under the conditions similar to those in the above-mentioned step M7.

Method P
The method P is a way to produce a compound represented by formula (P4) by inverting the 5-position of the compound represented by formula (H2) obtained from apramycin in 5 steps. The steps are shown as follows.

[Chem. 22]

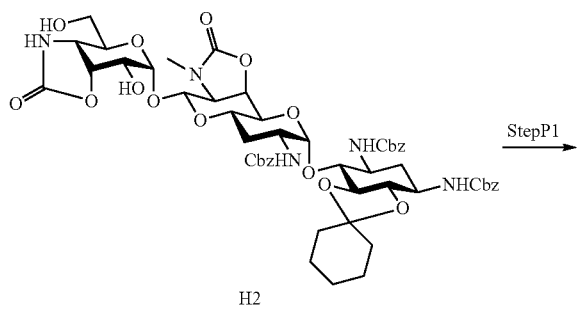

H2 →StepP1→

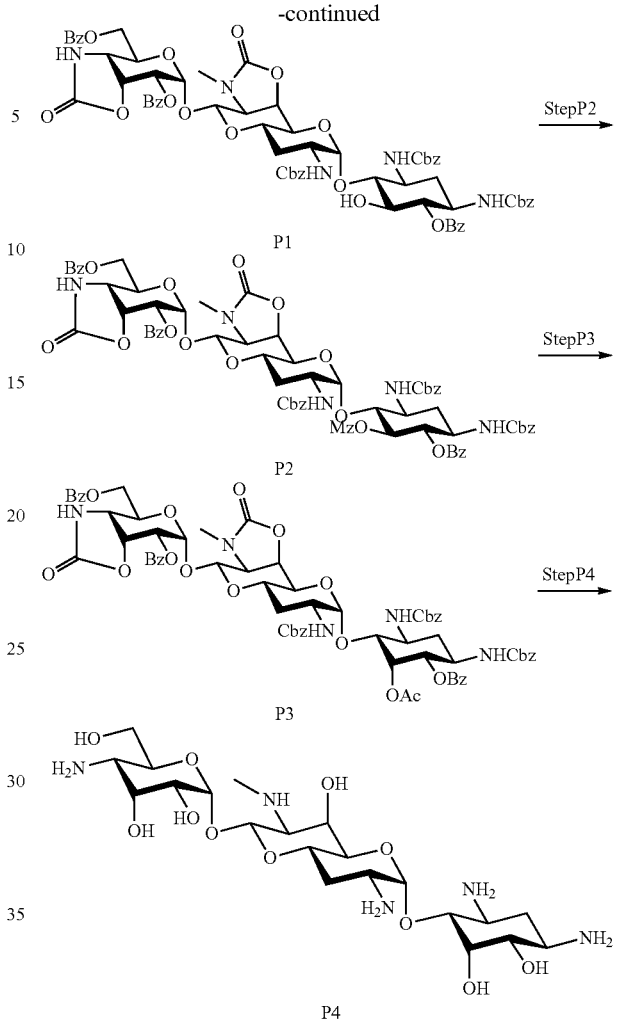

⟨?⟩ indicates text missing or illegible when filed

Step P1
The step P1 is a way to produce a compound represented by formula (P1) by eliminating the cyclohexylidene group at the 5- and 6-positions of the compound represented by formula (H2) and subsequently selectively protecting hydroxyl groups at the 6-, 2"- and 6"-positions with benzoyl groups. The removal of cyclohexylidene group and the benzoylation can be carried out under the conditions similar to those in the above-mentioned step M4.

Step P2
The step P2 is a way to produce a compound represented by formula (P2) by introducing a methanesulfonyl group into the free hydroxyl group at the 5-position of the compound represented by formula (P1). The methanesulphonylation can be carried out under the conditions similar to those in the above-mentioned step C1.

Step P3
The P3 step is a way to produce a compound represented by formula (P3) by inverting the 5-position of the compound represented by formula (P2). The reaction is achieved by the reaction of the compound represented by formula (P2) with cesium acetate. The solvents used in the present step include dioxane, N,N-dimethylformamide, 1,2-dimethoxyethane and the like, and preferably N, N-dimethylformamide. The reaction temperature is 80° C. to 100° C. The reaction time is 3 to 6 hours.

Step P4

The step P4 is a way to produce a compound represented by formula (P4) by removing the protecting group of the compound represented by formula (P3). The removal of protecting group can be carried out under the conditions similar to those in the above-mentioned step M7.

Method Q

The method Q is a way to produce a compound represented by formula (Q4) by selective chlorization of the hydroxyl group at the 6"-position of the compound represented by formula (C4) obtained from apramycin in 9 steps, followed by reduction and deprotection. The steps are shown as follows.

Step Q1

The step Q1 is a way to produce a compound represented by formula (Q1) by removing the benzoyl group of the compound represented by formula (C4). The removal of the benzoyl group can be carried out under the conditions similar to those in the above-mentioned step L1.

Step Q2

The step Q2 is a way to produce a compound represented by formula (Q2) by selectively chlorinating the hydroxy group at the 6"-position of the compound represented by formula (Q1). The chlorination can be carried out under the conditions similar to those in the above-mentioned step L2.

Step Q3

The step Q3 is a way to produce a compound represented by formula (Q3) by reducing the chloro group at the 6"-position of the compound represented by formula (Q2). The reduction can be carried out under the conditions similar to those in the above-mentioned step L3.

Step Q4

The step Q4 is a way to produce a compound represented by formula (Q4) by removing the protecting group of the compound represented by formula (Q3). The removal of protecting group can be carried out under the conditions similar to those in the above-mentioned steps L4 and B5.

Method R

The method R is a way to produce a compound represented by formula (R5) by selective chlorization of the hydroxyl group at the 6"-position of the compound represented by formula (C3) obtained from apramycin in 8 steps via a 5,6-dideoxy-5-eno derivative, followed by reduction and deprotection, and to produce a compound represented by formula (R6) by hydrogenating the 5- and 6-positions of this compound. The steps are shown as follows.

[Chem. 23]

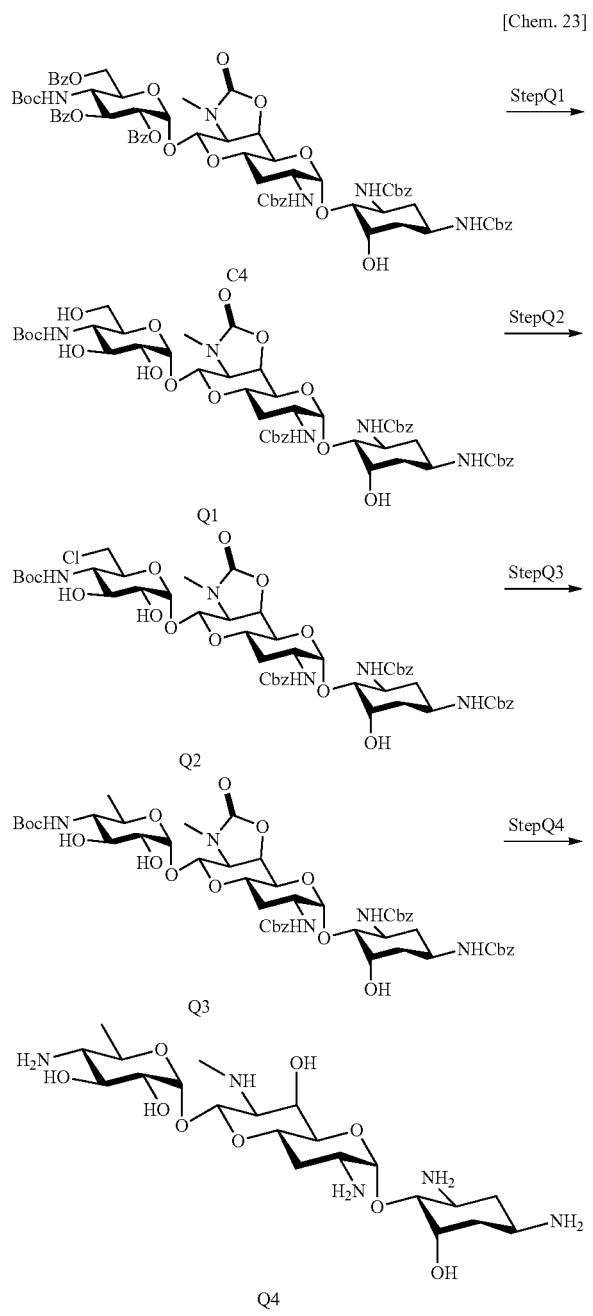

[Chem. 24]

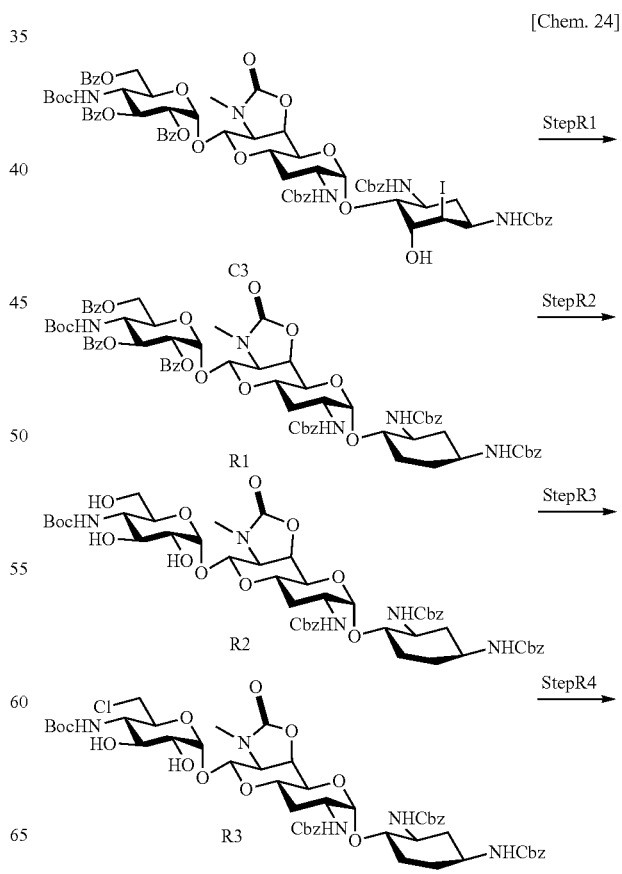

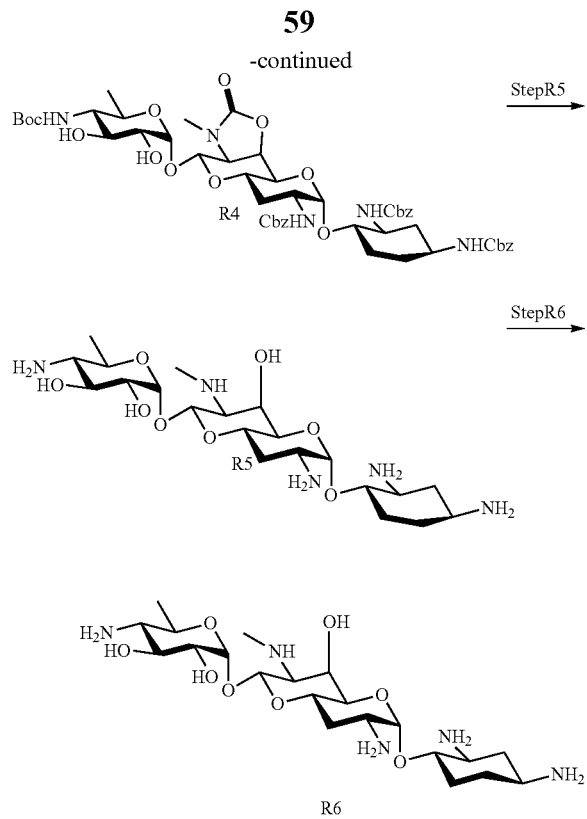

Step R1

The step R1 is a way to produce a compound represented by formula (R1) by benzylsulfonylation of the hydroxyl group at the 5-position of the compound represented by formula (C3), and then adding water followed by an elimination reaction. This step can be carried out under the conditions similar to those in the above-mentioned step N6.

Step R2

The step R2 is a way to produce a compound represented by formula (R2) by removing the benzoyl group of the compound represented by formula (R1). This step is achieved by reacting the compound represented by formula (R1) with a base. The removal of the benzoyl group can be carried out under the conditions similar to those in the above-mentioned step G5.

Step R3

The step R3 is a way to produce a compound represented by formula (R3) by selectively chlorinating the hydroxyl group at the 6"-position of the compound represented by formula (R2). The chlorination can be carried out under the conditions similar to those in the above-mentioned step L2.

Step R4

The step R4 is a way to produce a compound represented by formula (R4) by reducing the chloro group at the 6"-position of the compound represented by formula (R3). The reduction can be carried out under the conditions similar to those in the above-mentioned step L3.

Step R5

The step R5 is a way to produce a compound represented by formula (R5) by removing the t-butoxycarbonyl group, benzyloxycarbonyl group and cyclic carbamate of the compound represented by formula (R4). The removal of t-butoxycarbonyl group can be carried out under the conditions similar to those in the above-mentioned step L4. The removal of benzyloxycarbonyl group is achieved by reacting with metallic sodium in liquid ammonia. The reaction temperature is −70° C. to −30° C., and the reaction time is usually 1 to 2 hours. The cyclic carbamate can be eliminated by basic hydrolysis. The bases used include sodium hydroxide and potassium hydroxide. The reaction is carried out at the temperature of 90° C. to 110° C. and usually completed within the reaction time of 0.5 to 1 hour.

Step R6

The step R6 is a way to produce a compound represented by formula (R6) by hydrogenating the 5- and 6-positions of the compound represented by formula (R5). The hydrogenation is achieved by reacting with hydrogen and a catalytic hydrogen reduction catalyst. The catalytic reduction catalysts used for hydrogenation include palladium-carbon, palladium black, palladium hydroxide, platinum oxide and the like, and preferably platinum oxide. The solvent used is preferably water. The reaction temperature is 10° C. to 30° C., and the reaction time is usually 1 to 2 hours.

Method S

The method S is a way to produce a compound represented by a general formula (S1) by introducing a substituent into the amino group at the 4"-position of the compound represented by a general formula (S) and subsequent deprotecting. The steps are shown as follows.

[Chem. 25]

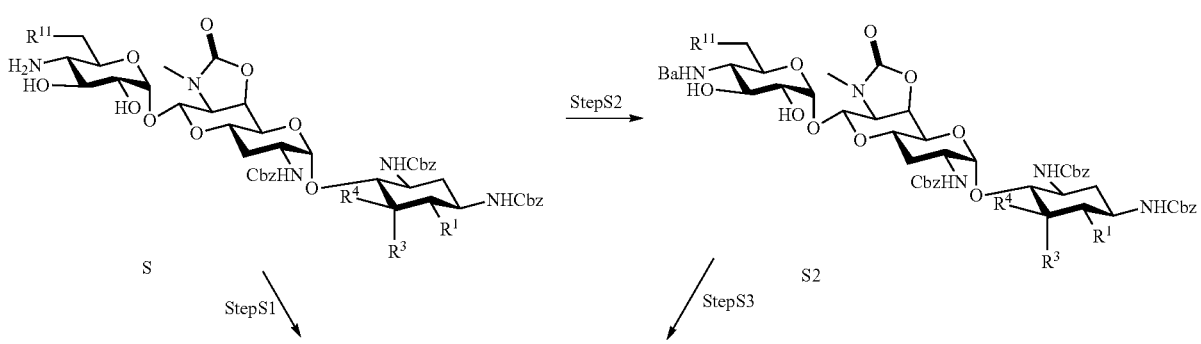

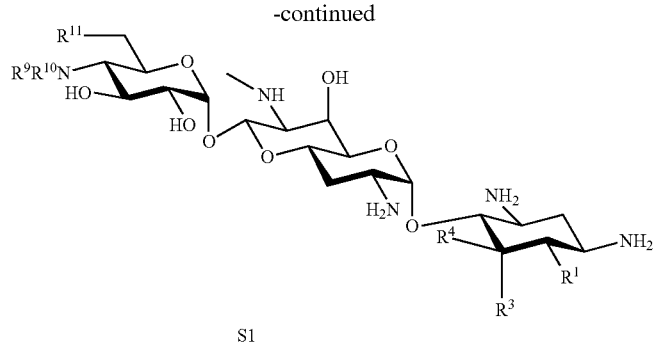

S1

Step S1

The step S1 is a way to produce a compound represented by general formula (S1) by alkylation or amidination of the amino group at the 4"-position of a compound represented by general formula (S) followed by deprotection. The step can be carried out under the conditions similar to those in the above-mentioned step A4.

Step S2

The step S2 is a way to produce a compound represented by general formula (S2) by preliminarily introducing a benzyl group into an amino group of the compound represented by general formula (S) for monoalkylation of the amino group at the 4"-position. The introduction of a benzyl group can be carried out under the conditions similar to those in the above-mentioned step A5.

Step S3

The step S3 is a way to produce a compound represented by general formula (S1) by alkylation of the amino group at the 4"-position of the compound represented by a general formula (S2) followed by deprotection. The step can be carried out under the conditions similar to those in the above-mentioned step A6.

Method T

The method T is a way to produce a compound represented by the general formula (T2) by introducing a substituent into the amino group at the 4"-position of the compound represented by formula (R1) obtained from apramycin in 9 steps and subsequent deprotection. The steps are shown as follows.

[Chem. 26]

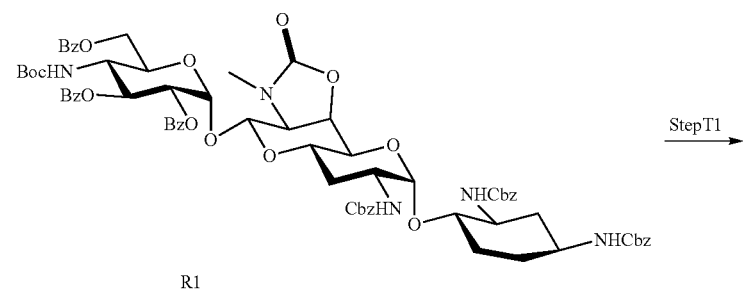

R1

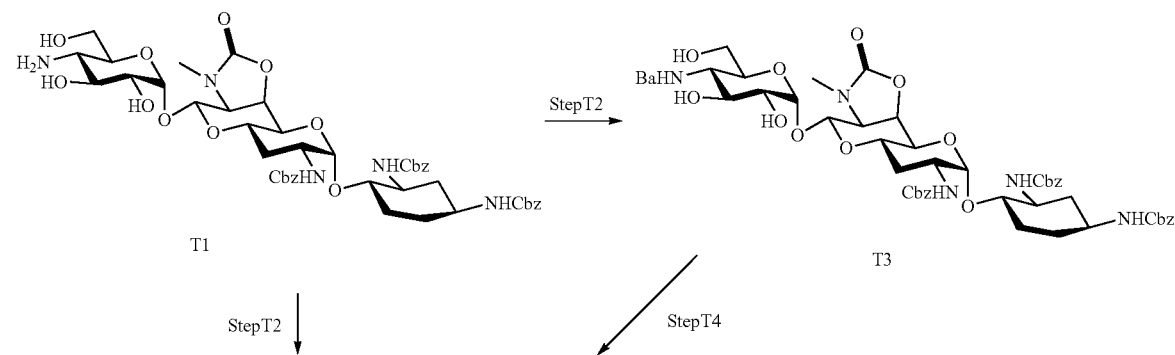

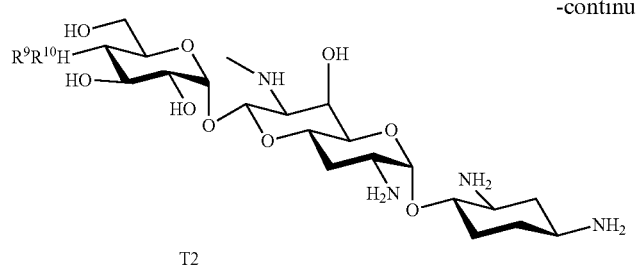

T2

Step T1

The step T1 is a way to produce a compound represented by formula (T1) by removing the benzoyl group and t-butoxycarbonyl group of the compound represented by formula (R1). The removal of protecting group can be carried out under the conditions similar to those in the above-mentioned step B4.

Step T2

The step T2 is a way to produce a compound represented by general formula (T2) by alkylation or amidination of the free amino group at the 4"-position of the compound represented by formula (T1) followed by deprotection. The step can be carried out under the conditions similar to those in the above-mentioned step A4.

Step T3

The step T3 is a way to produce a compound represented by formula (T3) by preliminarily introducing a benzyl group into an amino group of the compound represented by formula (T1) for monoalkylation of the amino group at the 4"-position. The introduction of benzyl group can be carried out under the conditions similar to those in the above-mentioned step A5.

Step T4

The step T4 is a way to produce a compound represented by general formula (T2) by alkylation of the benzylated amino group at the 4"-position of the compound represented by formula (T3) followed by deprotection of the benzyl group. This step can be carried out under the conditions similar to those in the above-mentioned step A6.

Method U

The method U is a way to produce a compound represented by general formula (U4) by first obtaining a free amino derivative at the 4"-position in 3 steps by using the compound represented by formula (M6) obtained from apramycin in 12 steps, and introducing a substituent into the amino group, followed by deprotection. The steps are shown as follows.

[Chem. 27]

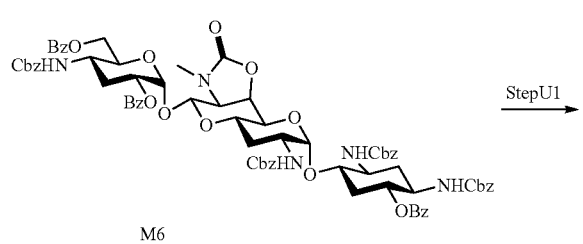

M6

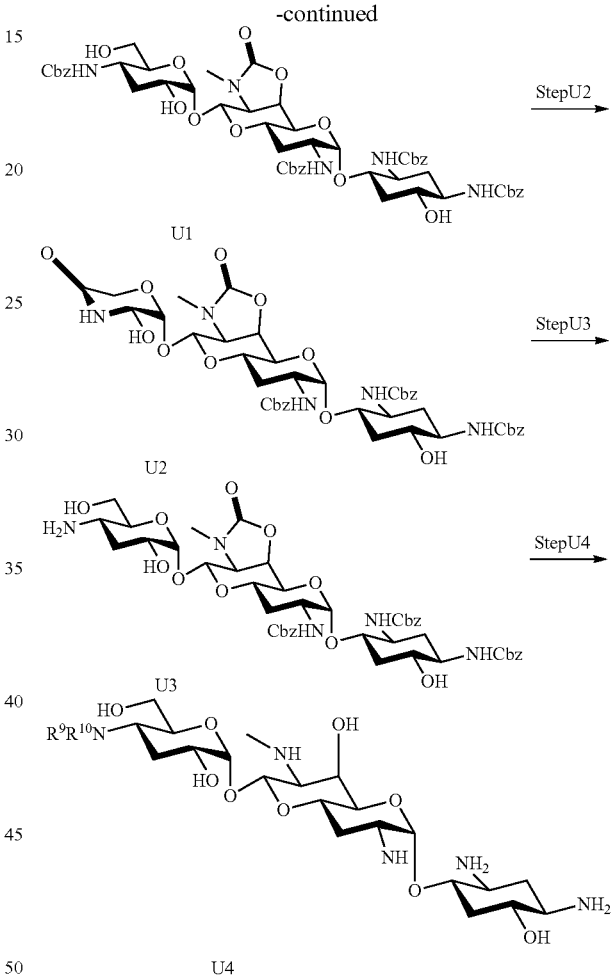

Step U1

The step U1 is a way to produce a compound represented by formula (U1) by removing the benzoyl group of the compound represented by formula (M6). The removal of the benzoyl group can be carried out under the conditions similar to those in the above-mentioned step L1.

Step U2

The step U2 is a way to produce a compound represented by formula (U2) by converting the 4"- and 6"-positions of the compound represented by formula (U1) into a cyclic carbamate. The conversion to cyclic carbamate can be carried out under the conditions similar to those in the above-mentioned step A2.

Step U3

The step U3 is a way to produce a compound represented by formula (U3) by hydrolyzing the cyclic carbamate at 4"- and 6"-positions of the compound represented by formula (U2) and liberating the amino group at the 4"-position and the hydroxyl group at the 6"-position. The removal of carbamate can be carried out under the conditions similar to those in the above-mentioned step A3.

Step U4

The step U4 is a way to produce a compound represented by general formula (U4) by alkylation or amidination of the amino group at the 4"-position of the compound represented by formula (U3) followed by deprotection. The step can be carried out under the conditions similar to those in the above-mentioned step A4.

Method V

The method V is a way to produce a compound represented by general formula (V1) by amidating the amino group at the 4"-position of the compound represented by the general formula (V) and subsequent deprotection. The steps are shown as follows.

[Chem. 28]

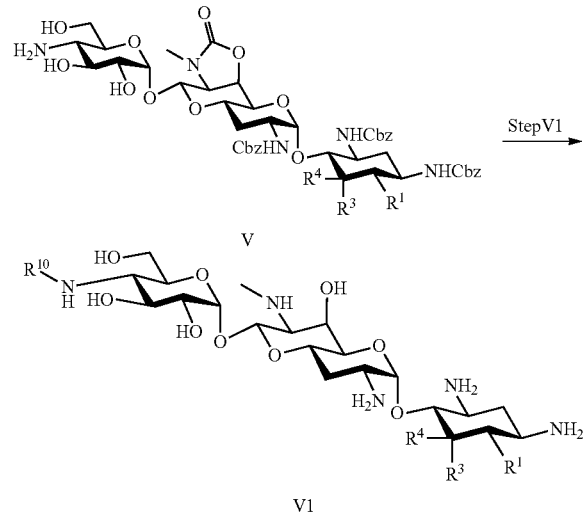

Step V1

The step V1 is a way to produce a compound represented by general formula (V1) by acylation of the amino group at the 4"-position of the compound represented by general formula (V) followed by deprotection. This step is achieved by reacting the compound of general formula (V) with various active esters of protected amino acids in the presence of a base followed by deprotection.

The active esters used in the present step include N-hydroxyamines, S-alkyls, S-phenyls and the like, and preferably N-hydroxysuccinimide ester among N-hydroxyamines. The base is preferably triethylamine. All the reaction temperatures are in the range of 10° C. to 30° C., and the reaction time is 1 to 24 hours.

The removal of t-butoxycarbonyl and p-methoxybenzyloxycarbonyl groups can be conducted under the conditions similar to those in the above-mentioned step L4. The removal of the benzyloxycarbonyl group and cyclic carbamate can be carried out under the conditions similar to those in the above-mentioned step A4.

Method W

The method W is a way to produce a compound represented by general formula (W2) by introducing a substituent to the amino group at the 4"-position of the compound represented by formula (D1) after the removal of protecting groups except the benzyloxycarbonyl group of the compound, followed by subsequent deprotection. The steps are shown as follows.

[Chem. 29]

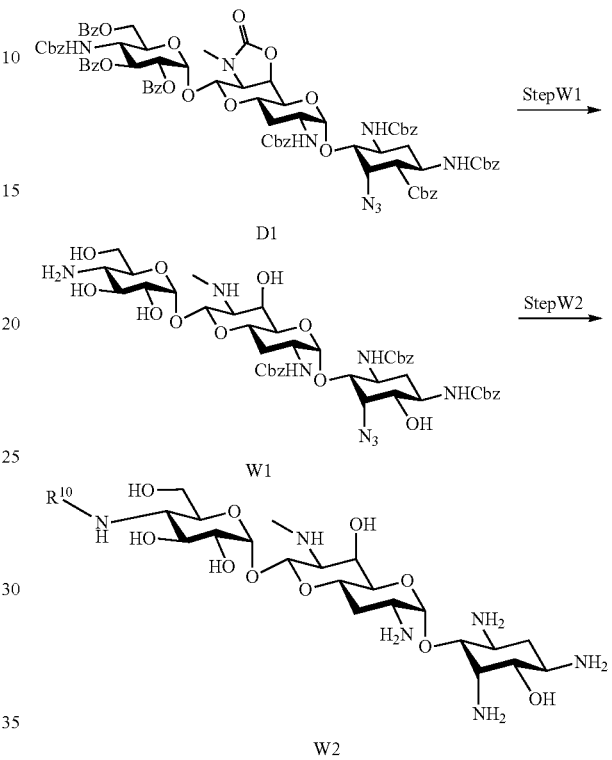

Step W1

The step W1 is a way to produce a compound represented by formula (W1) by removing the benzoyl group, t-butoxycarbonyl group and cyclic carbamate of the compound represented by formula (D1). The benzoyl group and cyclic carbamate can be removed by basic hydrolysis. The bases used include sodium hydroxide and potassium hydroxide. The reaction is carried out at the temperature of 10° C. to 100° C. and usually completed within the reaction time of 0.5 to 16 hours. The removal of a t-butoxycarbonyl group can be carried out under the conditions similar to those in the above-mentioned step L4.

Step W2

The step W2 is a way to produce a compound represented by general formula (W2) by acylation or amidination of the amino group at the 4"-position of the compound represented by general formula (W1) followed by deprotection. The amidination and deprotection of this step can be conducted under the conditions similar to those in the above-mentioned step A4, and acylation can be carried out under the conditions similar to those in the above-mentioned step V1.

Method X

The method X is a way to produce a compound represented by the general formula (X4) by using the compound represented by general formula (X) under the conditions similar to those in the method U. The steps are shown as follows.

[Chem. 30]

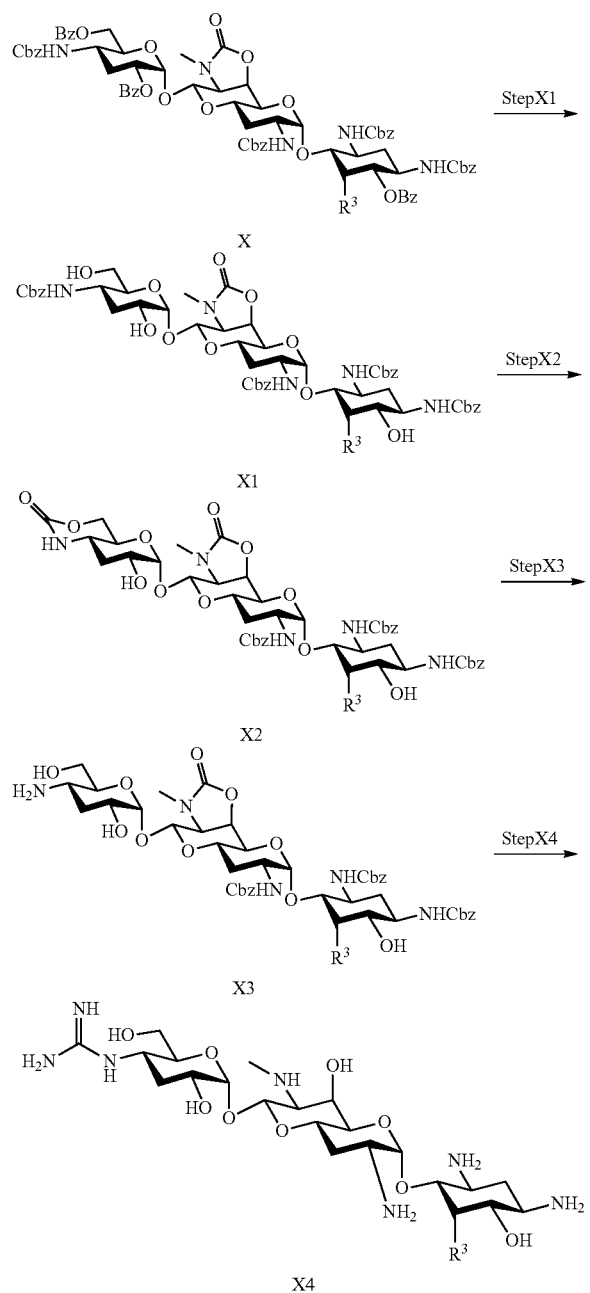

Step X1

The step X1 is a way to produce a compound represented by formula (X1) by removing the benzoyl group of the compound represented by the general formula (X). The removal of a benzoyl group can be carried out under the conditions similar to those in the above-mentioned step L1.

Step X2

The step X2 is a way to produce a compound represented by formula (X2) by converting the 4"- and 6"-positions of the compound represented by formula (X1) into cyclic carbamate. The conversion to cyclic carbamate can be carried out under the conditions similar to those in the above-mentioned step A2.

Step X3

The step X3 is a way to produce a compound represented by formula (X3) by hydrolyzing the cyclic carbamate at the 4"- and 6"-positions of the compound represented by formula (X2) and liberating the amino group at the 4"-position and the hydroxyl group at the 6"-position. The removal of carbamate can be carried out under the conditions similar to those in the above-mentioned step A3.

Step X4

The step X4 is a way to produce a compound represented by general formula (X4) by alkylation or amidination of the amino group at the 4"-position of the compound represented by formula (X3) followed by deprotection. The step can be carried out under the conditions similar to those in the above-mentioned step A4.

Method Y

The method Y is a way to produce a compound represented by formula (Y3) by using the compound represented by formula (O3) under the conditions similar to those in the method P. The steps are shown as follows.

[Chem. 31]

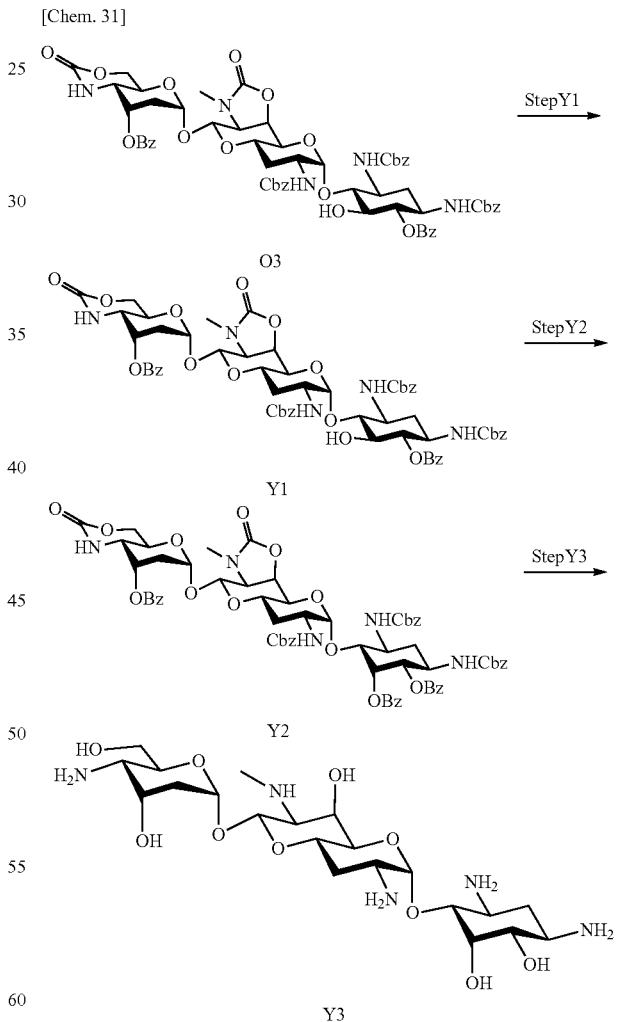

Step Y1

The step Y1 is a way to produce a compound represented by formula (Y1) by introducing a methanesulfonyl group into the free hydroxyl group at the 5-position of the compound represented by formula (O3). The methanesulphonylation can be carried out under the conditions similar to those in the above-mentioned step C1.
Step Y2
The step Y2 is a way to produce a compound represented by formula (Y2) by inverting the 5-position of the compound represented by formula (Y1). This reaction can be carried out under the conditions similar to those in the above-mentioned step P3.
Step Y3
The step Y3 is a way to produce a compound represented by formula (Y3) by removing the protecting group of the compound represented by formula (Y2). The removal of the protecting group can be carried out under the conditions similar to those in the above-mentioned step M7.

The compounds of the present invention and the above-mentioned compounds obtained in the production steps thereof can be purified and isolated in a conventional method of purification. As for a purification and isolation method, for example, a liquid separation method, a distillation method, a sublimation technique, a precipitation method, a crystallization method, normal-phase or reverse-phase column chromatography using silica gel as a packing material, column chromatography using ion exchange resin such as Amberlite CG-50, Dowex 50W×2 or CM-sephadex C-25 and the like, column chromatography using cellulose and the like, a preparative thin-layer chromatography method or high performance liquid chromatography method and the like can be used. In addition, the compounds obtained in the above-mentioned production steps can be also used for the subsequent steps appropriately without further isolation or purification.
Use of the Aminoglycoside Antibiotic The compound of the present invention or a pharmaceutically acceptable salt or solvate thereof has a wide antibacterial spectrum against a variety of gram-positive bacteria and gram-negative bacteria among pathogenicity bacteria. In addition, the compound of the present invention or a pharmaceutically acceptable salt or solvate thereof has excellent antibacterial activity against bacteria causing infectious diseases (MRSA, *Staphylococcus aureus*, *Escherichia coli*, *Klebsiella pneumonia*, *Pseudomonas aeruginosa* and the like), therefore can be used as an antimicrobial agent.

Thus, in accordance with other embodiments of the present invention, an antimicrobial agent comprising the compound of this present invention is provided. Furthermore, in accordance with another embodiment of the present invention, the use of a compound of the present invention or a pharmaceutically acceptable salt or solvate thereof to produce antimicrobial agent is provided.

As mentioned above, the compound of the present invention or a pharmaceutically acceptable salt or solvate thereof can be beneficially used as an antimicrobial agent or medicine to prevent or treat infectious diseases. Therefore, in accordance with another embodiment of the present invention, provided is a method to prevent or treat infectious diseases comprising administering a therapeutically effective amount of the compound of the present invention or a pharmaceutically acceptable salt or solvate thereof to animals including humans. The targeted infectious diseases are preferably bacterial infectious diseases including, for example, sepsis, infectious endocarditis, dermatological infections, surgical site infections, orthopedic surgical site infections, respiratory infections, urinary tract infections, enteral infections, peritonitis, meningitis, ophthalmological infections or otolaryngological infections, and preferably purulent skin diseases, secondary infections caused by burns/surgical incisions, pneumonia, endobronchial infections, tuberculosis, pyelonephritis, enteritis (including food poisonings), conjunctivitis, otitis media or the like. The targeted animals for prevention or treatment are preferably mammals, and more preferably humans. Also, the dose of the compound of the present invention or a pharmaceutically acceptable salt thereof is appropriately determined by those skilled in the art depending on administration, types of pathogens, age, sex and body weight of a patient and the severity of diseases. In the case of oral administration to a human, for example, the compound of the present invention can be administered to an adult at a dosage of 0.1 to 1000 mg/kg/day, and in the case of intravenous administration, it can be administered at a dosage of 0.01 to 100 mg/kg/day per adult.

In accordance with further embodiment of the present invention, the following inventions are provided.
(1) A compound of the present invention or a pharmaceutically acceptable salt or solvate thereof for use in therapy.
(2) A compound of the present invention or a pharmaceutically acceptable salt or solvate thereof for use in the prevention or treatment of infectious disease.
(3) Use of the compound of the present invention or a pharmaceutically acceptable salt or solvate thereof for the manufacture of a medicament for the prevention or treatment of infectious disease.
(4) Use of the compound of the present invention or a pharmaceutically acceptable salt or solvate thereof for the prevention or treatment of infectious disease.

The compound of the present invention or a pharmaceutically acceptable salt or solvate thereof has antibacterial activity against multidrug-resistant gram-positive and gram-negative bacteria that are untreatable with currently available antibiotics. The compound of the present invention or a pharmaceutically acceptable salt or solvate thereof is particularly useful to prevent or treat serious infectious diseases caused by MRSA or multidrug-resistant gram-negative bacteria and the like.

The compound of the present invention or a pharmaceutically acceptable salt or solvate thereof can be administered to an animal as a pharmaceutical composition comprising pharmaceutically acceptable additives, if desired. Therefore, in accordance with another embodiment of the present invention, provided is a composition, particularly a pharmaceutical composition comprising the compound of the present invention or a pharmaceutically acceptable salt or solvate thereof.

The pharmaceutical composition of the present invention can be administered via either oral or parenteral administration route (e.g., intravenous injection, intramuscular injection, subcutaneous administration, rectal administration, percutaneous administration, local eye administration, pulmonary administration) to all the mammals including humans depending on types of pathogens and diseases and the nature of the patient. Therefore, the pharmaceutical component of the present invention can be adjusted to a suitable formulation depending on administration routes. Such formulations, for example, can be as adjusted to parenteral injections mainly used for intravenous injections, intramuscular injections and the like; oral agent such as oral capsules, tablets, granules, powders, pills, fine granules, syrups, pastilles and the like; external preparation for parenteral administration such as ointments, eye drops, ear drops, nasal drops, eye ointments, mucocutaneous absorbents, dermatological agents, inhalants, suppositories and the like; other dry powders or nebulization aerosol formulations, and the like.

The above-mentioned formulation can be prepared by using additives such as excipients, bulking agents, binders, wetting agents, disintegrating agents, surfactants, lubricants, dispersing agents, buffer, preservatives, solubilizers, antiseptic agents, flavoring agents, analgesic agents, stabilizers and the like in a routine procedure. Specific examples of the available non-toxic additives include solubilizers or solubilization agents (distilled water for injections, saline, ethanol, glycerin, propylene glycol, corn oil, sesame oil and the like) that can constitute aqueous solutions or formulations to be dissolved before use for parenteral injection, eye drops, ear drops and nasal drops; pH regulators (mineral acid addition salts: trisodium orthophosphate, sodium bicarbonate and the like; organic acid salts: sodium citrate and the like, organic base salts: L-lysin, L-arginine and the like); isotonizing agents (sodium chloride, glucose, glycerin and the like); buffers (sodium chloride, benzalkonium chloride, sodium citrate and the like); surfactants (sorbitan monooleate, polysorbate 80 and the like); dispersing agents (D-mannitol and the like); stabilizers (antioxidants: ascorbic acid, sodium sulfite, sodium pyrosulfite and the like, chelating agents: citric acid, tartaric acid and the like). Also, appropriate formulation components as ointments, creams, and patches for eye ointments, mucocutaneous absorbents and dermatological agents include white petrolatum, macrogol, glycerin, liquid paraffin, cotton cloth and the like. Also, liquid inhalants include pH regulators (sodium citrate, sodium hydroxide and the like), isotonizing agents (sodium chloride, benzalkonium chloride, sodium citrate and the like) and buffers (sodium chloride, benzalkonium chloride, sodium citrate and the like), and powder inhalants include lactose and the like as a carrier. Also, orally administered agents and suppositories include excipients (lactose, D-mannitol, corn starch, crystalline cellulose and the like), disintegrating agents (carboxymethylcellulose, carboxymethylcellulose calcium and the like), binders (hydroxypropylcellulose, hydroxypropylmethylcellulose, polyvinylpyrrolidone and the like), lubricants (magnesium stearate, talc and the like), coating agents (purified shellac, hydroxypropylmethylcellulose, sucrose, titanium oxide and the like), plasticizers (glycerin, polyethylene glycol and the like), substrates (cacao butter, polyethylene glycol, hard fat and the like), and the like.

Also, when considering the improvement of the efficacy of the compound of the present invention to prevent or treat infectious diseases, other than a compound of the present invention, one or more clinically useful existing antibiotics (e.g., β-lactam antibiotics (carbapenems, cephalosporins, cephamycins, penicillins), glycopeptide antibiotics, ansamycins antibiotics, aminoglycoside antibiotics, quinolone antibiotics, monobactam antibiotics, macrolide antibiotics, tetracycline antibiotics, chloramphenicol antibiotics, lincomycin antibiotics, streptogramin antibiotics, oxazolidinone antibiotics, phosphomycins, novobiocins, cycloserines, moenomycins and the like) may be added to the pharmaceutical composition of the present invention. Alternatively, the compound of the present invention may be co-administered with above-mentioned antibiotics to living bodies. Furthermore, when considering expanding or improving the efficacy of the pharmaceutical composition of the present invention against gram-negative bacteria and drug-resistant bacteria against currently available antibiotics, the pharmaceutical composition of the present invention may comprise also a drug discharge pump (Efflux pump) inhibitor or an inhibitor of existing antibacterial degrading enzyme (R-lactamase and the like), and may be administered to living bodies together with these inhibitors. Further, when considering improving therapeutic or preventive effects for infectious diseases, the pharmaceutical composition of the present invention may be used in combination with compounds having no antibacterial activity (e.g. drugs for treating complications), and the present invention also includes such embodiment.

EXAMPLES

The present invention is explained in detail using Examples but is not limited to the Examples.

Example 1: Synthesis of 4″-N-benzyl-1,3,2′-tris-N-(benzyloxycarbonyl)-7′-N,6′-O-carbonylapramycin (A5) and 4″-N-methylapramycin (A4-a)

[Chem. 32]

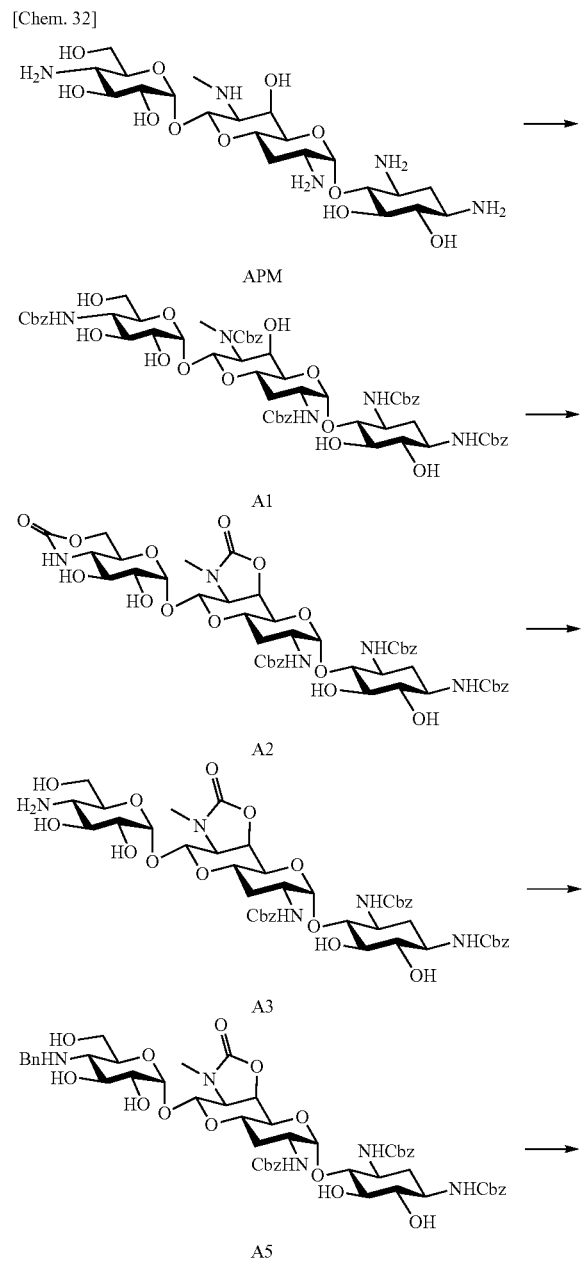

-continued

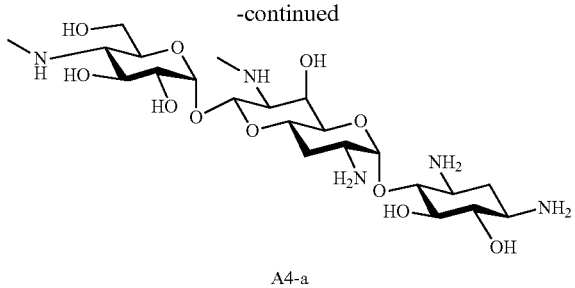

A4-a

Example 1-(i): Synthesis of 4"-N-benzyl-1,3,2'-tris-N-(benzyloxycarbonyl)-7'-N,6'-O-carbonylapramycin (A5)

A solution prepared by adding 15 ml of triethylamine and 6 ml of benzaldehyde to a solution of 20.4 g (21 mmol) of the compound represented by formula (A3) described in the US patent 2013/0165395A1 dissolved in 200 ml of methanol was stirred at room temperature for 2 hours. Then, after adding 1.6 g of NaBH$_4$, the resultant mixture was subjected to reaction at room temperature for 10 minutes. The reaction solution was concentrated under reduced pressure and washed with water. After drying, the resultant residue was washed with isopropyl ether to give 21.2 g (95%) of the title compound (A5) as a white solid.

MS (ESI) m/z: 1081 (M+Na)$^+$.

Example 1-(ii): Synthesis of 4"-N-methylapramycin (A4-a)

A mixture prepared by adding 0.1 ml of 37% formalin solution and 10 mg of NaBH$_3$CN to a solution of 550 mg (0.51 mmol) of the compound (A5) of Example 1-(i) dissolved in 10 ml of 10% acetic acid-methanol was subjected to reaction at room temperature for 13 hours. After completion of the reaction, the mixture was concentrated under reduced pressure and washed with water. After drying, the residue was dissolved in 5.2 ml of 50% aqueous 1,4-dioxane and 0.5 ml of acetic acid and palladium black were added to the solution, and catalytic reduction was performed in a hydrogen atmosphere at room temperature for 10 hours. After completion of the reaction, the reaction mixture was neutralized with NH$_4$OH and concentrated under reduced pressure after filtration. After drying, the residue was dissolved in 2.5 ml of water and the resulting mixture was heated to 110° C., to which 2.5 ml of 1 N aqueous potassium hydroxide was added. The mixture was subjected to reaction for 2 hours. After completion of the reaction, the reaction mixture was neutralized by adding 1 N aq. HCl under ice cooling and purified by ion exchange chromatography (CG50) to give 152 mg (54%) of the title compound (A4-a).

MS (ESI) m/z: 554 (M+1)$^+$; $^1$H NMR (25% ND$_3$-D$_2$O, 500 MHz): δ 2.77 (6H, s, 4"-NMe and 7'-NMe), 5.36 (1H, d, H-1') and 5.68 (1H, d, H-1").

Example 2: Synthesis of 4"-N-(3-aminopropyl)apramycin (A4-b)

[Chem. 33]

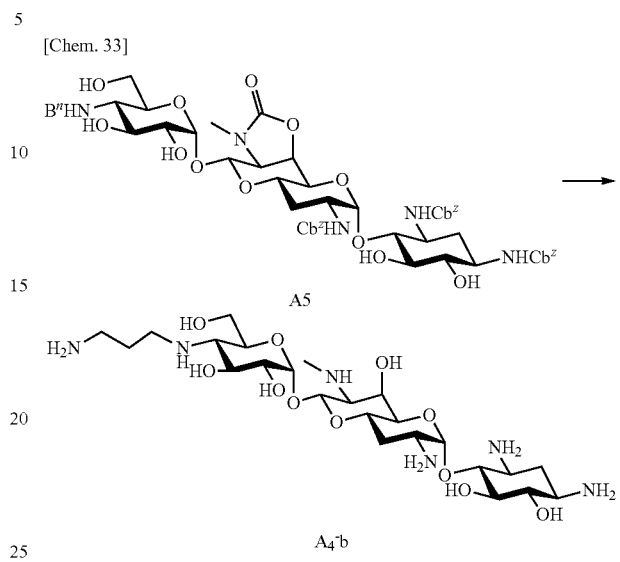

The title compound (A4-b) [87.1 mg (46%)] was obtained by a method similar to Example 1-(ii) using 333 mg (0.32 mmol) of the compound (A5) of Example 1-(i) and 80 mg of 3-[(benzyloxycarbonyl)amino]propionaldehyde.

MS (ESI) m/z: 597 (M+1)$^+$; $^1$H NMR (25% ND$_3$-D$_2$O, 500 MHz): δ 1.91-2.05 (3H, m, 4"-NH$_2$Pr(β) and H-3' ax), 2.94-3.09[6H, m, H-1 and 7' and 4"-NH$_2$Pr(α, γ)], 5.28 (1H, d, H-1") and 5.67 (1H, d, H-1').

Example 3: Synthesis of 4"-N-((1-aminocyclopentyl)methyl)apramycin (A4-c)

[Chem. 34]

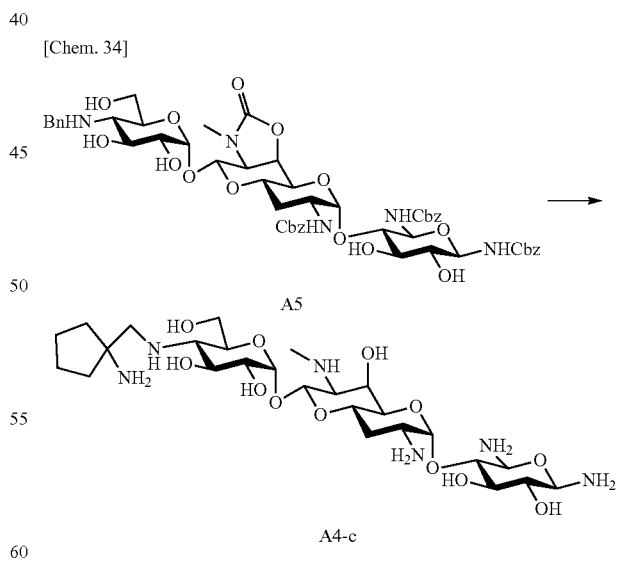

A mixture prepared by adding 80 mg of N-Boc-2-aminoacetaldehyde and 10 mg of NaBH$_3$CN to a solution of 300 mg (0.30 mmol) of the compound (A5) of Example 1-(i) dissolved in 6 ml of 10% acetic acid-methanol was subjected to reaction at room temperature for 16 hours. After completion of the reaction, the mixture was concentrated under reduced pressure and the residue was dissolved in 10 ml of 90% TFA-MeOH solution. The resultant mixture was subjected to reaction at room temperature for 2 hours. The reaction solution was concentrated under reduced pressure and washed with water. The residue was dissolved in 10 ml of 50% aqueous 1, 4-dioxane, and 0.5 ml of acetic acid and palladium black were added to the solution, and catalytic reduction was performed in a hydrogen atmosphere at room temperature for 10 hours. After completion of the reaction, the mixture was neutralized with NH₄OH and concentrated under reduced pressure after filtration. After drying, the residue was dissolved in 2.5 ml of water and the resulting mixture was heated to 110° C., to which 2.5 ml of 1 N aqueous potassium hydroxide was added. The mixture was subjected to reaction for 2 hours. After completion of the reaction, the reaction mixture was neutralized by adding 1 N aq. HCl under ice cooling and purified by ion exchange chromatography (CG50) to give 87.5 mg (46%) of the title compound (A4-c).

MS (ESI) m/z: 637 (M+1)⁺; ¹H NMR (TFA salt, 500 MHz, D₂O): δ 1.98 (1H, q, J=12 Hz, H-3' ax), 2.33 (1H, dt, J=4.5, 4.5 and 12 Hz, H-3' eq), 2.45 (1H, dt, J=4, 4 and 12.5 Hz, H-2eq), 2.74 (3H, s, NCH₃), 2.90 (1H, slightly br t, J=10 Hz, H-4"), 3.16 (1H, d, J=14 Hz), 3.22 (1H, d, J=14 Hz), 3.32 (1H, dd, J=3 and 8.5 Hz, H-7'), 3.71 (1H, dd, J=2.5 and 10 Hz, H-5'), 4.51 (1H, t, J=2.5 Hz, H-6'), 5.16 (1H, d, J=8.5 Hz, H-8'), 5.39 (1H, d, J=4 Hz, H-1") and 5.68 (1H, d, J=3.8 Hz, H-1').

Example 4: Synthesis of 4"-N-(1,3-diaminopropan-2-yl)apramycin (A4-d)

[Chem. 35]

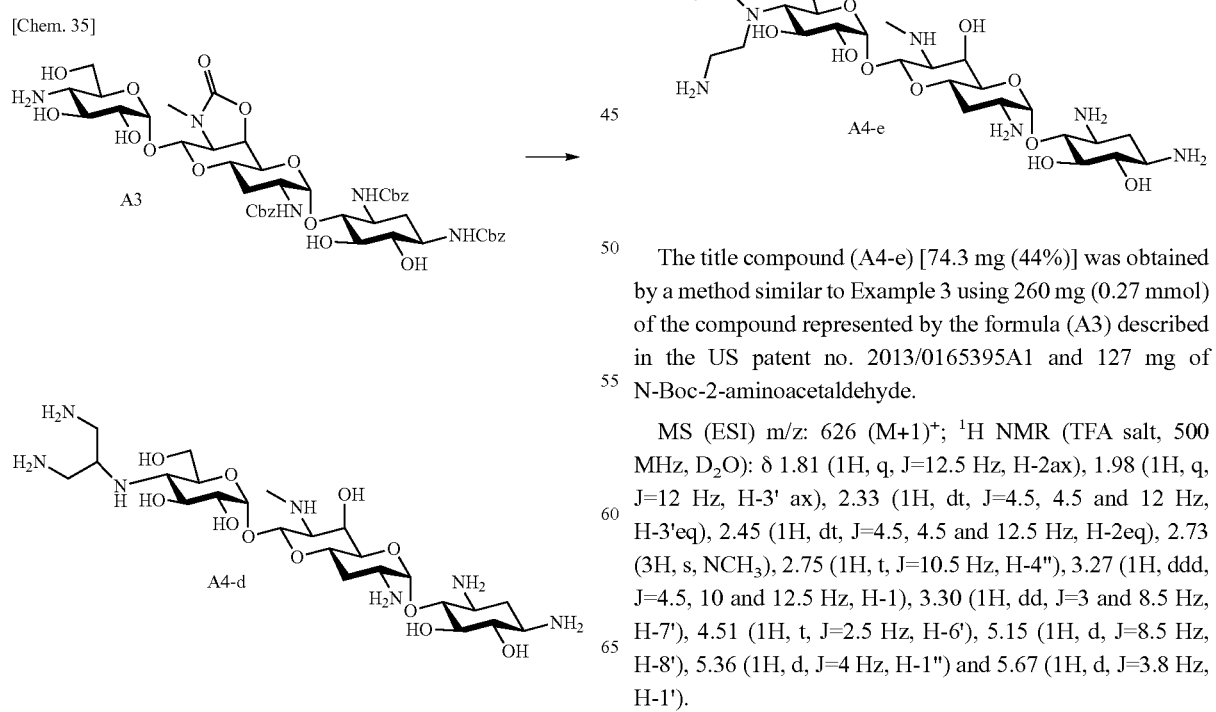

The title compound (A4-d) [80.6 mg (53%)] was obtained by a process similar to Example 1-(ii) using 250 mg (0.26 mmol) of the compound represented by the formula (A3) described in the US patent no. 2013/0165395A1 and 115 mg of 1,3-di-benzyloxycarbonylaminoacetone.

MS (ESI) m/z: 612 (M+1)⁺; ¹H NMR (TFA salt, 500 MHz, D₂O): δ 1.81 (1H, q, J=12.5 Hz, H-2ax), 1.98 (1H, q, J=12 Hz, H-3' ax), 2.33 (1H, dt, J=4, 4 and 12 Hz, H-3' eq), 2.45 (1H, dt, J=4, 4 and 12.5 Hz, H-2eq), 2.66 (1H, t, J=10.5 Hz, H-4"), 2.73 (3H, s, NCH₃), 3.31 (1H, dd, J=3 and 8.5 Hz, H-7'), 4.51 (1H, t, J=~3 Hz, H-6'), 5.15 (1H, d, J=8.5 Hz, H-8'), 5.37 (1H, d, J=4 Hz, H-1") and 5.67 (1H, d, J=3.8 Hz, H-1').

Example 5: Synthesis of 4"-N,N-bis(2-aminoethyl)apramycin (A4-e)

[Chem. 36]

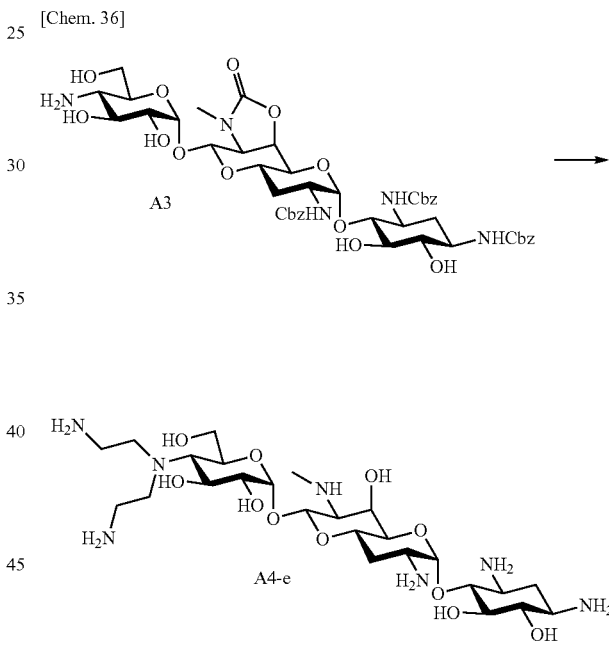

The title compound (A4-e) [74.3 mg (44%)] was obtained by a method similar to Example 3 using 260 mg (0.27 mmol) of the compound represented by the formula (A3) described in the US patent no. 2013/0165395A1 and 127 mg of N-Boc-2-aminoacetaldehyde.

MS (ESI) m/z: 626 (M+1)⁺; ¹H NMR (TFA salt, 500 MHz, D₂O): δ 1.81 (1H, q, J=12.5 Hz, H-2ax), 1.98 (1H, q, J=12 Hz, H-3' ax), 2.33 (1H, dt, J=4.5, 4.5 and 12 Hz, H-3'eq), 2.45 (1H, dt, J=4.5, 4.5 and 12.5 Hz, H-2eq), 2.73 (3H, s, NCH₃), 2.75 (1H, t, J=10.5 Hz, H-4"), 3.27 (1H, ddd, J=4.5, 10 and 12.5 Hz, H-1), 3.30 (1H, dd, J=3 and 8.5 Hz, H-7'), 4.51 (1H, t, J=2.5 Hz, H-6'), 5.15 (1H, d, J=8.5 Hz, H-8'), 5.36 (1H, d, J=4 Hz, H-1") and 5.67 (1H, d, J=3.8 Hz, H-1').

Example 6: Synthesis of 4''-N-[(1S,4S)-4-(t-butoxycarbonyl)aminocyclohexyl]-4''-N-benzyl-1,3,2'-tris-N-(benzyloxycarbonyl)-7'-N,6'-O-carbonylapramycin (A3-a), 4''-N-[(1R,4R)-4-(t-butoxycarbonyl) aminocyclohexyl]-4''-N-benzyl-1,3,2'-tris-N-(benzyloxycarbonyl)-7'-N,6'-O-carbonylapramycin (A3-b) and 4''-N-(cis-1,4-4-aminocyclohexyl) apramycin (A4-f)

[Chem. 37]

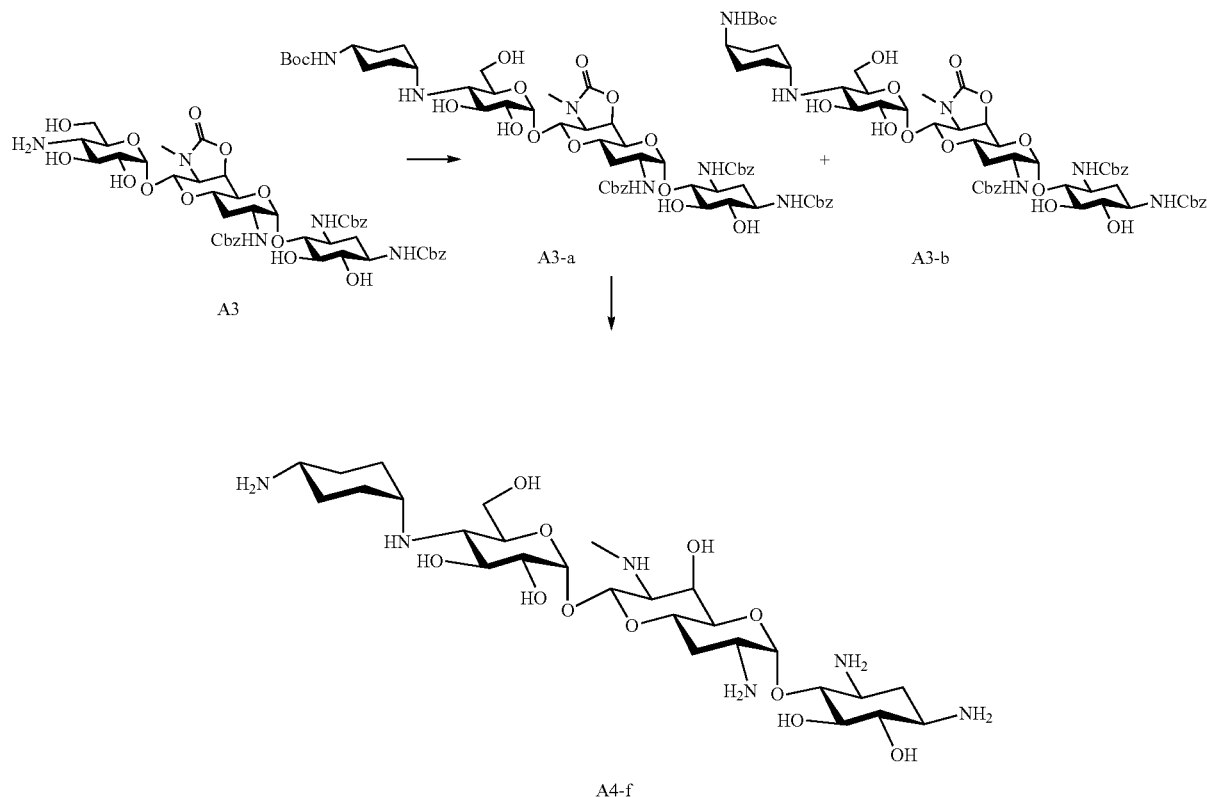

Examples 6-(i): Synthesis of 4''-N-[(1S,4S)-4-(t-butoxycarbonyl)aminocyclohexyl]-4''-N-benzyl-1,3,2'-tris-N-(benzyloxycarbonyl)-7'-N,6'-O-carbonylapramycin (A3-a) and 4''-N-[(1R,4R)-4-(t-butoxycarbonyl)aminocyclohexyl]-4''-N-benzyl-1,3,2'-tris-N-(benzyloxycarbonyl)-7'-N,6'-O-carbonylapramycin (A3-b)

A solution prepared by adding 85.2 mg of 4-(tert-butoxycarbonyl) aminocyclohexanone and 10 mg of NaBH$_3$CN to a solution of 260 mg (0.27 mmol) of the compound represented by formula (A3) dissolved in 5 ml of 10% acetic acid-methanol was subjected to reaction at room temperature for 16 hours. The reaction solution was concentrated under reduced pressure and a precipitate formed by adding saturated sodium bicarbonate solution was filtered. The resulting solid was purified on silica gel column chromatography (chloroform:methanol=10:1) to give 122 mg (36%) of the title compound (A3-a) and 97.1 mg (31%) of the title compound (A3-b).

MS (ESI) m/z: (A3-a), 1187 (M+Na)$^+$; (A3-b), 1187 (M+Na)$^+$.

Examples 6-(ii): Synthesis of 4''-N-(cis-1,4-4-aminocyclohexyl)apramycin (A4-f)

A solution prepared by dissolving 110 mg (0.095 mmol) of the title compound (A3-a) of Example 6-(i) dissolved in 1 ml of 90% TFA-MeOH was subjected to reaction at room temperature for 2 hours. The reaction solution was concentrated under reduced pressure and dissolved in 1 ml of 50% 1, 4-dioxane-water, and 0.1 ml of acetic acid and palladium black were added to this mixture. Next, the resultant mixture was subjected to catalytic reduction in a hydrogen atmosphere at room temperature for 10 hours. After completion of the reaction, the mixture was neutralized with NH$_4$OH and concentrated under reduced pressure after filtration. After drying, the residue was dissolved in water (1 ml) and heated to 110° C. and 1 N aqueous potassium hydroxide (0.5 ml) was added. The resultant mixture was subjected to reaction for 2 hours at the same temperature described above. After completion of the reaction, the reaction mixture was neutralized by adding 1 N aq. HCl under ice cooling and purified by ion exchange chromatography (CG50) to give 34.5 mg (52%) of the title compound (A4-f).

MS (ESI) m/z: 737 (M+1)$^+$; $^1$H NMR (TFA salt, 500 MHz, D$_2$O): δ 2.34 (1H, dt, J=4.5, 4.5 and 11.5 Hz, H-3' eq), 2.46 (1H, dt, J=4, 4 and 12.5 Hz, H-2eq), 2.76 (3H, s, NCH$_3$), 3.34 (1H, dd, J=3 and 8.5 Hz, H-7'), 3.40 (1H, t, J=10 Hz, H-4''), 3.95 (1H, t, J=10 Hz, H-3''), 4.53 (1H, slightly br t, J=~3 Hz, H-6'), 5.18 (1H, d, J=8.5 Hz, H-8'), 5.46 (1H, d, J=4 Hz, H-1'') and 5.68 (1H, d, J=3.8 Hz, H-1').

Example 7: Synthesis of 4"-N-(trans-1,4-4-amino-cyclohexyl)apramycin (A4-g)

[Chem. 38]

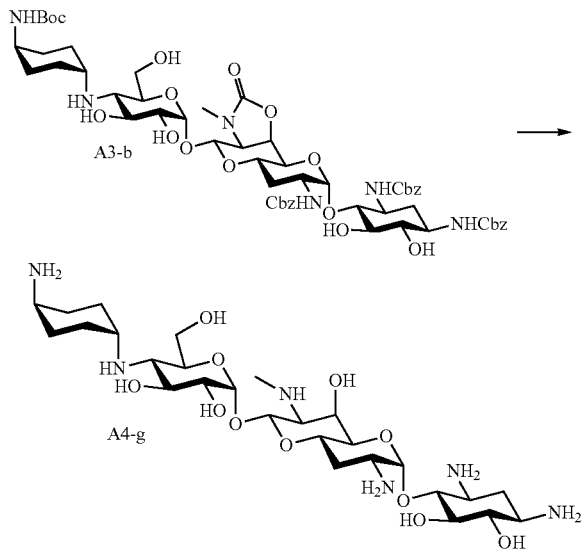

The title compound (A4-g) [26.8 mg (50%)] was obtained by a process similar to Example 6-(ii) using 90.1 mg (0.077 mmol) of the title compound (A3-b) of Example 6-(i).

MS (ESI) m/z: 737 (M+1)$^+$;

$^1$H NMR (TFA salt, 500 MHz, D$_2$O): δ 1.83 (1H, q, J=12.5 Hz, H-2ax), 1.99 (1H, q, J=12 Hz, H-3'ax), 2.46 (1H, dt, J=4, 4 and 12.5 Hz, H-2eq), 2.75 (3H, s, NCH$_3$), 3.33 (1H, dd, J=3 and 8.5 Hz, H-7'), 3.38 (1H, t, J=10 Hz, H-4"), 4.52 (1H, slightly br t, J=~2.5 Hz, H-6'), 5.18 (1H, d, J=8.5 Hz, H-8'), 5.45 (1H, d, J=4 Hz, H-1") and 5.69 (1H, d, J=3.8 Hz, H-1').

Example 8: Synthesis of 4"-N-(azetidin-3-yl)-1,3,2'-tris-N-(benzyloxycarbonyl)-7'-N,6'-O-carbonyl-apramycin (A3-c) and 4"-N-(azetidin-3-yl)apramycin (A4-h)

[Chem. 39]

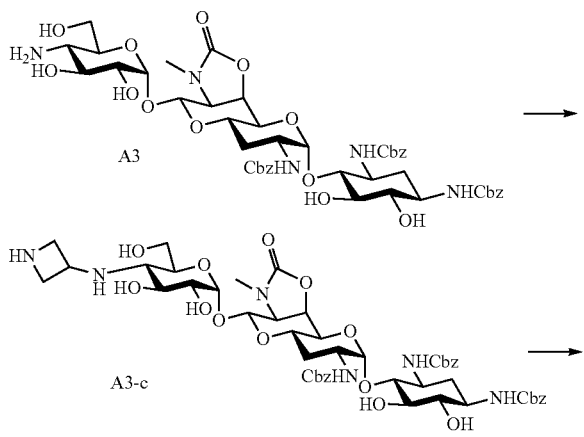

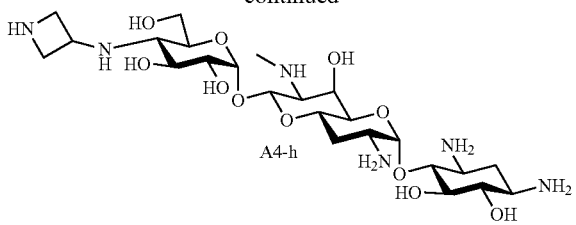

Examples 8-(i): Synthesis of 4"-N-(azetidin-3-yl)-1,3,2'-tris-N-(benzyloxycarbonyl)-7'-N,6'-O-carbonyl-apramycin (A3-c)

A solution prepared by adding 74.5 mg of 1-Boc-3-azetidinone and 10 mg of NaBH$_3$CN to a solution of 300 mg (0.29 mmol) of the compound represented by formula (A3) dissolved in 6 ml of 10% acetic acid methanol was subjected to reaction at room temperature for 16 hours. After completion of the reaction, the mixture was concentrated under reduced pressure and the residue was dissolved in 5 ml of 90% TFA-MeOH solution, and the resultant mixture was subjected to reaction at room temperature for 2 hours. The reaction solution was concentrated under reduced pressure and a precipitate formed by adding a saturated aqueous sodium bicarbonate solution to the residue was filtered, and the precipitate was dried under reduced pressure after filtration to give 284 mg (90%) of the title compound (A3-c) as a white solid.

MS (ESI) m/z: 1045 (M+Na)$^+$.

Examples 8-(ii): Synthesis of 4"-N-(azetidin-3-yl) apramycin (A4-h)

A mixture prepared by adding 0.2 ml of acetic acid and palladium black to a solution of 105 mg (0.1 mmol) of the title compound (A3-c) of Example 8-(i) dissolved in 2 ml of 50% of 1, 4-dioxane-water was subjected to catalytic reduction in a hydrogen atmosphere at room temperature for 10 hours. After completion of the reaction, the mixture was neutralized with NH$_4$OH and concentrated under reduced pressure after filtration. The residue was dissolved in water (1 ml) and heated to 110° C. and 1 N aqueous potassium hydroxide solution (1 ml) was added. The resultant mixture was subjected to reaction for 2 hours at the temperature. After completion of the reaction, the reaction mixture was neutralized by adding 1 N aq. HCl under ice cooling and purified by ion exchange chromatography (CG50) to give 36.2 mg (61%) of the title compound (A4-h).

MS (ESI) m/z: 595 (M+1)$^+$; $^1$H NMR (25% ND$_3$-D$_2$O, 500 MHz): δ 2.75 (3H, s, NMe), 3.5-3.75 (5H, m, azetidine), 5.51 (1H, d, J=3.5 Hz, H-1") and 5.73 (1H, d, J=3 Hz, H-1').

Example 9: Synthesis of 4"-N-(1-methylazetidin-3-yl)apramycin (A4-i)

[Chem. 40]

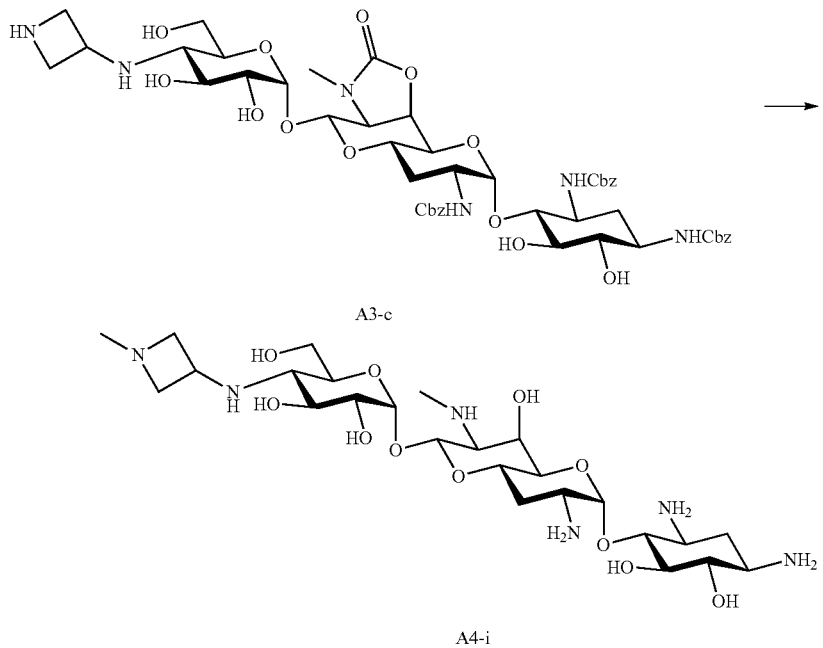

The title compound (A4-i) [33.2 mg (42%)] was obtained by deprotection operation similar to Example 1-(ii) using 130 mg (0.13 mmol) of the title compound (A3-c) of Example 8-(i).

MS (ESI) m/z: 609 (M+1)$^+$; $^1$H NMR (25% ND$_3$-D$_2$O, 500 MHz): δ 2.25 (3H, s, NMe), 2.75 (3H, s, NMe), 5.53 (1H, d, J=3.5 Hz, H-1") and 5.77 (1H, d, J=3 Hz, H-1').

Example 10: Synthesis of 4"-deamino-4"-guanidinoapramycin (A4-j)

[Chem. 41]

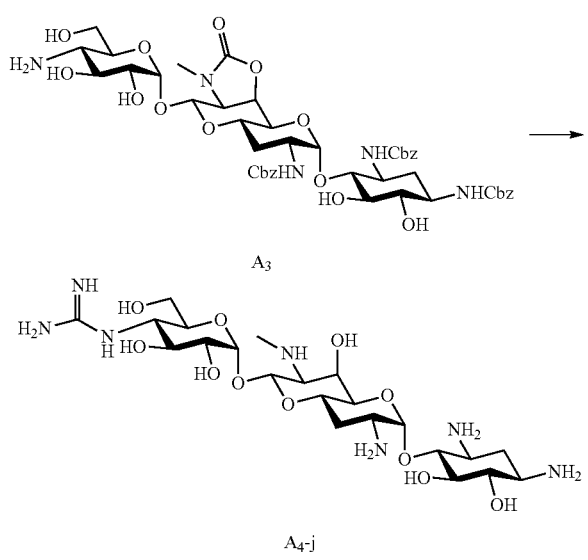

A solution prepared by adding 0.16 ml of triethylamine and 420 mg of 1,3-bis(tert-butoxycarbonyl)-2-(trifluoromethanesulfonyl) guanidine (Goodman's reagent) to a solution of 303 mg (0.31 mmol) of the compound represented by formula (A3) dissolved in 6.7 ml of a mixed solution of methylene chloride:methanol (10:1) was subjected to reaction at 40° C. for 48 hours. After completion of the reaction, the reaction solution was concentrated under reduced pressure and washed with water. After drying, the mixture was dissolved in 6 ml of 90% TFA-MeOH and the resultant mixture was subjected to reaction at room temperature for 1 hour. After completion of the reaction, the mixture was concentrated under reduced pressure. The residue was dissolved in 5.4 ml of 50% aqueous 1, 4-dioxane and 0.5 ml of acetic acid and palladium black were added, and the resultant mixture was subjected to catalytic reduction in a hydrogen atmosphere at room temperature for 10 hours. After completion of the reaction, the mixture was neutralized with NH$_4$OH and concentrated under reduced pressure after filtration. The residue was dissolved in 1 ml of water and 1 ml of 1 M aq. KOH heated to 105° C. was added and the mixture was subjected to reaction for 15 minutes. After completion of the reaction, the mixture was neutralized with 1 N HCl under ice cooling and concentrated under reduced pressure after filtration. The resulting residue was purified by ion exchange chromatography (CG50) to give 85 mg (47%) of the title compound (A4-j).

MS (ESI) m/z: 582 (M+1)$^+$; $^1$H NMR (TFA salt, 500 MHz, D$_2$O): δ 1.81 (1H, q, J=13 Hz, H-2ax), 1.99 (1H, q, J=12 Hz, H-3' ax), 2.33 (1H, dt, J=4.5, 4.5 and 12 Hz, H-3'eq), 2.45 (1H, dt, J=4, 4 and 13 Hz, H-2eq), 2.74 (3H, s, NCH$_3$), 3.32 (1H, dd, J=3 and 8.5 Hz, H-7'), 3.51 (1H, t, J=10 Hz, H-4"), 4.52 (1H, t, J=3 Hz, H-6'), 5.17 (1H, d, J=8.5 Hz, H-8'), 5.44 (1H, d, J=4 Hz, H-1") and 5.68 (1H, d, J=3.8 Hz, H-1'), $^{13}$C NMR (DCl-D$_2$O, 125 MHz) δ 157.52 (C=NH).

Example 11: Synthesis of 4''-N-(2-aminoethyl)-4''-N-benzyl-1,3,2'-tris-N-(benzyloxycarbonyl)-7'-N,6'-O-carbonylapramycin (A5-a) and 4''-N-guanidinoethylapramycin (A4-k)

[Chem. 42]

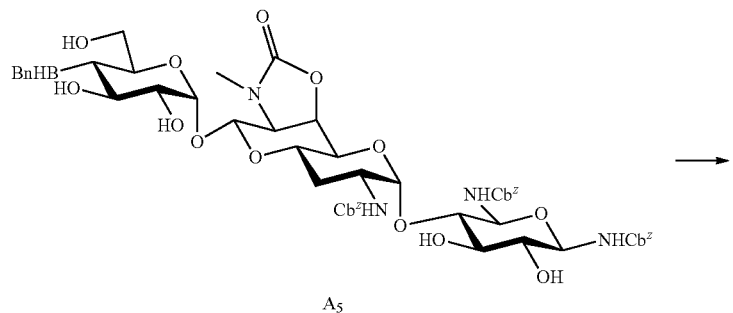

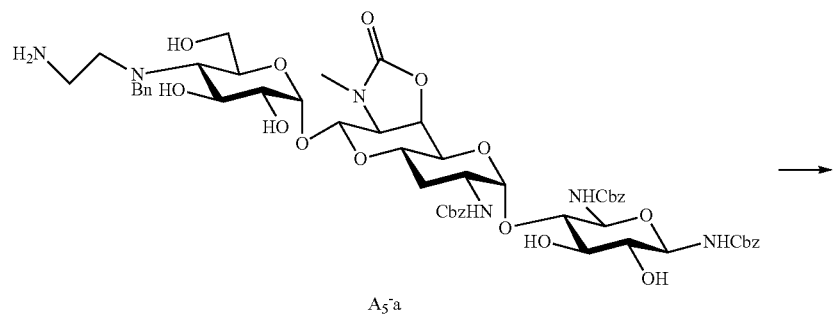

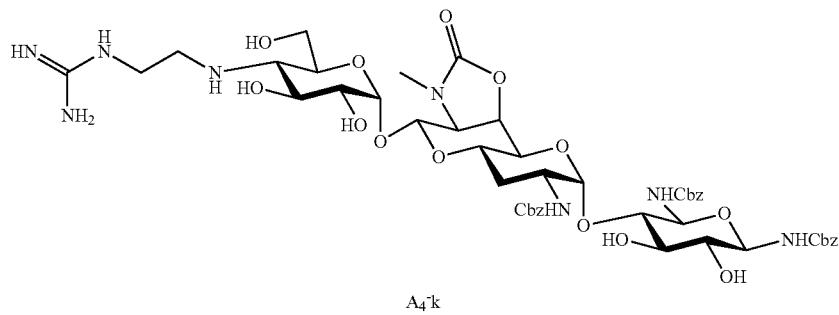

Example 11-(i): Synthesis of 4''-N-(2-aminoethyl)-4''-N-benzyl-1,3,2'-tris-N-(benzyloxycarbonyl)-7'-N,6'-O-carbonylapramycin (A5-a)

The title compound (A5-a) [644 mg (89%)] was obtained by a method similar to Example 8-(i) using 684 mg (0.66 mmol) of the title compound (A5) of Example 1-(i) and 100 mg of N-Boc-2-aminoacetaldehyde.
MS (ESI) m/z: 1123 (M+Na)$^+$.

Example 11-(ii): Synthesis of 4''-N-guanidinoethylapramycin (A4-k)

The title compound (A4-k) [96.8 mg (55%)] was obtained by a method similar to Example 10 using 300 mg (0.27 mmol) of the title compound (A5-a) of Example 11-(i) and 120 mg of N,N'-di-Boc-N''-triflylguanidine (Goodman's reagent).

MS (ESI) m/z: 625 (M+1)$^+$; $^1$H NMR (TFA salt, 500 MHz, D$_2$O): δ 1.81 (1H, q, J=12.5 Hz, H-2ax), 1.98 (1H, q, J=12 Hz, H-3' ax), 2.32 (1H, dt, J=4, 4 and 12 Hz, H-3'eq), 2.45 (1H, dt, J=4, 4 and 12.5 Hz, H-2eq), 2.74 (3H, s, NCH$_3$), 3.27 (1H, ddd, J=4, 10.5 and 12.5 Hz, H-1), 3.32 (1H, dd, J=3 and 8.5 Hz, H-7'), 3.37 (1H, t, J=10 Hz, H-4''), 4.52 (1H, t, J=3 Hz, H-6'), 5.16 (1H, d, J=8.5 Hz, H-8'), 5.43 (1H, d, J=4 Hz, H-1'') and 5.67 (1H, d, J=3.8 Hz, H-1'), $^{13}$C NMR (TFA salt, 125 MHz): δ 157.52 (C=NH).

Example 12: Synthesis of 1,3,2'-tris-N-(benzyloxycarbonyl)-4''-N-(t-butoxycarbonyl)-7'-N, 6'-O-carbonylapramycin (B1), 6,2'',3'',6''-tetra-O-benzoyl-1,3, 2'-tris-N-(benzyloxycarbonyl)-4''-N-(t-butoxycarbonyl)-7'-N,6'-O-carbonylapramycin (B2), 6,2'',3'',6''-tetra-O-benzoyl-1,3,2'-tris-N-(benzyloxycarbonyl)-4''-N-(t-butoxycarbonyl)-7'-N,6'-O-carbonyl-5-epiapramycin (B3), 6,2'',3'',6''-tetra-O-benzoyl-1,3,2'-tris-N-(benzyloxycarbonyl)-4''-N-(t-butoxycarbonyl)-7'-N,6'-O-carbonyl-5-deoxy-5-epi-5-fluoroapramycin (B3'), 1,3,2'-tris-N-(benzyloxycarbonyl)-7'-N,6'-O-carbonyl-5-epiapramycin (B4) and 5-epiapramycin (B5)

[Chem. 43]

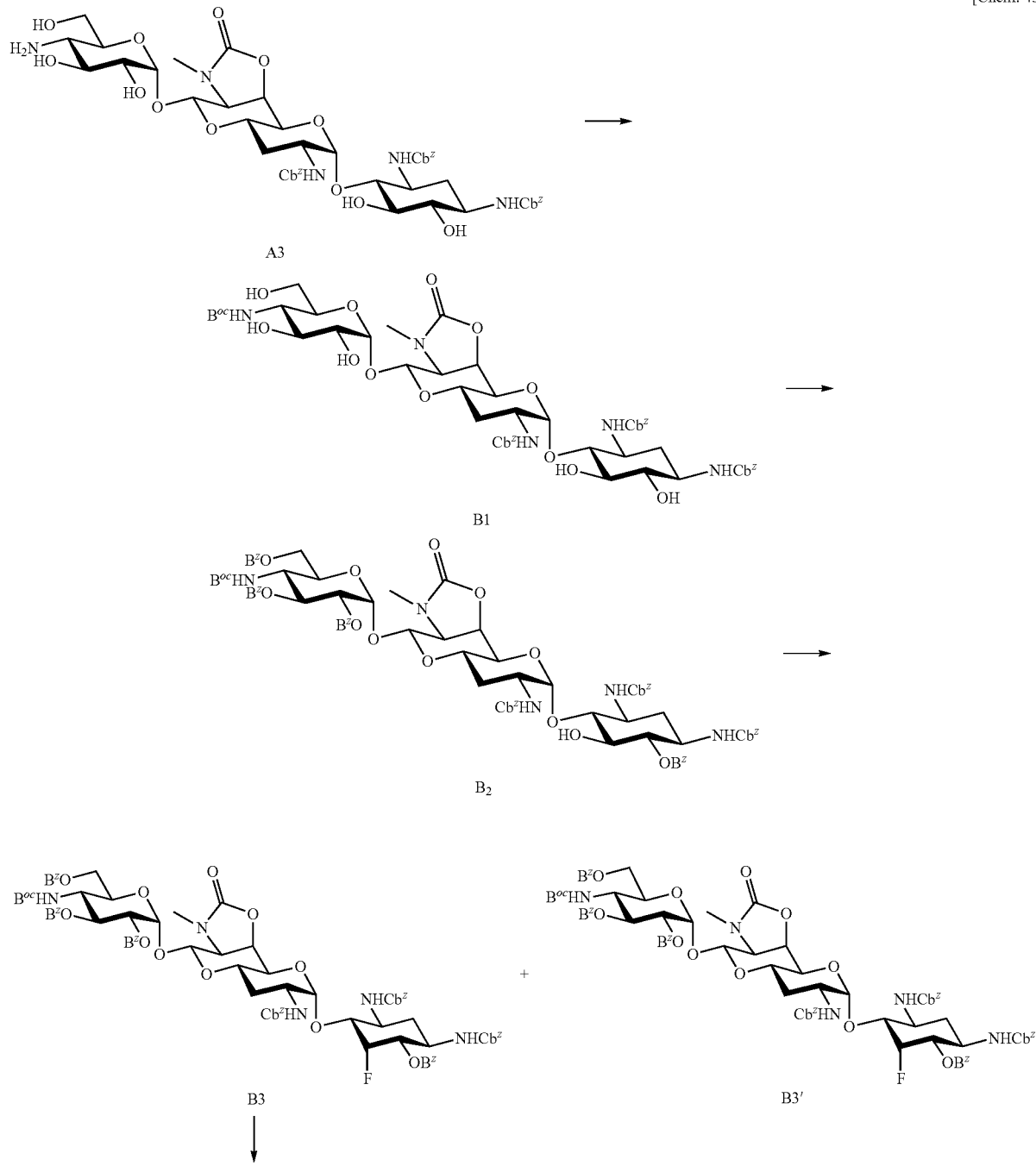

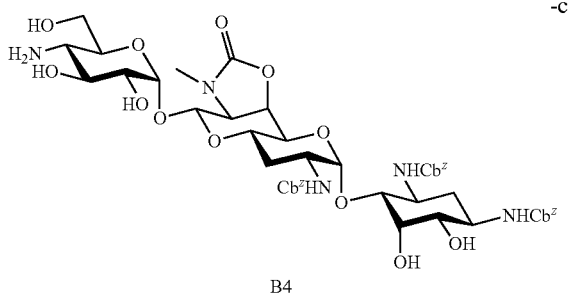 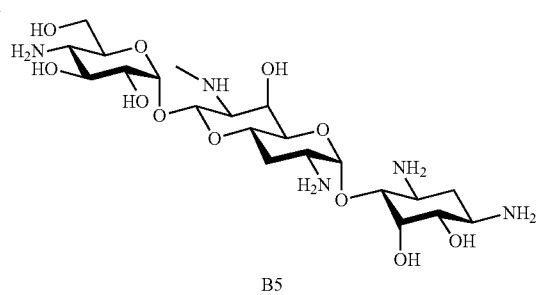

B4 → B5

Example 12-(i): Synthesis of 1,3,2'-tris-N-(benzyloxycarbonyl)-4"-N-(t-butoxycarbonyl)-7'-N, 6'-O-carbonylapramycin (B1)

A solution prepared by adding 13 ml of triethylamine and 8.5 g of $Boc_2O$ to a solution of 29.0 g (30 mmol) of the compound represented by formula (A3) dissolved in 200 ml of THF solution was subjected to reaction at 60° C. for 5 hours. After completion of the reaction, the mixture was concentrated under reduced pressure by adding conc. aqueous ammonia and the resulting residue was washed with water. After drying, 31.3 g (98%) of the title compound (B1) was obtained as a light brown solid.

MS (ESI) m/z: 1090 $(M+Na)^+$.

Example 12-(ii): Synthesis of 6,2",3",6"-tetra-O-benzoyl-1,3,2'-tris-N-(benzyloxycarbonyl)-4"-N-(t-butoxycarbonyl)-7'-N,6'-O-carbonylapramycin (B2)

A solution prepared by adding 24.9 ml (5.5 eq.) of benzoyl chloride under ice cooling to a solution of 41.9 g (39 mmol) of the title compound (B1) of Example 12-(i) dissolved in 220 ml of pyridine was subjected to reaction under ice cooling for 35 minutes. After completion of the reaction, the reaction mixture was concentrated under reduced pressure by adding water and the resulting residue was diluted with ethyl acetate. The organic layer was washed with 5% aq. $KHSO_4$, 5% aq. $NaHCO_3$ and brine successively, and dried with $Na_2SO_4$ and concentrated under reduced pressure to give 55.4 g (96%) of the title compound (B2) as a light yellow solid.

MS (ESI) m/z: 1507 $(M+Na)^+$; $^1H$ NMR (DMSO-$d_6$, 400 MHz): δ 1.15 (9H, m, t-Bu), 3.66 (1H, t, H-5), 4.53 (2H, m, H-6"), 5.21 (1H, dd, H-2"), 5.63 (1H, d, H-1") and 5.84 (1H, t, H-3").

Example 12-(iii): Synthesis of 6,2",3",6"-tetra-O-benzoyl-1,3,2'-tris-N-(benzyloxycarbonyl)-4"-N-(t-butoxycarbonyl)-7'-N,6'-O-carbonyl-5-epiapramycin (B3) and 6,2",3",6"-tetra-O-benzoyl-1,3,2'-tris-N-(benzyloxycarbonyl)-4"-N-(t-butoxycarbonyl)-7'-N,6'-O-carbonyl-5-deoxy-5-epi-5-fluoroapramycin (B3')

A solution prepared by adding 2.4 ml of DAST under ice cooling to a solution of 16.5 g (11 mmol) of the title compound (B2) of Example 12-(ii) dissolved in 90 ml of methylene chloride was subjected to reaction at room temperature for 1 hour. After completion of the reaction, the reaction solution was washed successively with saturated sodium bicarbonate solution and water, and concentrated under reduced pressure. The residue was purified on silica gel column chromatography (chloroform:methanol=25:1) to give 9.59 g (58%) of the title compound (B3) and 5.29 g (31.9%) of the title compound (B3').

MS (ESI) m/z: (B3), 1507 $(M+Na)^+$; (B3'), 1509 $(M+Na)^+$; $^1H$ NMR (DMSO-$d_6$, 400 MHz): (B3), δ 5.40 (1H, br s, H-5) and 5.63 (1H, d, H-1"); (B3'), δ 5.61 (1H, d, H-1") and 5.99 (1H, brd, H-5).

Example 12-(iv): Synthesis of 1,3,2'-tris-N-(benzyloxycarbonyl)-7'-N,6'-O-carbonyl-5-epiapramycin (B4)

A solution prepared by adding 0.35 ml of a 5 N NaOMe-methanol solution to a solution of 2.47 g (1.7 mmol) of the title compound (B3) of Example 12-(iii) dissolved in 24 ml of MeOH was subjected to reaction at room temperature for 2 hours. After completion of the reaction, the reaction solution was neutralized by adding 1 N HCl under ice cooling and concentrated under reduced pressure and washed with water. The solid obtained was washed with isopropyl ether and the residue was dissolved in 18 ml of 90% TFA-MeOH solution and the mixture was subjected to reaction at room temperature for 2 hours. The reaction solution was concentrated under reduced pressure and the residue was washed with isopropyl ether to give 1.72 g (93% as TFA salt) of the title compound (B4) as a colorless solid.

MS (ESI) m/z: 990 $(M+Na)^+$.

Example 12-(v): Synthesis of 5-epiapramycin (B5)

The title compound (B5) [203 mg (74%)] was obtained by a method similar to Example 8-(ii) using 550 mg (0.51 mmol as TFA salt) of the title compound (B4) of Example 12-(iv).

MS (ESI) m/z: 540 $(M+Na)^+$; $^1H$ NMR (25% $ND_3$-$D_2O$, 500 MHz) δ 4.53 (1H, t, H-5), 5.33 (1H, d, H-1') and 5.67 (1H, d, H-1"). 10 [0254]

Example 13: Synthesis of 1,3,2'-tris-N-(benzyloxycarbonyl)-7'-N,6'-O-carbonyl-5-deoxy-5-epi-5-fluoroapramycin (B6) and 5-deoxy-5-epi-5-fluoro-apramycin (B7)

[Chem. 44]

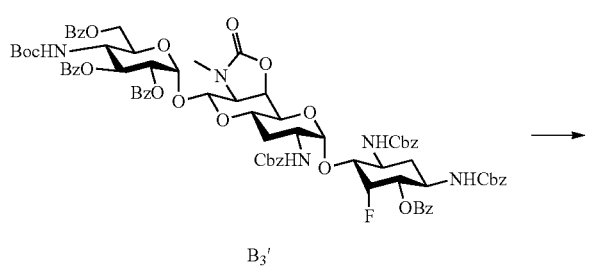

B3'

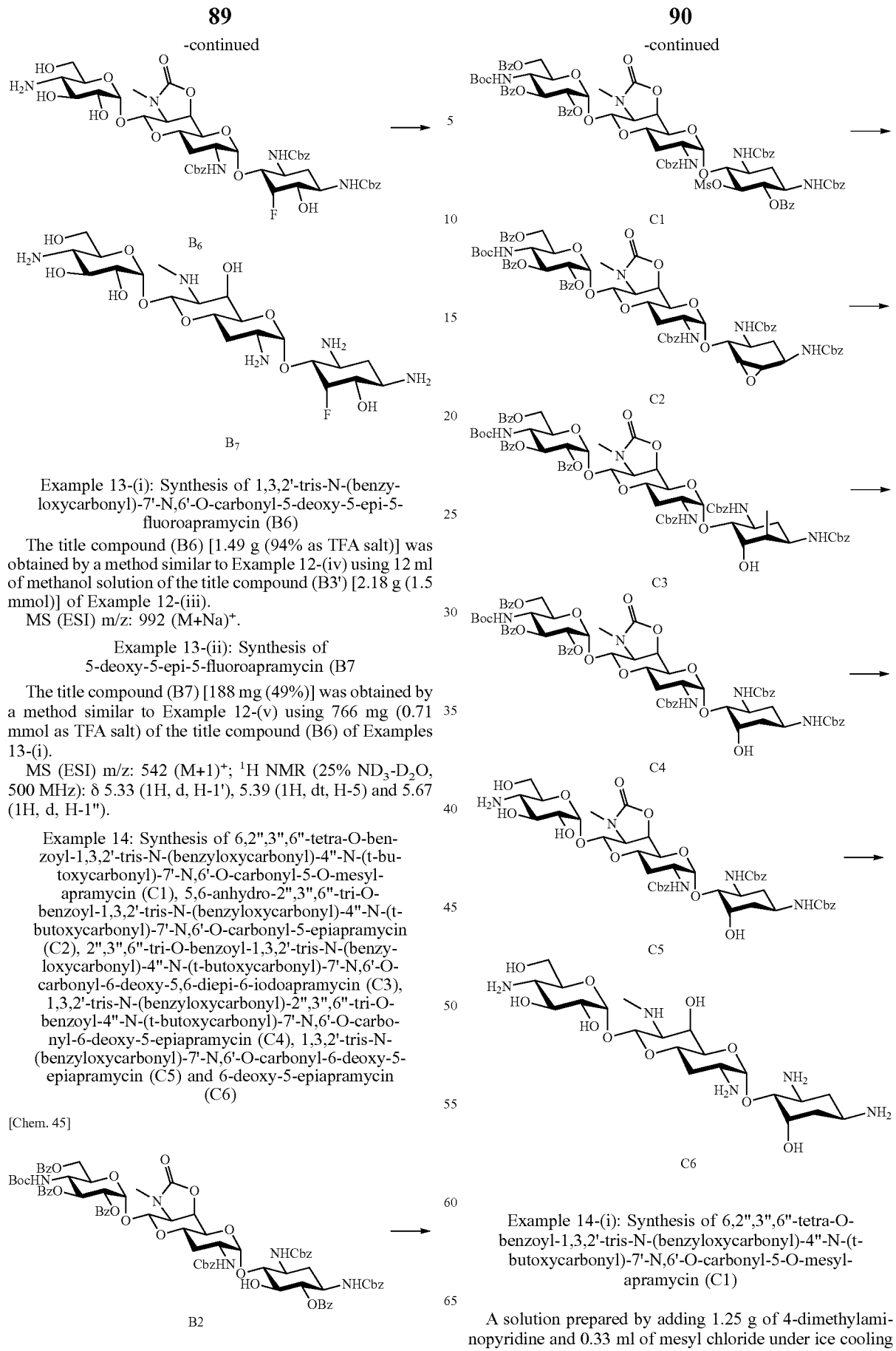

Example 13-(i): Synthesis of 1,3,2'-tris-N-(benzyloxycarbonyl)-7'-N,6'-O-carbonyl-5-deoxy-5-epi-5-fluoroapramycin (B6)

The title compound (B6) [1.49 g (94% as TFA salt)] was obtained by a method similar to Example 12-(iv) using 12 ml of methanol solution of the title compound (B3') [2.18 g (1.5 mmol)] of Example 12-(iii).

MS (ESI) m/z: 992 (M+Na)$^+$.

Example 13-(ii): Synthesis of 5-deoxy-5-epi-5-fluoroapramycin (B7

The title compound (B7) [188 mg (49%)] was obtained by a method similar to Example 12-(v) using 766 mg (0.71 mmol as TFA salt) of the title compound (B6) of Examples 13-(i).

MS (ESI) m/z: 542 (M+1)$^+$; $^1$H NMR (25% ND$_3$-D$_2$O, 500 MHz): δ 5.33 (1H, d, H-1'), 5.39 (1H, dt, H-5) and 5.67 (1H, d, H-1").

Example 14: Synthesis of 6,2",3",6"-tetra-O-benzoyl-1,3,2'-tris-N-(benzyloxycarbonyl)-4"-N-(t-butoxycarbonyl)-7'-N,6'-O-carbonyl-5-O-mesyl-apramycin (C1), 5,6-anhydro-2",3",6"-tri-O-benzoyl-1,3,2'-tris-N-(benzyloxycarbonyl)-4"-N-(t-butoxycarbonyl)-7'-N,6'-O-carbonyl-5-epiapramycin (C2), 2",3",6"-tri-O-benzoyl-1,3,2'-tris-N-(benzyloxycarbonyl)-4"-N-(t-butoxycarbonyl)-7'-N,6'-O-carbonyl-6-deoxy-5,6-diepi-6-iodoapramycin (C3), 1,3,2'-tris-N-(benzyloxycarbonyl)-2",3",6"-tri-O-benzoyl-4"-N-(t-butoxycarbonyl)-7'-N,6'-O-carbonyl-6-deoxy-5-epiapramycin (C4), 1,3,2'-tris-N-(benzyloxycarbonyl)-7'-N,6'-O-carbonyl-6-deoxy-5-epiapramycin (C5) and 6-deoxy-5-epiapramycin (C6)

[Chem. 45]

Example 14-(i): Synthesis of 6,2",3",6"-tetra-O-benzoyl-1,3,2'-tris-N-(benzyloxycarbonyl)-4"-N-(t-butoxycarbonyl)-7'-N,6'-O-carbonyl-5-O-mesyl-apramycin (C1)

A solution prepared by adding 1.25 g of 4-dimethylaminopyridine and 0.33 ml of mesyl chloride under ice cooling to a solution of 4.16 g (2.8 mmol) of the title compound (B2) of Example 12-(ii) dissolved in 21 ml of methylene chloride was subjected to reaction at room temperature for 2 hours. The reaction solution was successively washed with water, 10% aqueous potassium bisulfate solution, saturated sodium bicarbonate solution and water. Next the mixture was concentrated under reduced pressure to give 4.31 g (98%) of the title compound (C1) as a light yellow solid.

MS (ESI) m/z: 1584 (M+Na)$^+$.

Example 14-(ii): Synthesis of 5,6-anhydro-2″,3″,6″-tri-O-benzoyl-1,3,2′-tris-N-(benzyloxycarbonyl)-4″-N-(t-butoxycarbonyl)-7′-N,6′-O-carbonyl-5-epi-apramycin (C2)

A solution prepared by adding 2.7 ml of 5 N NaOMe-methanol solution to a solution of 4.28 g (2.7 mmol) of the title compound (C1) of Example 14-(i) dissolved in 20 ml of methanol was subjected to reaction at room temperature for 1 hour. After completion of the reaction, the reaction solution was neutralized by adding 1N HCl under ice cooling and concentrated under reduced pressure and washed with water. The solid obtained was washed with isopropyl ether and was dissolved in 20 ml of pyridine. To the mixture, 1.58 ml of benzoyl chloride was added under ice-cooling and the resulting mixture was subjected to reaction under ice-cooling for 35 minutes. Water was added to the reaction solution and the resulting residue obtained after concentration under reduced pressure was diluted with ethyl acetate. The organic layer was successively washed with water, 10% aqueous potassium bisulfate solution, saturated sodium bicarbonate solution and water. Next, the mixture was concentrated under reduced pressure to give 3.60 g (98%) of the title compound (C2) as a light yellow solid.

MS (ESI) m/z: 1384 (M+Na)$^+$.

Example 14-(iii): Synthesis of 2″,3″,6″-tri-O-benzoyl-1,3,2′-tris-N-(benzyloxycarbonyl)-4″-N-(t-butoxycarbonyl)-7′-N,6′-O-carbonyl-6-deoxy-5,6-diepi-6-iodoapramycin (C3)

A solution prepared by adding 1.2 g of sodium iodide and 87 mg of sodium acetate dissolved in 1.7 ml of acetic acid to a solution of 3.68 g (2.7 mmol) of the title compound (C2) of Example 14-(ii) dissolved in 14 ml of acetone was refluxed for 6 hours. To the residue obtained by concentrating the reaction solution was added ethyl acetate, and the organic layer was concentrated after washing with water to give 3.70 g (92%) of the title compound (C3) as a colorless solid.

MS (ESI) m/z: 1512 (M+Na)$^+$.

Example 14-(iv): Synthesis of 1,3,2′-tris-N-(benzyloxycarbonyl)-2″,3″,6″-tri-O-benzoyl-4″-N-(t-butoxycarbonyl)-7′-N,6′-O-carbonyl-6-deoxy-5-epi-apramycin (C4)

A solution prepared by adding 64 mg of AIBN and 1.5 ml of tributyltin hydride to a solution of 3.50 g (2.4 mmol) of the title compound (C3) of Example 14-(iii) dissolved in 15 ml of dioxane was subjected to reaction in N$_2$ atmosphere at 80° C. for 1.5 hours. The reaction solution was concentrated under reduced pressure and the resulting residue was dried under reduced pressure after washing it with isopropyl ether to give 2.19 g (67%) of the title compound (C4) as a colorless solid.

MS (ESI) m/z: 1386 (M+Na)$^+$; $^1$H NMR (DMSO-d$_6$, 400 MHz): δ 1.28-1.51 (11H, m, H-6ax, H-2ax, t-Bu), 1.83-1.98 (3H, m, H-6eq, H-2eq, H-3′eq), 4.82 (1H, d, H-1′) and 5.14 (1H, d, H-1″).

Example 14-(v): Synthesis of 1,3,2′-tris-N-(benzyloxycarbonyl)-7′-N,6′-O-carbonyl-6-deoxy-5-epi-apramycin (C5)

A solution prepared by adding 0.3 ml of 5 N NaOMe-methanol solution to a solution of 2.01 g (1.5 mmol) of the title compound (C4) of Example 14-(iv) dissolved in 20 ml of methanol was subjected to reaction at room temperature for 2 hours. The reaction solution was neutralized by adding 1 N HCl under ice cooling and concentrated under reduced pressure, and the residue was washed with water and further washed with isopropyl ether. The solid obtained was dissolved in 10 ml of 90% TFA-MeOH solution and the mixture was subjected to reaction at room temperature for 2 hours. The reaction solution was concentrated under reduced pressure and the residue was washed with isopropyl ether to give 1.43 g (90% as TFA salt) of the title compound (C5) as a colorless solid.

MS (ESI) m/z: 974 (M+Na)$^+$.

Example 14-(vi): Synthesis of 6-deoxy-5-epiapramycin (C6)

The title compound (C6) [115 mg (47%)] was obtained by a method similar to Example 8-(ii) using 500 mg (0.47 mmol as TFA salt) of the title compound (C5) of Example 14-(vi).

MS (ESI) m/z: 546 (M+Na)$^+$; $^1$H NMR (25% ND$_3$-D$_2$O, 500 MHz): δ 1.70 (1H, ddd, H-6ax), 2.31-2.41 (2H, m, H-2eq and H-6eq), 4.64 (2H, m, H-6′ and H-5), 5.32 (1H, d, H-1′) and 5.68 (1H, d, H-1″).

Example 15: Synthesis of 1,3,2′-tris-N-(benzyloxycarbonyl)-7′-N,6′-O-carbonyl-5,6-dideoxy-5-fluoro-apramycin (C7) and 5,6-dideoxy-5-fluoroapramycin (C8)

[Chem. 46]

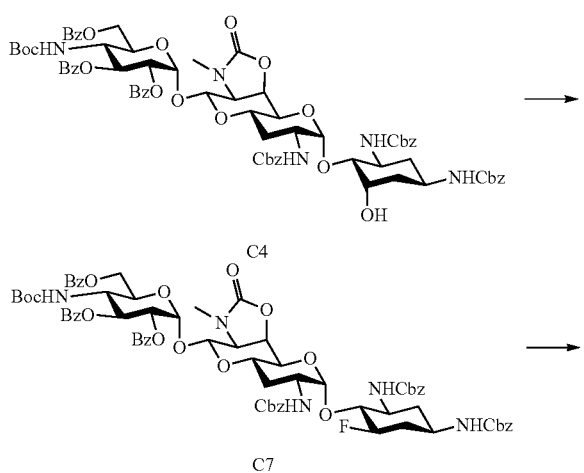

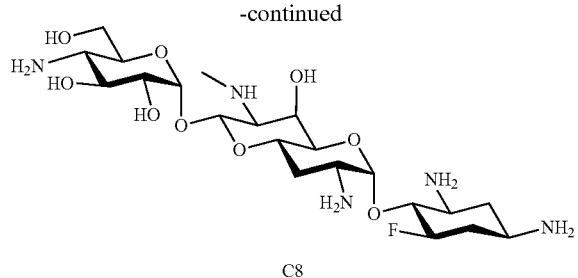

C8

Example 15-(i): Synthesis of 1,3,2'-tris-N-(benzyloxycarbonyl)-7'-N,6'-O-carbonyl-5,6-dideoxy-5-fluoroapramycin (C7)

The title compound (C7) [995 mg (92%)] was obtained by a process similar to Examples 12-(iii) and (iv) using 1.07 g (0.08 mmol) of the title compound (C4) of Example 14-(iv).

MS (ESI) m/z: 1388 (M+Na)$^+$.

Example 15-(ii): Synthesis of 5,6-dideoxy-5-fluoroapramycin (C8)

A solution prepared by adding 0.13 ml of 5 N NaOMe-methanol to a solution of 844 mg (0.62 mmol) of the title compound (C7) of Example 15-(i) dissolved in 8.4 ml of methanol was subjected to reaction at room temperature for 2 hours. After completion of the reaction, the reaction solution was neutralized by adding 1 N HCl under ice cooling and concentrated under reduced pressure and the residue was washed with water and further washed with isopropyl ether. The residue was dissolved in 5 ml of 90% TFA-MeOH solution and the mixture was subjected to reaction at room temperature for 2 hours. After concentrating the reaction solution under reduced pressure, the resulting residue was washed with isopropyl ether and dissolved in 10 ml of 50% dioxane-water and a mixture prepared by adding 0.5 ml of acetic acid and palladium black to the solution was subjected catalytic reduction in a hydrogen atmosphere at room temperature for 10 hours. After completion of the reaction, the mixture was neutralized with NH$_4$OH and the filtrate was concentrated after filtration. The residue was dissolved in water (3 ml) and heated to 110° C. and 1 N aqueous potassium hydroxide solution (1 ml) was added. The mixture was subjected to reaction for 2 hours at the temperature. After completion of the reaction, the reaction mixture was neutralized by adding 1 N aq. HCl under ice cooling and purified by ion exchange chromatography (CG50) to give 244 mg (63%) of the title compound (C8).

MS (ESI) m/z: 526 (M+1)$^+$; $^1$H NMR (25% ND$_3$-D$_2$O, 500 MHz): δ 1.85 (1H, dddd, H-6ax), 2.64 (1H, m, H-6eq), 5.04 (1H, dddd, H-5), 5.48 (1H, d, H-1') and 5.70 (1H, d, H-1").

Example 16: Synthesis of 5-azide-1,3,2'-tris-N-(benzyloxycarbonyl)-6,2",3",6"-tetra-O-benzoyl-4"-N-(t-butoxycarbonyl)-7'-N,6'-O-carbonyl-5-deoxy-5-epiapramycin (D1) and 5-amino-5-deoxy-5-epiapramycin (D2)

[Chem. 47]

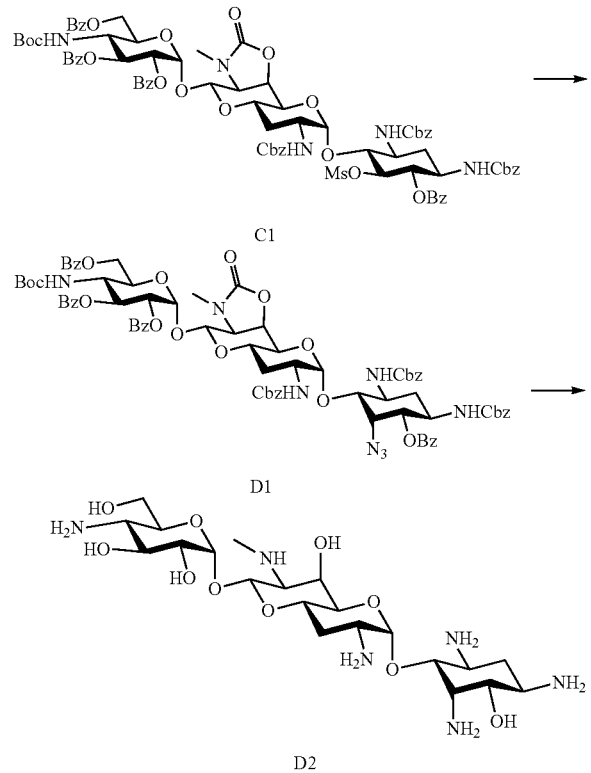

Example 16-(i): Synthesis of 5-azide-1,3,2'-tris-N-(benzyloxycarbonyl)-6,2",3",6"-tetra-O-benzoyl-4"-N-(t-butoxycarbonyl)-7'-N,6'-O-carbonyl-5-deoxy-5-epiapramycin (D1)

A solution prepared by adding 30.1 mg of NaN$_3$ to a solution of 330 mg (0.21 mmol) of the title compound (C1) of Example 14-(i) dissolved in 4 ml of DMF was subjected to reaction at 100° C. for 6 hours. After the reaction solution was concentrated under reduced pressure and a residue was washed with water, the residue was purified by silica gel column chromatography (developing solvent, CHCl$_3$: MeOH=30:1) to give 264 mg (83%) of the title compound (D1) as a light yellow solid.

MS (ESI) m/z: 1531 (M+Na)$^+$.

Example 16-(ii): Synthesis of 5-amino-5-deoxy-5-epiapramycin (D2)

The title compound (D2) [47.6 mg (52%)] was obtained by a method similar to Example 15-(ii) using 260 mg (0.17 mmol) of the title compound (D1) of Example 16-(i).

MS (ESI) m/z: 539 (M+1)$^+$; $^1$H NMR (25% ND$_3$-D$_2$O, 500 MHz): δ 3.93-4.05 (5H, m, H-2", -5', -3", -5 and -5"), 5.36 (1H, d, H-1') and 5.74 (1H, d, H-1").

Example 17: Synthesis of 6,2",3",6"-tetra-O-benzoyl-1,3,2'-tris-N-(benzyloxycarbonyl)-4"-N-(t-butoxycarbonyl)-7'-N,6'-O-carbonyl-5-chloro-5-deoxy-5-epiapramycin (E1), 5-azide-1,3,2'-tris-N-(benzyloxycarbonyl)-6,2",3",6"-tetra-O-benzoyl-4"-N-(t-butoxycarbonyl)-7'-N,6'-O-carbonyl-5-deoxyapramycin (E2) and 5-amino-5-deoxyapramycin (E3)

[Chem. 48]

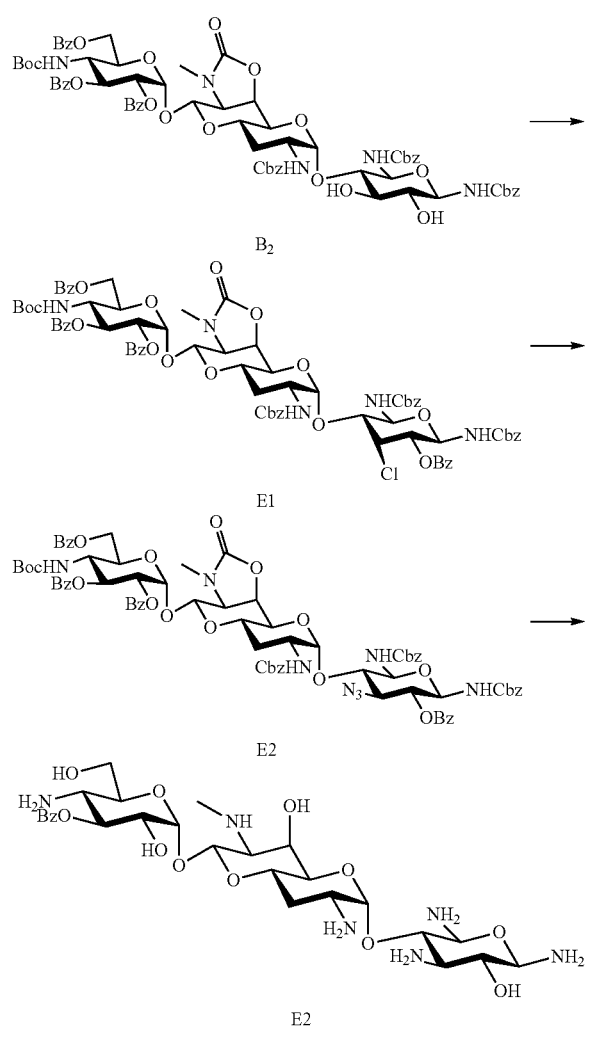

Example 17-(i): Synthesis of 6,2",3",6"-tetra-O-benzoyl-1,3,2'-tris-N-(benzyloxycarbonyl)-4"-N-(t-butoxycarbonyl)-7'-N,6'-O-carbonyl-5-chloro-5-deoxy-5-epiapramycin (E1)

A solution was prepared by adding 400 ml of pyridine and further 0.17 ml (2.1 eq.) of sulfuryl chloride under ice cooling to a solution of 1.49 g (1.0 mmol) of the title compound (B2) of Example 12-(ii) in 15 ml of methylene chloride. After 5 minutes, the resulting solution was brought back to room temperature and the mixture was subjected to reaction for 1.5 hours. After MeOH was added to the reaction solution under ice cooling, the mixture was concentrated under reduced pressure and the residue obtained was diluted with ethyl acetate. The organic layer was washed with aq. $Na_2SO_3$, aq. $NaCO_3$ and brine successively, and was dried with $Na_2SO_4$ and concentrated under reduced pressure to give 1.1 g (98%) of the title compound (E1) as a light yellow solid.

MS (ESI) m/z: 1523 $(M+Na)^+$.

Example 17-(ii): Synthesis of 5-azide-1,3,2'-tris-N-(benzyloxycarbonyl)-6,2",3",6"-tetra-O-benzoyl-4"-N-(t-butoxycarbonyl)-7'-N,6'-O-carbonyl-5-deoxyapramycin (E2)

The title compound (E2) [264 mg (83%)] was obtained by a process similar to Example 16-(i) using 330 mg (0.21 mmol) of the title compound (E1) of Example 17-(i).

MS (ESI) m/z: 1531 $(M+Na)^+$.

Example 17-(iii): Synthesis of 5-amino-5-deoxyapramycin (E3)

The title compound (E3) [47.6 mg (52%)] was obtained by a method similar to Example 15-(ii) using 260 mg (0.17 mmol) of the title compound (E2) of Example 17-(ii).

MS (ESI) m/z: 539 $(M+1)^+$; $^1H$ NMR (25% $ND_3$-$D_2O$, 500 MHz): δ 3.93-4.05 (5H, m, H-2", -5', -3", -5 and -5"), 5.36 (1H, d, H-1') and 5.74 (1H, d, H-1").

Example 18: Synthesis of 6-azide-1,3,2'-tris-N-(benzyloxycarbonyl)-6,2",3",6"-tetra-O-benzoyl-4"-N-(t-butoxycarbonyl)-7'-N,6'-O-carbonyl-5-deoxy-5,6-diepi-5-epiapramycin (F1), 6-azide-1,3,2'-tris-N-(benzyloxycarbonyl)-6,2",3",6"-tetra-O-benzoyl-4"-N-(t-butoxycarbonyl)-7'-N,6'-O-carbonyl-5,6-dideoxy-5,6-diepi-5-fluoroapramycin (F2) and 6-amino-5,6-dideoxy-5,6-diepi-5-fluoroapramycin (F3)

[Chem. 49]

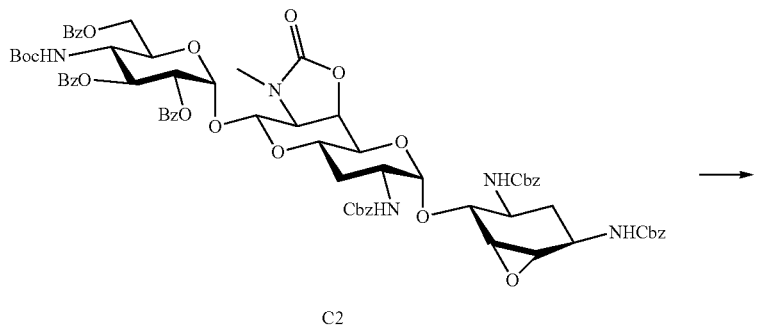

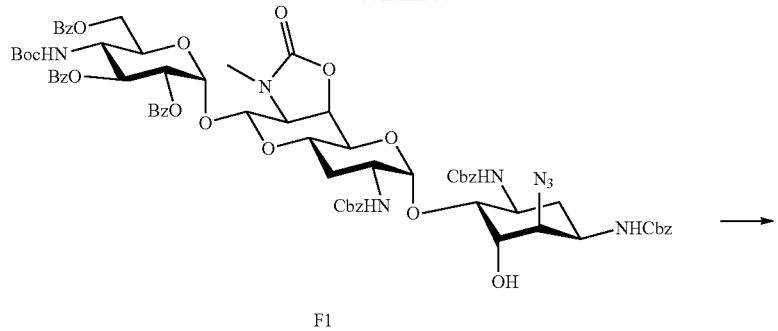

F1

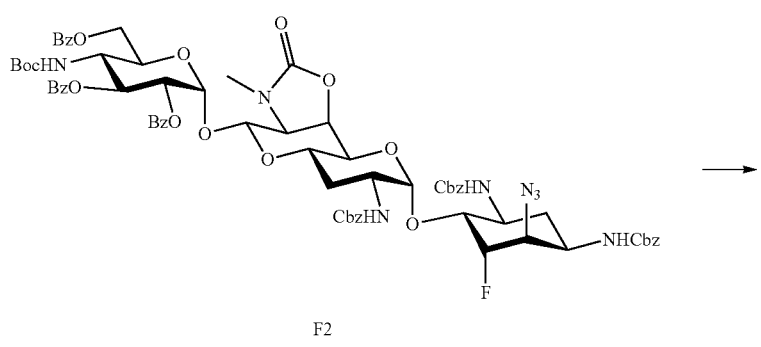

F2

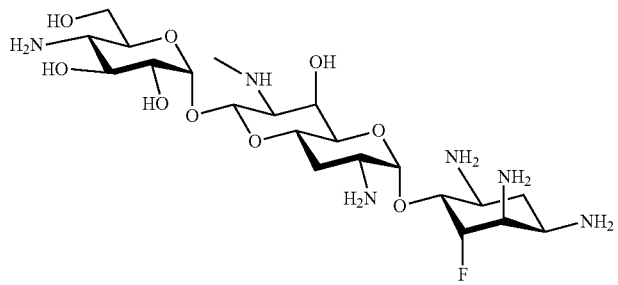

F3

Example 18-(i): Synthesis of 6-azide-1,3,2'-tris-N-(benzyloxycarbonyl)-6,2",3",6"-tetra-O-benzoyl-4"-N-(t-butoxycarbonyl)-7'-N,6'-O-carbonyl-5-deoxy-5,6-diepi-5-epiapramycin (F1)

A solution prepared by adding 43 mg of NH$_4$Cl and 72 mg of NaN$_3$ to a solution of 980 mg (0.72 mmol) of the title compound (C2) of Example 14-(ii) dissolved in 4 ml of DMF was subjected to reaction at 100° C. for 2 hours. The reaction solution was concentrated under reduced pressure and the residue was washed with water. The residue was purified by silica gel column chromatography (developing solvent, CHCl$_3$:MeOH=30:1) to give 778 mg (77%) of the title compound (F1) as a light yellow solid.

MS (ESI) m/z: 1427 (M+Na)$^+$.

Example 18-(ii): Synthesis of 6-azide-1,3,2'-tris-N-(benzyloxycarbonyl)-6,2",3",6"-tetra-O-benzoyl-4"-N-(t-butoxycarbonyl)-7'-N,6'-O-carbonyl-5,6-dideoxy-5,6-diepi-5-fluoroapramycin (F2)

The title compound (F2) [442 mg (60%)] was obtained by a method similar to Examples 12-(iii) and (iv) using 730 mg (0.52 mmol) of the title compound (F1) of Example 18-(i).

MS (ESI) m/z: 1429 (M+Na)$^+$.

Example 18-(iii): Synthesis of 6-amino-5,6-dideoxy-5,6-diepi-5-fluoroapramycin (F3)

The title compound (F3) [96.5 mg (63%)] was obtained by a method similar to Example 15-(ii) using 400 mg (0.28 mmol) of the title compound (F2) of Example 18-(ii).

MS (ESI) m/z: 541 (M+1)$^+$; $^1$H NMR (25% ND$_3$-D$_2$O, 500 MHz): δ 3.90-4.01 (5H, m, H-2", -5', -3", -6 and -5"), 5.37 (1H, d, H-1'), 5.51 (1H, m, H-5) and 5.71 (1H, d, H-1").

Example 19: Synthesis of 1,3,2'-tris-N-(benzyloxy-carbonyl)-6,2",3",6"-tetra-O-benzoyl-4"-N-(t-butoxycarbonyl)-7'-N,6'-O-carbonyl-6-deoxy-5-epi-5-O-mesylapramycin (C9), 5-azide-1,3,2'-tris-N-(benzyloxycarbonyl)-6,2",3",6"-tetra-O-benzoyl-4"-N-(t-butoxycarbonyl)-7'-N,6'-O-carbonyl-5,6-dideoxyapramycin (C10) and 5-amino-5,6-deoxyapramycin (C11)

[Chem. 50]

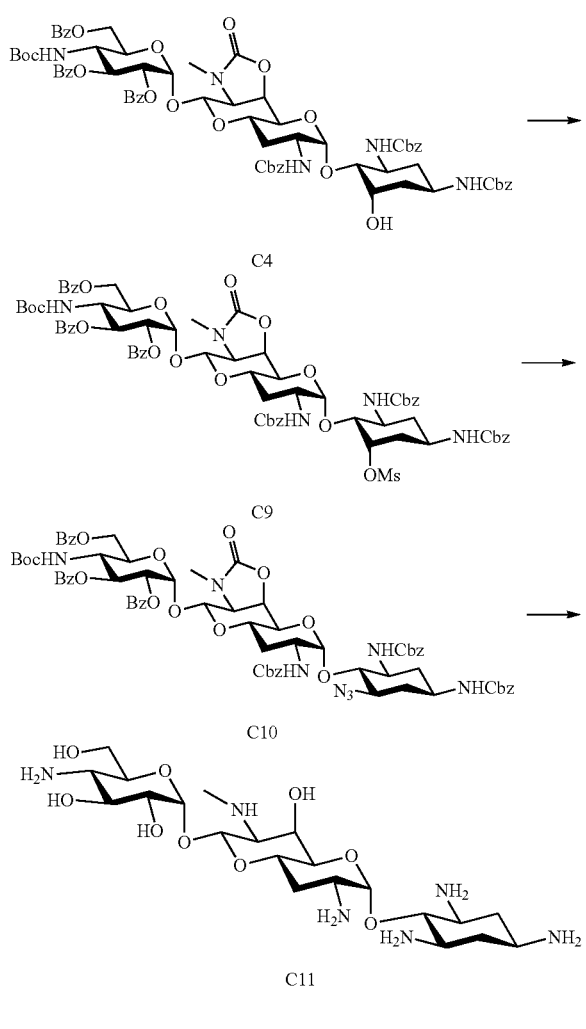

Examples 19-(i): Synthesis of 1,3,2'-tris-N-(benzyloxycarbonyl)-6,2",3",6"-tetra-O-benzoyl-4"-N-(t-butoxycarbonyl)-7'-N,6'-O-carbonyl-6-deoxy-5-epi-5-O-mesylapramycin (C9)

The title compound (C9) [403 mg (85%)] was obtained by a method similar to Example 14-(i) using 450 mg (0.33 mmol) of the title compound (C4) of Example 14-(iv).
MS (ESI) m/z: 1464 (M+Na)$^+$.

Example 19-(ii): Synthesis of 5-azide-1,3,2'-tris-N-(benzyloxycarbonyl)-6,2",3",6"-tetra-O-benzoyl-4"-N-(t-butoxycarbonyl)-7'-N,6'-O-carbonyl-5,6-dideoxyapramycin (C10)

The title compound (C10) [342 mg (88%)] was obtained by a method similar to Example 16-(i) using 401 mg (0.28 mmol) of the title compound (C9) of Example 19-(i).
MS (ESI) m/z: 1411 (M+Na)$^+$.

Example 19-(iii): Synthesis of 5-amino-5,6-dideoxyapramycin (C11)

The title compound (C11) [54.2 mg (88%)] was obtained by a method similar to Example 15-(ii) using 342 mg (0.25 mmol) of the title compound (C10) of Example 19-(ii).
MS (ESI) m/z: 523 (M+1)$^+$; $^1$H NMR (25% ND$_3$-D$_2$O, 500 MHz): δ 1.47-1.64 (2H, m, H-2ax and H-6ax), 2.32-2.46 (2H, m, H-2eq and H-6eq), 3.22-3.33 (2H, m, H-1 and H-5), 3.43 (1H, dt, H-2'), 3.52 (1H, t, H-4), 5.42 (1H, d, H-1') and 5.76 (1H, d, H-1").

Example 20: Synthesis of 1,3,2',7',4"-pentakis-N-(benzyloxycarbonyl)-5,6-O-cyclohexylideneapramycin (G1), 1,3,2'-tris-N-(benzyloxycarbonyl)-7'-N,6'-O-carbonyl-4"-N,6"-O-carbonyl-5,6-O-cyclohexylideneapramycin (G2), 2"-O-benzoyl-1,3,2'-tris-N-(benzyloxycarbonyl)-7'-N,6'-O-carbonyl-4"-N,6"-O-carbonyl-5,6-O-cyclohexylideneapramycin (G3), 2"-O-benzoyl-1,3,2'-tris-N-(benzyloxycarbonyl)-3"-O-benzylsulfonyl-7'-N,6'-O-carbonyl-4"-N,6"-O-carbonyl-5,6-O-cyclohexylideneapramycin (G4), 2",3"-anhydro-1,3,2',4"-tetrakis-N-(benzyloxycarbonyl)-7'-N,6'-O-carbonyl-5,6-O-cyclohexylidene-3"-epiapramycin (G5), 2"-azide-1,3,2'-tris-N-(benzyloxycarbonyl)-7'-N,6'-O-carbonyl-4",N-6"-O-carbonyl-5,6-O-cyclohexylidene-2"-deoxy-2",3"-diepiapramycin (G6), 3"-azide-1,3,2'-tris-N-(benzyloxycarbonyl)-7'-N,6'-O-carbonyl-4"-N,6"-O-carbonyl-5,6-O-cyclohexylidene-3"-deoxyapramycin (G6') and 2"-amino-2"-deoxy-2",3"-diepiapramycin (G7)

[Chem. 51]

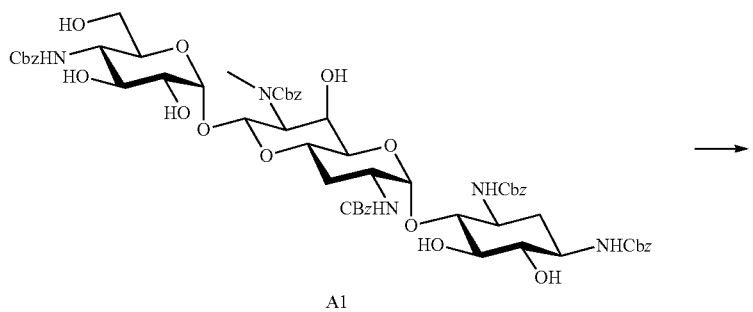

-continued
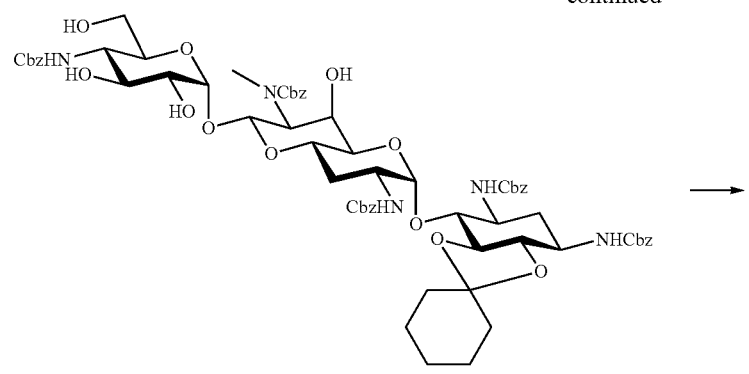
G1
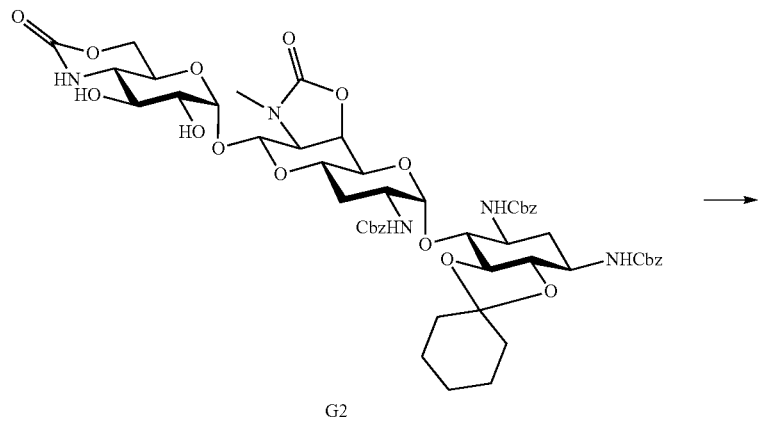
G2
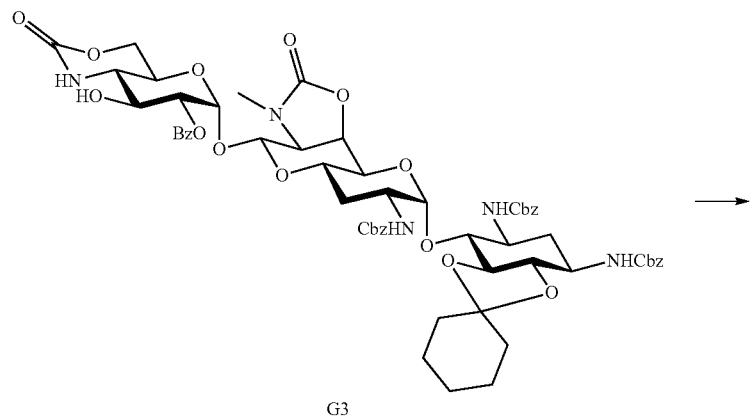
G3
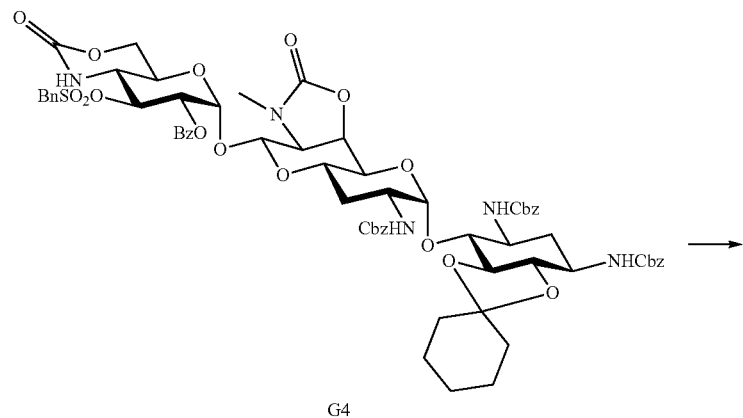
G4

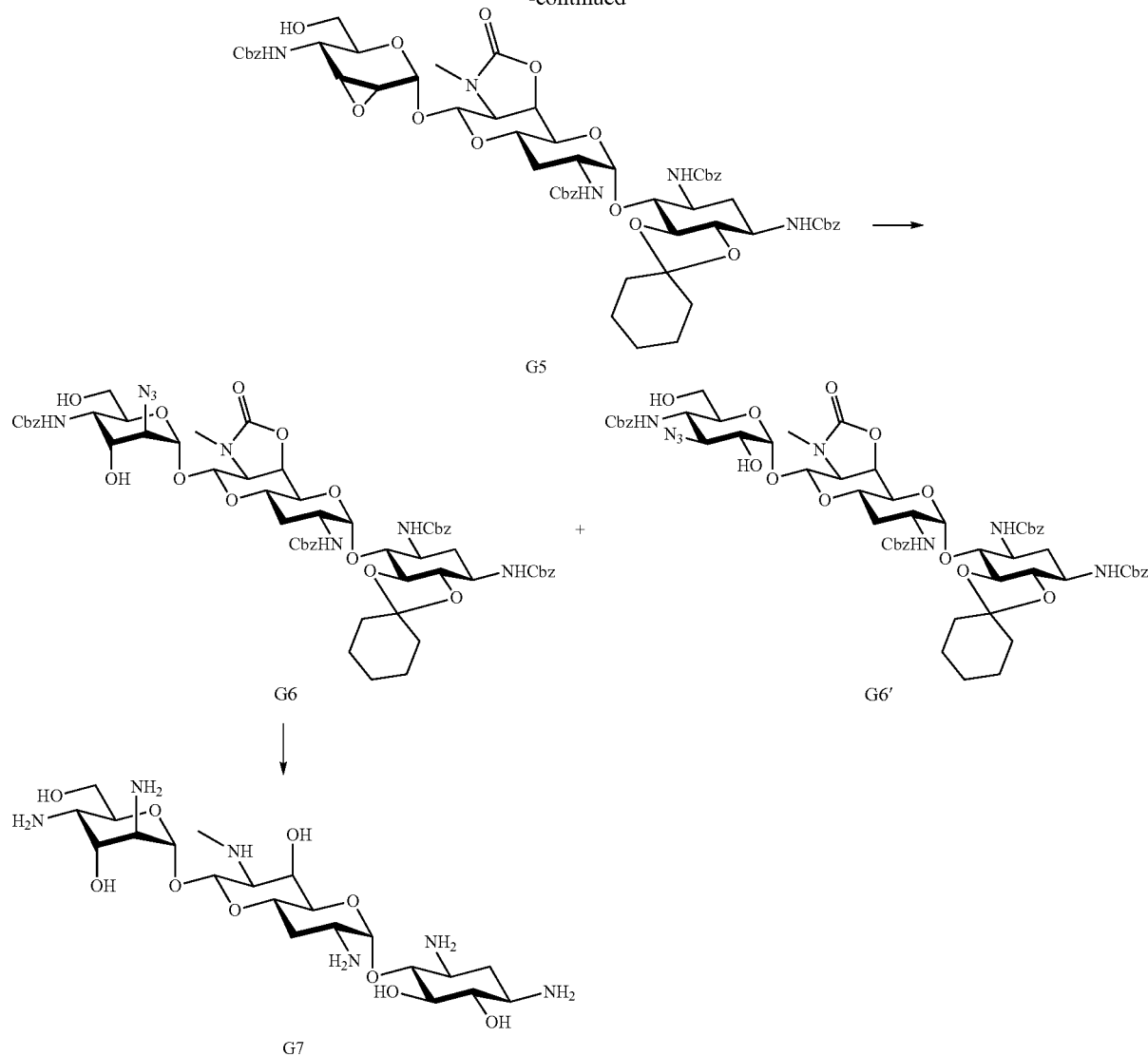

Example 20-(i): Synthesis of 1,3,2',7',4''-pentakis-N-(benzyloxycarbonyl)-5,6-O-cyclohexylideneapramycin (G1)

A solution prepared by adding 1.0 g of p-toluenesulfonic acid monohydrate and 20 ml of 1,1-dimethoxycyclohexane to a solution of 20.0 g (16.5 mmol) of the compound represented by formula (A1) dissolved in 100 ml of DMF was subjected to reaction at 60° C. for 4 hours. The reaction solution was neutralized by adding triethylamine and the residue obtained by concentrating under reduced pressure was diluted with ethyl acetate. The organic layer was washed with water and concentrated, and the residue was dissolved in 200 ml of dioxane. The resultant solution prepared by adding 100 ml of 20% aqueous acetic acid to the solution was subjected to reaction at room temperature for 18 hours. The reaction solution was concentrated under reduced pressure and the residue was crystallized with methanol to give 17.7 g (83%) of the title compound (G1).

MS (ESI) m/z: 1312 (M+Na)$^+$.

Example 20-(ii): Synthesis of 1,3,2'-tris-N-(benzyloxycarbonyl)-7'-N,6'-O-carbonyl-4''-N,6''-O-carbonyl-5,6-O-cyclohexylideneapramycin (G2)

The title compound (G2) [12.2 g (92%)] as a colorless solid was obtained by a method similar to Example 1-(ii) using 16.0 g (12.4 mmol) of the title compound (G1) of Example 20-(i).

MS(ESI) m/z: 1096 (M+Na)$^+$.

Example 20-(iii): Synthesis of 2''-O-benzoyl-1,3,2'-tris-N-(benzyloxycarbonyl)-7'-N,6'-O-carbonyl-4''-N,6''-O-carbonyl-5,6-O-cyclohexylideneapramycin (G3)

A solution prepared by adding 2 ml (1.5 eq.) of benzoyl chloride to a solution of 12.0 g (11.3 mmol) of the title compound (G2) of Example 20-(ii) dissolved in 60 ml of pyridine was treated in a method similar to Example 12-(ii) to give 12.7 g (96%) of the title compound (G3) as a colorless solid.

MS (ESI) m/z: 1200 (M+Na)$^+$.

Examples 20-(iv): Synthesis of 2''-O-benzoyl-1,3,2'-tris-N-(benzyloxycarbonyl)-3''-O-benzylsulfonyl-7'-N,6'-O-carbonyl-4''-N,6''-O-carbonyl-5,6-O-cyclohexylideneapramycin (G4)

A solution prepared by adding 2.85 g of benzylsulfonyl chloride at −10 to 0° C. to a solution of 12.0 g (10.2 mmol) of the title compound (G3) of Example 20-(iii) dissolved in 60 ml of pyridine was subjected to reaction at the same temperature as mentioned above for 1 hour. After adding water to the reaction solution, the residue obtained by concentration under reduced pressure was diluted with ethyl acetate. The organic layer was washed with 5% aq. $KHSO_4$, 5% aq. $NaHCO_3$ and brine successively, and dried with $Na_2SO_4$ and concentrated under reduced pressure to give 12.9 g (93%) of the title compound (G4) as a light yellow solid.

MS (ESI) m/z: 1377 $(M+Na)^+$.

Example 20-(v): Synthesis of 2'',3''-anhydro-1,3,2',4''-tetrakis-N-(benzyloxycarbonyl)-7'-N,6'-O-carbonyl-5,6-O-cyclohexylidene-3''-epiapramycin (G5)

A solution prepared by adding 27 ml (3eq) of 1 N NaOBn-benzyl alcohol solution to a solution of 12.5 g (9.2 mmol) of the title compound (G4) of Example 20-(iv) dissolved in 100 ml of chloroform was subjected to reaction at room temperature for 1 hour. The reaction solution was neutralized with 1 N hydrochloric acid after adding water to it, and an organic layer was washed with water and concentrated under reduced pressure. The resultant precipitation after isopropyl ether was added to the residue was filtered, and dried to give 10.1 g (94%) of the title compound (G5).

MS (ESI) m/z: 1186 $(M+Na)^+$.

Examples 20-(vi): Synthesis of 2''-azide-1,3,2'-tris-N-(benzyloxycarbonyl)-7'-N,6'-O-carbonyl-4''-N,6''-O-carbonyl-5,6-O-cyclohexylidene-2''-deoxy-2'',3''-diepiapramycin (G6) and 3''-azide-1,3,2'-tris-N-(benzyloxycarbonyl)-7'-N,6'-O-carbonyl-4''-N,6''-O-carbonyl-5,6-O-cyclohexylidene-3''-deoxyapramycin (G6')

The title compounds (G6) [452 mg (21%)] and (G6') [1.16 g (53%)] as colorless solids were obtained by a method similar to Example 18-(i) using 2.05 g (1.8 mmol) of the title compound (G5) of Example 20-(v).

MS (ESI) m/z: (G6), 1229 $(M+Na)^+$, (G6'), 1229 $(M+Na)^+$.

Examples 20-(vii): Synthesis of 2''-amino-2''-deoxy-2'',3''-diepiapramycin (G7)

A solution prepared by dissolving 402 mg (0.33 mmol) of the title compound (G6) of Example 20-(vi) in 80% aqueous acetic acid was subjected to reaction at 80° C. for 0.5 hours. After completion of the reaction, the mixture was concentrated under reduced pressure and the residue was dissolved in 10 ml of 50% dioxane-water. A mixture prepared by adding 0.5 ml of acetic acid and palladium black to the solution was subjected to catalytic reduction in a hydrogen atmosphere at room temperature for 10 hours. After completion of the reaction, the mixture was neutralized with $NH_4OH$ and the filtrate was concentrated under reduced pressure after filtration. The residue was dissolved in water (3 ml) and heated to 110° C. and 1 N aqueous potassium hydroxide solution (3 ml) was added. The resulting mixture was subjected to reaction for 2 hours at the temperature. After completion of the reaction, the reaction mixture was neutralized by adding 1 N aq. HCl under ice cooling and purified by ion exchange chromatography (CG50) to give 66.5 mg (37%) of the title compound (G7).

MS (ESI) m/z: 539 $(M+1)^+$; $^1$H NMR (25% $ND_3$-$D_2O$, 500 MHz): δ 3.28 (1H, dd, J=3.5 and 9.5 Hz, H-4''), 4.18 (1H, dd, J=3.5 and 4 Hz, H-3''), 3.34 (1H, dd, J=2 and 4 Hz, H-2''), 5.31 (1H, d, J=2 Hz, H-1'') and 5.38 (1H, d, J=3.5 Hz, H-1').

Example 21: Synthesis of 3''-amino-3''-deoxyapramycin (G8)

[Chem. 52]

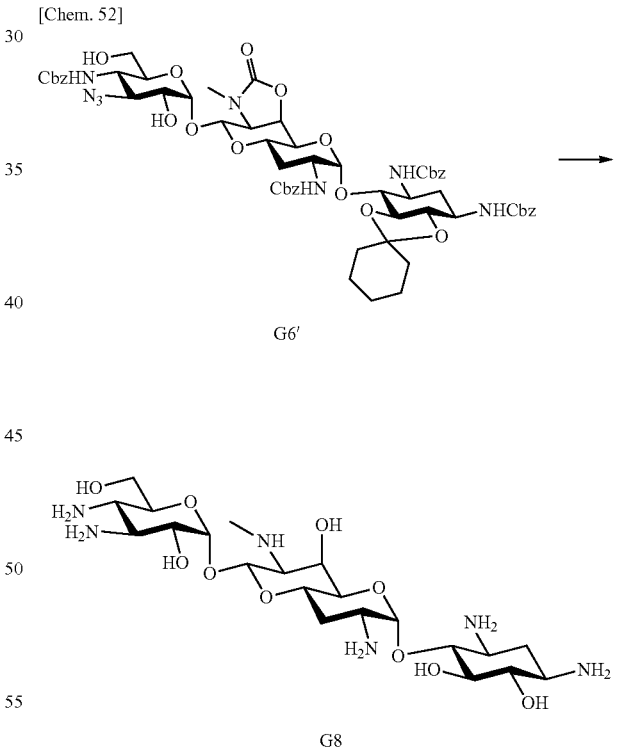

The title compound (G8) [125 mg (51%)] was obtained by a method similar to Example 20-(viii) using 551 mg (0.46 mmol) of the title compound (G6') of Example 20-(vi).

MS (ESI) m/z: 539 $(M+1)^+$; $^1$H NMR (25% $ND_3$-$D_2O$, 500 MHz): δ 3.18 (1H, t, 10 Hz, H-3''), 3.76 (1H, dd, J=4 and 10 Hz, H-2''), 5.42 (1H, d, J=3.5 Hz, H-1') and 5.60 (1H, d, J=4 Hz, H-1'').

Example 22: Synthesis of 2"-O-benzoyl-1,3,2'-tris-N-(benzyloxycarbonyl)-7'-N,6'-O-carbonyl-4"-N,6"-O-carbonyl-5,6-O-cyclohexylidene-3"-trifluoromethanesulfonylapramycin (H1), 1,3,2'-tris-N-(benzyloxycarbonyl)-7'-N,6'-O-carbonyl-4"-N,3"-O-carbonyl-5,6-O-cyclohexylidene-3"-epiapramycin (H2) and 3"-epiapramycin (H3)
[Chem. 53]
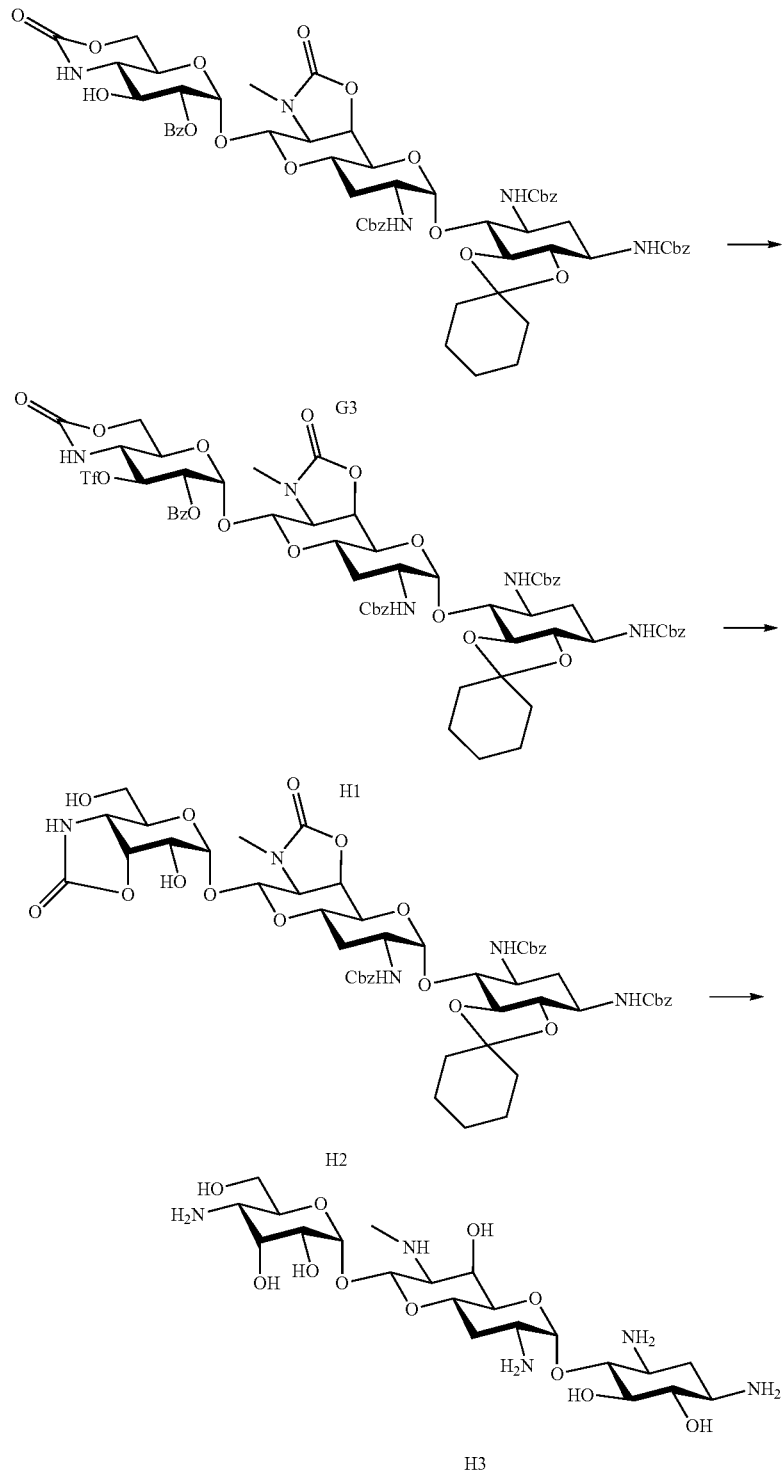

Examples 22-(i): Synthesis of 2''-O-benzoyl-1,3,2'-tris-N-(benzyloxycarbonyl)-7'-N,6'-O-carbonyl-4''-N,6''-O-carbonyl-5,6-O-cyclohexylidene-3''-trifluoromethanesulfonylapramycin (H1)

A solution prepared by adding 2 ml of pyridine and 0.95 ml of trifluoromethanesulfonic anhydride under ice cooling to a solution of 4.55 g (3.87 mmol) of the title compound (G3) of Example 20-(iii) in 50 ml of methylene chloride was subjected to reaction under ice cooling for 1 hour. The reaction solution was successively washed with 10% aq. KHSO$_4$, 5% aq. NaHCO$_3$ and water followed by concentration under reduced pressure to give 4.99 g (98%) of the title compound (H1) as a light yellow solid.
MS (ESI) m/z: 1332 (M+Na)$^+$.

Example 22-(ii): Synthesis of 1,3,2'-tris-N-(benzyloxycarbonyl)-7'-N,6'-O-carbonyl-4''-N,3''-O-carbonyl-5,6-O-cyclohexylidene-3''-epiapramycin (H2)

A solution prepared by adding 2.33 g of cesium acetate to a solution of 4.67 g (3.57 mmol) of the title compound (H1) of Example 22-(i) dissolved in 25 ml of DMF was subjected to reaction at 80° C. for 3 hours. Ethyl acetate was added to the reaction mixture and the resulting mixture was washed with water and concentrated under reduced pressure. The residue was dissolved in 30 ml of chloroform and 1 ml of 5 N NaOMe-methanol solution was added, and the resulting mixture was subjected to reaction at room temperature for 1 hour. The reaction solution was concentrated under reduced pressure after neutralization with 1 N hydrochloric acid, and purified by silica gel column chromatography (developing solvent, CHCl$_3$:MeOH=30:1) to give 2.75 g (72%) of the title compound (H2).
MS (ESI) m/z: 1096 (M+Na)$^+$.

Example 22-(iii): Synthesis of 3''-epiapramycin (H3)

The title compound (H3) [115 mg (52%)] was obtained by a method similar to Example 20-(viii) using 440 mg (0.41 mmol) of the title compound (H2) of Example 22-(ii).
MS (ESI) m/z: 540 (M+1)$^+$; $^1$H NMR (25% ND$_3$-D$_2$O, 500 MHz): δ 4.18 (1H, t, J=3 Hz, H-3''), 5.32 (1H, d, J=3.5 Hz, H-1') and 5.46 (1H, d, J=4.5 Hz, H-1'').

Example 23: Synthesis of 2'',3''-anhydro-1,3,2'-tris-N-(benzyloxycarbonyl)-7'-N,6'-O-carbonyl-4''-N,6''-O-carbonyl-5,6-O-cyclohexylideneapramycin (I1), 1,3,2'-tris-N-(benzyloxycarbonyl)-7'-N,6'-O-carbonyl-4''-N,6''-O-carbonyl-2'',3''-diepiapramycin (I2) and 2'',3''-diepiapramycin (I3)

[Chem. 54]

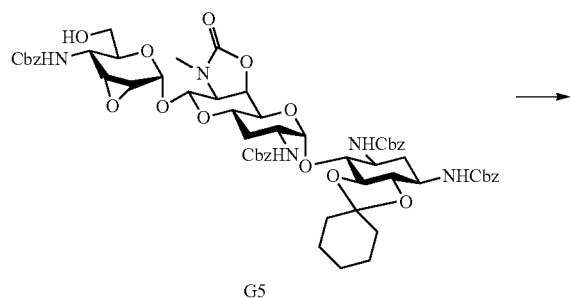

G5

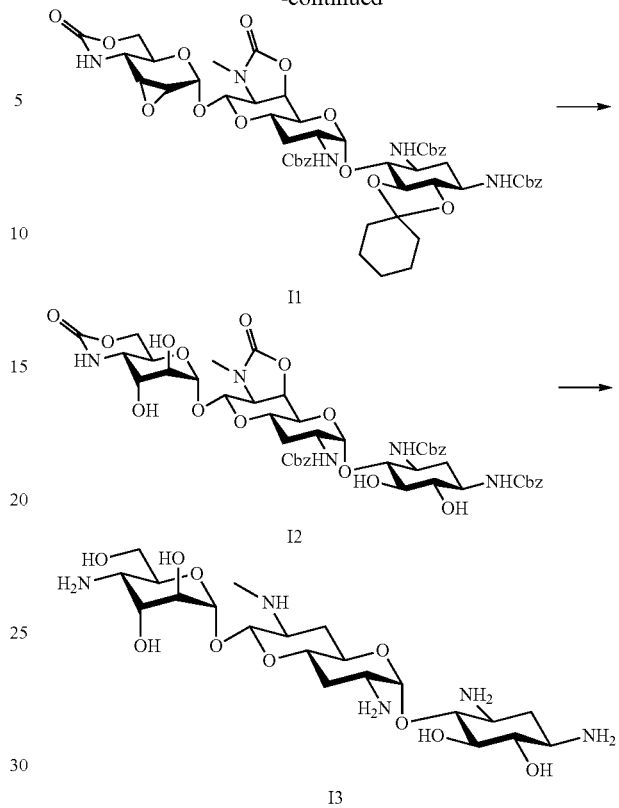

Examples 23-(i): Synthesis of 2'',3''-anhydro-1,3,2'-tris-N-(benzyloxycarbonyl)-7'-N,6'-O-carbonyl-4''-N,6''-O-carbonyl-5,6-O-cyclohexylideneapramycin (I1)

The title compound (I1) [1.38 g (93%)] was obtained by a method similar to Example 1-(ii) using 1.63 g (1.40 mmol) of the title compound (G5) of Example 20-(v).
MS (ESI) m/z: 1078 (M+Na)$^+$.

Example 23-(ii): Synthesis of 1,3,2'-tris-N-(benzyloxycarbonyl)-7'-N,6'-O-carbonyl-4''-N,6''-O-carbonyl-2'',3''-diepiapramycin (I2)

A solution prepared by dissolving 622 mg (0.58 mmol) of the title compound (I1) of Example 23-(i) in 80% aqueous acetic acid was subjected to reaction at 80° C. for 0.5 hours. After the reaction solution was concentrated under reduced pressure, the resulting residue was washed with isopropyl ether and dried to give 548 mg (95%) of the title compound (I2).
MS (ESI) m/z: 1016 (M+Na)$^+$.

Example 23-(iii): Synthesis of 2'',3''-diepiapramycin (I3)

The title compound (I3) [226 mg (68%)] was obtained by a method similar to Example 8-(ii) using 600 mg (0.60 mmol) of the title compound (I2) of Example 23-(ii).
MS (ESI) m/z: 540 (M+1)$^+$; $^1$H NMR (25% ND$_3$-D$_2$O, 500 MHz): δ 3.27 (1H, dd, J=3 and 10 Hz, H-4''), 4.05-4.18 (3H, m, H-4', -2'',-3''), 5.38 (1H, d, J=3.5 Hz, H-1') and 5.40 (1H, d, J=4.5 Hz, H-1'').

Example 24: Synthesis of 1,3,2',7',4"-pentakis-N-(benzyloxycarbonyl)-5,6:2",3"-di-O-cyclohexylideneapramycin (J1), 1,3,2',4"-tetrakis-N-(benzyloxycarbonyl)-7'-N,6'-O-carbonyl-5,6:2",3"-di-O-cyclohexylideneapramycin (J2), 1,3,2',4"-tetrakis-N-(benzyloxycarbonyl)-7'-N,6'-O-carbonyl-5,6:2",3"-di-O-cyclohexylidene-6"-deoxy-6"-fluoroapramycin (J3) and 6"-deoxy-6"-fluoroapramycin (J4)

[Chem. 55]

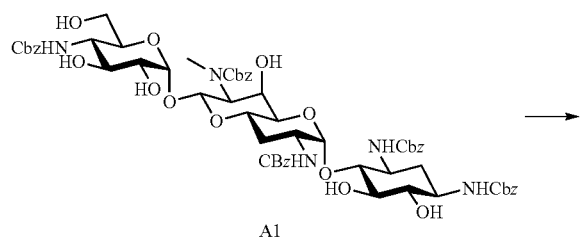
A1

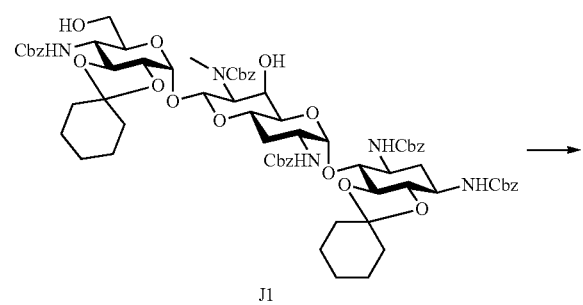
J1

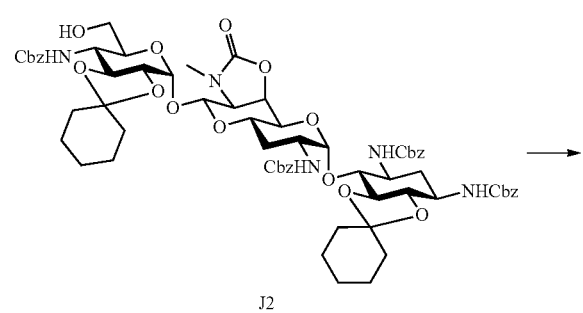
J2

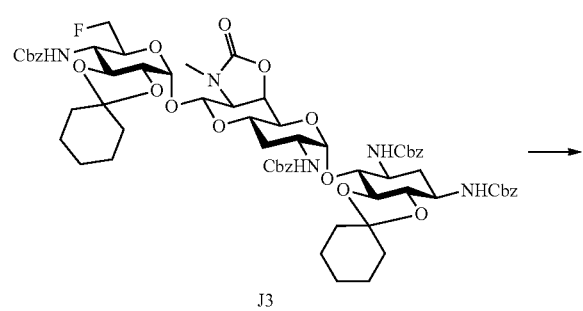
J3

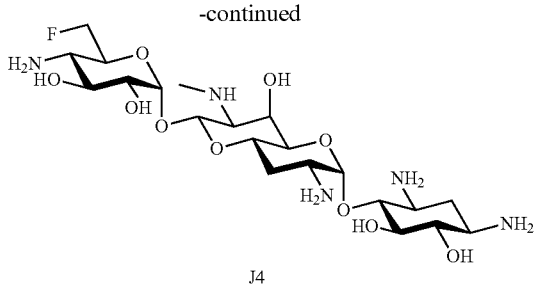
J4

Example 24-(i): Synthesis of 1,3,2',7',4"-pentakis-N-(benzyloxycarbonyl)-5,6:2",3"-di-O-cyclohexylideneapramycin (J1)

A solution prepared by adding 250 mg of p-toluenesulfonic acid monohydrate and 5 ml of 1,1-dimethoxycyclohexane to a solution of 5.0 g (4.13 mmol) of the compound represented by formula (A1) dissolved in 25 ml of DMF was subjected to reaction under reduced pressure at 60° C. for 4 hours. The reaction solution was neutralized by adding triethylamine and the residue obtained by concentrating under reduced pressure was diluted with ethyl acetate. The organic layer was washed with water and the residue obtained by concentration was dissolved in 50 ml of dioxane. A mixture prepared by adding 25 ml of 20% aqueous acetic acid to this solution was subjected to reaction at room temperature for 18 hours. The reaction solution was concentrated and the residue was washed with isopropyl ether, and dried to give 5.55 g (98%) of the title compound (J1).

MS (ESI) m/z: 1392 (M+Na)$^+$.

Example 24-(ii): Synthesis of 1,3,2',4"-tetrakis-N-(benzyloxycarbonyl)-7'-N,6'-O-carbonyl-5,6:2",3"-di-O-cyclohexylideneapramycin (J2)

The title compound (J2) [4.61 g (93%)] was obtained by a method similar to Example 1-(ii) using 5.40 g (3.94 mmol) of the title compound (J1) of Example 24-(i).

MS (ESI) m/z: 1284 (M+Na)$^+$.

Example 24-(iii): Synthesis of 1,3,2',4"-tetrakis-N-(benzyloxycarbonyl)-7'-N,6'-O-carbonyl-5,6:2",3"-di-O-cyclohexylidene-6"-deoxy-6"-fluoroapramycin (J3)

The title compound (J3) [896 mg (92%)] was obtained by a method similar to Examples 12-(iii) and (iv) using 977 mg (0.77 mmol) of the title compound (J2) of Example 24-(ii).

MS (ESI) m/z: 1286 (M+Na)$^+$.

Example 24-(iv): Synthesis of 6"-deoxy-6"-fluoroapramycin (J4)

The title compound (J4) [133 mg (55%)] was obtained by a method similar to Example 20-(viii) using 565 mg (0.45 mmol) of the title compound (J3) of Example 24-(iii).

MS (ESI) m/z: 542 (M+1)$^+$; $^1$H NMR (25% ND$_3$-D$_2$O, 500 MHz): δ 3.85-4.05 (2H, m, H-6"), 5.32 (1H, d, J=4.5 Hz, H-1') and 5.46 (1H, d, J=4 Hz, H-1").

Example 25: Synthesis of 2″,3″-anhydro-1,3,2′,4″-tetrakis-N-(benzyloxycarbonyl)-6″-O-benzylsulfonyl-7′-N,6′-O-carbonyl-5,6-O-cyclohexylidene-3″-epiapramycin (K1), 1,3,2′,4″-tetrakis-N-(benzyloxycarbonyl)-7′-N,6′-O-carbonyl-5,6-O-cyclohexylidene-3″,6″-dideoxy-3″,6″-diiodoapramycin (K2), 1,3,2′,4″-tetrakis-N-(benzyloxycarbonyl)-7′-N,6′-O-carbonyl-5,6-O-cyclohexylidene-3″,6″-dideoxyapramycin (K3) and 3″,6″-dideoxyapramycin (K4)

[Chem. 56]

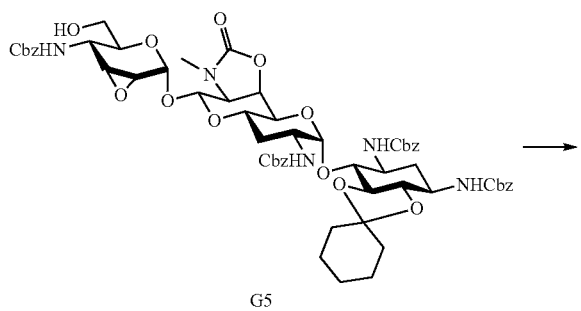

G5

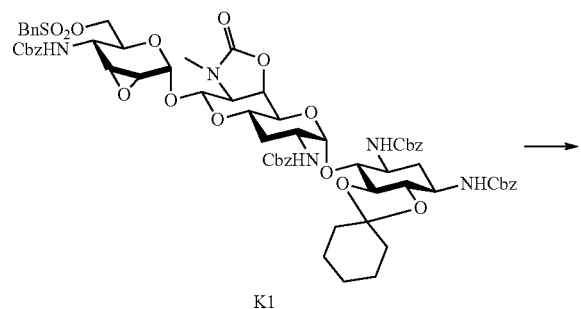

K1

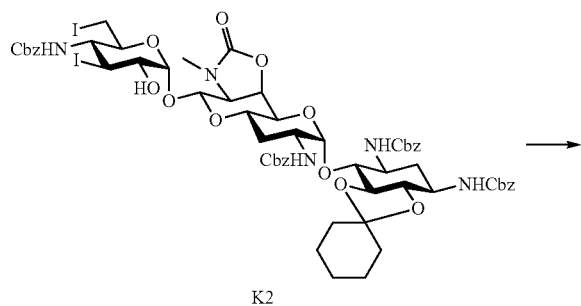

K2

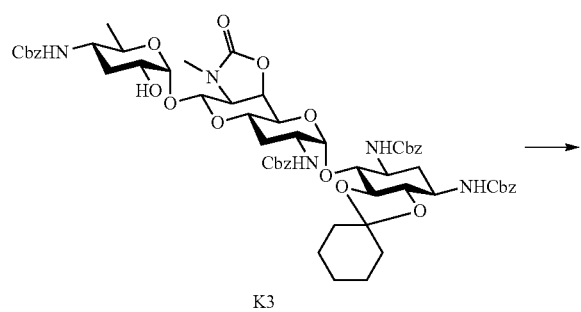

K3

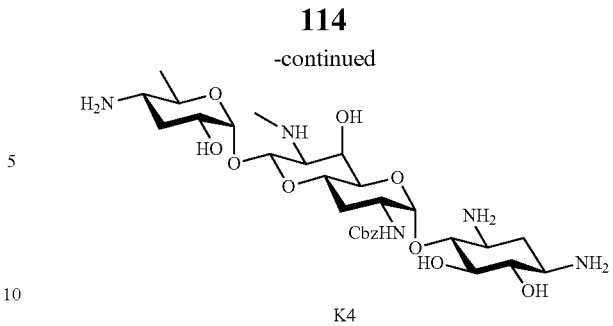

K4

Example 25-(i): Synthesis of 2″,3″-anhydro-1,3,2′,4″-tetrakis-N-(benzyloxycarbonyl)-6″-O-benzylsulfonyl-7′-N,6′-O-carbonyl-5,6-O-cyclohexylidene-3″-epiapramycin (K1)

The title compound (K1) [926 mg (96%)] was obtained by a method similar to Example 20-(iv) using 850 mg (0.73 mmol) of the title compound (G5) of Example 20-(v).

MS (ESI) m/z: 1340 (M+Na)$^+$.

Example 25-(ii): Synthesis of 1,3,2′,4″-tetrakis-N-(benzyloxycarbonyl))-7′-N,6′-O-carbonyl-5,6-O-cyclohexylidene-3″,6″-dideoxy-3″,6″-diiodoapramycin (K2)

The title compound (K2) [889 mg (93%)] was obtained by a method similar to Example 14-(iii) using 900 mg (0.68 mmol) of the title compound (K1) of Example 25-(i).

MS (ESI) m/z: 1424 (M+Na)$^+$.

Example 25-(iii): Synthesis of 1,3,2′,4″-tetrakis-N-(benzyloxycarbonyl)-7′-N,6′-O-carbonyl-5,6-O-cyclohexylidene-3″,6″-dideoxyapramycin (K3)

The title compound (K3) [645 mg (92%)] was obtained by a method similar to Example 14-(iv) using 850 mg (0.61 mmol) of the title compound (K2) of Example 25-(ii).

MS (ESI) m/z: 1172 (M+Na)$^+$.

Example 25-(iv): Synthesis of 3″,6″-dideoxyapramycin (K4)

The title compound (K4) [155 mg (59%)] was obtained by a method similar to Example 20-(viii) using 600 mg (0.52 mmol) of the title compound (K3) of Example 25-(iii).

MS (ESI) m/z: 508 (M+1)$^+$; $^1$H NMR (25% ND$_3$-D$_2$O, 500 MHz): δ 1.47 (3H, d, CH$_3$-6″), 1.99 (1H, q, H-3″ax), 2.27 (1H, dt, H-3″eq), 5.31 (1H, d, H-1′) and 5.72 (1H, d, H-1″).

Example 26: Synthesis of 1,3,2'-tris-N-(benzyloxycarbonyl)-4''-N-(t-butoxycarbonyl)-7'-N, 6'-O-carbonyl-5-chloro-5-deoxy-5-epiapramycin (L1), 1,3,2'-tris-N-(benzyloxycarbonyl)-4''-N-(t-butoxycarbonyl)-7'-N, 6'-O-carbonyl-5,6''-dichloro-5,6''-dideoxy-5-epiapramycin (L2), 1,3,2'-tris-N-(benzyloxycarbonyl)-4''-N-(t-butoxycarbonyl)-7'-N, 6'-O-carbonyl-5,6''-dideoxyapramycin (L3), 1,3,2'-tris-N-(benzyloxycarbonyl)-7'-N,6'-O-carbonyl-5,6''-dideoxyapramycin (L4) and 5,6''-dideoxyapramycin (L5)

[Chem. 57]

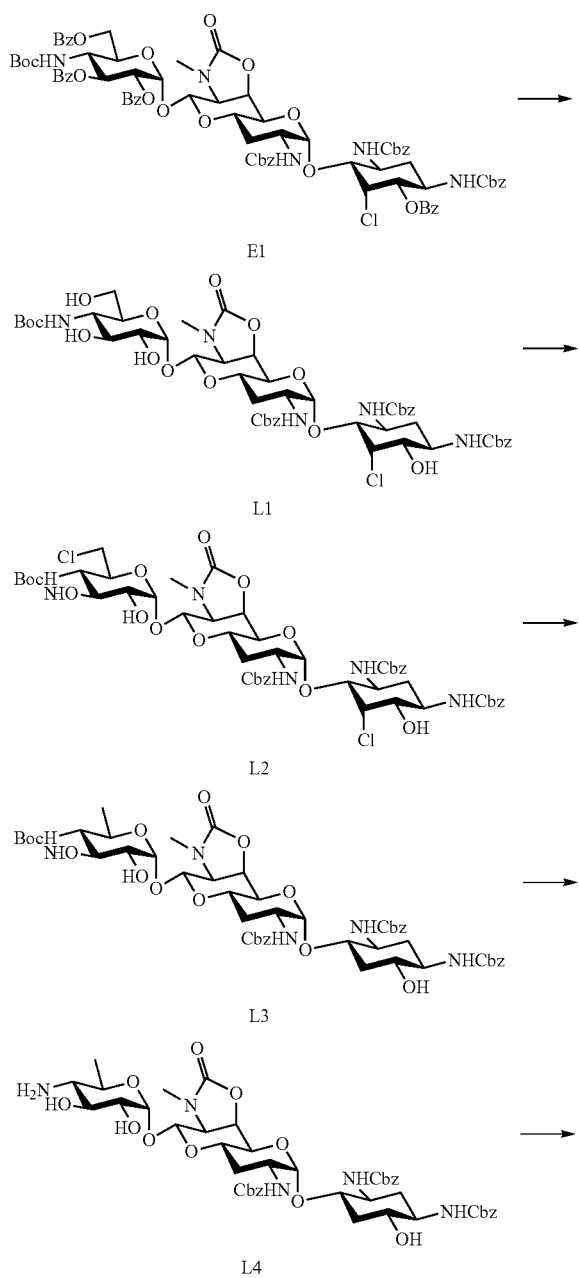

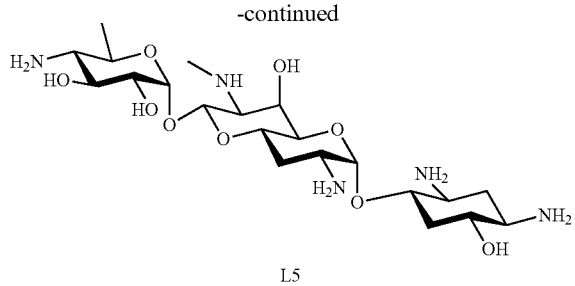

Example 26-(i): Synthesis of 1,3,2'-tris-N-(benzyloxycarbonyl)-4''-N-(t-butoxycarbonyl)-7'-N, 6'-O-carbonyl-5-chloro-5-deoxy-5-epiapramycin (L1)

A solution prepared by adding 3 ml of 5 N NaOMe-methanol to a solution of 100 mg (0.067 mmol) of the title compound (E1) of Example 17-(i) dissolved in 2 ml of methanol was subjected to reaction at room temperature for 1 hour. The reaction solution was neutralized by adding 1 N HCl and concentrated under reduced pressure and the residue was washed with water. The residue was further washed with isopropyl ether and dried to give 65.9 mg (91%) of the title compound (L1) as a colorless solid.

MS (ESI) m/z: 1108 (M+Na)$^+$.

Example 26-(ii): Synthesis of 1,3,2'-tris-N-(benzyloxycarbonyl)-4''-N-(t-butoxycarbonyl)-7'-N, 6'-O-carbonyl-5,6''-dichloro-5,6''-dideoxy-5-epiapramycin (L2)

A solution prepared by adding 1.1 ml of pyridine, 6.7 ml of carbon tetrachloride and 1.81 g of triphenylphosphine to a solution of 1.50 g (1.38 mmol) of the title compound (L1) of Example 26-(i) dissolved in 30 ml of THF was subjected to reaction at 50° C. for 2 hours. The reaction solution was concentrated under reduced pressure, and the residue was dissolved in chloroform. The organic layer was successively washed with 5% aq. KHSO$_4$, 5% aq. NaHCO$_3$ and brine and dried with Na$_2$SO$_4$ followed by concentration. The residue was purified by silica gel column chromatography (developing solvent, CHCl$_3$:acetone=1:1) to give 1.10 g (72%) of the title compound (L2) as a colorless solid.

MS (ESI) m/z: 1126 (M+Na)$^+$.

Example 26-(iii): Synthesis of 1,3,2'-tris-N-(benzyloxycarbonyl)-4''-N-(t-butoxycarbonyl)-7'-N, 6'-O-carbonyl-5,6''-dideoxyapramycin (L3)

The title compound (L3) [184 mg (98%)] was obtained by a method similar to Example 14-(iv) using 200 mg (0.18 mmol) of the title compound (L2) of Example 26-(ii).

MS (ESI) m/z: 1058 (M+Na)$^+$.

Examples 26-(iv): Synthesis of 1,3,2'-tris-N-(benzyloxycarbonyl)-7'-N,6'-O-carbonyl-5,6''-dideoxyapramycin (L4)

The title compound (L4) [147 mg (79% as TFA salt)] was obtained by a method similar to Example 14-(vi) using 184 mg (0.17 mmol) of the title compound (L3) of Example 26-(iii).

MS (ESI) m/z: 936 (M+1)$^+$.

Example 26-(v): Synthesis of 5,6"-dideoxyapramycin (L5)

The title compound (L5) [19.0 mg (67%)] was obtained by a method similar to Example 8-(ii) using 91.1 mg (0.087 mmol as TFA salt) of the title compound (L4) of Example 26-(iv).

MS (ESI) m/z: 508 (M+1)$^+$; $^1$H NMR (DCl-D$_2$O, 500 MHz): δ 1.27 (3H, d, CH$_3$-6"), 1.42 (1H, q, H-5ax), 2.61 (1H, ddd, H-5eq), 5.29 (1H, d, H-1') and 5.37 (1H, d, H-1").

Example 27: Synthesis of 1,3,2',4"-tetrakis-N-(benzyloxycarbonyl)-7'-N,6'-O-carbonyl-5,6-O-cyclohexylidene-3"-deoxy-3"-iodoapramycin (M1), 1,3,2',4"-tetrakis-N-(benzyloxycarbonyl)-7'-N,6'-O-carbonyl-5,6-O-cyclohexylidene-3"-deoxyapramycin (M2), 2",6"-di-O-benzoyl-1,3,2',4"-tetrakis-N-(benzyloxycarbonyl)-7'-N,6'-O-carbonyl-5,6-O-cyclohexylidene-3"-deoxyapramycin (M3), 5,2",6"-tri-O-benzoyl-1,3,2',4"-tetrakis-N-(benzyloxycarbonyl)-7'-N,6'-O-carbonyl-3"-deoxyapramycin (M4), 5,2",6"-tri-O-benzoyl-1,3,2',4"-tetrakis-N-(benzyloxycarbonyl)-7'-N,6'-O-carbonyl-5-chloro-5,3"-dideoxy-5-epiapramycin (M5), 5,2",6"-tri-O-benzoyl-1,3,2',4"-tetrakis-N-(benzyloxycarbonyl)-7'-N,6'-O-carbonyl-5,3"-dideoxyapramycin (M6) and 5,3"-dideoxyapramycin (M7)

[Chem. 58]

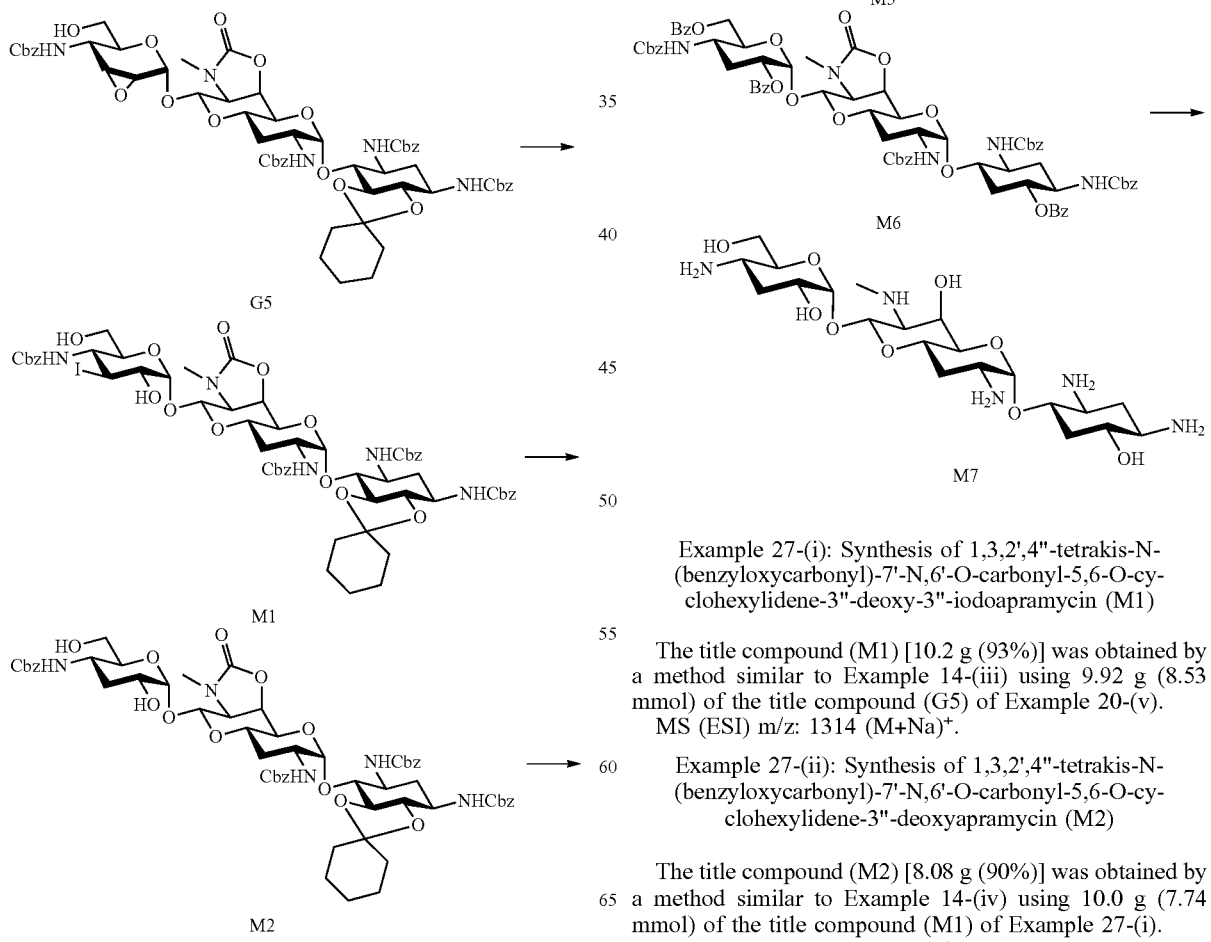

Example 27-(i): Synthesis of 1,3,2',4"-tetrakis-N-(benzyloxycarbonyl)-7'-N,6'-O-carbonyl-5,6-O-cyclohexylidene-3"-deoxy-3"-iodoapramycin (M1)

The title compound (M1) [10.2 g (93%)] was obtained by a method similar to Example 14-(iii) using 9.92 g (8.53 mmol) of the title compound (G5) of Example 20-(v).
MS (ESI) m/z: 1314 (M+Na)$^+$.

Example 27-(ii): Synthesis of 1,3,2',4"-tetrakis-N-(benzyloxycarbonyl)-7'-N,6'-O-carbonyl-5,6-O-cyclohexylidene-3"-deoxyapramycin (M2)

The title compound (M2) [8.08 g (90%)] was obtained by a method similar to Example 14-(iv) using 10.0 g (7.74 mmol) of the title compound (M1) of Example 27-(i).
MS (ESI) m/z: 1188 (M+Na)$^+$.

Example 27-(iii): Synthesis of 2",6"-di-O-benzoyl-1,3,2',4"-tetrakis-N-(benzyloxycarbonyl)-7'-N,6'-O-carbonyl-5,6-O-cyclohexylidene-3"-deoxyapramycin (M3)

The title compound (M3) [11.2 g (97%)] as a colorless solid was obtained by a method similar to Example 12-(ii) using 50 ml pyridine solution of the title compound (M2) [9.80 g (8.4 mmol)] of Example 27-(ii) and 4 ml (3eq.) of benzoyl chloride.
MS (ESI) m/z: 1396 (M+Na)$^+$.

Example 27-(iv): Synthesis of 5,2",6"-tri-O-benzoyl-1,3,2',4"-tetrakis-N-(benzyloxycarbonyl)-7'-N,6'-O-carbonyl-3"-deoxyapramycin (M4)

A solution prepared by dissolving 11.0 g (8 mmol) of the title compound (M3) of Example 27-(iii) in 50 ml of 80% aqueous acetic acid was subjected to reaction at 80° C. for 30 minutes. The reaction solution was concentrated and the organic layer was neutralized with NaHCO$_3$ after the residue was diluted with ethyl acetate, and further washed with water and concentrated. Next, a solution prepared by dissolving the residue in 50 ml of pyridine and adding 3.7 ml (4eq.) of benzoyl chloride to the mixture under ice cooling was subjected to reaction under ice cooling for 35 minutes. The reaction solution was concentrated after adding water and the residue was diluted with ethyl acetate. The organic layer was successively washed with 5% aq. KHSO$_4$, 5% aq. NaHCO$_3$ and water and concentrated to give 11.1 g (99%) of the title compound (M4) as a light yellow solid.
MS (ESI) m/z: 1420 (M+Na)$^+$.

Example 27-(v): Synthesis of 5,2",6"-tri-O-benzoyl-1,3,2',4"-tetrakis-N-(benzyloxycarbonyl)-7'-N,6'-O-carbonyl-5-chloro-5,3"-dideoxy-5-epiapramycin (M5)

The title compound (M5) [904 mg (90%)] was obtained by a method similar to Example 17-(i) using 1.00 g (0.71 mmol) of the title compound (M4) of Example 27-(iv).
MS (ESI) m/z: 1438 (M+Na)$^+$.

Example 27-(vi): Synthesis of 5,2",6"-tri-O-benzoyl-1,3,2',4"-tetrakis-N-(benzyloxycarbonyl)-7'-N,6'-O-carbonyl-5,3"-dideoxyapramycin (M6)

The title compound (M6) [762 mg (89%)] was obtained by a method similar to Example 14-(iv) using 880 mg (0.62 mmol) of the title compound (M5) of Example 27-(v).
MS (ESI) m/z: 1404 (M+Na)$^+$.

Example 27-(vii): Synthesis of 5,3"-dideoxyapramycin (M7)

A solution prepared by adding 0.2 ml of 5 N NaOMe-methanol to a solution of 750 mg (0.54 mmol) of the title compound (M6) of Example 27-(vi) dissolved in 10 ml of methanol was subjected to reaction at room temperature for 2 hours. After completion of the reaction, the reaction solution was neutralized with 1 N hydrochloric acid and concentrated under reduced pressure. The residue was dissolved in 10 ml of 50% aqueous 1, 4-dioxane. A mixture prepared by adding 0.5 ml of acetic acid and palladium black was subjected to catalytic reduction in a hydrogen atmosphere at room temperature for 10 hours. The reaction solution was neutralized with NH$_4$OH and filtered and the filtrate was concentrated. The residue was dissolved in 5 ml of water and heated to 110° C. and 5 ml of 1 N aqueous potassium hydroxide solution was added. The resulting mixture was heated for 0.5 hours. The reaction mixture was neutralized by adding 1 N aq. HCl under ice cooling and purified by ion exchange chromatography (CG50) to give 121 mg (44%) of the title compound (M7).
MS (ESI) m/z: 508 (M+1)$^+$; $^1$H NMR (25% ND$_3$-D$_2$O, 500 MHz): δ 1.66 (1H, q, H-5ax), 1.98 (1H, q, H-3"ax), 2.30 (1H, dt, H-3" eq), 2.68-2.75 (4H, m, H-5eq and 7'-NMe), 5.30 (1H, d, H-1') and 5.69 (1H d, H-1").

Example 28: Synthesis of 5,2",6"-tri-O-benzoyl-1,3,2',4"-tetrakis-N-(benzyloxycarbonyl)-7'-N,6'-O-carbonyl-3"-deoxy-5-epiapramycin (M8), 5,2",6"-tri-O-benzoyl-1,3,2',4"-tetrakis-N-(benzyloxycarbonyl)-7'-N,6'-O-carbonyl-5,3"-dideoxy-5-epi-5-fluoroapramycin (M8') and 3"-deoxy-5-epiapramycin (M9)

[Chem. 59]

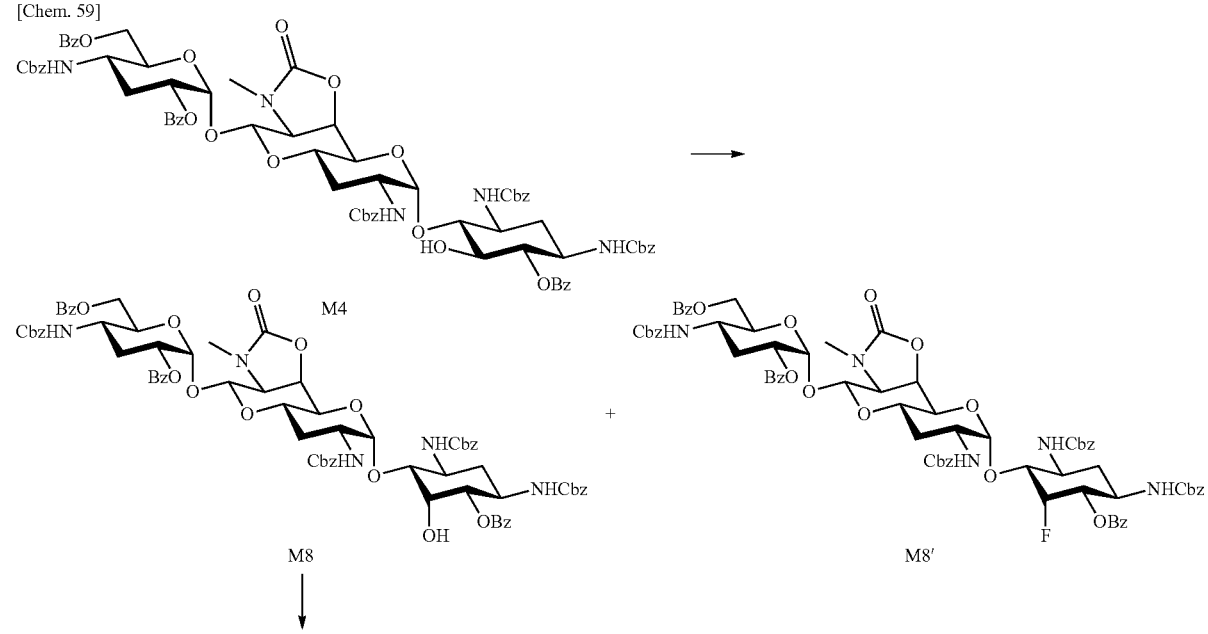

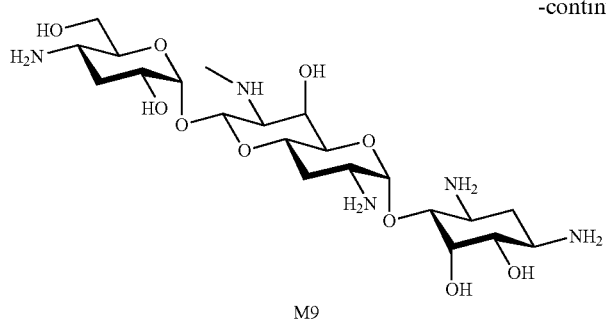

M9

Example 28-(i): Synthesis of 5,2",6"-tri-O-benzoyl-1,3,2',4"-tetrakis-N-(benzyloxycarbonyl)-7'-N,6'-O-carbonyl-3"-deoxy-5-epiapramycin (M8) and 5,2",6"-tri-O-benzoyl-1,3,2',4"-tetrakis-N-(benzyloxycarbonyl)-7'-N,6'-O-carbonyl-5,3"-dideoxy-5-epi-5-fluoroapramycin (M8')

The title compounds (M8) [1.12 g (56%)] and (M8') [445 mg (22%)] were obtained by a method similar to Examples 12-(iii) using 2.01 g (1.43 mmol) of the title compound (M4) of Example 27-(iv).

MS (ESI) m/z: (M8), 1420 (M+Na)$^+$; (M8'), 1422 (M+Na)$^+$.

Example 28-(ii): Synthesis of 3"-deoxy-5-epiapramycin (M9)

The title compound (M9) [78.6 mg (52%)] was obtained by a method similar to Example 27-(vii) using 410 mg (0.29 mmol) of the title compound (M8) of Example 28-(i).

MS (ESI) m/z: 524 (M+1)$^+$; $^1$H NMR (25% ND$_3$-D$_2$O, 500 MHz): δ 1.95 (1H, q, J=12.5 Hz, H-3"ax), 2.27 (1H, dt, J=4 and 12.5 Hz, H-3"eq), 4.51 (1H, t, J=2.5 Hz, H-5), 5.21 (1H, d, J=3.5 Hz, H-1') and 5.51 (1H, J=4 Hz, d, H-1").

Example 29: Synthesis of 5,3"-dideoxy-5-epi-5-fluoroapramycin (M10)

The title compound (M10) [70.5 mg (50%)] was obtained by a method similar to Example 27-(vii) using 380 mg (0.27 mmol) of the title compound (M8') of Example 28-(i).

MS (ESI) m/z: 526 (M+1)$^+$; $^1$H NMR (25% ND$_3$-D$_2$O, 500 MHz): δ 1.95 (1H, q, J=12.5 Hz, H-3"ax), 2.30 (1H, dt, J=4 and 12.5 Hz, H-3"eq), 5.28 (1H, d, J=3.5 Hz, H-1'), 5.35 (1H, br d, J=55 Hz, H-5) and 5.51 (1H, d, J=4 Hz, H-1").

Example 30: Synthesis of 5,2",6"-tri-O-benzoyl-1,3,2',4"-tetrakis-N-(benzyloxycarbonyl)-7'-N,6'-O-carbonyl-3"-deoxy-5-O-mesylapramycin (N1), 5,6-anhydro-2",6"-di-O-benzoyl-1,3,2',4"-tetrakis-N-(benzyloxy carbonyl)-7'-N,6'-O-carbonyl-3"-deoxy-5-epiapramycin (N2), 2",6"-di-O-benzoyl-1,3,2',4"-tetrakis-N-(benzyloxycarbonyl)-7'-N,6'-O-carbonyl-6,3"-dideoxy-5,6-diepi-6-iodoapramycin (N3), 2",6"-di-O-benzoyl-1,3,2',4"-tetrakis-N-(benzyloxycarbonyl)-7'-N,6'-O-carbonyl-6,3"-dideoxy-5-epiapramycin (N4), and 6,3"-dideoxy-5-epiapramycin (N5)

[Chem. 61]

[Chem. 60]

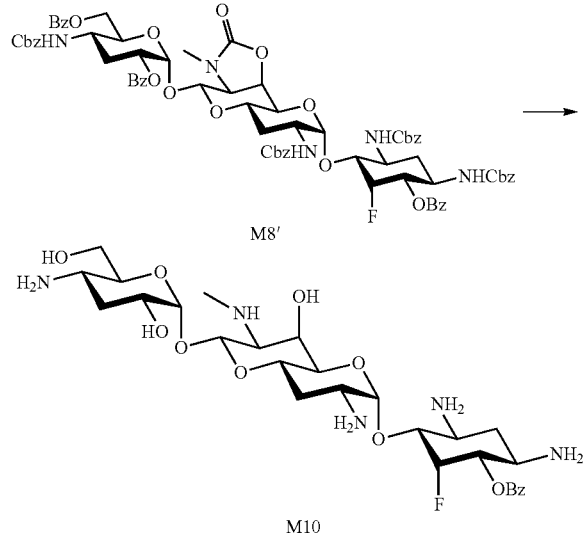

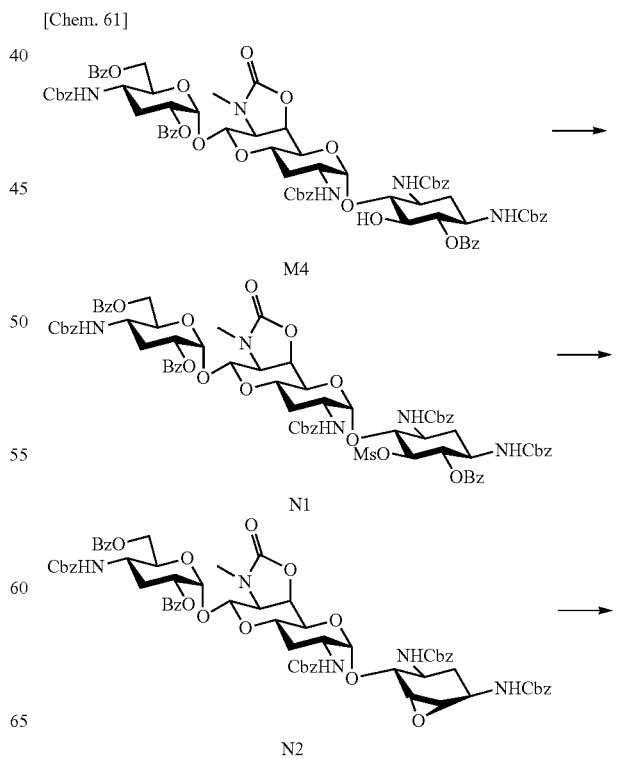

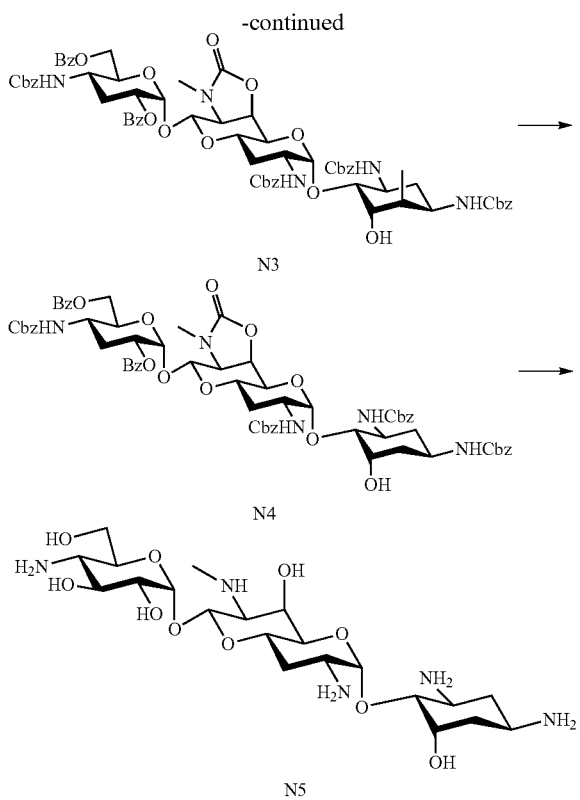

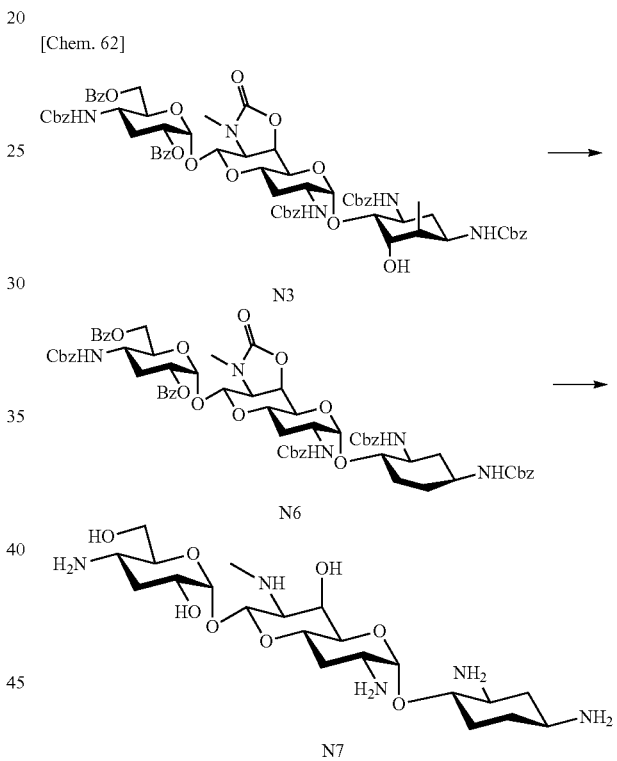

Example 30-(i): Synthesis of 5,2",6"-tri-O-benzoyl-1,3,2',4"-tetrakis-N-(benzyloxycarbonyl)-7'-N,6'-O-carbonyl-3"-deoxy-5-O-mesylapramycin (N1)

The title compound (N1) [2.31 g (97%)] was obtained by a method similar to Example 14-(i) using 2.25 g (1.61 mmol) of the title compound (M4) of Example 27-(v).

MS (ESI) m/z: 1498 (M+Na)$^+$.

Example 30-(ii): Synthesis of 5,6-anhydro-2",6"-di-O-benzoyl-1,3,2',4"-tetrakis-N-(benzyloxy carbonyl)-7'-N,6'-O-carbonyl-3"-deoxy-5-epiapramycin (N2)

The title compound (N2) [1.46 g (82%)] was obtained by a method similar to Example 14-(ii) using 2.02 g (1.40 mmol) of the title compound (N1) of Example 30-(i).

MS (ESI) m/z: 1298 (M+Na)$^+$.

Example 30-(iii): Synthesis of 2",6"-di-O-benzoyl-1,3,2',4"-tetrakis-N-(benzyloxycarbonyl)-7'-N,6'-O-carbonyl-6,3"-dideoxy-5,6-diepi-6-iodoapramycin (N3)

The title compound (N3) [1.37 g (92%)] was obtained by a method similar to Example 14-(iii) using 1.35 g (1.06 mmol) of the title compound (N2) of Example 30-(ii).

MS (ESI) m/z: 1426 (M+Na)$^+$.

Example 30-(iv): Synthesis of 2",6"-di-O-benzoyl-1,3,2',4"-tetrakis-N-(benzyloxycarbonyl)-7'-N,6'-O-carbonyl-6,3"-dideoxy-5-epiapramycin (N4)

The title compound (N4) [331 mg (88%)] was obtained by a method similar to Example 14-(iv) using 417 mg (0.29 mmol) of the title compound (N3) of Example 30-(iii).

MS (ESI) m/z: 1300 (M+Na)$^+$.

Example 30-(v): Synthesis of 6,3"-dideoxy-5-epiapramycin (N5)

The title compound (N5) [66.8 mg (55%)] was obtained by a method similar to Example 27-(vii) using 310 mg (0.24 mmol) of the title compound (N4) of Example 30-(iv).

MS (ESI) m/z: 508 (M+1)$^+$; $^1$H NMR (25% ND$_3$-D$_2$O, 500 MHz): δ 1.37 (1H, q, J=12.5 Hz, H-6ax), 1.62 (1H, t, J=12.5 Hz, H-6eq), 1.93 (1H, q, J=12.5 Hz, H-3"ax), 2.33 (1H, dt, J=4 and 12.5 Hz, H-3"eq), 4.57 (2H, br s, H-5 and H-6'), 5.24 (1H, d, J=3 Hz, H-1') and 5.50 (1H, d, J=3.5 Hz, H-1").

Example 31: Synthesis of 2",6"-di-O-benzoyl-1,3,2',4"-tetrakis-N-(benzyloxycarbonyl)-7'-N,6'-O-carbonyl-5,6,3"-trideoxy-5-enoapramycin (N6) and 5,6,3"-trideoxyapramycin (N7)

[Chem. 62]

Example 31-(i): Synthesis of 2",6"-di-O-benzoyl-1,3,2',4"-tetrakis-N-(benzyloxycarbonyl)-7'-N,6'-O-carbonyl-5,6,3"-trideoxy-5-enoapramycin (N6)

A solution prepared by adding 200 mg of benzylsulfonyl chloride at −10 to 0° C. to a solution of 952 mg (0.67 mmol) of the title compound (N3) of Example 30-(iii) dissolved in 5 ml of pyridine was subjected to reaction at the same temperature as mentioned above for 1 hour. Next, 0.5 ml of water was added to the reaction solution and the mixture was heated at 80° C. for 2 hours. The reaction solution was concentrated, and the precipitation resulting from adding water was filtered. Subsequently, the precipitation was purified by silica gel column chromatography (developing solvent, CHCl$_3$:MeOH=30:1) to give 578 mg (67%) of the title compound (N6).

MS (ESI) m/z: 1282 (M+Na)$^+$.

Example 31-(ii): Synthesis of 5,6,3''-trideoxyapramycin (N7)

The title compound (N7) [81.3 mg (61%)] was obtained by a method similar to Example 27-(vii) using 480 mg (0.27 mmol) of the title compound (N6) of Example 31-(i).

MS (ESI) m/z: 492 (M+1)$^+$. $^1$H NMR (25% ND$_3$-D$_2$O, 500 MHz): δ 1.60 (1H, q, J=12.5 Hz, H-6ax), 1.65 (1H, q, J=12 Hz, H-5ax), 1.95 (1H, q, J=12.5 Hz, H-3''ax), 2.20-2.32 (2H, m, H-6eq and H-3'' eq), 2.29 (1H, m, H-6eq), 5.37 (1H, d, J=3.6 Hz, H-1') and 5.69 (1H, d, J=3.9 Hz, H-1'').

Example 32: Synthesis of 5-azide-2'',6''-di-O-benzoyl-1,3,2',4''-tetrakis-N-(benzyloxycarbonyl)-7'-N,6'-O-carbonyl-5,3''-dideoxy-5-epiapramycin (N8) and 5-amino-5,3''-dideoxy-5-epiapramycin (N9)

[Chem. 63]

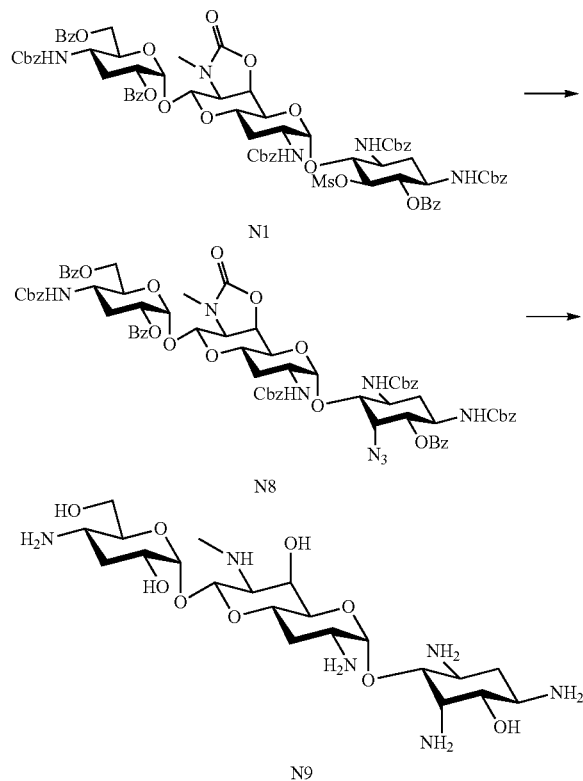

Examples 32-(i): Synthesis of 5-azide-2'',6''-di-O-benzoyl-1,3,2',4''-tetrakis-N-(benzyloxycarbonyl)-7'-N,6'-O-carbonyl-5,3''-dideoxy-5-epiapramycin (N8)

The title compound (N8) [375 mg (70%)] was obtained by a method similar to Example 16-(i) using 552 mg (0.37 mmol) of the title compound (N1) of Example 30-(i).
MS (ESI) m/z: 1445 (M+Na)$^+$.

Example 32-(ii): Synthesis of 5-amino-5,3''-dideoxy-5-epiapramycin (N9)

The title compound (N9) [66.8 mg (55%)] was obtained by a method similar to Example 27-(vii) using 322 mg (0.23 mmol) of the title compound (N8) of Example 32-(i).

MS (ESI) m/z: 523 (M+1)$^+$; $^1$H NMR (25% ND$_3$-D$_2$O, 500 MHz): δ 1.95 (1H, q, J=12.5 Hz, H-3''ax), 2.30 (1H, dt, J=4 and 12.5 Hz, H-3''eq), 3.93-4.05 (5H, m, H-2'', -5', -3'', -5 and -5''), 5.36 (1H, d, J=3.6 Hz, H-1') and 5.73 (1H, d, J=3.9 Hz, H-1'').

Example 33: Synthesis of 1,3,2'-tris-N-(benzyloxycarbonyl)-7'-N,6'-O-carbonyl-4''-N,6''-O-carbonyl-2''-deoxy-2'',3''-diepi-5,6-O-cyclohexylidene-3''-iodoapramycin (O1), 1,3,2'-tris-N-(benzyloxycarbonyl)-7'-N,6'-O-carbonyl-4''-N,6''-O-carbonyl-2''-deoxy-5,6-O-cyclohexylidene-3''-epiapramycin (O2), 6,3''-di-O-benzoyl-1,3,2'-tris-N-(benzyloxycarbonyl)-7'-N,6'-O-carbonyl-4''-N,6''-O-carbonyl-2''-deoxy-3''-epiapramycin (O3), 6,3''-di-O-benzoyl-1,3,2'-tris-N-(benzyloxycarbonyl)-7'-N,6'-O-carbonyl-4''-N,6''-O-carbonyl-5,2''-dideoxy-5,3''-diepi-5-fluoroapramycin (O4) and 5,2''-dideoxy-5,3''-diepi-5-fluoroapramycin (O5)

[Chem. 64]

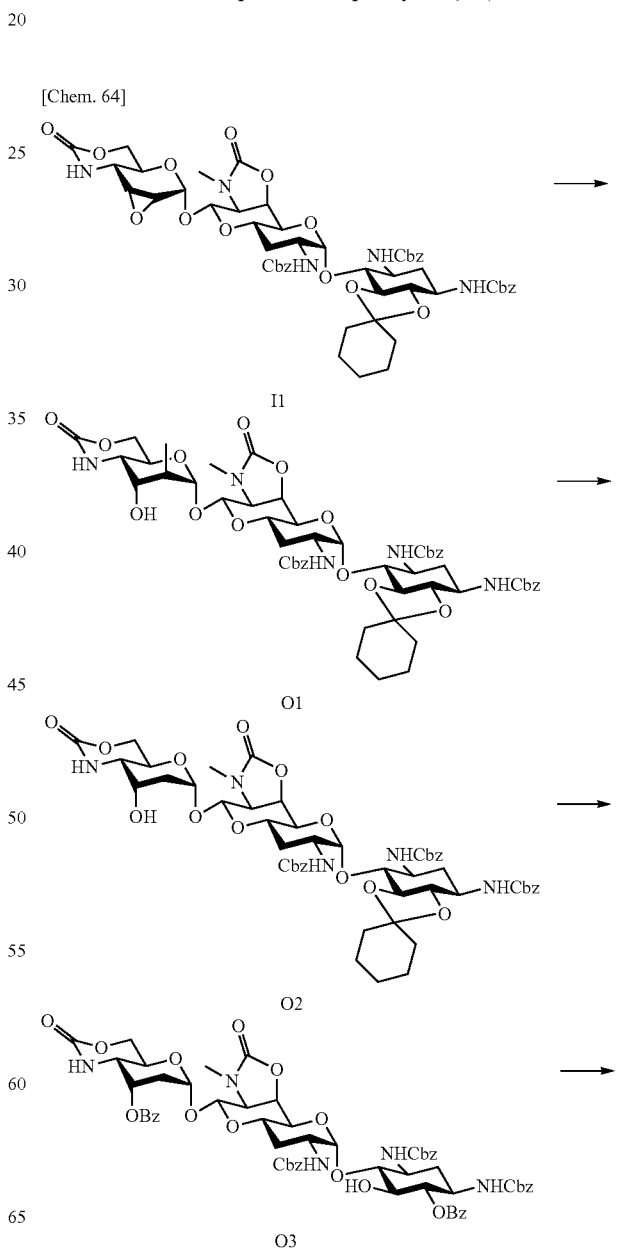

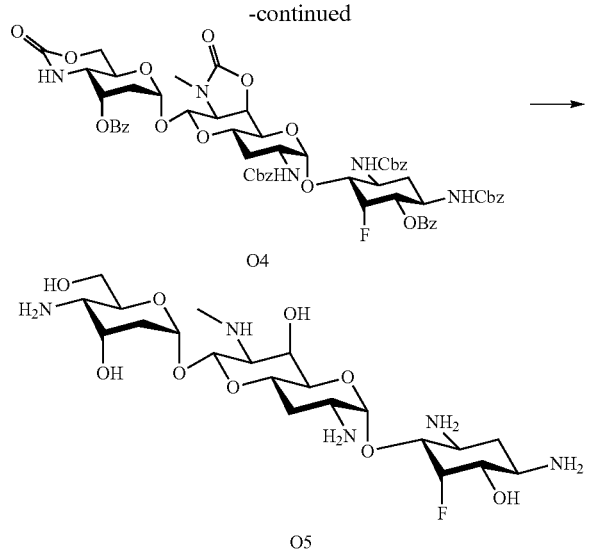

Examples 33-(i): Synthesis of 1,3,2'-tris-N-(benzyloxycarbonyl)-7'-N,6'-O-carbonyl-4"-N,6"-O-carbonyl-2"-deoxy-2",3"-diepi-5,6-O-cyclohexylidene-3"-iodoapramycin (O1)

The title compound (O1) [5.70 g (91%)] was obtained by a method similar to Example 14-(iii) using 5.60 g (5.30 mmol) of the title compound (I1) of Example 23-(i).
MS (ESI) m/z: 1206 (M+Na)$^+$.

Example 33-(ii): Synthesis of 1,3,2'-tris-N-(benzyloxycarbonyl)-7'-N,6'-O-carbonyl-4"-N,6"-O-carbonyl-2"-deoxy-5,6-O-cyclohexylidene-3"-epiapramycin (O2)

The title compound (O2) [4.94 g (99%)] was obtained by a method similar to Example 14-(iv) using 5.55 g (4.70 mmol) of the title compound (O1) of Example 33-(i).
MS (ESI) m/z: 1080 (M+Na)$^+$.

Example 33-(iii): Synthesis of 6,3"-di-O-benzoyl-1,3,2'-tris-N-(benzyloxycarbonyl)-7'-N,6'-O-carbonyl-4"-N,6"-O-carbonyl-2"-deoxy-3"-epiapramycin (O3)

The title compound (O3) [5.09 g (94%)] was obtained by a method similar to Example 27-(iv) using 4.85 g (4.59 mmol) of the title compound (O2) of Example 33-(ii).
MS (ESI) m/z: 1208 (M+Na)$^+$.

Example 33-(iv): Synthesis of 6,3"-di-O-benzoyl-1,3,2'-tris-N-(benzyloxycarbonyl)-7'-N,6'-O-carbonyl-4"-N,6"-O-carbonyl-5,2"-dideoxy-5,3"-diepi-5-fluoroapramycin (O4)

The title compound (O4) [332 mg (33%)] was obtained by a method similar to Examples 12-(iii) and (iv) using 1.00 g (0.84 mmol) of the title compound (O3) of Example 33-(iii).
MS (ESI) m/z: 1210 (M+Na)$^+$.

Example 33-(v): Synthesis of 5,2"-dideoxy-5,3"-diepi-5-fluoroapramycin (O5)

The title compound (O5) [48.5 mg (37%)] was obtained by a method similar to Example 27-(vii) using 300 mg (0.25 mmol) of the title compound (O4) of Example 33-(iv).

MS (ESI) m/z: 526 (M+1)$^+$; $^1$H NMR (25% ND$_3$-D$_2$O, 500 MHz): δ 2.30-2.40 (1H, m, H-2"ax), 2.37 (1H, dt, H-2"eq), 4.30 (1H, dd, H-3"), 5.31 (1H, d, H-1'), 5.35 (1H, d, H-5) and 5.60 (1H, d, H-1").

Example 34: Synthesis of 6,2",6"-tri-O-benzoyl-1,3,2'-tris-N-(benzyloxycarbonyl)-7'-N,6'-O-carbonyl-4"-N,3"-O-carbonyl-3"-epiapramycin (P1), 6,2",6"-tri-O-benzoyl-1,3,2'-tris-N-(benzyloxycarbonyl)-7'-N,6'-O-carbonyl-4"-N,3"-O-carbonyl-3"-epi-5-O-mesylapramycin (P2), 5-O-acetyl-6,2",6"-tri-O-benzoyl-1,3,2'-tris-N-(benzyloxycarbonyl)-7'-N,6'-O-carbonyl-4"-N,3"-O-carbonyl-5,3"-diepiapramycin (P3) and 5,3"-diepiapramycin (P4)

[Chem. 65]

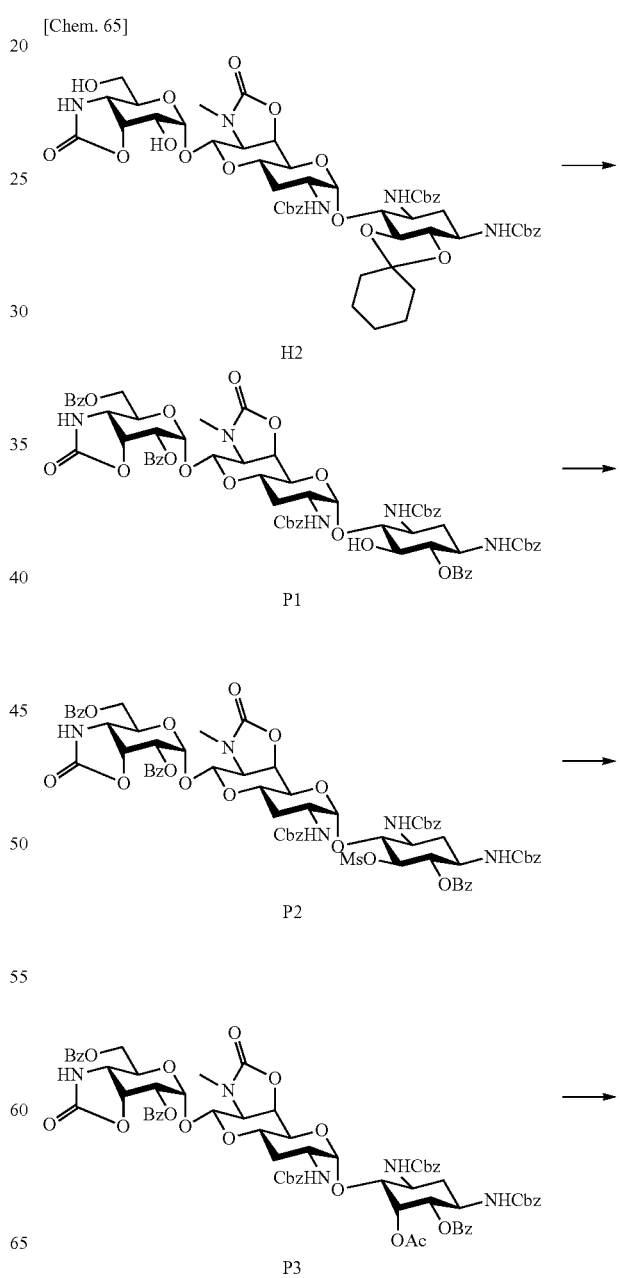

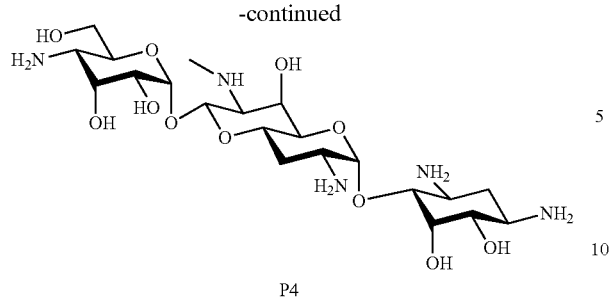

P4

Example 34-(i): Synthesis of 6,2″,6″-tri-O-benzoyl-1,3,2′-tris-N-(benzyloxycarbonyl)-7′-N,6′-O-carbonyl-4″-N,3″-O-carbonyl-3″-epiapramycin (P1)

The title compound (P1) [3.02 g (54%)] was obtained by a method similar to Example 27-(iv) using 2.60 g (2.41 mmol) of the title compound (H2) of Example 22-(ii).

MS (ESI) m/z: 1328 (M+Na)+.

Example 34-(ii): Synthesis of 6,2″,6″-tri-O-benzoyl-1,3,2′-tris-N-(benzyloxycarbonyl)-7′-N,6′-O-carbonyl-4″-N,3″-O-carbonyl-3″-epi-5-O-mesylapramycin (P2)

The title compound (P2) [3.05 g (95%)] was obtained by a method similar to Example 14-(i) using 2.92 g (2.24 mmol) of the title compound (P1) of Example 34-(i).

MS (ESI) m/z: 1406 (M+Na)+.

Example 34-(iii): Synthesis of 5-O-acetyl-6,2″,6″-tri-O-benzoyl-1,3,2′-tris-N-(benzyloxycarbonyl)-7′-N,6′-O-carbonyl-4″-N,3″-O-carbonyl-5,3″-diepiapramycin (P3)

A solution prepared by adding 745 mg of cesium acetate to a solution of 1.47 g (1.06 mmol) of the title compound (P2) of Example 34-(ii) dissolved in 15 ml of DMF was subjected to reaction at 90° C. for 5 hours. Ethyl acetate was added to the reaction solution and the mixture was washed with water twice and concentrated under reduced pressure. The resultant residue was purified by silica gel column chromatography (developing solvent, CHCl$_3$:MeOH=40:1) to give 1.07 g (75%) of the title compound (P3).

MS (ESI) m/z: 1370 (M+Na)+.

Examples 34-(iv): Synthesis of 5,3″-diepiapramycin (P4)

The title compound (P4) [168 mg (48%)] was obtained by a method similar to Example 27-(vii) using 886 mg (0.66 mmol) of the title compound (P3) of Example 34-(iii).

MS (ESI) m/z: 540 (M+1)+;

$^1$H NMR (25% ND$_3$-D$_2$O, 500 MHz): δ 1.92 (1H, q, H-2″ax), 4.18 (1H, t, H-3″), 4.48 (1H, t, H-5), 5.32 (1H, d, H-1′) and 5.46 (1H, d, H-1″).

Example 35: Synthesis of 1,3,2′-tris-N-(benzyloxycarbonyl)-4″-N-(t-butoxycarbonyl)-7′-N, 6′-O-carbonyl-6-deoxy-5-epiapramycin (Q1), 1,3,2′-tris-N-(benzyloxycarbonyl)-4″-N-(t-butoxycarbonyl)-7′-N, 6′-O-carbonyl-6″-chloro-6,6″-dideoxy-5-epiapramycin (Q2), 1,3,2′-tris-N-(benzyloxycarbonyl)-4″-N-(t-butoxycarbonyl)-7′-N, 6′-O-carbonyl-6,6″-dideoxy-5-epiapramycin (Q3) and 6,6″-dideoxy-5-epiapramycin (Q4)

[Chem. 66]

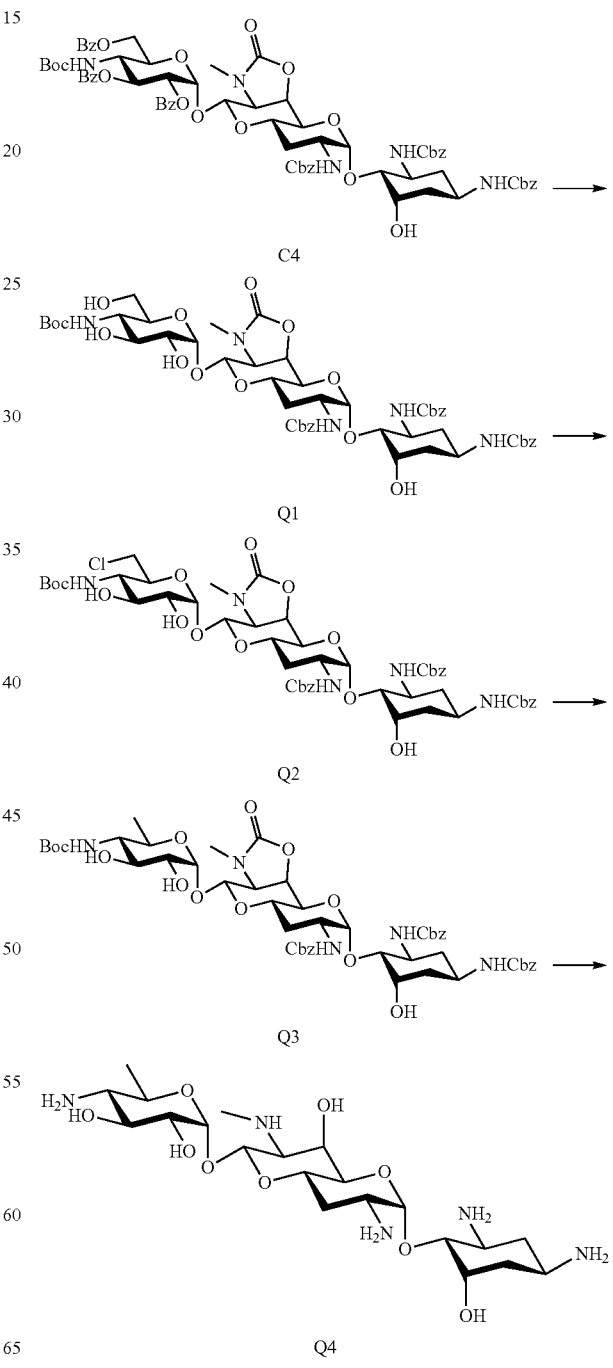

Example 35-(i): Synthesis of 1,3,2'-tris-N-(benzyloxycarbonyl)-4"-N-(t-butoxycarbonyl)-7'-N, 6'-O-carbonyl-6-deoxy-5-epiapramycin (Q1)

A solution prepared by adding 0.3 ml of 5 N NaOMe-methanol to a solution of 2.01 g (1.5 mmol) of the title compound (C4) of Example 14-(iv) dissolved in 20 ml of MeOH was subjected to reaction at room temperature for 2 hours. The reaction solution was concentrated under reduced pressure after neutralization with 1 N HCl under ice cooling, and the residue was washed with water. The residue was further washed with isopropyl ether and dried under reduced pressure to give 1.45 g (92%) of the title compound (Q1) as a colorless solid.

MS(ESI) m/z: 1074 (M+Na)$^+$.

Example 35-(ii): Synthesis of 1,3,2'-tris-N-(benzyloxycarbonyl)-4"-N-(t-butoxycarbonyl)-7'-N,6'-O-carbonyl-6"-chloro-6,6"-dideoxy-5-epiapramycin (Q2)

The title compound (Q2) [804 mg (87%)] was obtained by a method similar to Example 26-(ii) using 965 mg (0.86 mmol) of the title compound (Q1) of Example 35-(i).

MS (ESI) m/z: 1092 (M+Na)$^+$.

Example 35-(iii): Synthesis of 1,3,2'-tris-N-(benzyloxycarbonyl)-4"-N-(t-butoxycarbonyl)-7'-N,6'-O-carbonyl-6,6"-dideoxy-5-epiapramycin (Q3)

The title compound (Q3) (706 mg (93%)) was obtained by a method similar to Example 14-(iv) using 785 mg (0.73 mmol) of the title compound (Q2) of Example 35-(ii).

MS (ESI) m/z: 1058 (M+Na)$^+$.

Example 35-(iv): Synthesis of 6,6"-dideoxy-5-epiapramycin (Q4)

The title compound (Q4) (143 mg (41%)) was obtained by a method similar to Example 6-(iii) using 702 mg (0.68 mmol) of the title compound (Q3) of Example 35-(iii).

MS (ESI) m/z: 508 (M+1)$^+$; $^1$H NMR (25% ND$_3$-D$_2$O, 500 MHz): δ 1.32 (1H, q, J=12.5 Hz, H-6ax), 1.43 (3H, d, H-6"), 1.52 (1H, t, J=12.5 Hz, H-6eq), 4.49 (2H, br s, H-5 and H-6'), 5.16 (1H, d, J=3.5 Hz, H-1') and 5.47 (1H, d, J=3.5 Hz, H-1").

Example 36: Synthesis of 2",3",6"-tri-O-benzoyl-1,3,2'-tris-N-(benzyloxycarbonyl)-4"-N-(t-butoxycarbonyl)-7'-N,6'-O-carbonyl-5,6-dideoxy-5-enoapramycin (R1), 1,3,2'-tris-N-(benzyloxycarbonyl)-4"-N-(t-butoxycarbonyl)-7'-N, 6'-O-carbonyl-5,6-dideoxy-5-enoapramycin (R2), 1,3,2'-tris-N-(benzyloxycarbonyl)-4"-N-(t-butoxycarbonyl)-7'-N, 6'-O-carbonyl-6"-chloro-5-eno-5,6,6"-trideoxy-apramycin (R3), 1,3,2'-tris-N-(benzyloxycarbonyl)-4"-N-(t-butoxycarbonyl)-7'-N, 6'-O-carbonyl-5-eno-5,6,6"-trideoxyapramycin (R4) and 5-eno-5,6,6"-trideoxyapramycin (R5)

[Chem. 67]

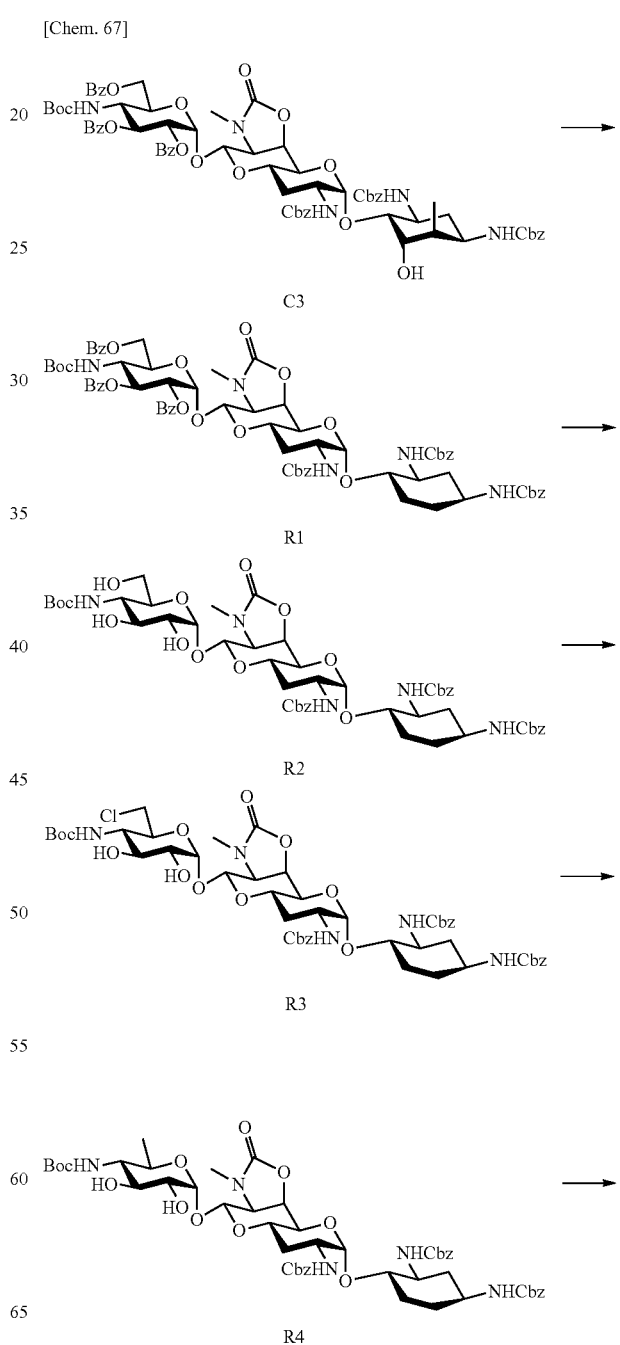

-continued

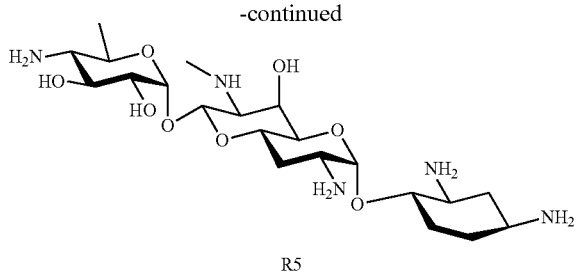

R5

Example 36-(i): Synthesis of 2",3",6"-tri-O-benzoyl-1,3,2'-tris-N-(benzyloxycarbonyl)-4"-N-(t-butoxycarbonyl)-7'-N,6'-O-carbonyl-5,6-dideoxy-5-enoapramycin (R1)

The title compound (R1) (2.24 g (82%)) was obtained by a method similar to Example 31-(i) using 3.01 g (2.02 mmol) of the title compound (C3) of Example 14-(iii).
MS (ESI) m/z: 1368 (M+Na)$^+$.

Example 36-(ii): Synthesis of 1,3,2'-tris-N-(benzyloxycarbonyl)-4"-N-(t-butoxycarbonyl)-7'-N, 6'-O-carbonyl-5,6-dideoxy-5-enoapramycin (R2)

The title compound (R2) (1.51 g (98%)) was obtained by a method similar to Example 26-(i) using 2.02 g (1.50 mmol) of the title compound (R1) of Example 36-(i).
MS (ESI) m/z: 1056 (M+Na)$^+$.

Example 36-(iii): Synthesis of 1,3,2'-tris-N-(benzyloxycarbonyl)-4"-N-(t-butoxycarbonyl)-7'-N, 6'-O-carbonyl-6"-chloro-5-eno-5,6,6"-trideoxyapramycin (R3)

The title compound (R3) (1.22 g (85%)) was obtained by a method similar to Example 26-(ii) using 1.40 g (1.36 mmol) of the title compound (R2) of Example 36-(ii).
MS (ESI) m/z: 1074 (M+Na)$^+$.

Example 36-(iv): Synthesis of 1,3,2'-tris-N-(benzyloxycarbonyl)-4"-N-(t-butoxycarbonyl)-7'-N, 6'-O-carbonyl-5-eno-5,6,6"-trideoxyapramycin (R4)

The title compound (R4) [976 mg (91%)] was obtained by a method similar to Example 14-(iv) using 1.10 g (1.05 mmol) of the title compound (R3) of Example 36-(iii).
MS (ESI) m/z: 1040 (M+Na)$^+$.

Example 36-(v): Synthesis of 5-eno-5,6,6"-trideoxyapramycin

A mixture prepared by adding 500 mg of metallic sodium and a solution of 1.00 g (0.98 mmol) of the title compound (R4) of Example 36-(iv) dissolved in 5 ml of THF to 50 ml of liquid ammonia at −50° C. was subjected to reaction at the same temperature as mentioned above for 0.5 hours. MeOH was added to the reaction solution until the color of the solution disappeared and concentrated. A mixture prepared by adding 10 ml of water to the residue was heated at 110° C. for 0.5 hours. After completion of the reaction, the reaction mixture was neutralized by adding 1 N aq. HCl under ice cooling and purified by ion exchange chromatography (CG50) to give 186 mg (39%) of the title compound (R5).

MS (ESI) m/z: 490 (M+1)$^+$; $^1$H NMR (25% ND$_3$-D$_2$O, 500 MHz): δ 1.44 (3H, d, H-6"), 5.25 (1H, d, H-1'), 5.51 (1H, d, H-1") and 6.03 (2H, s, H-5 and H-6).

Example 37: Synthesis of 5,6,6"-trideoxyapramycin (R6)

[Chem. 68]

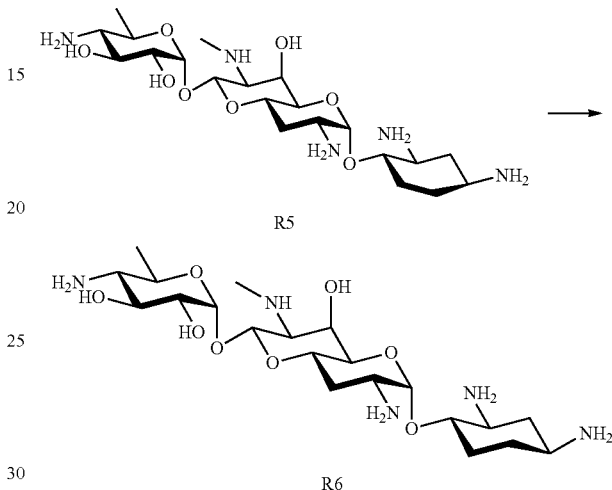

A mixture prepared by adding platinum oxide to a 10 ml aqueous solution of 100 mg (0.20 mmol) of the title compound (R5) of Example 36-(v) was subjected to catalytic reduction in a hydrogen atmosphere at room temperature for 3 hours. After filtration, the reaction solution was purified by ion exchange chromatography (CG50) to give 92.1 mg (92%) of the title compound (R6).

MS (ESI) m/z: 492 (M+1)$^+$; $^1$H NMR (25% ND$_3$-D$_2$O, 500 MHz): δ 1.46 (3H, d, H-6"), 1.42-1.67 (3H, m, H-2ax, -6ax and -5ax), 2.25 (1H, m, H-6eq), 2.41-2.52 (2H, m, H-3'eq and -5eq), 5.34 (1H, d, H-1') and 5.70 (1H, d, H-1").

Example 38: Synthesis of 1,3,2'-tris-N-(benzyloxycarbonyl)-7'-N,6'-O-carbonyl-5-deoxyapramycin (S-a), 4"-N-benzyl-1,3,2'-tris-N-(benzyloxycarbonyl)-7'-N,6'-O-carbonyl-5-deoxyapramycin (S2-a) and 5-deoxy-4"-N-methylapramycin (S1-a)

[Chem. 69]

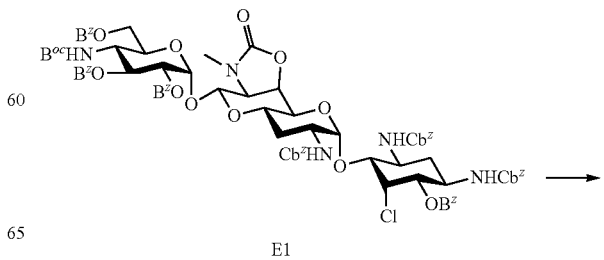

E1

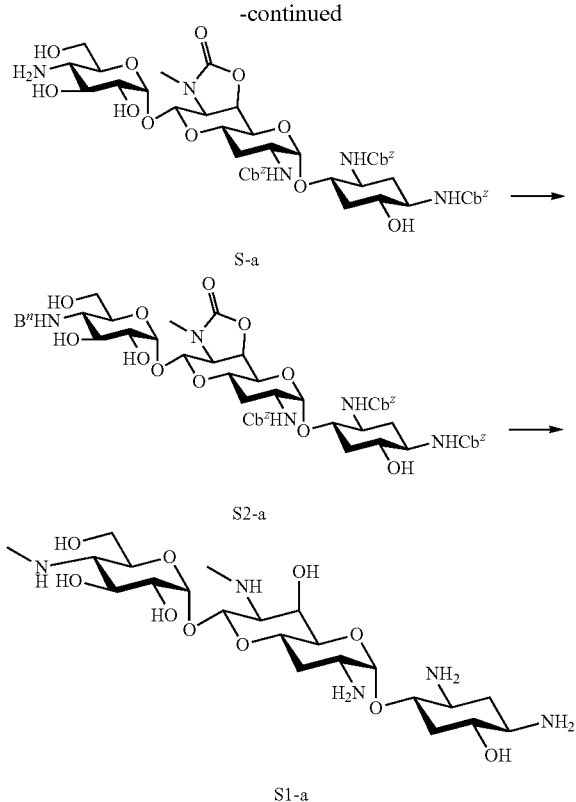

S-a

S2-a

S1-a

Example 38-(i): Synthesis of 1,3,2'-tris-N-(benzyloxycarbonyl)-7'-N,6'-O-carbonyl-5-deoxyapramycin (S-a)

The title compound (S-a) [939 mg (93% as TFA salt)] was obtained by a method similar to Example 14-(iv) and Example 12-(v) using 1.46 g (0.97 mmol) of the title compound (E1) of Example 17-(i).

MS (ESI) m/z: 974 (M+Na)⁺.

Example 38-(ii): Synthesis of 4''-N-benzyl-1,3,2'-tris-N-(benzyloxycarbonyl)-7'-N,6'-O-carbonyl-5-deoxyapramycin (S2-a)

The title compound (S2-a) [209 mg (95%)] as a colorless solid was obtained by a method similar to Example 1-(iv) using 221 mg (0.21 mmol as TFA salt) of the title compound (S-a) of Example 38-(i).

MS (ESI) m/z: 1064 (M+Na)⁺.

Example 38-(iii): Synthesis of 5-deoxy-4''-N-methylapramycin (S1-a)

The title compound (S1-a) [38 mg (47%)] was obtained by a method similar to Example 1-(v) using 150 mg (0.15 mmol) of the title compound (S2-a) of Example 38-(ii).

MS (ESI) m/z: 538 (M+H)⁺;

¹H NMR (25% ND$_3$-D$_2$O, 500 MHz): δ 1.65 (1H, q, H-5ax), 2.64-2.79 (7H, m, H-5eq, 7'-NMe and 4''-NMe), 5.29 (1H, d, H-1') and 5.67 (1H, d, H-1'').

Example 39: Synthesis of 4''-N-(2-aminoethyl)-5-deoxyapramycin (S1-b)

[Chem. 70]

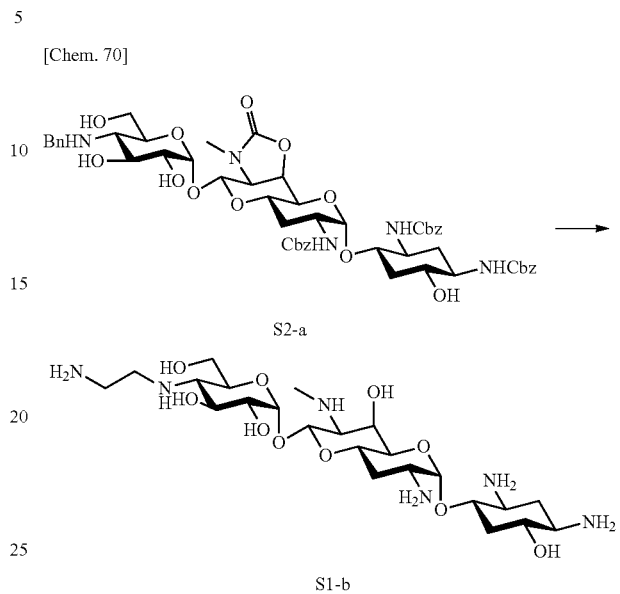

S1-b

The title compound (S1-b) [34 mg (72%)] was obtained by a method similar to Example 3 using 96 mg (0.09 mmol) of the title compound (S2-a) of Example 38-(ii) and 18 mg of N-Boc-2-aminoacetaldehyde.

MS (ESI) m/z: 567 (M+1)⁺;

¹H NMR (25% ND$_3$-D$_2$O, 500 MHz): δ 1.66 (1H, q, H-5ax), 2.68-2.78 (4H, m, H-5eq and 7'-NMe), 2.92 (1H, t, H-4''), 3.01-3.13 [5H, m, H-1 and 4''-NH$_2$Et(β, α)], 5.30 (1H, d, H-1') and 5.69 (1H, d, H-1'').

Example 40: Synthesis of 4''-N-(3-aminopropyl)-5-deoxyapramycin (S1-c)

[Chem. 71]

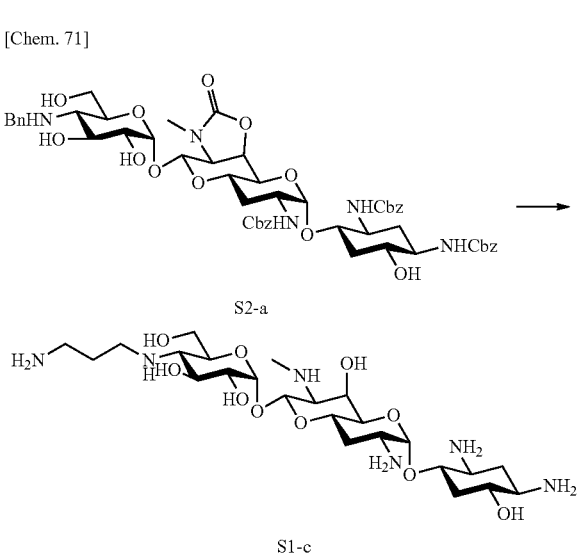

S1-c

The title compound (S1-c) [62.5 mg (53%)] was obtained by a method similar to Example 1-(v) using 200 mg (0.2 mmol as TFA salt) of the title compound (S2-a) of Example 38-(i) and 48 mg of 3-[(benzyloxycarbonyl)amino] propionaldehyde.

MS (ESI) m/z: 581 (M+1)$^+$; $^1$H NMR (25% ND$_3$-D$_2$O, 500 MHz): δ 1.91-2.05 [2H, m, 4"-NH$_2$Pr(β) and H-3'ax], 2.65-2.78 (4H, m, H-5eq and 7'-NMe), 2.88 (1H, t, H-4"), 2.94-3.09 [6H, m, H-1, -7' and 4"-NH$_2$Pr(α, γ)], 3.63 (1H, dd, H-6), 5.28 (1H, d, H-1') and 5.67 (1H, d, H-1").

Example 41: Synthesis of 4"-N-(1,3-diaminopropan-2-yl)-5-deoxyapramycin (S1-d)

[Chem. 72]

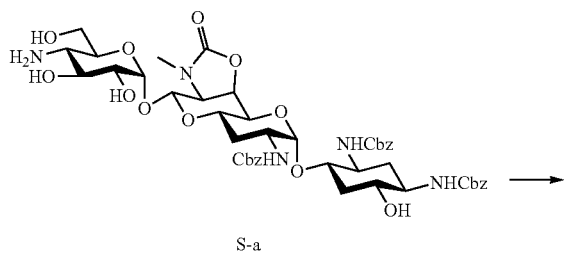

S-a

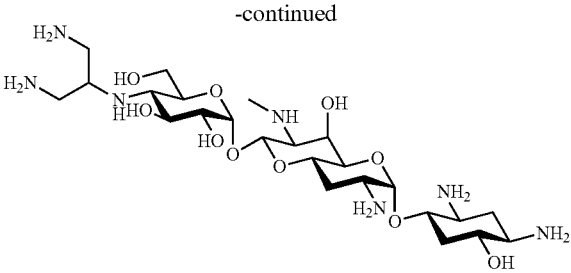

S1-d

The title compound (S1-d) [70.5 mg (59%)] was obtained by a method similar to Example 1-(v) using 190 mg (0.2 mmol as TFA salt) of the title compound (S-a) of Example 38-(i) and 90 mg of 1,3-bis[(benzyloxycarbonyl)amino] propan-2-one.

MS (ESI) m/z: 596 (M+1)$^+$; $^1$H NMR (DCl-D$_2$O, 500 MHz): δ 1.45 (1H, q, J=12 Hz, H-5ax), 1.75 (1H, q, J=12.5 Hz, H-2ax), 2.01 (1H, q, J=12 Hz, H-3'ax), 2.35 (1H, dt, J=4.5, 4.5 and 12 Hz, H-3'eq), 2.45 (1H, dt, J=4, 4 and 12.5 Hz, H-2eq), 2.67 (1H, t, J=10 Hz, H-4"), 2.75 (3H, s, NCH$_3$), 3.34 (1H, dd, J=3 and 8.5 Hz, H-7'), 4.55 (1H, t, J=3 Hz, H-6'), 5.13 (1H, d, J=8.5 Hz, H-8'), 5.35 (1H, d, J=3.8 Hz, H-1') and 5.38 (1H, d, J=4 Hz, H-1").

Example 42: Synthesis of 4"-deamino-5-deoxy-4"-guanidinoapramycin (S1-e)

[Chem. 73]

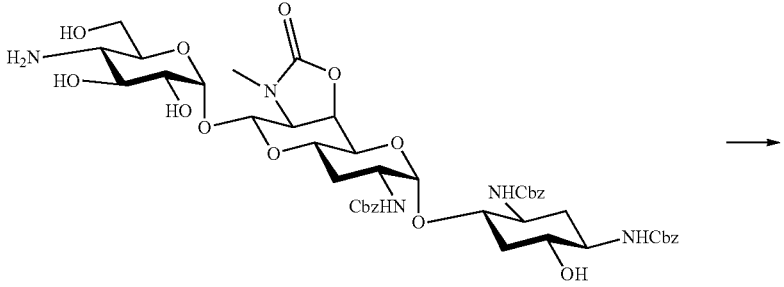

S-a

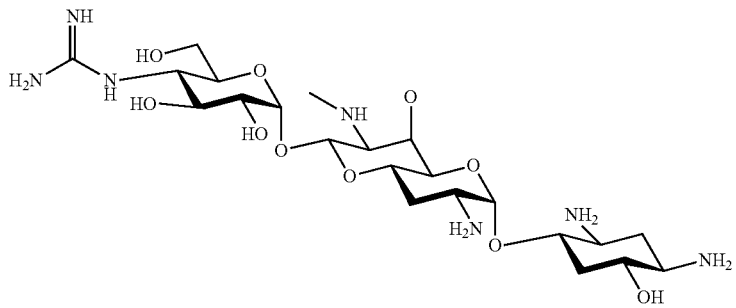

S1-e

The title compound (S1-e) [76.2 mg (45%)] was obtained by a method similar to Example 10 using 290 mg (0.3 mmol as TFA salt) of the title compound (S-a) of Examples 38-(i) and 310 mg of Goodman's reagent.

MS (ESI) m/z: 566 (M+1)+; $^1$H NMR (DCl-D$_2$O, 500 MHz): δ 1.76 (1H, q, H-5ax), 2.46 (1H, ddd, H-5eq), 5.36 (1H, d, H-1') and 5.45 (1H, d, H-1"), $^{13}$C NMR (DCl-D$_2$O, 125 MHz): δ 157.52 (C=NH).

Example 43: Synthesis of 4"-N-benzyl-1,3,2'-tris-N-(benzyloxycarbonyl)-7'-N,6'-O-carbonyl-5-epi-apramycin (S2-b) and 5-epi-4"-N-methylapramycin (S1-f)

[Chem. 74]

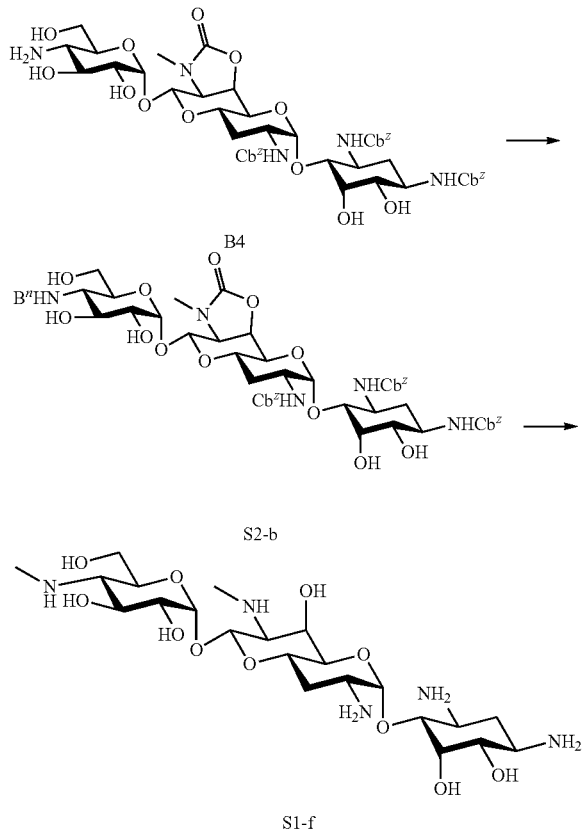

Example 43-(i): Synthesis of 4"-N-benzyl-1,3,2'-tris-N-(benzyloxycarbonyl)-7'-N,6'-O-carbonyl-5-epiapramycin (S2-b)

The title compound (S2-b) [2.34 g (96%)] as a colorless solid was obtained by a method similar to Example 1-(iv) using 2.52 g (2.3 mmol as TFA salt) of the title compound (B4) of Example 12-(v).

MS (ESI) m/z: 1080 (M+Na)+.

Example 43-(ii): Synthesis of 5-epi-4"-N-methyl-apramycin (S1-f)

The title compound (S1-f) [113 mg (72%)] was obtained by a method similar to Example 1-(v) using 320 mg (0.30 mmol) of the title compound (S2-b) of Example 43-(i) and 0.1 ml of 37% formalin.

MS (ESI) m/z: 554 (M+1)+; $^1$H NMR (25% ND$_3$-D$_2$O, 500 MHz): δ 2.77 (6H, s, 4"-NMe and 7'-NMe), 4.55 (1H, t, H-5), 5.35 (1H, d, H-1') and 5.68 (1H, d, H-1").

Example 44: Synthesis of 4"-N-(2-aminoethyl)-5-epiapramycin (S1-g)

[Chem. 75]

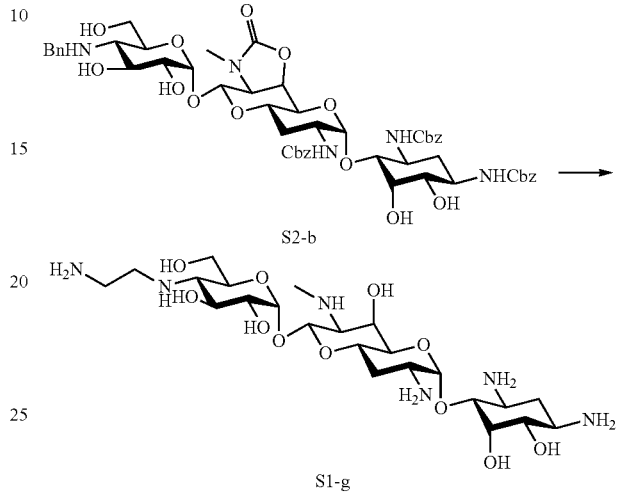

The title compound (S1-g) [94.5 mg (51%)] was obtained by a method similar to Example 3 using 342 mg (0.32 mmol) of the title compound (S2-b) of Example 43-(i) and 52 mg of N-Boc-2-aminoacetaldehyde.

MS (ESI) m/z: 583 (M+1)+; $^1$H NMR (25% ND$_3$-D$_2$O, 500 MHz): δ 3.02-3.14 (4H, m, 4"-NH$_2$Et(β, α)), 4.57 (1H, m, H-5), 5.34 (1H, d, H-1') and 5.70 (1H, d, H-1").

Example 45: Synthesis of 4"-N-(3-aminopropyl)-5-epiapramycin (S1-h)

[Chem. 76]

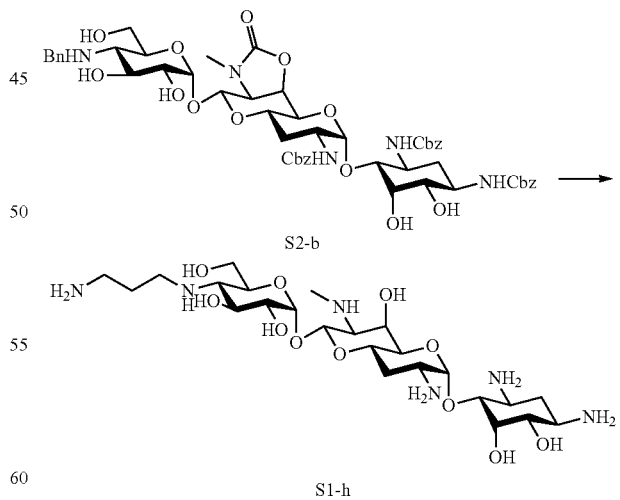

The title compound (S1-h) [87.1 mg (48%)] was obtained by a method similar to Example 1-(v) using 333 mg (0.31 mmol) of the title compound (S2-b) of Example 43-(i) and 80 mg of 3-[(benzyloxycarbonyl)amino]propionaldehyde.

MS (ESI) m/z: 597 (M+1)+; $^1$H NMR (25% ND$_3$-D$_2$O, 500 MHz): δ 1.98 [2H, m, 4"-NH$_2$Pr(β)], 2.92-3.08 (5H, m,

H-7' and 4"-NH$_2$Pr($\alpha$, $\gamma$)), 4.65 (1H, m, H-5), 5.33 (1H, d, H-1') and 5.66 (1H, d, H-1").

Example 46: Synthesis of 4"-N-(1,3-diaminopropan-2-yl)-5-epiapramycin (S1-i)

[Chem. 77]

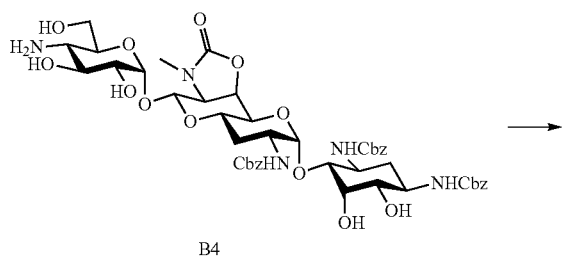

B4

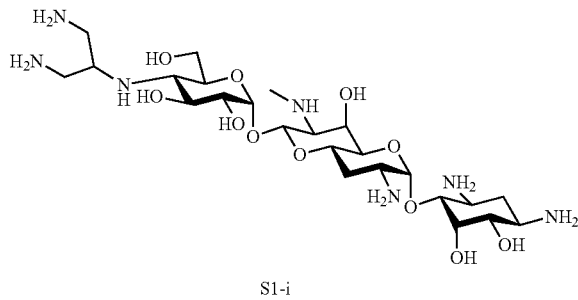

S1-i

The title compound (S1-i) [73.4 mg (54%)] was obtained by a method similar to Example 1-(v) using 250 mg (0.23 mmol as TFA salt) of the title compound (B4) of Example 12-(v) and 90 mg of 1,3-bis[(benzyloxycarbonyl)amino]propan-2-one.

MS (ESI) m/z: 596 (M+1)$^+$; $^1$H NMR (TFA salt, 500 MHz, D$_2$O): δ 1.70 (1H, q, J=12.5 Hz, H-2ax), 2.03 (1H, q, J=12 Hz, H-3"ax), 2.36 (1H, dt, J=4.5, 4.5 and 12 Hz, H-3'eq), 2.43 (1H, dt, J=4.5, 4.5 and 12.5 Hz, H-2eq), 2.65 (1H, t, J=10 Hz, H-4"), 2.73 (3H, s, NCH$_3$), 3.29 (1H, dd, J=3 and 8.5 Hz, H-7"), 3.95 (1H, dd, J=2.5 and 11 Hz, H-4), 4.46 (1H, t, J=2.5 Hz, H-5eq), 4.50 (1H, t, J=3 Hz, H-6'), 5.16 (1H, d, J=8.5 Hz, H-8') and 5.37 (2H, d, J=4 Hz, H-1' and H-1").

Example 47: Synthesis of 4"-deamino-5-epi-4"-guanidinoapramycin (S1-j)

[Chem. 78]

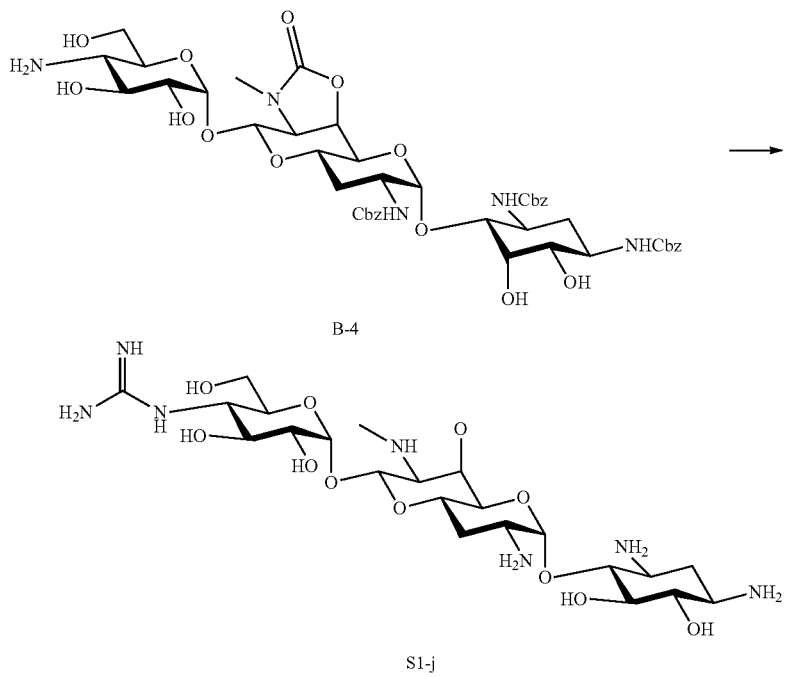

The title compound (S1-j) [65.8 mg (43%)] was obtained by a method similar to Example 10 using 285 mg (0.26 mmol as TFA salt) of the title compound (B4) of Example 12-(v) and 273 mg of Goodman's reagent.

MS (ESI) m/z: 550 (M+1)$^+$; $^1$H NMR (TFA salt, 500 MHz, D$_2$O): δ 1.71 (1H, q, J=12.5 Hz, H-2ax), 2.05 (1H, q, J=12 Hz, H-3' ax), 2.38 (1H, dt, J=4.5, 4.5 and 12 Hz, H-3'eq), 2.46 (1H, dt, J=4.5, 4.5 and 12.5 Hz, H-2eq), 2.75 (3H, s, NCH$_3$), 3.31 (1H, dd, J=3 and 8.5 Hz, H-7'), 3.52 (1H, t, J=10 Hz, H-4"), 4.47 (1H, slightly br t, J=~2.5 Hz, H-5), 4.51 (1H, slightly br t, J=~3 Hz, H-6'), 5.19 (1H, d, J=8.5 Hz, H-8'), 5.39 (1H, d, J=3.8 Hz, H-1') and 5.45 (1H, d, J=4 Hz, H-1").

Example 48: Synthesis of 4"-deamino-5-deoxy-5-epi-5-fluoro-4"-guanidinoapramycin (S1-k)

[Chem. 79]

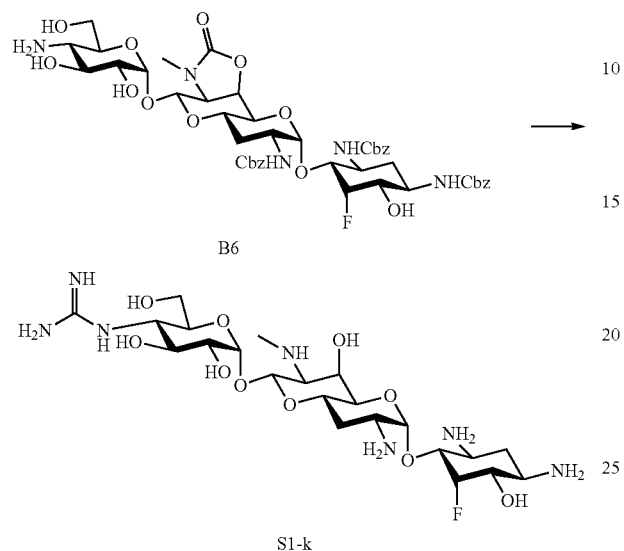

The title compound (S1-k) [77.1 mg (45%)] was obtained by a method similar to Example 10 using 305 mg (0.32 mmol as TFA salt) of the title compound (B6) of Example 13-(i) and 280 mg of Goodman's reagent.

MS (ESI) m/z: 552 (M+1)$^+$; $^1$H NMR (TFA salt, 500 MHz, D$_2$O): δ 1.80 (1H, q, J=12.5 Hz, H-2ax), 2.05 (1H, q, J=12 Hz, H-3'ax), 2.38 (1H, dt, J=4.5, 4.5 and 12 Hz, H-3'eq), 2.51 (1H, dt, J=4.5, 4.5 and 12.5 Hz, H-2eq), 2.74 (3H, s, NCH$_3$), 3.32 (1H, dd, J=2.5 and 8.5 Hz, H-7'), 3.52 (1H, t, J=10 Hz, H-4"), 4.14 (1H, ddd, J=~1.5, 11 and 26 Hz, H-4), 4.52 (1H, slightly br t, J=~3 Hz, H-6'), 5.35 (1H, slightly br dt, J=~2,~2 and 52 Hz, H-5), 5.19 (1H, d, J=8.5 Hz, H-8') and 5.43-5.57 (2H, H-1' and H-1").

Example 49: Synthesis of 1,3,2'-tris-N-(benzyloxycarbonyl)-7'-N,6'-O-carbonyl-5,6-dideoxy-5-enoapramycin (T1), 4"-N-benzyl-1,3,2'-tris-N-(benzyloxycarbonyl)-7'-N,6'-O-carbonyl-5,6-dideoxy-5-enoapramycin (T3) and 5,6-dideoxy-4"-N-methylapramycin (T2-a)

[Chem. 80]

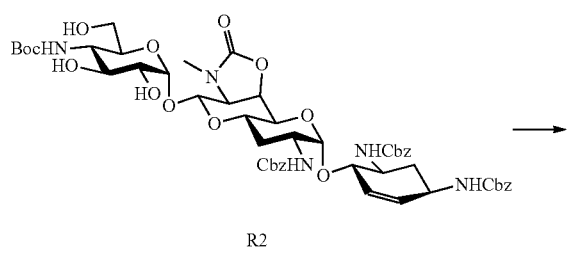

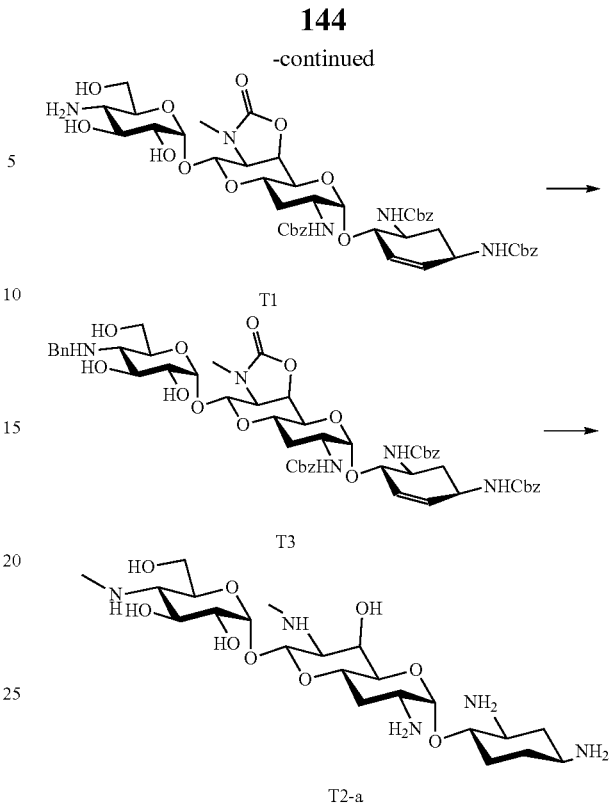

Examples 49-(i): Synthesis of 1,3,2'-tris-N-(benzyloxycarbonyl)-7'-N,6'-O-carbonyl-5,6-dideoxy-5-enoapramycin (T1)

The title compound (T1) [2.58 g (94% as TFA salt)] was obtained by a method similar to Example 14-(vi) using 3.50 g (2.6 mmol) of the title compound (R2) of Example 36-(ii).

MS (ESI) m/z: 956 (M+Na)$^+$.

Example 49-(ii): Synthesis of 4"-N-benzyl-1,3,2'-tris-N-(benzyloxycarbonyl)-7'-N,6'-O-carbonyl-5,6-dideoxy-5-enoapramycin (T3)

The title compound (T3) [1.38 g (92%)] as a colorless solid was obtained by a method similar to Example 1-(iv) using 1.46 g (1.3 mmol as TFA salt) of title compound of Example 49-(i).

MS (ESI) m/z: 1046 (M+Na)$^+$.

Example 49-(iii): Synthesis of 5,6-dideoxy-4"-N-methylapramycin (T2-a)

The title compound (T2-a) [97.3 mg (62%)] was obtained by a method similar to Example 1-(v) using 310 mg (0.30 mmol) of the title compound (T3) of Example 49-(ii) and 0.1 ml of 37% formalin.

MS (ESI) m/z: 522 (M+1)$^+$; $^1$H NMR (25% ND$_3$-D$_2$O, 500 MHz): δ 1.42-1.67 (3H, m, H-2ax, -6ax and -5ax), 2.25 (1H, m, H-6eq), 2.41-2.52 (2H, m, H-3'eq and -5eq), 2.75 (6H, s, 4"-NMe and 7'-NMe), 5.32 (1H, d, H-1') and 5.71 (1H, d, H-1").

Example 50: Synthesis of 4''-N-(2-aminoethyl)-5,6-dideoxyapramycin (T2-b)

[Chem. 81]

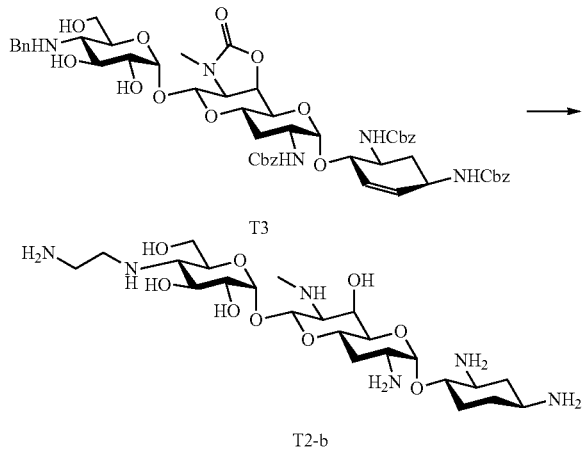

The title compound (T2-b) [96.5 mg (61%)] was obtained by a method similar to Example 3 using 300 mg (0.29 mmol) of the title compound (T3) of Example 49-(ii) and 50 mg of N-Boc-2-aminoacetaldehyde.

MS (ESI) m/z: 551 (M+1)$^+$;

$^1$H NMR (25% ND$_3$-D$_2$O, 500 MHz): δ 1.43-1.67 (3H, m, H-2ax, -6ax and -5ax), 2.25 (1H, m, H-6eq), 2.39-2.51 (2H, m, H-3'eq and -5eq), 3.02-3.14 [4H, m, 4''-NH$_2$Et(α, β)], 5.32 (1H, d, H-1') and 5.70 (1H, d, H-1'').

Example 51: Synthesis of 4''-N-(3-aminopropyl)-5,6-dideoxyapramycin (T2-c)

[Chem. 82]

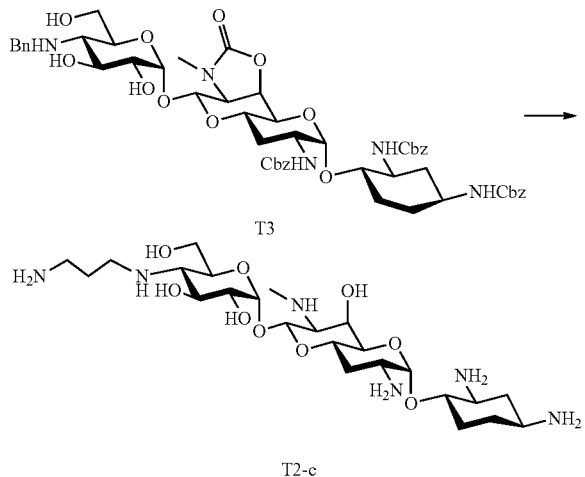

The title compound (T2-c) [88.2 mg (54%)] was obtained by a method similar to Example 1-(v) using 303 mg (0.29 mmol) of the title compound (T3) of Example 49-(ii) and 80 mg of 3-[(benzyloxycarbonyl)amino]propionaldehyde.

MS (ESI) m/z: 565 (M+1)$^+$; $^1$H NMR (25% ND$_3$-D$_2$O, 500 MHz): δ 1.43-1.67 (3H, m, H-2ax, -6ax and -5ax), 2.25 (1H, m, H-6eq), 2.39-2.50 (2H, m, H-3'eq and H-5eq), 2.92-3.08 [5H, m, H-7' and 4''-NH$_2$Pr(α, γ)], 5.31 (1H, d, H-1') and 5.70 (1H, d, H-1'').

Example 52: Synthesis of 4''-N-(1,3-diaminopropan-2-yl)-5,6-dideoxyapramycin (T2-d)

[Chem. 83]

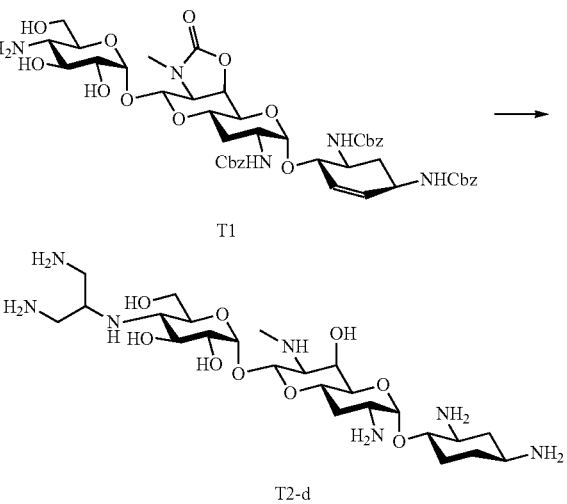

The title compound (T2-d) [76.4 mg (47%)] was obtained by a method similar to Example 1-(v) using 301 mg (0.29 mmol as TFA salt) of the title compound (T3) of Example 49-(i) and 100 mg of 1,3-bis[(benzyloxycarbonyl)amino]propan-2-one.

MS (ESI) m/z: 580 (M+1)$^+$; $^1$H NMR (TFA salt, 500 MHz, D$_2$O): δ 1.33 (1H, slightly br dq, J=~3.5,~12,~12 and ~12 Hz, H-5ax), 1.52 (1H, dq, J=3, 13, 13 and 13 Hz, H-6ax), 1.72 (1H, q, J=12 Hz, H-2ax), 2.00 (1H, q, J=12 Hz, H-3'ax), 2.15 (1H, m, H-6eq), 2.34 (1H, dt, J=4, 4 and 12 Hz, H-3'eq), 2.42 (2H, m, H-2eq and H-5eq), 2.67 (1H, t, J=10 Hz, H-4''), 2.75 (3H, s, NCH$_3$), 3.34 (1H, dd, J=3 and 8.5 Hz, H-7'), 4.54 (1H, t, J=3 Hz, H-6'), 5.16 (1H, d, J=8.5 Hz, H-8'), 5.34 (1H, d, J=4 Hz, H-1') and 5.38 (1H, d, J=4 Hz, H-1'').

Example 53: Synthesis of 4''-deamino-5,6-dideoxy-4''-guanidinoapramycin (T2-e)

[Chem. 84]

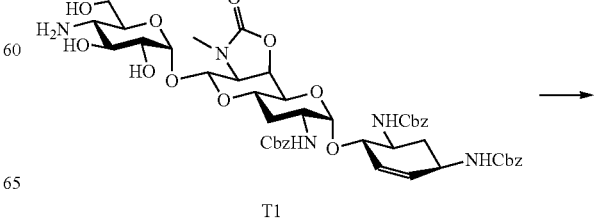

-continued

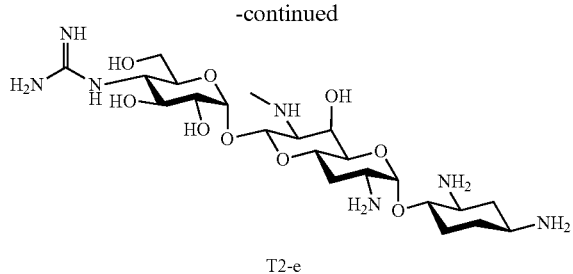

T2-e

The title compound (T2-e) [61.3 mg (43%)] was obtained by a method similar to Example 10 using 275 mg (0.26 mmol as TFA salt) of the title compound (T3) of Example 49-(i) and 270 mg of Goodman's reagent.
MS (ESI) m/z: 550 (M+1)+.

Example 54: Synthesis of 4"-N-benzyl-1,3,2'-tris-N-(benzyloxycarbonyl)-7'-N,6'-O-carbonyl-6-deoxy-5-epiapramycin (S2-c) and 6-deoxy-5-epi-4"-N-methylapramycin (S1-I)

[Chem. 85]

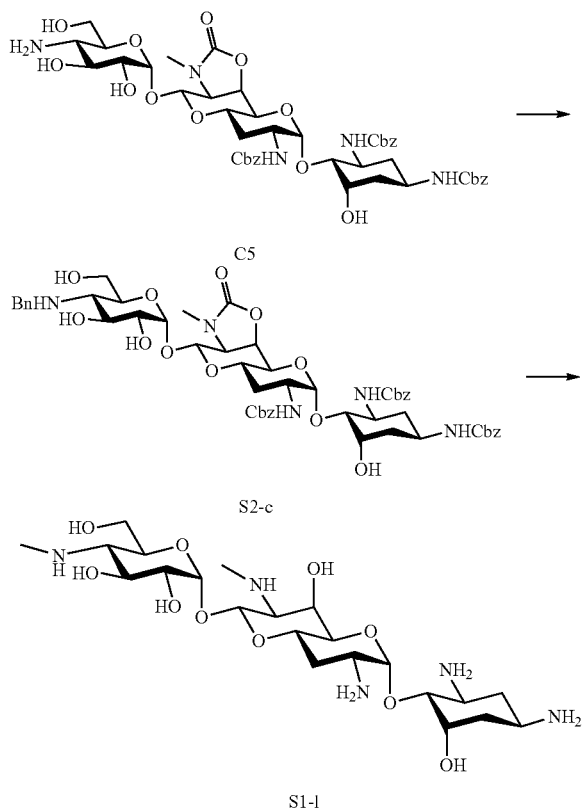

Example 54-(i): Synthesis of 4"-N-benzyl-1,3,2'-tris-N-(benzyloxycarbonyl)-7'-N,6'-O-carbonyl-6-deoxy-5-epiapramycin (S2-c)

The title compound (S2-c) [1.63 g (92%)] as a colorless solid was obtained by a method similar to Example 1-(iv) using 1.78 g (1.7 mmol as TFA salt) of the title compound (C5) of Example 14-(iv).
MS (ESI) m/z: 1064 (M+Na)+.

Example 54-(ii): Synthesis of 6-deoxy-5-epi-4"-N-methylapramycin (S1-1)

The title compound (S1-I) [105 mg (67%)] was obtained by a method similar to Example 1-(v) using 300 mg (0.29 mmol) of the title compound (S2-c) of Example 54-(i) and 0.1 ml of 37% formalin.
MS (ESI) m/z: 538 (M+1)+; $^1$H NMR (25% ND$_3$-D$_2$O, 500 MHz): δ 1.72 (1H, ddd, H-6ax), 2.35-2.43 (2H, m, H-2eq and H-6eq), 2.75 (6H, s, 4"-NMe and 7'-NMe), 4.67 (1H, m, H-5), 5.34 (1H, d, H-1') and 5.70 (1H, d, H-1").

Example 55: Synthesis of 6-deoxy-4"-N-(2-aminoethyl)-5-epiapramycin (S1-m)

[Chem. 86]

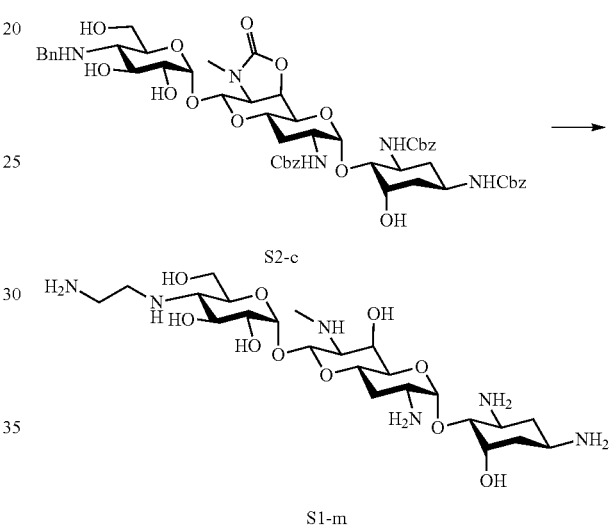

The title compound (S1-m) [87.0 mg (53%)] was obtained by a method similar to Examples 3 using 302 mg (0.29 mmol) of the title compound (S2-c) of Example 54-(i) and 52 mg of N-Boc-2-aminoacetaldehyde.
MS (ESI) m/z: 566 (M+1)+; $^1$H NMR (25% ND$_3$-D$_2$O, 500 MHz): δ 1.70 (1H, ddd, H-6ax), 2.32-2.41 (2H, m, H-2eq and 6eq), 3.02-3.14 [4H, m, 4"-NH$_2$Et(α,β)], 4.62-4.68 (2H, m, H-6' and H-5), 5.24 (1H, d, H-8'), 5.32 (1H, d, H-1'), 5.68 (1H, d, H-1").

Example 56: Synthesis of 6-deoxy-4"-N-(3-aminopropyl)-5-epiapramycin (S1-n)

[Chem. 87]

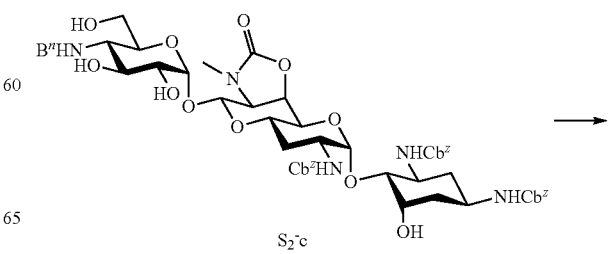

-continued

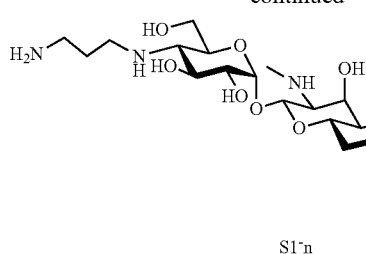

S1-n

The title compound (S1-n) [79.1 mg (47%)] was obtained by a method similar to Example 1-(v) using 303 mg (0.29 mmol) of the title compound (S2-c) of Example 54-(i) and 83 mg of 3-[(benzyloxycarbonyl)amino]propionaldehyde.

MS (ESI) m/z: 581 (M+1)$^+$; $^1$H NMR (25% ND$_3$-D$_2$O, 500 MHz): δ 1.68 (1H, ddd, H-6ax), 1.92-1.98 (2H, m, 4″-NH$_2$Pr(β)), 2.31-2.40 (2H, m, H-2eq and -6eq), 2.92-3.08 (5H, m, H-7′ and 4″-NH$_2$Pr(α, γ)), 4.65 (1H, m, H-5), 5.30 (1H, d, H-1′) and 5.66 (1H, d, H-1″).

Example 57: Synthesis of 4″-deamino-6-deoxy-5-epi-4″-guanidinoapramycin (S1-o)

[Chem. 88]

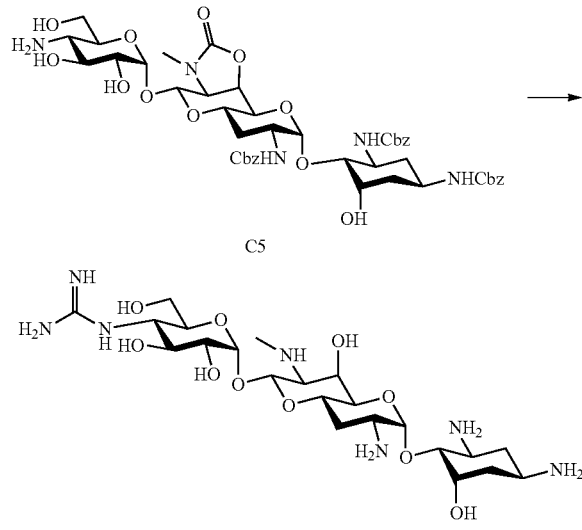

S1-o

The title compound (S1-o) [67.5 mg (46%)] was obtained by a method similar to Example 10 using 285 mg (0.26 mmol as TFA salt) of the title compound (C5) of Example 14-(vi) and 273 mg of Goodman's reagent.

MS (ESI) m/z: 566 (M+1)$^+$; $^1$H NMR (25% ND$_3$-D$_2$O, 500 MHz): δ 1.74 (1H, ddd, H-6ax), 2.36-2.42 (2H, m, H-2eq and -6eq), 4.68 (1H, m, H-5), 5.35 (1H, d, H-1′) and 5.75 (1H, d, H-1″), $^{13}$C NMR (25% ND$_3$-D$_2$O, 125 MHz): δ 158.3 (C=NH).

Example 58: Synthesis of 4″-N-(1,3-diaminopropan-2-yl)-5,6″-dideoxyapramycin (S1-p)

[Chem. 89]

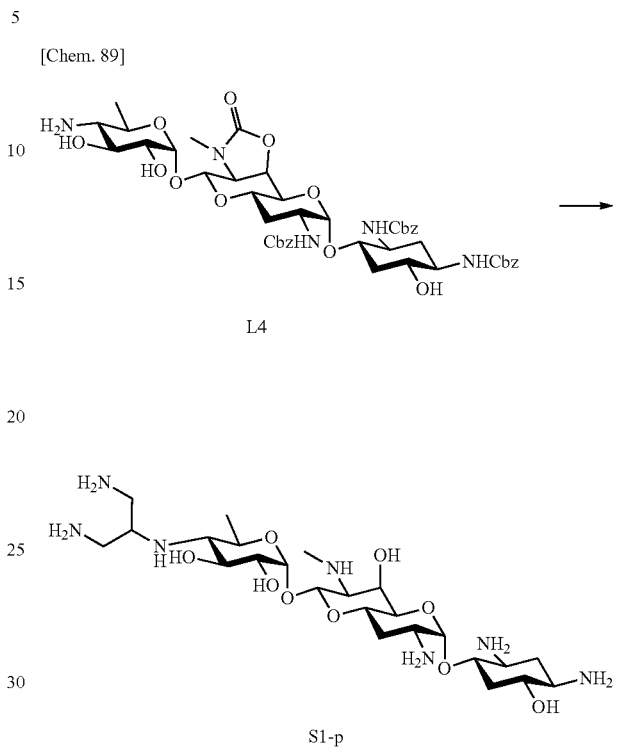

S1-p

The title compound (S1-p) [18.1 mg (39%)] was obtained by a method similar to Example 1-(v) using 83.9 mg (0.081 mmol as TFA salt) of the title compound (L4) of Example 26-(iv) and 57 mg of 1,3-bis[(benzyloxycarbonyl)amino]propan-2-one.

MS (ESI) m/z: 580 (M+1)$^+$; $^1$H NMR (DCl-D$_2$O, 500 MHz): δ 1.22 (3H, d, J=6 Hz, CH$_3$-6″), 1.45 (1H, q, J=12 Hz, H-5ax), 1.75 (1H, q, J=12.5 Hz, H-2ax), 2.00 (1H, q, J=12 Hz, H-3′ ax), 2.38 (1H, t, J=10 Hz, H-4″), 2.45 (1H, dt, J=4, 4 and 12.5 Hz, H-2eq), 2.67 (1H, dt, J=4.5, 4.5 and 12 Hz, H-5eq), 2.75 (3H, s, NCH$_3$), 3.34 (1H, dd, J=2.5 and 8.5 Hz, H-7′), 4.55 (1H, t, J=2.5 Hz, H-6′), 5.13 (1H, d, J=8.5 Hz, H-8′), 5.32 (1H, d, J=4 Hz, H-1″) and 5.35 (1H, d, J=3.8 Hz, H-1′).

Example 59: Synthesis of 4″-deamino-5,6″-dideoxy-4″-guanidinoapramycin (S1-a)

[Chem. 90]

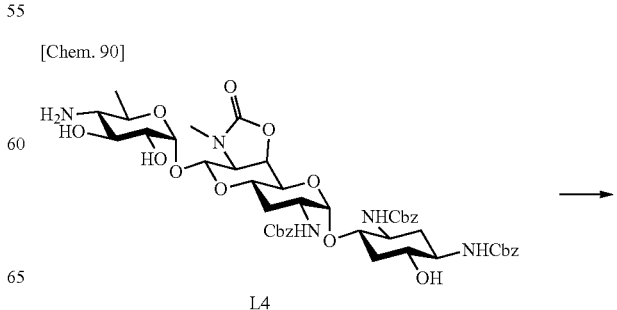

L4

-continued

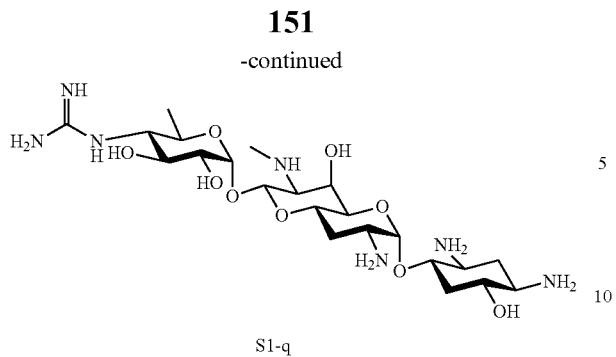

S1-q

The title compound (S1-q) [12.2 mg (23%)] was obtained by a method similar to Example 10 using 100 mg (0.095 mmol as TFA salt) of the title compound (L4) of Example 26-(iv) and 81.8 mg of Goodman's reagent.

MS (ESI) m/z: 550 (M+1)$^+$; $^1$H NMR (DCl-D$_2$O, 500 MHz): δ 1.21 (3H, d, H-6"), 1.78 (1H, q, H-5ax), 2.45 (1H, ddd, H-5eq), 5.35 (1H, d, H-1') and 5.38 (1H, d, H-1"), $^{13}$C NMR (DCl-D$_2$O, 125 MHz): δ 157.41 (C=NH).

Example 60: Synthesis of 1,3,2',4"-tetrakis-N-(benzyloxycarbonyl)-7'-N,6'-O-carbonyl-5,3"-dideoxyapramycin (U1), 1,3,2'-tri-N-(benzyloxycarbonyl)-7'-N,6'-O-carbonyl-4"-N,6"-O-carbonyl-5,3"-dideoxyapramycin (U2), 1,3,2'-tris-N-(benzyloxycarbonyl)-7'-N,6'-O-carbonyl-5,3"-dideoxyapramycin (U3) and 4"-deamino-5,3"-dideoxy-4"-guanidinoapramycin (U4-a)

[Chem. 91]

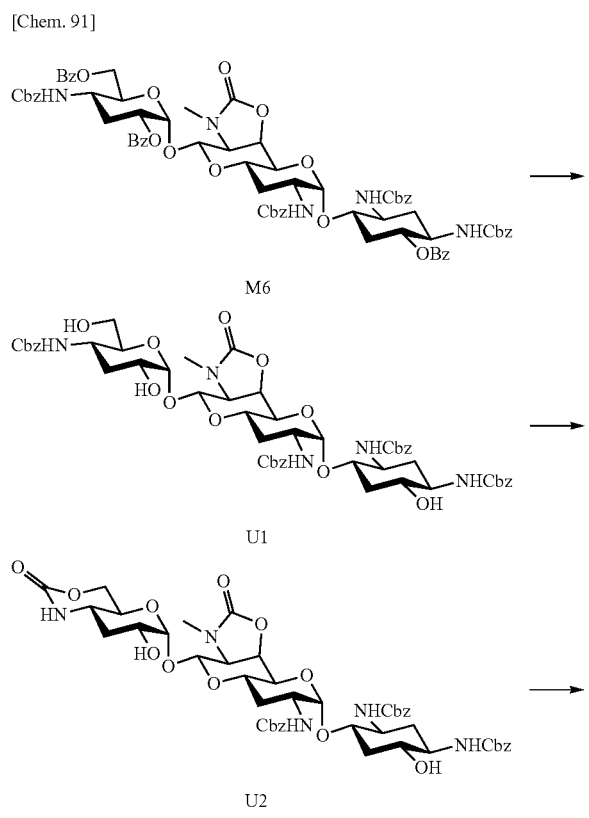

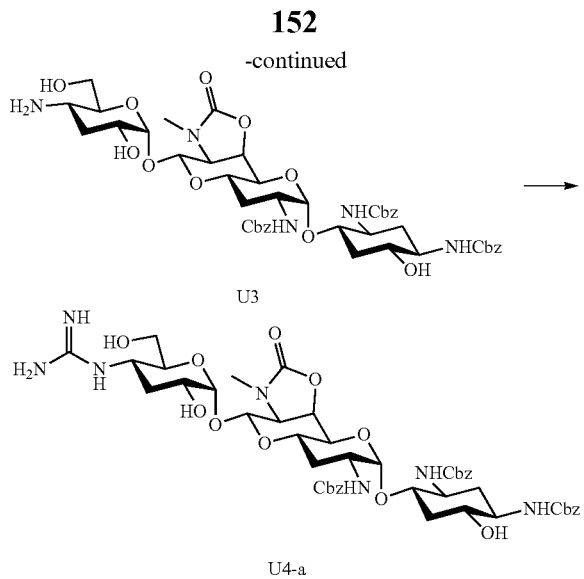

Example 60-(i): Synthesis of 1,3,2',4"-tetrakis-N-(benzyloxycarbonyl)-7'-N,6'-O-carbonyl-5,3"-dideoxyapramycin (U1)

The title compound (U1) [1.09 g (97%)] was obtained by a method similar to Example 14-(v) using 1.45 g (1.05 mmol) of the title compound (M6) of Example 27-(vii).
MS (ESI) m/z: 1092 (M+Na)$^+$.

Example 60-(ii): Synthesis of 1,3,2'-tri-N-(benzyloxycarbonyl)-7'-N,6'-O-carbonyl-4"-N,6"-O-carbonyl-5,3"-dideoxyapramycin (U2)

The title compound (U2) [866 mg (96%)] was obtained by a method similar to Example 1-(ii) using 1.00 g (0.94 mmol) of the title compound (U1) of Example 60-(i) and 45 mg of NaH.
MS (ESI) m/z: 984 (M+Na)$^+$.

Example 60-(iii): Synthesis of 1,3,2'-tri-N-(benzyloxycarbonyl)-7'-N,6'-O-carbonyl-5,3"-dideoxyapramycin (U3)

The title compound (U3) [713 mg (92%)] was obtained by a method similar to Example 1-(iii) using 801 mg (0.83 mmol) of the title compound (U2) of Examples 60-(ii).
MS (ESI) m/z: 958 (M+Na)$^+$.

Examples 60-(iv): Synthesis of 4"-deamino-5,3"-dideoxy-4"-guanidinoapramycin (U4-a)

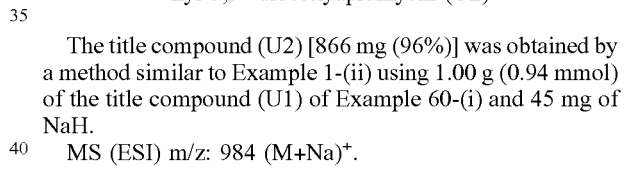

The title compound (U4-a) [174 mg (45%)] was obtained by a method similar to Example 10 using 735 mg (0.70 mmol as TFA salt) of the title compound (U3) of Example 60-(iii) and 550 mg of Goodman's reagent.
MS (ESI) m/z: 550 (M+Na)$^+$; $^1$H NMR (TFA salt, 500 MHz, D$_2$O): δ 1.46 (1H, q, J=12 Hz, H-5ax), 1.73 (1H, q, J=12.5 Hz, H-2ax), 1.84 (1H, q, J=12 Hz, H-3"ax), 2.00 (1H, q, J=12 Hz, H-3'ax), 2.15 (1H, dt, J=4, 4 and 12 Hz, H-3"eq), 2.36 (1H, dt, J=4.5, 4.5 and 12 Hz, H-3'eq), 2.46 (1H, dt, J=4, 4 and 12.5 Hz, H-2eq), 2.67 (1H, dt, J=4.5, 4.5 and 12 Hz, H-5eq), 2.77 (3H, s, NCH$_3$), 3.32 (1H, dd, J=3 and 8.5 Hz, H-7'), 4.52 (1H, slightly br t, J=~2.5 Hz, H-6'), 5.22 (1H, d, J=8.5 Hz, H-8'), 5.33 (1H, d, J=4 Hz, H-1") and 5.35 (1H, d, J=3.8 Hz, H-1').

Example 61: Synthesis of 4"-N-glycylapramycin (V1-a)

[Chem. 92]

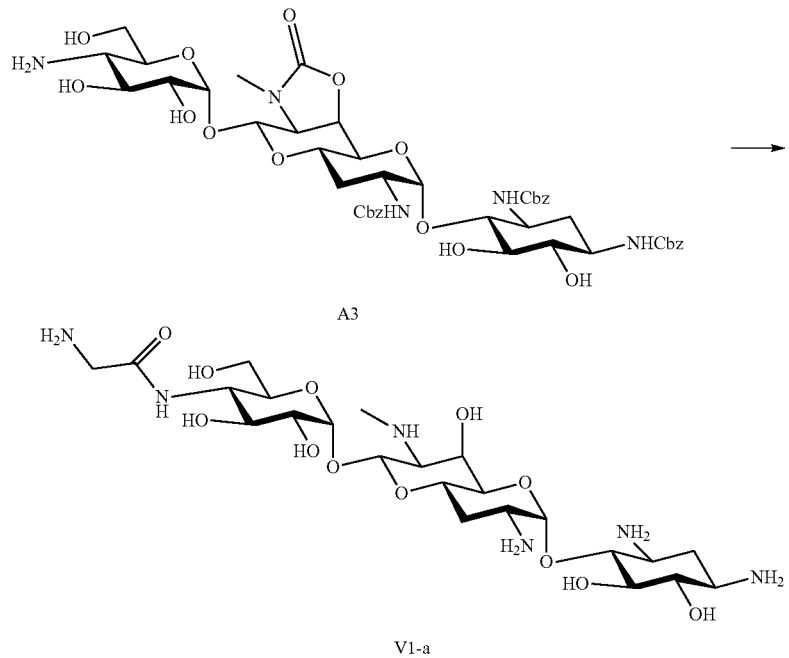

A3

V1-a

A solution prepared by adding 0.16 ml of triethylamine and 122 mg of N-hydroxysuccinimide ester of N-(tert-butoxycarbonyl)glycine to a solution of 300 mg (0.31 mmol) of the compound represented by formula (A3) dissolved in 2 ml of DMF was subjected to reaction at room temperature for 8 hours. After completion of the reaction, the reaction mixture was concentrated under reduced pressure and dissolved in 1-butanol followed by washing with water. After the organic layer was concentrated under reduced pressure, the concentrated organic layer was treated in a method similar to Example 10 to give 131 mg (71%) of the title compound (V1-a).

MS (ESI) m/z: 597 (M+1)$^+$; $^1$H NMR (25% ND$_3$-D$_2$O, 500 MHz): δ 1.58 (1H, q, H-2ax), 2.03 (1H, q, J=12 Hz, H-3'ax), 2.34 (1H, dt, H-3' eq), 2.50 (1H, dt, H-2eq), 2.75 (3H, s, NCH$_3$), 3.62 (2H, s, CH$_2$ (glycyl)), 5.28 (1H, d, H-8'), 5.50 (1H, d, H-1') and 5.75 (1H, d, H-1").

Example 62: Synthesis of 4"-N-sarcosylapramycin (V1-b)

[Chem. 93]

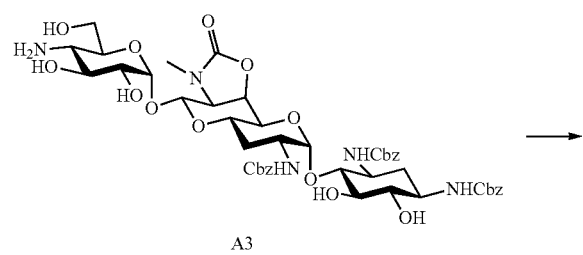

A3

-continued

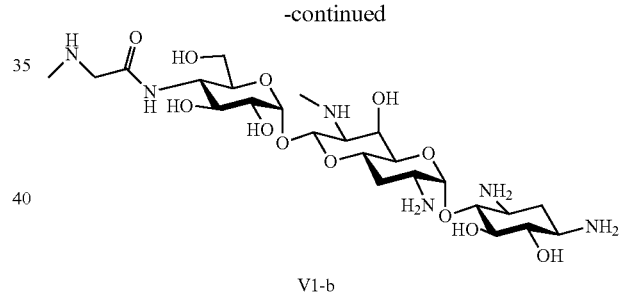

V1-b

The title compound (V1-b) [125 mg (66%)] was obtained by a method similar to Example 61 using 300 mg (0.31 mmol) of the compound represented by the formula (A3) and 122 mg of N-hydroxysuccinimide ester of N-(tert-butoxycarbonyl)sarcosine.

MS (ESI) m/z: 611 (M+1)$^+$; $^1$H NMR (25% ND$_3$-D$_2$O, 500 MHz): δ 1.58 (1H, q, H-2ax), 2.05 (1H, q, H-3'ax), 2.33 (1H, dt, H-3'eq), 2.51 (1H, dt, J=4, 4 and 12.5 Hz, H-2eq), 2.75 (3H, s, 7'-NCH$_3$), 2.65 (3H, s, NCH$_3$(sarcosyl)), 3.60 and 3.64 (each 1H, each d, CH$_2$(sarcosyl)), 5.29 (1H, d, H-8'), 5.52 (1H, d, H-1') and 5.76 (1H, d, H-1").

Example 63: Synthesis of 4"-N-(L-alanyl)apramycin (V1-c)

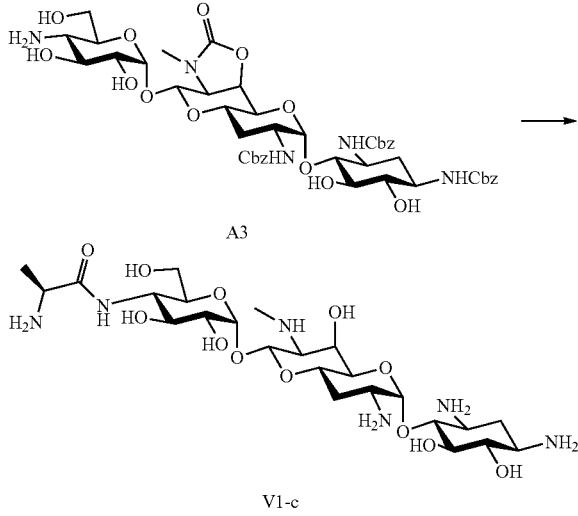

The title compound (V1-c) [121 mg (64%)] was obtained by a method similar to Example 61 using 300 mg (0.31 mmol) of the compound represented by the formula (A3) and 125 mg of N-hydroxysuccinimide ester of N-(tert-butoxycarbonyl)-L-alanine.

MS (ESI) m/z: 611 (M+1)$^+$; $^1$H NMR (25% ND$_3$-D$_2$O, 500 MHz): δ 1.58 (1H, q, H-2ax), 1.65 (3H, d, C—CH$_3$ (alanyl)), 2.04 (1H, q, H-3'ax), 2.35 (1H, dt, H-3' eq), 2.50 (1H, dt, H-2eq), 2.76 (3H, s, 7'-NCH$_3$), 3.83-3.89 (1H, m, CH(alanyl)), 5.27 (1H, d, H-8'), 5.50 (1H, d, H-1') and 5.75 (1H, d, H-1").

Example 64: Synthesis of 4"-N-(D-alanyl)apramycin (V1-d)

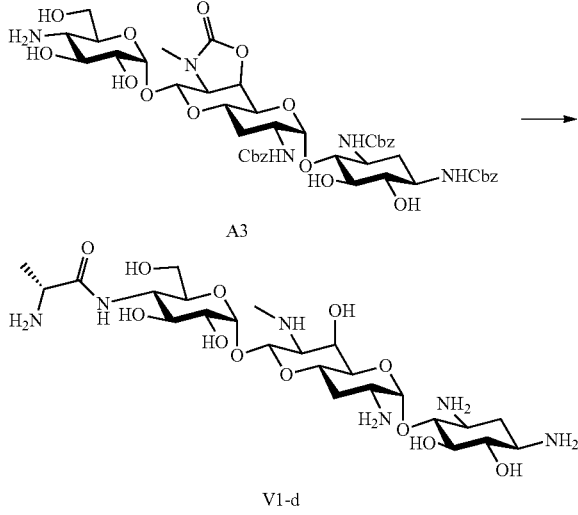

The title compound (V1-d) [115 mg (61%)] was obtained by a method similar to Example 61 using 300 mg (0.31 mmol) of the compound represented by the formula (A3) and 125 mg of N-hydroxysuccinimide ester of N-(tert-butoxycarbonyl)-D-alanine.

MS (ESI) m/z: 611 (M+1)$^+$; $^1$H NMR (25% ND$_3$-D$_2$O, 500 MHz): δ 1.58 (1H, q, H-2ax), 1.65 (3H, d, Me(alanyl)), 2.04 (1H, q, H-3'ax), 2.35 (1H, dt, H-3'eq), 2.50 (1H, dt, H-2eq), 2.76 (3H, s, 7'-NCH$_3$), 3.83-3.89 (1H, m, CH(alanyl)), 5.27 (1H, d, H-8'), 5.50 (1H, d, H-1') and 5.75 (1H, d, H-1").

Example 65: Synthesis of 4"-N-(L-seryl)apramycin (V1-e)

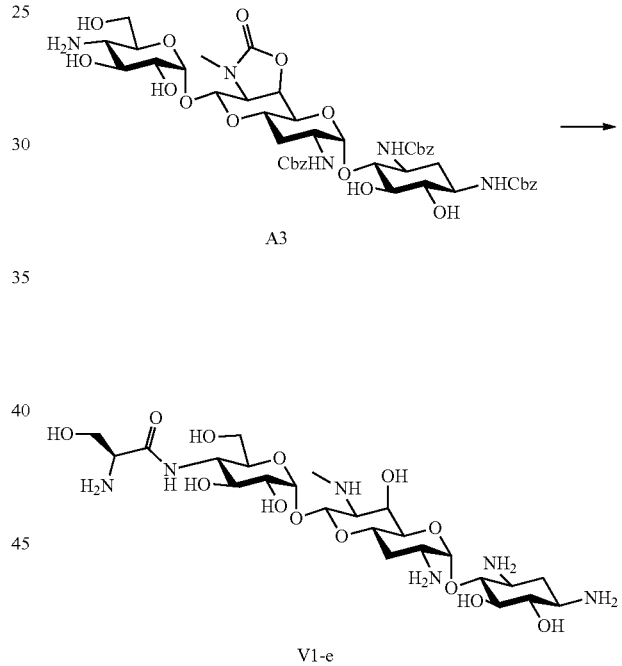

The title compound (V1-e) [128 mg (66%)] was obtained by a method similar to Example 61 using 300 mg (0.31 mmol) of the compound represented by the formula (A3) and 138 mg of N-hydroxysuccinimide ester of N-(tert-butoxycarbonyl)-L-serine.

MS (ESI) m/z: 627 (M+1)$^+$; $^1$H NMR (25% ND$_3$-D$_2$O, 500 MHz): δ 1.58 (1H, q, H-2ax), 2.03 (1H, q, H-3'ax), 2.35 (1H, dt, H-3'eq), 2.50 (1H, dt, H-2eq), 2.75 (3H, s, 7'-NCH$_3$), 4.13-4.20 (2H, m, CH$_2$(seryl)), 4.30 (1H, t, CH(seryl)), 5.28 (1H, d, H-8'), 5.50 (1H, d, H-1') and 5.76 (1H, d, H-1").

Example 66: Synthesis of 4"-N-(D-seryl)apramycin (V1-f)

[Chem. 97]

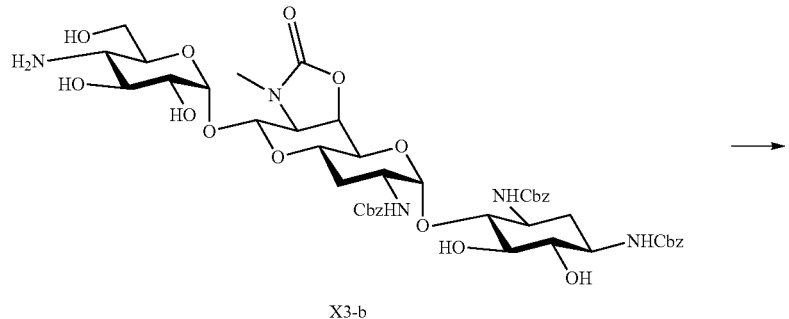

X3-b

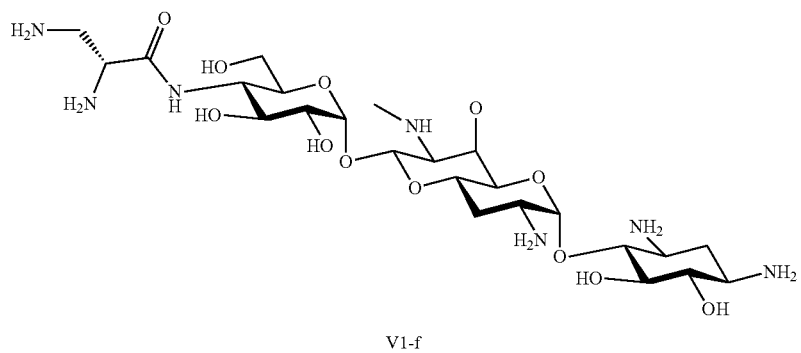

V1-f

The title compound (V1-f) [122 mg (63%)] was obtained by a method similar to Example 61 using 300 mg (0.31 mmol) of the compound represented by the formula (A3) and 138 mg of N-hydroxysuccinimide ester of N-(tert-butoxycarbonyl)-D-serine.

MS (ESI) m/z: 627 (M+1)$^+$; $^1$H NMR (25% $ND_3$-$D_2O$, 500 MHz): δ 1.57 (1H, q, H-2ax), 2.03 (1H, q, H-3'ax), 2.34 (1H, dt, H-3'eq), 2.50 (1H, dt, H-2eq), 2.76 (3H, s, 7'-$NCH_3$), 4.13-4.20 (2H, m, $CH_2$(seryl)), 4.30 (1H, t, CH(seryl)), 5.28 (1H, d, H-8'), 5.50 (1H, d, H-1') and 5.76 (1H, d, H-1").

Example 67: Synthesis of 4"-N-(D-alanyl)apramycin (V1-q)

[Chem. 98]

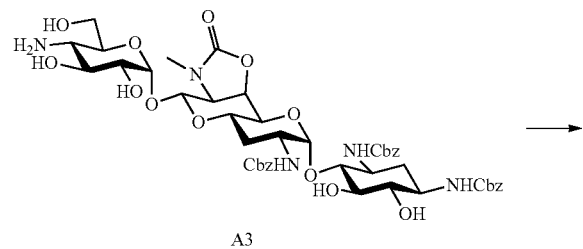

A3

-continued

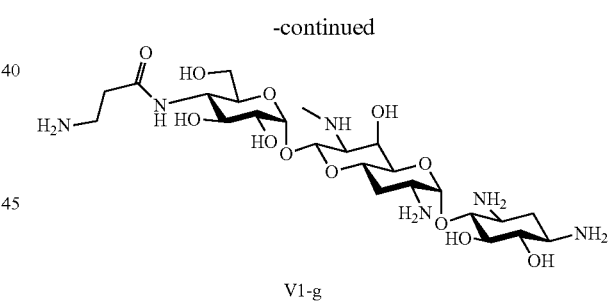

V1-g

The title compound (V1-g) [120 mg (63%)] was obtained by a method similar to Example 61 using 300 mg (0.31 mmol) of the compound represented by the formula (A3) and 125 mg of N-hydroxysuccinimide ester of N-(tert-butoxycarbonyl)-β-alanine.

MS (ESI) m/z: 611 (M+1)$^+$; $^1$H NMR (25% $ND_3$-$D_2O$, 500 MHz): δ 1.58 (1H, q, H-2ax), 2.03 (1H, q, H-3'ax), 2.35 (1H, dt, H-3'eq), 2.50 (1H, dt, H-2eq), 2.65 (2H, t, $CH_2$(β-alanyl)), 2.75 (3H, s, 7'-$NCH_3$), 3.17 (2H, t, $CH_2$(β-alanyl)), 5.28 (1H, d, H-8'), 5.50 (1H, d, H-1') and 5.75 (1H, d, H-1").

Example 68: Synthesis of 4"-N-(L-isoseryl)apramycin (V1-h)

[Chem. 99]

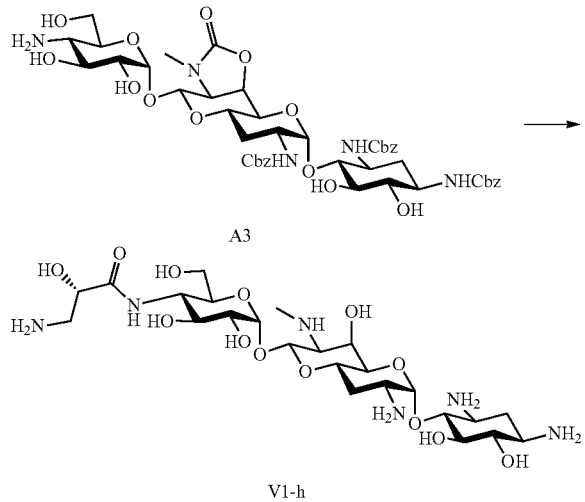

The title compound (V1-h) [105 mg (54%)] was obtained by a method similar to Example 61 using 300 mg (0.31 mmol) of the compound represented by the formula (A3) and 158 mg of N-hydroxysuccinimide ester of N-(p-methoxybenzyloxycarbonyl)-L-isoserine.

MS (ESI) m/z: 627 (M+1)$^+$; $^1$H NMR (25% ND$_3$-D$_2$O, 500 MHz): δ 1.57 (1H, q, H-2ax), 2.03 (1H, q, H-3'ax), 2.35 (1H, dt, H-3'eq), 2.50 (1H, dt, H-2eq), 2.75 (3H, s, 7'-NCH$_3$), 3.20 (1H, dd, CH$_2$(isoseryl)), 3.33 (1H, dd, CH$_2$(isoseryl)), 4.55 (1H, t, CH(isoseryl)), 5.27 (1H, d, H-8'), 5.52 (1H, d, H-1') and 5.76 (1H, d, H-1").

Example 69: Synthesis of 5-epi-4"-N-glycylapramycin (V1-i)

[Chem. 100]

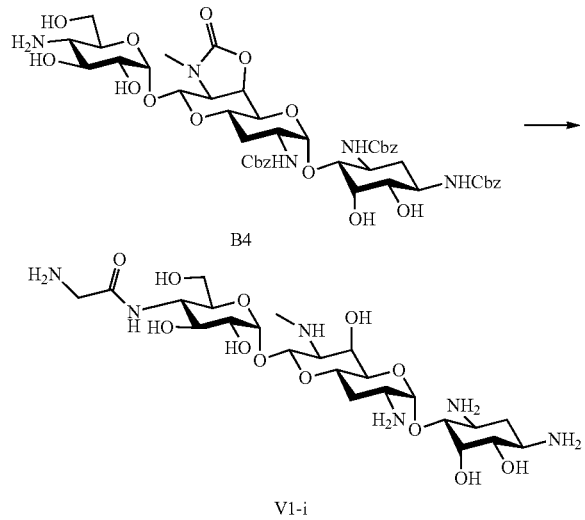

The title compound (V1-i) [76.1 mg (64%)] was obtained by a method similar to Example 61 using 200 mg (0.20 mmol) of the compound represented by the formula (B4) and 88.2 mg of N-hydroxysuccinimide ester of N-(tert-butoxycarbonyl)glycine.

MS (ESI) m/z: 597 (M+1)$^+$; $^1$H NMR (25% ND$_3$-D$_2$O, 500 MHz): δ 1.35 (1H, q, H-2ax), 1.99 (1H, q, H-3'ax), 2.25 (1H, dt, H-3'eq), 2.34 (1H, dt, H-2eq), 2.64 (3H, s, 7'-NCH$_3$), 3.63 (2H, s, CH$_2$(glycyl)), 4.53 (1H, t, H-5), 5.18 (1H, H-8'), 5.25 (1H, d, H-1') and 5.67 (1H, d, H-1").

Example 70: Synthesis of 5-epi-4"-N-sarcosylapramycin (V1-j)

[Chem. 101]

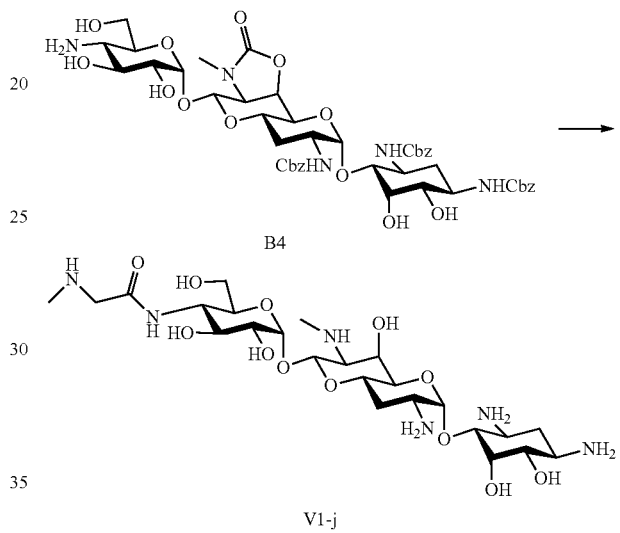

The title compound (V1-j) [81.5 mg (65%)] was obtained by a method similar to Example 61 using 200 mg (0.20 mmol) of the compound represented by the formula (B4) and 95.2 mg of N-hydroxysuccinimide ester of N-(tert-butoxycarbonyl)sarcosine.

MS (ESI) m/z: 611 (M+1)$^+$; $^1$H NMR (25% ND$_3$-D$_2$O, 500 MHz): δ 1.40 (1H, q, H-2ax), 2.04 (1H, q, H-3'ax), 2.30 (1H, dt, H-3'eq), 2.43 (1H, dt, H-2eq), 2.64 (3H, s, 7'-NCH$_3$), 2.70 (3H, s, NCH$_3$(sarcosyl)), 3.57 and 3.62 (each 1H, each d, CH$_2$(sarcosyl)), 4.56 (1H, t, H-5), 5.22 (1H, d, J=8.5 Hz, H-8'), 5.32 (1H, d, H-1') and 5.69 (1H, d, H-1").

Example 71: Synthesis of 4"-N-(L-alanyl)-5-epi-apramycin (V1-k)

[Chem. 102]

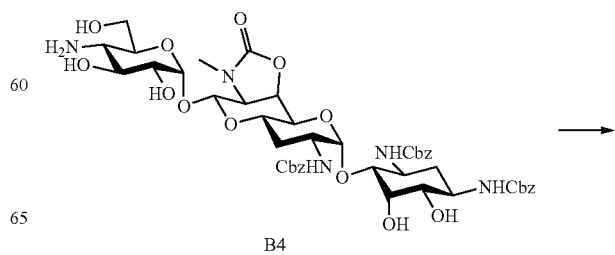

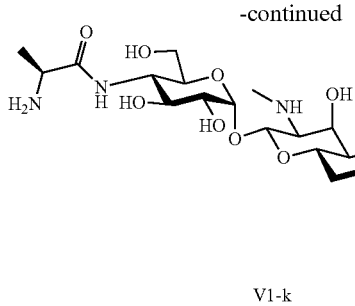

V1-k

The title compound (V1-k) [121 mg (64%)] was obtained by a method similar to Example 61 using 200 mg (0.20 mmol) of the compound represented by the formula (B4) and 96.3 mg of N-hydroxysuccinimide ester of N-(tert-butoxycarbonyl)-L-alanine.

MS (ESI) m/z: 611 (M+1)$^+$; $^1$H NMR (25% ND$_3$-D$_2$O, 500 MHz): δ 1.39 (1H, q, H-2ax), 1.65 (3H, d, CH$_3$(alanyl)), 2.03 (1H, q, H-3'ax), 2.31 (1H, dt, H-3'eq), 2.43 (1H, dt, H-2eq), 2.65 (3H, s, 7'-NCH$_3$), 3.85-3.90 (1H, m, CH(alanyl)), 4.53 (1H, t, H-5), 5.21 (1H, d, H-8'), 5.31 (1H, d, H-1') and 5.67 (1H, d, H-1").

Example 72: Synthesis of 5-epi-4"-N-(L-seryl) apramycin (V1-l)

[Chem. 103]

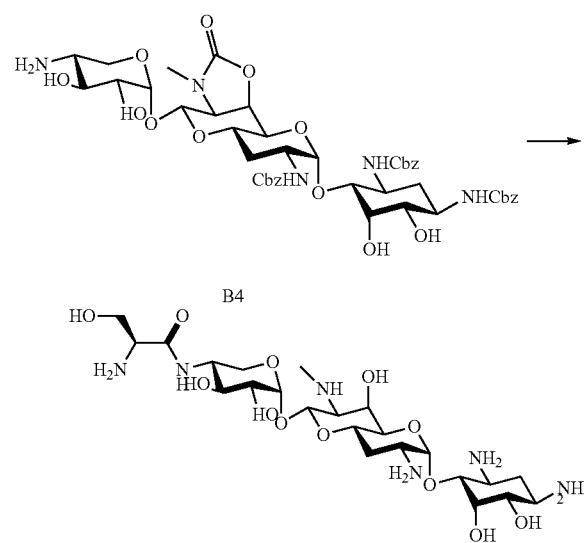

The title compound (V1-l) [83.4 mg (65%)] was obtained by a method similar to Example 61 using 200 mg (0.31 mmol) of the compound represented by the formula (B4) and 92.0 mg of N-hydroxysuccinimide ester of N-(tert-butoxycarbonyl)-L-serine.

MS (ESI) m/z: 627 (M+1)$^+$; $^1$H NMR (25% ND$_3$-D$_2$O, 500 MHz): δ 1.39 (1H, q, H-2ax), 2.03 (1H, q, H-3'ax), 2.31 (1H, dt, H-3'eq), 2.43 (1H, dt, H-2eq), 2.65 (3H, s, 7'-NCH$_3$), 4.13-4.20 (2H, m, CH$_2$(seryl)), 4.30 (1H, t, CH(seryl)), 4.55 (1H, t, H-5), 5.21 (1H, d, H-8'), 5.30 (1H, d, H-1') and 5.68 (1H, d, H-1").

Example 73: Synthesis of 4"-N-(β-alanyl)-5-epi-apramycin (V1-m)

[Chem. 104]

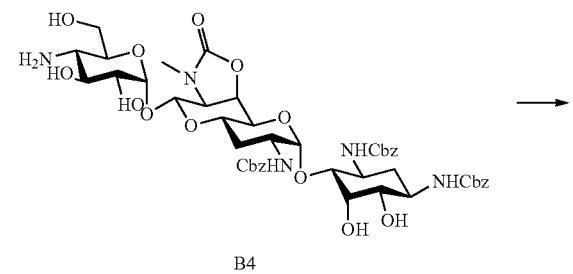

B4

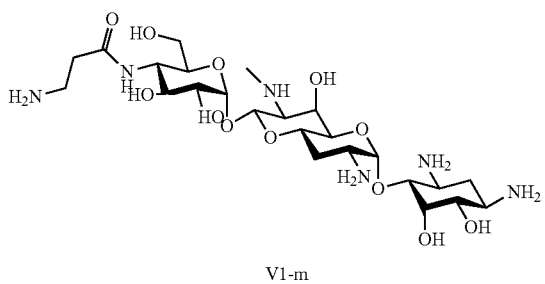

V1-m

The title compound (V1-m) [79.6 mg (65%)] was obtained by a method similar to Example 61 using 200 mg (0.20 mmol) of the compound represented by the formula (B4) and 95.5 mg of N-hydroxysuccinimide ester of N-(tert-butoxycarbonyl)-β-alanine.

MS (ESI) m/z: 611 (M+1)$^+$; $^1$H NMR (25% ND$_3$-D$_2$O, 500 MHz): δ 1.35 (1H, q, H-2ax), 1.99 (1H, q, H-3'ax), 2.25 (1H, dt, H-3'eq), 2.38 (1H, dt, H-2eq), 2.64 (3H, s, 7'-NCH$_3$), 2.67 (2H, t, CH$_2$(β-alanyl)), 3.15 (2H, t, CH$_2$(β-alanyl)), 5.16 (1H, d, H-8'), 4.50 (1H, t, H-5), 5.25 (1H, d, H-1') and 5.63 (1H, d, H-1").

Example 74: Synthesis of 5-epi-4"-N-(L-isoseryl) apramycin (V1-n)

[Chem. 105]

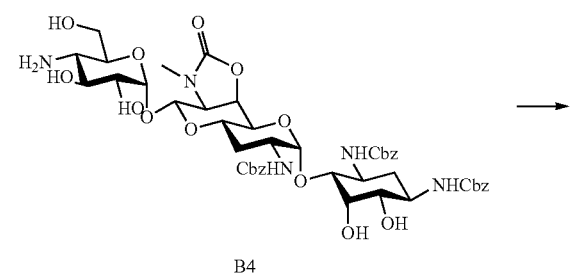

B4

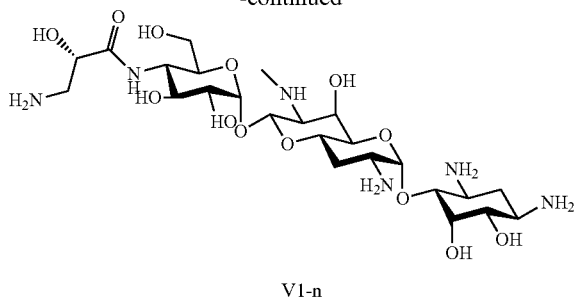

V1-n

The title compound (V1-n) [77.5 mg (62%)] was obtained by a method similar to Example 61 using 200 mg (0.20 mmol) of the compound represented by the formula (B4) and 105 mg of N-hydroxysuccinimide ester of N-(p-methoxybenzyloxycarbonyl)-L-isoserine.

MS (ESI) m/z: 627 (M+1)$^+$; $^1$H NMR (25% ND$_3$-D$_2$O, 500 MHz): δ 1.34 (1H, q, H-2ax), 1.98 (1H, q, H-3'ax), 2.24 (1H, dt, H-3'eq), 2.37 (1H, dt, H-2eq), 2.61 (3H, s, 7'-NCH$_3$), 3.08 (1H, dd, CH$_2$(isoseryl)), 3.33 (1H, dd, CH$_2$(isoseryl)), 4.43 (1H, t, CH(isoseryl)), 4.51 (1H, t, H-5), 5.15 (1H, d, H-8'), 5.24 (1H, d, H-1') and 5.65 (1H, d, H-1").

Example 75: Synthesis of
6-deoxy-5-epi-4"-N-glycylapramycin (V1-o)

[Chem. 106]

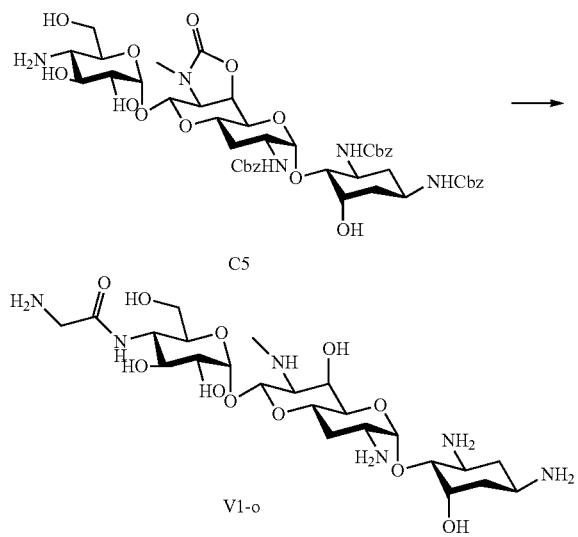

V1-o

The title compound (V1-o) [77.5 mg (74%)] was obtained by a method similar to Example 61 using 170 mg (0.18 mmol) of the compound represented by the formula (C5) and 79.4 mg of N-hydroxysuccinimide ester of N-(tert-butoxycarbonyl)glycine.

MS (ESI) m/z: 581 (M+1)$^+$; $^1$H NMR (25% ND$_3$-D$_2$O, 500 MHz): δ 1.48 (1H, q, H-2ax), 1.72 (1H, q, H-6ax), 2.07 (1H, q, H-3'ax), 2.37 (1H, dt, H-3'eq), 2.40 (1H, dt, H-6eq), 2.48 (1H, dt, H-2eq), 2.63 (3H, s, 7'-NCH$_3$), 3.72 (2H, s, CH$_2$(glycyl)), 4.69 (1H, dd, H-5), 5.26 (1H, d, H-8'), 5.35 (1H, d, H-1') and 5.74 (1H, d, H-1").

Example 76: Synthesis of
6-deoxy-5-epi-4"-N-sarcosylapramycin (V1-i)

[Chem. 107]

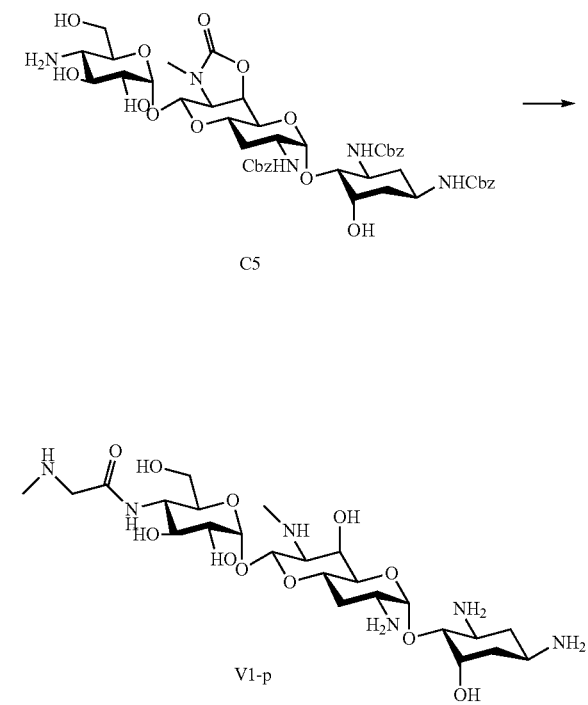

V1-p

The title compound (V1-p) [70.6 mg (66%)] was obtained by a method similar to Example 61 using 170 mg (0.18 mmol) of the compound represented by the formula (C5) and 85.5 mg of N-hydroxysuccinimide ester of N-(tert-butoxycarbonyl)sarcosine.

MS (ESI) m/z: 611 (M+1)$^+$; $^1$H NMR (25% ND$_3$-D$_2$O, 500 MHz): δ 1.48 (1H, q, H-2ax), 1.72 (1H, q, H-6ax), 2.08 (1H, q, H-3'ax), 2.37 (1H, dt, H-3'eq), 2.40 (1H, dt, H-6eq), 2.48 (1H, dt, H-2eq), 2.68 (3H, s, 7'-NCH$_3$), 2.73 (3H, s, NMe(sarcosyl)), 3.63 and 3.67 (each 1H, each d, CH$_2$ (sarcosyl)), 4.65 (1H, dd, H-5), 5.26 (1H, d, H-8'), 5.35 (1H, d, H-1') and 5.75 (1H, d, H-1").

Example 77: Synthesis of 4"-N-(i-alanyl)-6-deoxy-5-epiapramycin (V1-q)

[Chem. 108]

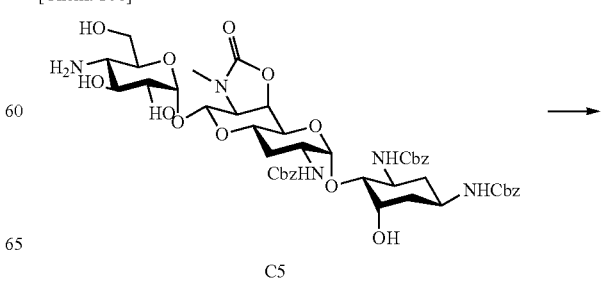

C5

-continued

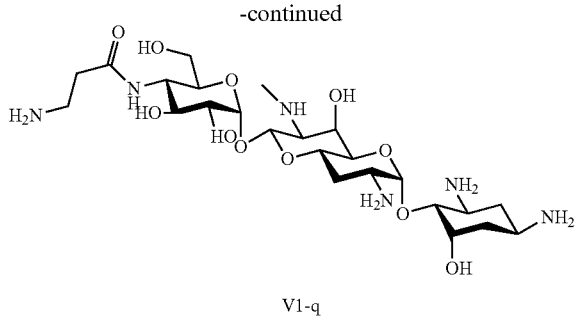

V1-q

The title compound (V1-q) [72.1 mg (67%)] was obtained by a method similar to Example 61 using 170 mg (0.18 mmol) of the compound represented by the formula (C5) and 86.0 mg of N-hydroxysuccinimide ester of N-(tert-butoxycarbonyl)-β-alanine.

MS (ESI) m/z: 595 (M+1)$^+$; $^1$H NMR (25% ND$_3$-D$_2$O, 500 MHz): δ 1.48 (1H, q, H-2ax), 1.73 (1H, q, H-6ax), 2.08 (1H, q, H-3'ax), 2.37 (1H, dt, H-3'eq), 2.42 (1H, dt, H-6eq), 2.48 (1H, dt, H-2eq), 2.70 (3H, s, 7'-NCH$_3$), 2.73 (2H, t, CH$_2$(β-alanyl)), 3.18 (2H, t, CH$_2$(S-alanyl)), 4.69 (1H, dd, H-5), 5.26 (1H, d, H-8'), 5.37 (1H, d, H-1') and 5.77 (1H, d, H-1").

Example 78: Synthesis of 6-deoxy-5-epi-4"-N-(L-isoseryl)apramycin (V1-r)

[Chem. 109]

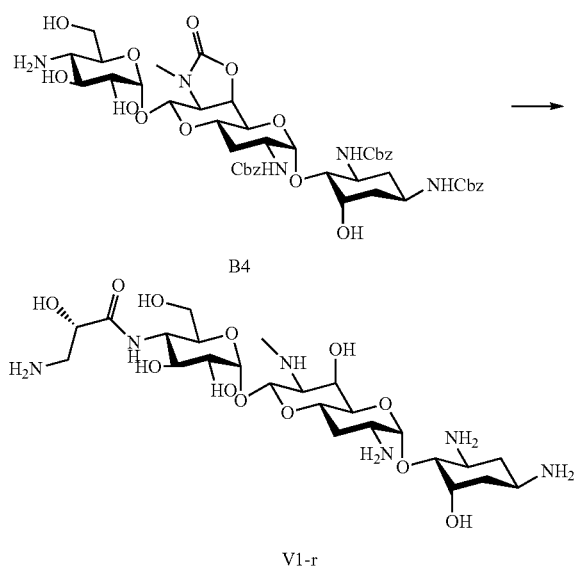

V1-r

The title compound (V1-r) [70.5 mg (64%)] was obtained by a method similar to Example 61 using 170 mg (0.18 mmol) of the compound represented by the formula (C5) and 94.5 mg of N-hydroxysuccinimide ester of N-(p-methoxybenzyloxycarbonyl)-L-isoserine.

MS (ESI) m/z: 611 (M+1)$^+$; $^1$H NMR (25% ND$_3$-D$_2$O, 500 MHz): δ 1.48 (1H, q, H-2ax), 1.73 (1H, q, H-6ax), 2.08 (1H, q, H-3'ax), 2.37 (1H, dt, H-3'eq), 2.42 (1H, dt, H-6eq), 2.48 (1H, dt, H-2eq), 2.74 (3H, s, 7'-NCH$_3$), 3.20 (1H, dd, CH$_2$(isoseryl)), 3.45 (1H, dt, CH$_2$(isoseryl)), 4.54 (1H, q, CH(isoseryl)), 4.69 (1H, dd, H-5), 5.26 (1H, d, H-8'), 5.37 (1H, d, H-1') and 5.77 (1H, d, H-1").

Example 79: Synthesis of 5-azide-1,3,2'-tris-N-(benzyloxycarbonyl)-5-deoxy-5-epiapramycin (W1) and 5-amino-4"-deamino-5-deoxy-5-epi-4"-guanidinoapramycin (W2-a)

[Chem. 110]

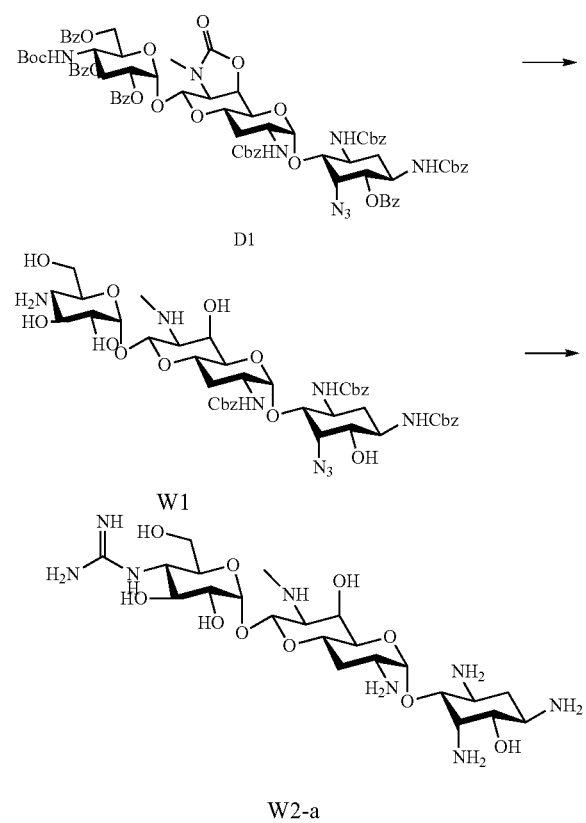

Examples 79-(i): Synthesis of 5-azide-1,3,2'-tris-N-(benzyloxycarbonyl)-5-deoxy-5-epiapramycin (W1)

A solution prepared by adding 3.4 ml of 4 N aqueous NaOH solution to a solution of 1.31 g (0.87 mmol) of the title compound (D1) of Example 16-(i) dissolved in 20 ml of 1,4-dioxane was subjected to reaction at room temperature for 2 hours. The reaction solution was neutralized by adding 2 N HCl and concentrated under reduced pressure and the residue was washed with water and further washed with isopropyl ether. The solid obtained was dissolved in 10 ml of 90% TFA-MeOH solution and the mixture was subjected to reaction at room temperature for 2 hours. The reaction solution was concentrated under reduced pressure and the residue was washed with isopropyl ether and dried to give 937 mg (90% as TFA salt) of the title compound (W1) as a colorless solid.

MS (ESI) m/z: 967 (M+1)$^+$.

Example 79-(ii): Synthesis of 5-amino-4"-deamino-5-deoxy-5-epi-4"-guanidinoapramycin (W2-a)

The title compound (W2-a) [45.5 mg (37%)] was obtained by a method similar to Example 10 using 254 mg (0.21 mmol as 2TFA salt) of the title compound (W1) of Example 79-(i) and 253 mg of Goodman's reagent.

MS (ESI) m/z: 581 (M+1)+; 1H NMR (TFA salt, 500 MHz, D2O): δ 1.82 (1H, q, J=12.5 Hz, H-2ax), 2.03 (1H, q, J=12 Hz, H-3'ax), 2.40 (1H, dt, J=4.5, 4.5 and 12 Hz, H-3'eq), 2.53 (1H, dt, J=4.5, 4.5 Hz, H-2eq), 2.74 (3H, s, NCH3), 3.30 (1H, dd, J=3 and 8.5 Hz, H-7'), 3.52 (1H, t, J=10 Hz, H-4"), 3.58 (1H, dd, J=2.5 and 10 Hz, H-5'), 3.80 (1H, t, J=10 Hz, H-3"), 4.04 (1H, dd, J=4 and 11 Hz, H-6), 4.18 (1H, t, J=4 Hz, H-5), 4.23 (1H, dd, J=4 and 11 Hz, H-4), 4.54 (1H, slightly br t, J=2.5 Hz, H-6'), 5.19 (1H, d, J=8.5 Hz, H-8'), 5.41 (1H, d, J=3.8 Hz, H-1') and 5.44 (1H, d, J=4 Hz, H-1").

Example 80: Synthesis of 5-amino-5-deoxy-5-epi-4"-N-glycylapramycin (W2-b)

[Chem. 111]

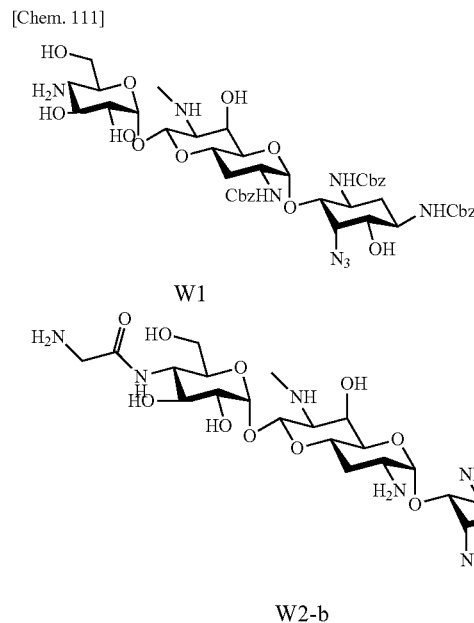

W2-b

The title compound (W2-b) [40.1 mg (34%)] was obtained by a method similar to Example 61 using 254 mg (0.21 mmol as 2TFA salt) of the title compound (W1) of Example 79-(i) and 90.0 mg of N-hydroxysuccinimide ester of N-(tert-butoxycarbonyl)glycine.

MS (ESI) m/z: 596 (M+1)+; 1H NMR (TFA salt, 500 MHz, D2O): δ 1.81 (1H, q, J=12.5 Hz, H-2ax), 2.03 (1H, q, J=12 Hz, H-3'ax), 2.40 (1H, dt, J=4.5, 4.5 and 12 Hz, H-3'eq), 2.54 (1H, dt, J=4.5, 4.5 and 12.5 Hz, H-2eq), 2.75 (3H, s, NCH3), 3.31 (1H, dd, J=3 and 8.5 Hz, H-7'), 3.95 (1H, dt, J=4.5, 4.5 and 11 Hz, H-4'), 4.04 (1H, dd, J=4 and 11 Hz, H-6), 4.14 (1H, dd, J=4 and 11 Hz, H-4), 4.18 (1H, t, J=4 Hz, H-5), 4.54 (1H, slightly br t, J=~2.5 Hz, H-6'), 5.20 (1H, d, J=8.5 Hz, H-8'), 5.41 (1H, d, J=3.8 Hz, H-1') and 5.44 (1H, d, J=4 Hz, H-1").

Example 81: Synthesis of 5-amino-5-deoxy-5-epi-4"-N-(L-isoseryl)apramycin (W2-c)

[Chem. 112]

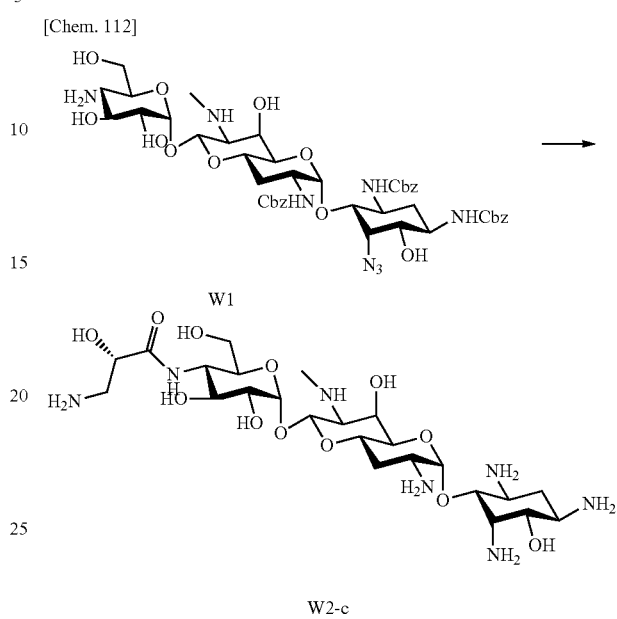

W2-c

The title compound (W2-c) [46.6 mg (49%)] was obtained by a method similar to Example 61 using 254 mg (0.21 mmol as 2TFA salt) of the title compound (D2) of Example 79-(i) and 105 mg of N-hydroxysuccinimide ester of N-(p-methoxycarbonyl)-L-isoserine.

MS (ESI) m/z: 626 (M+1)+; 1H NMR (TFA salt, 500 MHz, D2O): δ 1.87 (1H, q, J=12.5 Hz, H-2ax), 2.03 (1H, q, J=12 Hz, H-3'ax), 2.42 (1H, dt, J=4.5, 4.5 and 12 Hz, H-3'eq), 2.57 (1H, dt, J=4.5, 4.5 and 12.5 Hz, H-2eq), 2.75 (3H, s, NCH3), 4.42 (1H, dd, J=4 and 8 Hz, COCH(OH)), 4.56 (1H, slightly br t, J=~3 Hz, H-6'), 5.20 (1H, d, J=8.5 Hz, H-8'), 5.42 (1H, d, J=4 Hz, H-1') and 5.44 (1H, d, J=4 Hz, H-1").

Example 82: Synthesis of 1,3,2',4"-tetrakis-N-(benzyloxycarbonyl)-7'-N,6'-O-carbonyl-3"-deoxy-5-epiapramycin (X1-a), 1,3,2'-tri-N-(benzyloxycarbonyl)-7'-N,6'-O-carbonyl-4"-N,6"-O-carbonyl-3"-deoxy-5-epiapramycin (X2-a), 1,3,2'-tris-N-(benzyloxycarbonyl)-7'-N,6'-O-carbonyl-3"-deoxy-5-epiapramycin (X3-a) and 4"-deamino-3"-deoxy-5-epi-4"-guanidinoapramycin (X4-a)

[Chem. 113]

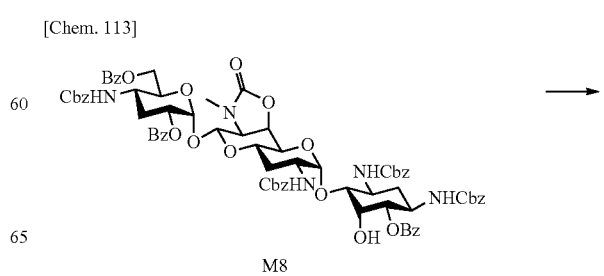

M8

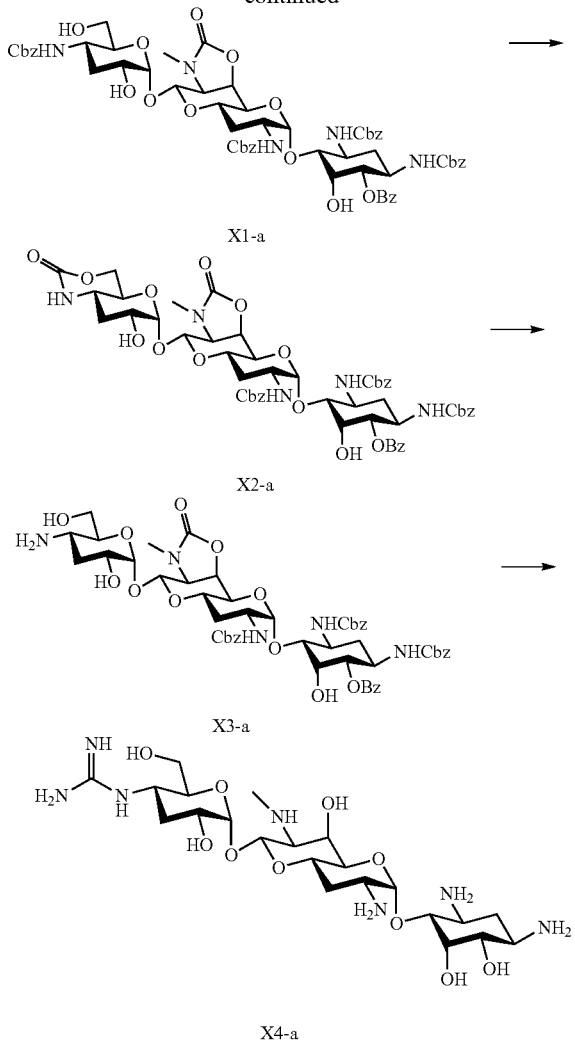

Example 82-(i): Synthesis of 1,3,2',4''-tetrakis-N-(benzyloxycarbonyl)-7'-N,6'-O-carbonyl-3''-deoxy-5-epiapramycin (X1-a)

The title compound (X1-a) [1.08 g (95%)] was obtained by a method similar to Example 14-(v) using 1.47 g (1.05 mmol) of the title compound (M8) of Example 28-(i).
MS (ESI) m/z: 1108 (M+Na)$^+$.

Example 82-(ii): Synthesis of 1,3,2'-tris-N-(benzyloxycarbonyl)-7'-N,6'-O-carbonyl-4''-N,6''-O-carbonyl-3''-deoxy-5-epiapramycin (X2-a)

The title compound (X2-a) [891 mg (96%)] was obtained by a method similar to Example 1-(ii) using 1.03 g (0.95 mmol) of the title compound (X1-a) of Example 82-(i) and 45 mg of NaH.
MS (ESI) m/z: 1000 (M+Na)$^+$.

Example 82-(iii): Synthesis of 1,3,2'-tris-N-(benzyloxycarbonyl)-7'-N,6'-O-carbonyl-3''-deoxy-5-epiapramycin (X3-a)

The title compound (X3-a) [881 mg (93% as TFA salt)] was obtained by a method similar to Example 1-(iii) using 870 mg (0.89 mmol) of the title compound (X2-a) of Example 82-(ii).
MS (ESI) m/z: 974 (M+Na)$^+$.

Example 82-(iv): Synthesis of 4''-deamino-3''-deoxy-5-epi-4''-guanidinoapramycin (X4-a)

The title compound (X4-a) [201 mg (47%)] was obtained by a method similar to Example 10 using 800 mg (0.75 mmol as TFA salt) of the title compound (X3-a) of Example 82-(iii) and 600 mg of Goodman's reagent.
MS (ESI) m/z: 566 (M+H)$^+$; $^1$H NMR (TFA salt, 500 MHz, D$_2$O): δ 1.69 (1H, q, J=12.5 Hz, H-2ax), 1.82 (1H, q, J=12 Hz, H-3''ax), 2.10 (1H, q, J=12 Hz, H-3'ax), 2.12 (1H, dt, J=4, 4 and 12 Hz, H-3''eq), 2.35 (1H, dt, J=4, 4 and 12 Hz, H-3'eq), 2.42 (1H, dt, J=4, 4 and 12.5 Hz, H-2eq), 2.74 (3H, s, NCH$_3$), 3.29 (1H, dd, J=2.5 and 8.5 Hz, H-7'), 4.44 (1H, slightly br t, J=~2 Hz, H-5), 4.49 (1H, slightly br t, J=~2.5 Hz, H-6'), 5.19 (1H, d, J=8.5 Hz, H-8'), 5.30 (1H, d, J=3.5 Hz, H-1'') and 5.36 (1H, d, J=4 Hz, H-1').

Example 83: Synthesis of 1,3,2',4''-tetrakis-N-(benzyloxycarbonyl)-7'-N,6'-O-carbonyl-5,3''-dideoxy-5-epi-5-fluoroapramycin (X1-b), 1,3,2'-tri-N-(benzyloxycarbonyl)-7'-N,6'-O-carbonyl-4''-N,6''-O-carbonyl-5,3''-dideoxy-5-epi-5-fluoroapramycin (X2-b), 1,3,2'-tris-N-(benzyloxycarbonyl)-7'-N,6'-O-carbonyl-5,3''-dideoxy-5-epi-5-fluoroapramycin (X3-b) and 4''-deamino-5,3''-dideoxy-5-epi-5-fluoro-4''-guanidinoapramycin (X4-b)

[Chem. 114]

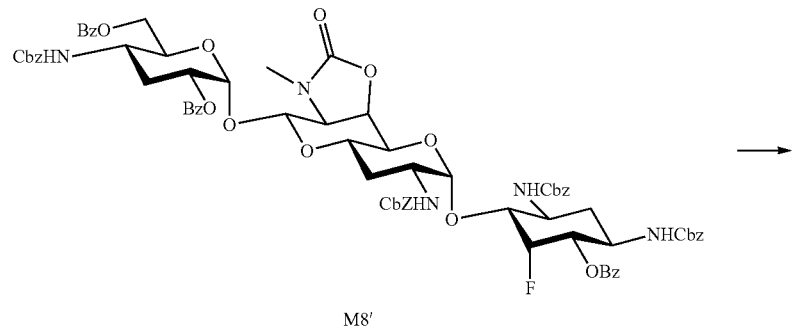

M8'

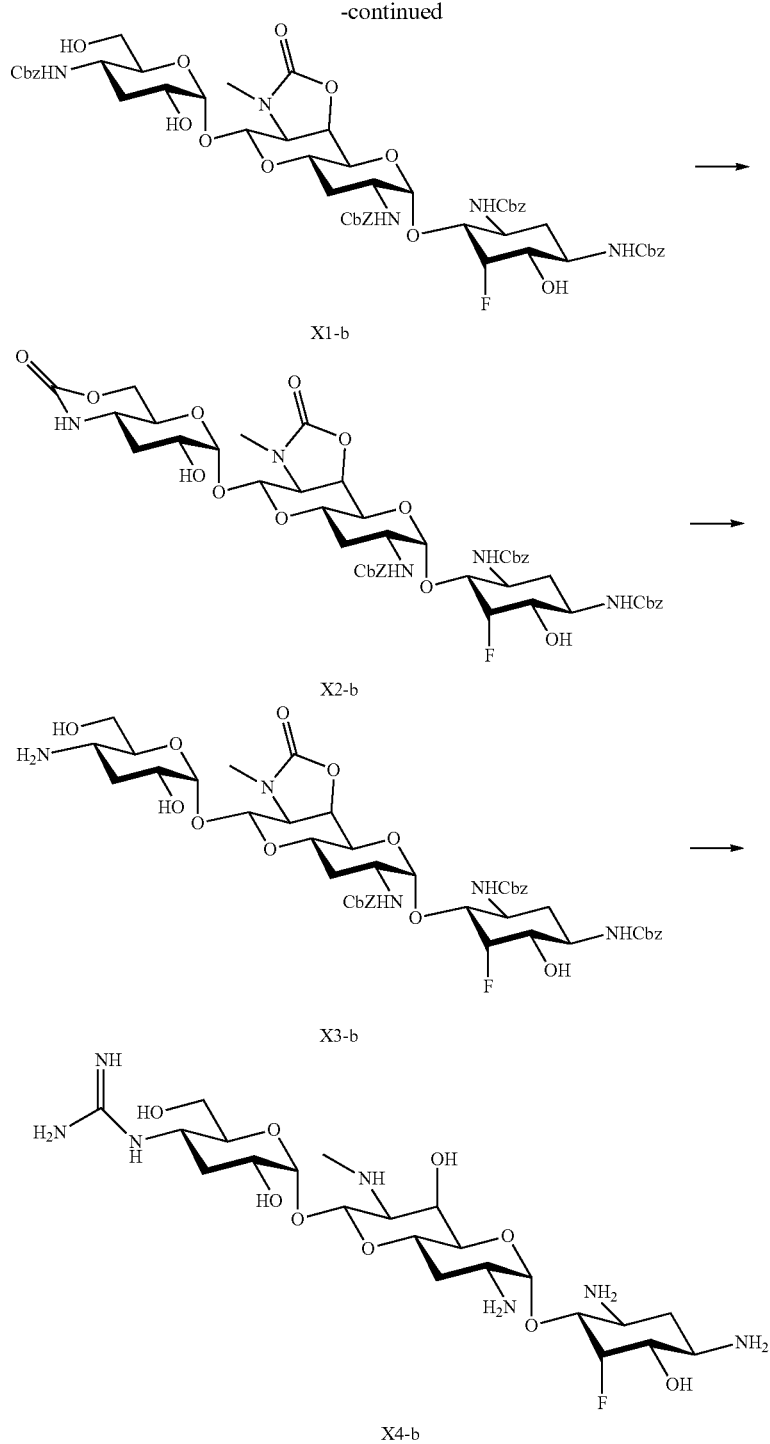

Example 83-(i): Synthesis of 1,3,2',4"-tetrakis-N-(benzyloxycarbonyl)-7'-N,6'-O-carbonyl-5,3"-dideoxy-5-epi-5-fluoroapramycin (X1-b)

The title compound (X1-b) [544 mg (96%)] was obtained by a method similar to Example 14-(v) using 722 mg (0.52 mmol) of the title compound (M8') of Example 28-(i).

MS (ESI) m/z: 1110 (M+Na)$^+$.

Example 83-(ii): Synthesis of 1,3,2'-tris-N-(benzyloxycarbonyl)-7'-N,6'-O-carbonyl-4"-N,6"-O-carbonyl-5,3"-dideoxy-5-epi-5-fluoroapramycin (X2-b)

The title compound (X2-b) [451 mg (92%)] was obtained by a method similar to Example 1-(ii) using 500 mg (0.46 mmol) of the title compound (X1-b) of Example 83-(i) and 22 mg of NaH.

MS (ESI) m/z: 1002 (M+Na)$^+$.

Examples 83-(iii): Synthesis of 1,3,2'-tris-N-(benzyloxycarbonyl)-7'-N,6'-O-carbonyl-5,3"-dideoxy-5-epi-5-fluoroapramycin (X3-b)

The title compound (X3-b) [438 mg (91% as TFA salt)] was obtained by a method similar to Example 1-(iii) using 440 mg (0.45 mmol) of the title compound (X2-b) of Example 83-(ii).
MS (ESI) m/z: 976 (M+Na)+.

Example 83-(iv): Synthesis of 4"-deamino-5,3"-dideoxy-5-epi-5-fluoro-4"-guanidinoapramycin (X4-b)

The title compound (X4-b) [105 mg (50%)] was obtained by a method similar to Example 10 using 400 mg (0.37 mmol as TFA salt) of the title compound (X3-b) of Example 83-(iii) and 600 mg of Goodman's reagent.
MS (ESI) m/z: 568 (M+H)+; $^1$H NMR (TFA salt, 500 MHz, D$_2$O): δ 1.76 (1H, q, J=12.5 Hz, H-2ax), 1.81 (1H, q, J=12 Hz, H-3"ax), 2.02 (1H, q, J=12 Hz, H-3'ax), 2.12 (1H, dt, J=4, 4 and 12 Hz, H-3"eq), 2.35 (1H, dt, J=4.5, 4.5 and 12 Hz, H-3'eq), 2.47 (1H, dt, J=4, 4 and 12.5 Hz, H-2eq), 2.74 (3H, s, NCH$_3$), 3.30 (1H, dd, J=3 and 8.5 Hz, H-7'), 4.10 (1H, apparently dd, J=11 and 26 Hz, H-4), 4.49 (1H, slightly br t, J=~2.5 Hz, H-6'), 5.19 (1H, d, J=8.5 Hz, H-8'), 5.30 (1H, d, J=3.5 Hz, H-1"), 5.32 (1H, apparently d, J=52 Hz, H-5) and 5.43 (1H, d, J=4 Hz, H-1').

Example 84: Synthesis of 6,3"-di-O-benzoyl-1,3,2'-tris-N-(benzyloxycarbonyl)-7'-N,6'-O-carbonyl-4"-N,6"-O-carbonyl-2"-deoxy-3"-epi-5-O-mesyl-apramycin (Y1), 5-O-acetyl-6,3"-di-O-benzoyl-1,3,2'-tris-N-(benzyloxycarbonyl)-7'-N,6'-O-carbonyl-4"-N,6"-O-carbonyl-2"-deoxy-5,3"-diepiapramycin (Y2) and 2"-deoxy-5,3"-diepiapramycin (Y3)

[Chem. 115]

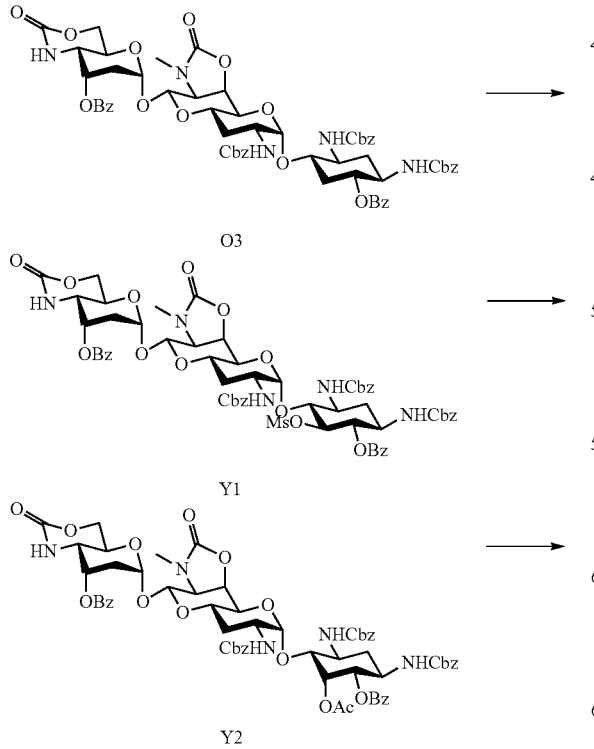

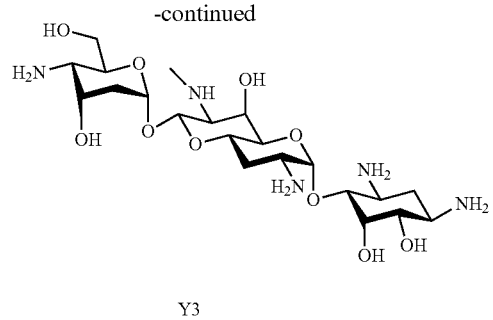

Y3

Example 84-(i): Synthesis of 6,3"-di-O-benzoyl-1,3,2'-tris-N-(benzyloxycarbonyl)-7'-N,6'-O-carbonyl-4"-N,6"-O-carbonyl-2"-deoxy-3"-epi-5-O-mesyl-apramycin (Y1)

The title compound (Y1) [1.05 g (99%)] was obtained by a method similar to Example 14-(i) using 1.00 g (0.84 mmol) of the title compound (O3) of Example 33-(iii).
MS (ESI) m/z: 1286 (M+Na)+.

Examples 84-(ii): Synthesis of 5-O-acetyl-6,3"-di-O-benzoyl-1,3,2'-tris-N-(benzyloxycarbonyl)-7'-N,6'-O-carbonyl-4"-N,6"-O-carbonyl-2"-deoxy-5,3"-diepiapramycin (Y2)

The title compound (Y2) [732 mg (79%)] was obtained by a method similar to Example 34-(iii) using 955 mg (0.76 mmol) of the title compound (Y1) of Example 84-(i).
MS (ESI) m/z: 1250 (M+Na)+.

Examples 84-(iii): Synthesis of 2"-deoxy-5,3"-diepiapramycin (Y3)

The title compound (Y3) [77.5 mg (45%)] was obtained by a method similar to Example 27-(vii) using 400 mg (0.33 mmol) of the title compound (Y2) of Example 84-(ii).
MS (ESI) m/z: 524 (M+1)+; $^1$H NMR (25% ND$_3$-D$_2$O, 500 MHz): δ 1.38 (1H, q, H-2ax), 1.83 (1H, q, J=12 Hz, H-3'ax), 2.15 (1H, dt, H-2eq), 2.21-2.27 (1H, m, H-2"ax), 2.28 (1H, dt, H-3'eq), 3.08 (1H, dd, H-2"eq), 4.18 (1H, t, H-3"), 4.31 (1H, q, H-3"), 4.53 (1H, t, H-5), 5.19 (1H, d, J=8.5 Hz, H-8'), 5.07 (1H, d, H-1"), 5.28 (1H, d, H-1') and 5.63 (1H, d, H-1").

Example 85: Synthesis of 5-epi-4"-N-(D-isoseryl)apramycin (V1-s)

[Chem. 116]

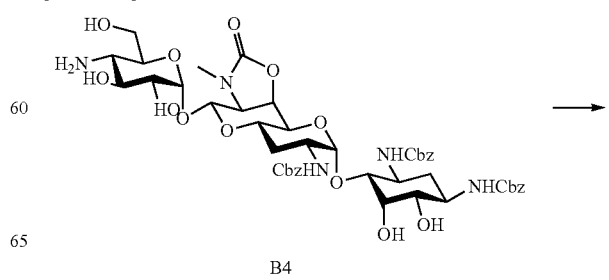

B4

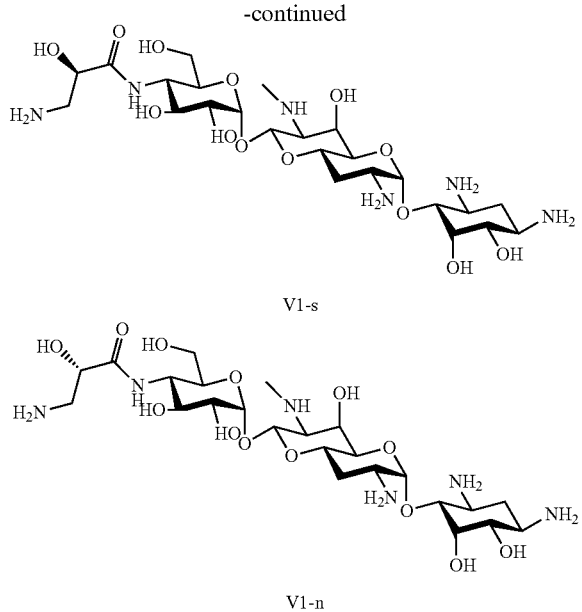

V1-s

V1-n

The title compound (V1-s) [22.5 mg (18%)] and the title compound (V1-n) [20.8 mg (17%)] of Example 74 were obtained by a method similar to Example 61 using 200 mg (0.20 mmol) of the compound represented by the formula (B4) and 105 mg of N-hydroxysuccinimide ester of N-(tert-butoxycarbonyl)-DL-isoserine.

MS (ESI) m/z: 627 (M+1)$^+$; $^1$H NMR (25% ND$_3$-D$_2$O, 500 MHz): δ 1.33 (1H, q, H-2ax), 1.97 (1H, q, H-3'ax), 2.23 (1H, dt, H-3'eq), 2.36 (1H, dt, H-2eq), 2.61 (3H, s, 7'-NCH$_3$), 3.03 (1H, dd, CH$_2$(isoseryl)), 3.23 (1H, dd, CH$_2$(isoseryl)), 4.20 (1H, t, H-4''), 4.44 (1H, dd, CH(isoseryl)), 4.49 (1H, t, H-5), 5.13 (1H, d, H-8'), 5.23 (1H, d, H-1') and 5.63 (1H, d, H-1'').

Test Example 1

Antibacterial Activity

As for the representative compounds of a new aminoglycoside antibiotic of the present invention described in Examples, the minimal inhibitory concentration (MIC, μg/mL) was measured for various assay strains of bacteria using an agar plate dilution method in accordance with the method described in the Japan Society of Chemotherapy. The results are provided in Tables 1 to 6.

TABLE 1

| Test bacterium Abbreviated Name[1] | Compound Abbreviation[2] | A4-a | A4-b | A4-c | A4-d | A4-e | A4-f | A4-g | A4-h | A4-i | A4-j | A4-k | B5 | B7 | C6 | C8 | D2 |
|---|---|---|---|---|---|---|---|---|---|---|---|---|---|---|---|---|---|
| S. aureus RN4220 | Sensitive bacterium | 4 | 4 | 4 | 2 | 2 | 4 | 4 | 4 | 4 | 2 | 2 | 4 | 4 | 4 | 2 | 4 |
| S. aureus RN4220/pMS520 | MRSA | 4 | 4 | 4 | 2 | 2 | 4 | 4 | 4 | 4 | 2 | 2 | 2 | 4 | 4 | 2 | 4 |
| S. aureus MF490 | MRSA | 16 | 8 | 16 | 4 | 4 | 8 | 16 | 16 | 16 | 8 | 16 | 8 | 16 | 8 | 8 | 8 |
| E. faecium ATCC19434 | | 32 | 16 | 16 | 8 | 16 | 32 | 32 | 32 | 32 | 16 | 16 | 16 | 32 | 16 | 16 | 32 |
| E. coli JM109/pMW218 | Sensitive bacterium | 2 | 2 | 1 | 1 | 1 | 1 | 2 | 2 | 1 | 1 | 0.5 | 1 | 1 | 1 | 1 | 2 |
| K. pneumoniae ATCC BAA-1705 | KPC-producing strain | 2 | 2 | 1 | 2 | 2 | 2 | 2 | 4 | 2 | 2 | 1 | 1 | 2 | 2 | 1 | 2 |
| K. pneumoniae ATCC BAA-2146 | NDM-producing strain | 2 | 2 | 1 | 1 | 2 | 1 | 2 | 2 | 2 | 1 | 1 | 1 | 2 | 1 | 1 | 2 |
| A. baumannii ATCC BAA-1710 | MDRA | 16 | 8 | 32 | 4 | 4 | 32 | 32 | 16 | 16 | 8 | 8 | 8 | 8 | 8 | 8 | 8 |
| S. marcescens TH-0447 | AMK-resistant | 8 | 8 | 8 | 8 | 8 | 16 | 16 | 16 | 16 | 8 | 8 | 8 | 16 | 8 | 8 | 8 |
| S. marcescens GN6944 | GM-resistant | 8 | 8 | 8 | 4 | 8 | 8 | 16 | 8 | 8 | 4 | 4 | 8 | 8 | 4 | 4 | 4 |
| P. aeruginosa PAO1 | Sensitive bacterium | 8 | 4 | 16 | 4 | 4 | 16 | 16 | 8 | 8 | 4 | 8 | 4 | 4 | 4 | 4 | 4 |
| P. aeruginosa PAO1/GN315 | AMK-resistant | 8 | 8 | 16 | 4 | 4 | 16 | 16 | 16 | 16 | 8 | 8 | 4 | 8 | 4 | 4 | 4 |
| P. aeruginosa MSC17707 | AMK-resistant | 8 | 8 | 32 | 4 | 8 | 16 | 32 | 16 | 16 | 8 | 16 | 4 | 8 | 8 | 4 | 8 |
| P. aeruginosa MSC01035 | ABK-resistant | 8 | 8 | 16 | 8 | 8 | 16 | 32 | 16 | 16 | 8 | 16 | 4 | 8 | 8 | 8 | 4 |

[1]The name of each test bacterium is as follows. S. aureus: Staphylococcus aureus, E. faecium: Enterococcus faecium, E. coli: Escherichia coli, K. pneumonia: Klebsiella pneumonia, A. baumannii: Acinetobacter baumannii, S. marcescens: Serratia marcescens, P. aeruginosa: Pseudomonas aeruginosa.

[1]Characteristics of each test bacterium is as follows. Sensitive bacterium: strains showing sensitivity against antibiotics, MRSA: methicillin-resistant Staphylococcus aureus, KPC-producing strain: Klebsiella pneumoniae carbapenemase-producing strain, NDM-producing strain: New Ddlhi metallo-β-lactamase-producing strain, MDRA: Multiple drug-resistant Acinetobacter, AMK-resistant: amikacin- resistant, GM-resistant: gentamicin-resistnat, ABK-resistant: arbekacin-resistant.

[2]The compound abbreviations in this Table correspond to the compound abbreviations of the title in each Example of the description described in parenthesis.

TABLE 2

| Test bacterium Abbreviated Name[1] | Compound Abbreviation[2] | E3 | F3 | C11 | G7 | G8 | H3 | I3 | J4 | K4 | L5 | M7 | M9 | M10 | N5 | N7 | N9 |
|---|---|---|---|---|---|---|---|---|---|---|---|---|---|---|---|---|---|
| S. aureus RN4220 | Sensitive bacterium | 8 | 8 | 8 | 4 | 8 | 4 | 8 | 8 | 2 | 2 | 2 | 1 | 2 | 2 | 2 | 2 |
| S. aureus RN4220/pMS520 | MRSA | 8 | 8 | 8 | 8 | 8 | 4 | 8 | 4 | 2 | 1 | 1 | 2 | 2 | 2 | 2 | 2 |
| S. aureus MF490 | MRSA | 16 | 32 | 16 | 16 | 32 | 8 | 32 | 16 | 8 | 4 | 4 | 4 | 8 | 4 | 8 | 8 |
| E. faecium ATCC19434 | | 64 | 64 | 32 | 16 | 32 | 16 | 32 | 32 | 8 | 8 | 16 | 8 | 8 | 8 | 16 | 16 |
| E. coli JM109/pMW218 | Sensitive bacterium | 4 | 8 | 2 | 1 | 2 | 2 | 4 | 2 | 1 | 1 | 0.5 | 1 | 0.5 | 1 | 1 | 1 |
| K. pneumoniae ATCC BAA-1705 | KPC-producing strain | 4 | 4 | 4 | 2 | 4 | 2 | 4 | 2 | 2 | 1 | 1 | 1 | 1 | 2 | 1 | 2 |
| K. pneumoniae ATCC BAA-2146 | NDM-producing strain | 4 | 4 | 4 | 4 | 4 | 2 | 4 | 2 | 1 | 1 | 1 | 1 | 1 | 2 | 1 | 1 |
| A. baumannii ATCC BAA-1710 | MDRA | 16 | 16 | 16 | 8 | 16 | 8 | 16 | 32 | 16 | 8 | 8 | 4 | 8 | 8 | 8 | 8 |
| S. marcescens TH-0447 | AMK-resistant | 16 | 16 | 16 | 8 | 16 | 8 | 32 | 16 | 8 | 4 | 8 | 4 | 8 | 8 | 8 | 8 |
| S. marcescens GN6944 | GM-resistant | 16 | 16 | 16 | 8 | 16 | 8 | 16 | 16 | 4 | 4 | 4 | 4 | 4 | 4 | 4 | 8 |
| P. aeruginosa PAO1 | Sensitive bacterium | 16 | 16 | 16 | 8 | 8 | 8 | 16 | 8 | 8 | 4 | 4 | 2 | 4 | 4 | 4 | 4 |
| P. aeruginosa PAO1/GN315 | AMK-resistant | 16 | 16 | 16 | 8 | 16 | 8 | 32 | 8 | 8 | 4 | 4 | 4 | 4 | 4 | 4 | 4 |
| P. aeruginosa MSC17707 | AMK-resistant | 16 | 16 | 16 | 8 | 16 | 8 | 32 | 16 | 16 | 8 | 4 | 4 | 4 | 8 | 8 | 8 |
| P. aeruginosa MSC01035 | ABK-resistant | 16 | 32 | 32 | 16 | 16 | 8 | 64 | 16 | 16 | 8 | 4 | 4 | 4 | 8 | 8 | 8 |

[1] The name of each test bacterium is as follows. *S. aureus*: *Staphylococcus aureus*, *E. faecium*: *Enterococcus faecium*, *E. coli*: *Escherichia coli*, *K. pneumonia*: *Klebsiella pneumonia*, *A. baumannii*: *Acinetobacter baumannii*, *S. marcescens*: *Serratia marcescens*, *P. aeruginosa*: *Pseudomonas aeruginosa*.
[1] Characteristics of each test bacterium is as follows. Sensitive bacterium: strains showing sensitivity against antibiotics, MRSA: methicillin-resistant *Staphylococcus aureus*, KPC-producing strain: *Klebsiella pneumoniae* carbapenemase-producing strain, NDM-producing strain: New Ddlhi metallo-β-lactamase-producing strain, MDRA: Multiple drug-resistant *Acinetobacter*, AMK-resistant: amikacin-resistant, GM-resistant: gentamicin-resistnat, ABK-resistant: arbekacin-resistant.
[2] The compound abbreviations in this Table correspond to the compound abbreviations of the title in each Example of the description described in parenthesis.

TABLE 3

| Test bacterium Abbreviated Name[1] | Compound Abbreviation[2] | O5 | P4 | Q4 | R6 | S1-a | S1-b | S1-c | S1-d | S1-e | S1-f | S1-g | S1-h | S1-i | S1-j | S1-k |
|---|---|---|---|---|---|---|---|---|---|---|---|---|---|---|---|---|
| S. aureus RN4220 | Sensitive bacterium | 1 | 2 | 2 | 2 | 2 | 2 | 2 | 1 | 1 | 2 | 4 | 2 | 2 | 2 | 1 |
| S. aureus RN4220/pMS520 | MRSA | 1 | 2 | 1 | 2 | 2 | 1 | 2 | 1 | 1 | 2 | 2 | 2 | 2 | 1 | 1 |
| S. aureus MF490 | MRSA | 4 | 4 | 4 | 8 | 8 | 4 | 4 | 4 | 4 | 8 | 8 | 8 | 4 | 4 | 4 |
| E. faecium ATCC19434 | | 8 | 16 | 8 | 16 | 32 | 8 | 8 | 16 | 4 | 16 | 16 | 16 | 4 | 8 | 16 |
| E. coli JM109/pMW218 | Sensitive bacterium | 0.5 | 2 | 0.5 | 1 | 1 | 0.5 | 1 | 1 | 0.5 | 1 | 1 | 1 | 1 | 0.5 | 0.5 |
| K. pneumoniae ATCC BAA-1705 | KPC-producing strain | 1 | 2 | 1 | 2 | 1 | 1 | 1 | 1 | 2 | 2 | 2 | 2 | 1 | 1 | 1 |
| K. pneumoniae ATCC BAA-2146 | NDM-producing strain | 0.5 | 2 | 1 | 1 | 1 | 1 | 1 | 1 | 0.5 | 1 | 2 | 1 | 2 | 1 | 1 |
| A. baumannii ATCC BAA-1710 | MDRA | 4 | 8 | 8 | 8 | 8 | 4 | 8 | 8 | 4 | 8 | 4 | 8 | 4 | 4 | 8 |
| S. marcescens TH-0447 | AMK-resistant | 4 | 8 | 4 | 8 | 8 | 8 | 8 | 8 | 4 | 8 | 8 | 8 | 8 | 4 | 8 |
| S. marcescens GN6944 | GM-resistant | 2 | 8 | 4 | 4 | 4 | 4 | 8 | 4 | 4 | 4 | 8 | 8 | 4 | 4 | 4 |
| P. aeruginosa PAO1 | Sensitive bacterium | 2 | 4 | 4 | 8 | 4 | 4 | 4 | 2 | 4 | 4 | 4 | 4 | 2 | 2 | 8 |
| P. aeruginosa PAO1/GN315 | AMK-resistant | 2 | 4 | 4 | 8 | 4 | 4 | 4 | 4 | 4 | 4 | 4 | 4 | 4 | 4 | 8 |

TABLE 3-continued

| Test bacterium Abbreviated Name[1]| Compound Abbreviation[2] | O5 | P4 | Q4 | R6 | S1-a | S1-b | S1-c | S1-d | S1-e | S1-f | S1-g | S1-h | S1-i | S1-j | S1-k |
|---|---|---|---|---|---|---|---|---|---|---|---|---|---|---|---|---|
| P. aeruginosa MSC17707 | AMK-resistant | 4 | 4 | 8 | 16 | 4 | 4 | 8 | 4 | 8 | 8 | 4 | 4 | 2 | 4 | 8 |
| P. aeruginosa MSC01035 | ABK-resistant | 4 | 8 | 8 | 16 | 4 | 4 | 8 | 4 | 8 | 8 | 8 | 8 | 4 | 4 | 8 |

[1] The name of each test bacterium is as follows. S. aureus: Staphylococcus aureus, E. faecium: Enterococcus faecium, E. coli: Escherichia coli, K. pneumonia: Klebsiella pneumonia, A. baumannii: Acinetobacter baumannii, S. marcescens: Serratia marcescens, P. aeruginosa: Pseudomonas aeruginosa.
[1] Characteristics of each test bacterium is as follows. Sensitive bacterium: strains showing sensitivity against antibiotics, MRSA: methicillin-resistant Staphylococcus aureus, KPC-producing strain: Klebsiella pneumoniae carbapenemase-producing strain, NDM-producing strain: New Ddlhi metallo-β-lactamase-producing strain, MDRA: Multiple drug-resistant Acinetobacter, AMK-resistant: amikacin-resistant, GM-resistant: gentamicin-resistnat, ABK-resistant: arbekacin-resistant.
[2] The compound abbreviations in this Table correspond to the compound abbreviations of the title in each Example of the description described in parenthesis.

TABLE 4

| Test bacterium Abbreviated Name[1]| Compound Abbreviation[2] | T2-a | T2-b | T2-c | T2-d | T2-e | S1-l | S1-m | S1-n | S1-o | S1-p | S1-q | U4-a | ABK[3] | AMK[3] | GM[3] |
|---|---|---|---|---|---|---|---|---|---|---|---|---|---|---|---|---|
| S. aureus RN4220 | Sensitive bacterium | 2 | 4 | 2 | 2 | 1 | 2 | 2 | 2 | 1 | 1 | 1 | 1 | 1 | 2 | 0.5 |
| S. aureus RN4220/pMS520 | MRSA | 1 | 4 | 2 | 1 | 0.5 | 1 | 2 | 2 | 1 | 1 | 1 | 1 | 1 | 64 | 0.5 |
| S. aureus MF490 | MRSA | 8 | 8 | 8 | 4 | 2 | 8 | 8 | 8 | 2 | 2 | 4 | 4 | 64 | >64 | >64 |
| E. faecium ATCC19434 | | 8 | 16 | 8 | 4 | 4 | 16 | 16 | 8 | 8 | 4 | 4 | 4 | 8 | 32 | 8 |
| E. coli JM109/pMW218 | Sensitive bacterium | 0.5 | 1 | 1 | 1 | 0.5 | 0.5 | 1 | 1 | 0.5 | 1 | 0.5 | 0.5 | 0.5 | 0.5 | 0.25 |
| K. pneumoniae ATCC BAA-1705 | KPC-producing strain | 1 | 2 | 1 | 2 | 1 | 1 | 2 | 1 | 1 | 1 | 1 | 1 | 16 | 32 | 2 |
| K. pneumoniae ATCC BAA-2146 | NDM-producing strain | 1 | 2 | 1 | 2 | 0.5 | 0.5 | 1 | 1 | 0.5 | 1 | 0.5 | 0.5 | >64 | >64 | >64 |
| A. baumannii ATCC BAA-1710 | MDRA | 4 | 8 | 4 | 8 | 4 | 4 | 4 | 4 | 4 | 8 | 16 | 8 | 32 | 64 | >64 |
| S. marcescens TH-0447 | AMK-resistant | 4 | 8 | 8 | 8 | 4 | 4 | 4 | 4 | 4 | 8 | 4 | 4 | 64 | >64 | 32 |
| S. marcescens GN6944 | GM-resistant | 4 | 8 | 4 | 8 | 2 | 2 | 8 | 4 | 2 | 4 | 4 | 2 | 8 | 8 | 64 |
| P. aeruginosa PAO1 | Sensitive bacterium | 4 | 8 | 4 | 4 | 4 | 4 | 4 | 4 | 2 | 2 | 4 | 4 | 2 | 2 | 2 |
| P. aeruginosa PAO1/GN315 | AMK-resistant | 4 | 8 | 4 | 4 | 4 | 4 | 8 | 4 | 4 | 4 | 8 | 4 | 8 | 64 | 8 |
| P. aeruginosa MSC17707 | AMK-resistant | 4 | 8 | 4 | 8 | 4 | 4 | 8 | 8 | 4 | 4 | 8 | 8 | 4 | 32 | 8 |
| P. aeruginosa MSC01035 | ABK-resistant | 4 | 16 | 8 | 8 | 8 | 4 | 8 | 4 | 4 | 4 | 8 | 8 | >64 | >64 | >64 |

[1] The name of each test bacterium is as follows. S. aureus: Staphylococcus aureus, E. faecium: Enterococcus faecium, E. coli: Escherichia coli, K. pneumonia: Klebsiella pneumonia, A. baumannii: Acinetobacter baumannii, S. marcescens: Serratia marcescens, P. aeruginosa: Pseudomonas aeruginosa.
[1] Characteristics of each test bacterium is as follows. Sensitive bacterium: strains showing sensitivity against antibiotics, MRSA: methicillin-resistant Staphylococcus aureus, KPC-producing strain: Klebsiella pneumoniae carbapenemase-producing strain, NDM-producing strain: New Ddlhi metallo-β-lactamase-producing strain, MDRA: Multiple drug-resistant Acinetobacter, AMK-resistant: amikacin-resistant, GM-resistant: gentamicin-resistnat, ABK-resistant: arbekacin-resistant.
[2] The compound abbreviations in this Table correspond to the compound abbreviations of the title in each Example of the description described in parenthesis.
[3] Compounds in three columns from the rightmost column are existing antibiotics. The corresponding common name of each antibiotic is as follows. ABK: arbekacin, AMK: amikacin, GM: gentamicin.

TABLE 5

| Test bacterium Abbreviated Name[1]| Compound Abbreviation[2] | V1-a | V1-b | V1-c | V1-d | V1-e | V1-f | V1-g | V1-h | V1-i | V1-j | V1-k | V1-l | V1-m | V1-n | V1-o |
|---|---|---|---|---|---|---|---|---|---|---|---|---|---|---|---|---|
| S. aureus RN4220 | Sensitive bacterium | 4 | 2 | 4 | 4 | 8 | 8 | 4 | 4 | 2 | 2 | 4 | 4 | 2 | 2 | 1 |
| S. aureus RN4220/pMS520 | MRSA | 4 | 2 | 4 | 4 | 8 | 8 | 2 | 4 | 2 | 2 | 4 | 4 | 2 | 2 | 1 |
| S. aureus MF490 | MRSA | 16 | 8 | 16 | 16 | 32 | 32 | 8 | 8 | 8 | 4 | 8 | 8 | 8 | 8 | 4 |
| E. faecium ATCC19434 | | 32 | 16 | 32 | 64 | 64 | 64 | 32 | 32 | 16 | 8 | 16 | 32 | 16 | 16 | 8 |

TABLE 5-continued

| Test bacterium Abbreviated Name[1] | Compound Abbreviation[2] | V1-a | V1-b | V1-c | V1-d | V1-e | V1-f | V1-g | V1-h | V1-i | V1-j | V1-k | V1-l | V1-m | V1-n | V1-o |
|---|---|---|---|---|---|---|---|---|---|---|---|---|---|---|---|---|
| E. coli JM109/pMW218 | Sensitive bacterium | 2 | 1 | 2 | 2 | 2 | 2 | 1 | 2 | 1 | 1 | 1 | 1 | 1 | 0.5 | 0.5 |
| K. pneumoniae ATCC BAA-1705 | KPC-producing strain | 2 | 2 | 4 | 2 | 4 | 4 | 2 | 2 | 2 | 1 | 1 | 1 | 1 | 1 | 1 |
| K. pneumoniae ATCC BAA-2146 | NDM-producing strain | 2 | 1 | 2 | 2 | 2 | 2 | 1 | 2 | 1 | 1 | 1 | 1 | 1 | 1 | 1 |
| A. baumannii ATCC BAA-1710 | MDRA | 8 | 8 | 8 | 8 | 16 | 8 | 8 | 8 | 4 | 8 | 8 | 8 | 8 | 8 | 4 |
| S. marcescens TH-0447 | AMK-resistant | 8 | 16 | 16 | 16 | 16 | 16 | 16 | 16 | 8 | 8 | 16 | 8 | 8 | 8 | 8 |
| S. marcescens GN6944 | GM-resistant | 8 | 8 | 8 | 8 | 8 | 16 | 8 | 8 | 8 | 8 | 8 | 8 | 8 | 8 | 4 |
| P. aeruginosa PAO1 | Sensitive bacterium | 4 | 4 | 16 | 4 | 8 | 4 | 4 | 16 | 2 | 2 | 4 | 4 | 2 | 2 | 2 |
| P. aeruginosa PAO1/GN315 | AMK-resistant | 4 | 4 | 8 | 8 | 8 | 8 | 4 | 8 | 4 | 4 | 4 | 4 | 4 | 4 | 2 |
| P. aeruginosa MSC17707 | AMK-resistant | 8 | 4 | 8 | 8 | 8 | 8 | 4 | 4 | 2 | 2 | 4 | 4 | 2 | 2 | 2 |
| P. aeruginosa MSC01035 | ABK-resistant | 4 | 4 | 8 | 8 | 8 | 8 | 4 | 4 | 4 | 4 | 8 | 8 | 4 | 4 | 4 |

[1] The name of each test bacterium is as follows. S. aureus: Staphylococcus aureus, E. faecium: Enterococcus faecium, E. coli: Escherichia coli, K. pneumonia: Klebsiella pneumonia, A. baumannii: Acinetobacter baumannii, S. marcescens: Serratia marcescens, P. aeruginosa: Pseudomonas aeruginosa.
[1] Characteristics of each test bacterium is as follows. Sensitive bacterium: strains showing sensitivity against antibiotics, MRSA: methicillin-resistant Staphylococcus aureus, KPC-producing strain: Klebsiella pneumoniae carbapenemase-producing strain, NDM-producing strain: New Ddlhi metallo-β-lactamase-producing strain, MDRA: Multiple drug-resistant Acinetobacter, AMK-resistant: amikacin-resistant, GM-resistant: gentamicin-resistnat, ABK-resistant: arbekacin-resistant.
[2] The compound abbreviations in this Table correspond to the compound abbreviations of the title in each Example of the description described in parenthesis.

TABLE 6

| Test bacterium Abbreviated Name[1] | Compound Abbreviation[2] | V1-p | V1-q | V1-r | V1-s | W2-a | W2-b | X4-a | X4-b | Y3 | ABK[3] | AMK[3] | GM[3] |
|---|---|---|---|---|---|---|---|---|---|---|---|---|---|
| S. aureus RN4220 | Sensitive bacterium | 1 | 1 | 1 | 1 | 1 | 4 | 1 | 1 | 2 | 1 | 2 | 0.5 |
| S. aureus RN4220/pMS520 | MRSA | 1 | 1 | 1 | 1 | 1 | 2 | 1 | 1 | 2 | 1 | 64 | 0.5 |
| S. aureus MF490 | MRSA | 4 | 4 | 4 | 4 | 4 | 16 | 4 | 4 | 4 | 64 | >64 | >64 |
| E. faecium ATCC19434 | | 8 | 8 | 8 | 16 | 8 | 32 | 8 | 8 | 8 | 8 | 32 | 8 |
| E. coli JM109/pMW218 | Sensitive bacterium | 1 | 1 | 0.5 | 0.5 | 1 | 1 | 0.5 | 1 | 1 | 0.5 | 0.5 | 0.25 |
| K. pneumoniae ATCC BAA-1705 | KPC-producing strain | 1 | 1 | 1 | 0.5 | 1 | 2 | 1 | 1 | 2 | 16 | 32 | 2 |
| K. pneumoniae ATCC BAA-2146 | NDM-producing strain | 1 | 1 | 1 | 1 | 1 | 2 | 1 | 1 | 2 | >64 | >64 | >64 |
| A. baumannii ATCC BAA-1710 | MDRA | 4 | 4 | 4 | 4 | 8 | 8 | 4 | 16 | 8 | 32 | 64 | >64 |
| S. marcescens TH-0447 | AMK-resistant | 8 | 8 | 8 | 8 | 4 | 16 | 4 | 4 | 8 | 64 | >64 | 32 |
| S. marcescens GN6944 | GM-resistant | 4 | 4 | 8 | 4 | 4 | 8 | 4 | 4 | 4 | 8 | 8 | 64 |
| P. aeruginosa PAO1 | Sensitive bacterium | 2 | 2 | 2 | 1 | 4 | 2 | 4 | 4 | 4 | 2 | 2 | 2 |
| P. aeruginosa PAO1/GN315 | AMK-resistant | 4 | 4 | 2 | 2 | 4 | 4 | 4 | 8 | 8 | 8 | 64 | 8 |
| P. aeruginosa MSC17707 | AMK-resistant | 2 | 2 | 2 | 2 | 8 | 4 | 8 | 8 | 8 | 4 | 32 | 8 |
| P. aeruginosa MSC01035 | ABK-resistant | 4 | 4 | 4 | 4 | 4 | 4 | 8 | 16 | 16 | >64 | >64 | >64 |

[1] The name of each test bacterium is as follows. S. aureus: Staphylococcus aureus, E. faecium: Enterococcus faecium, E. coli: Escherichia coli, K. pneumonia: Klebsiella pneumonia, A. baumannii: Acinetobacter baumannii, S. marcescens: Serratia marcescens, P. aeruginosa: Pseudomonas aeruginosa.
[1] Characteristics of each test bacterium is as follows. Sensitive bacterium: strains showing sensitivity against antibiotics, MRSA: methicillin-resistant Staphylococcus aureus, KPC-producing strain: Klebsiella pneumoniae carbapenemase-producing strain, NDM-producing strain: New Ddlhi metallo-β-lactamase-producing strain, MDRA: Multiple drug-resistant Acinetobacter, AMK-resistant: amikacin-resistant, GM-resistant: gentamicin-resistnat, ABK-resistant: arbekacin-resistant.
[2] The compound abbreviations in this Table correspond to the compound abbreviations of the title in each Example of the description described in parenthesis.
[3] Compounds in three columns from the rightmost column are existing antibiotics. The corresponding common name of each antibiotic is as follows. ABK: arbekacin, AMK: amikacin, GM: gentamicin.

Results in Tables 1 to 6 have shown that the compounds of the present invention have antibacterial activities against both gram-positive and gram-negative bacteria. Also, it has been demonstrated that the compounds of the present invention have strong antimicrobial activities against resistance strains or low sensitive strains of Staphylococcus aureus, Klebsiella pneumoniae, Acinetobacter, Serratia and Pseudomonas aeruginosa that are either resistant or low sensitive to existing antibiotics such as arbekacin (ABK), amikacin (AMK) and gentamicin (GM).

The invention claimed is:

1. A method for the treatment of bacterial infectious disease comprising administering a therapeutically effective dose of a compound represented by a formula (I) or a pharmaceutically acceptable salt or hydrate thereof:

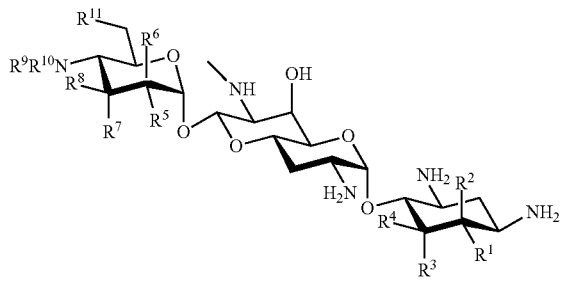

(I)

wherein,
$R^1$ is a hydrogen atom or a hydroxyl group,
$R^2$ is a hydrogen atom or an amino group,
$R^3$ is a hydrogen atom, a halogen atom, a hydroxyl group or an amino group,
$R^4$ is a hydrogen atom, a halogen atom or an amino group, wherein $R^1$ and $R^4$ may form a double bond together,
$R^5$ is a hydrogen atom, a hydroxyl group or an amino group,
$R^6$ is a hydrogen atom, a hydroxyl group or an amino group,
$R^7$ is a hydrogen atom, a hydroxyl group or an amino group,
$R^8$ is a hydrogen atom, a hydroxyl group or an amino group,
$R^9$ and $R^{10}$ are each independently a hydrogen atom, a $C_{1-6}$ alkyl group, an amino-$C_{1-6}$ alkyl group, a guanidino-$C_{1-6}$ alkyl group, an amino-$C_{3-7}$ cycloalkyl group, an amino-$C_{3-7}$ cycloalkyl-$C_{1-6}$ alkyl group, an amidino group, an azetidino group optionally substituted with a $C_{1-6}$ alkyl group, a glycyl group, a sarcosyl group, an L-alanyl group, a D-alanyl group, an L-seryl group, a D-seryl group, a β-alanyl group, an L-isoseryl group or a D-isoseryl group; and
$R^{11}$ is a hydrogen atom, a hydroxyl group or a fluorine atom,
except when
(i) $R^5$, $R^8$, and $R^{11}$ are hydroxyl groups, $R^1$, $R^2$, $R^3$, $R^4$, $R^6$, $R^7$, $R^9$, and $R^{10}$ are hydrogen atoms, or
(ii) $R^1$, $R^5$, $R^8$, and $R^{11}$ are hydroxyl groups, $R^2$, $R^3$, $R^4$, $R^6$, $R^7$, $R^9$, and $R^{10}$ are hydrogen atoms.

* * * * *